United States Patent
Kim et al.

(10) Patent No.: US 12,091,403 B2
(45) Date of Patent: Sep. 17, 2024

(54) COMPOUND FOR ORGANIC ELECTRIC ELEMENT, ORGANIC ELECTRIC ELEMENT USING SAME, AND ELECTRONIC DEVICE THEREOF

(71) Applicant: DUK SAN NEOLUX CO., LTD, Cheonan-si (KR)

(72) Inventors: Yu Ri Kim, Wonju-si (KR); Jong Gwang Park, Cheonan-si (KR); Yun Suk Lee, Seongnam-si (KR); Yong Wook Park, Anseong-si (KR); Hyun Ji Oh, Cheonan-si (KR)

(73) Assignee: Duk San Neolux Co., Ltd. (KR)

( * ) Notice: Subject to any disclaimer, the term of this patent is extended or adjusted under 35 U.S.C. 154(b) by 694 days.

(21) Appl. No.: 17/287,556

(22) PCT Filed: Oct. 23, 2019

(86) PCT No.: PCT/KR2019/013993
§ 371 (c)(1),
(2) Date: Apr. 22, 2021

(87) PCT Pub. No.: WO2020/085797
PCT Pub. Date: Apr. 30, 2020

(65) Prior Publication Data
US 2021/0380568 A1 Dec. 9, 2021

(30) Foreign Application Priority Data
Oct. 23, 2018 (KR) .................. 10-2018-0126915

(51) Int. Cl.
*C07D 409/12* (2006.01)
*C07D 407/12* (2006.01)
(Continued)

(52) U.S. Cl.
CPC ......... *C07D 409/12* (2013.01); *C07D 407/12* (2013.01); *H10K 85/615* (2023.02);
(Continued)

(58) Field of Classification Search
None
See application file for complete search history.

(56) References Cited

U.S. PATENT DOCUMENTS 9,691,990 B2 6/2017 Mun et al.
10,297,758 B2 5/2019 Lee et al.
(Continued)

FOREIGN PATENT DOCUMENTS

CN 107382960 A 11/2017
CN 107406402 A 11/2017
(Continued)

OTHER PUBLICATIONS

Machine translation of WO-2017095075-A1, translation generated Nov. 2023, 30 pages. (Year: 2023).*

(Continued)

*Primary Examiner* — Robert S Loewe
(74) *Attorney, Agent, or Firm* — Harness, Dickey & Pierce, P.L.C.

(57) ABSTRACT

The present invention relates to a compound for an organic electric element, an organic electric element using same, and an electronic device thereof. According to the present invention, high light-emitting efficiency, low driving voltage, and high heat resistance can be achieved in the element, and the color purity and lifespan of the element can be improved.

10 Claims, 2 Drawing Sheets

(51) Int. Cl.
  *H10K 85/60* (2023.01)
  *H10K 50/11* (2023.01)
  *H10K 50/15* (2023.01)
  *H10K 50/16* (2023.01)
  *H10K 50/17* (2023.01)
  *H10K 101/10* (2023.01)
  *H10K 101/40* (2023.01)

(52) U.S. Cl.
  CPC ......... *H10K 85/633* (2023.02); *H10K 85/636* (2023.02); *H10K 85/6572* (2023.02); *H10K 85/6574* (2023.02); *H10K 85/6576* (2023.02); *H10K 50/11* (2023.02); *H10K 50/15* (2023.02); *H10K 50/16* (2023.02); *H10K 50/171* (2023.02); *H10K 2101/10* (2023.02); *H10K 2101/40* (2023.02)

(56) References Cited

U.S. PATENT DOCUMENTS

| | | | |
|---|---|---|---|
| 2015/0322337 A1* | 11/2015 | Hattori | C07F 9/65586 548/440 |
| 2017/0288148 A1* | 10/2017 | Park | H10K 85/636 |
| 2018/0072695 A1 | 3/2018 | Byun et al. | |
| 2018/0358563 A1 | 12/2018 | Park et al. | |
| 2019/0047992 A1* | 2/2019 | Park | H10K 50/11 |
| 2019/0157560 A1 | 5/2019 | Lee et al. | |
| 2020/0020863 A1 | 1/2020 | Park et al. | |
| 2020/0136052 A1 | 4/2020 | So et al. | |
| 2020/0152874 A1 | 5/2020 | Park et al. | |
| 2020/0172524 A1 | 6/2020 | Park et al. | |
| 2021/0184129 A1 | 6/2021 | Mun et al. | |

FOREIGN PATENT DOCUMENTS

| | | | |
|---|---|---|---|
| CN | 110997650 A | 4/2020 | |
| CN | 112055740 A | 12/2020 | |
| KR | 20150007476 A | 1/2015 | |
| KR | 20150081451 A | 7/2015 | |
| KR | 101614739 B1 | 4/2016 | |
| KR | 20170083765 A | 7/2017 | |
| KR | 20190105437 A | 9/2019 | |
| WO | WO-2017095075 A1 * | 6/2017 | ........... C07D 209/82 |
| WO | 2018016786 A1 | 1/2018 | |

OTHER PUBLICATIONS

International Search Report (in English and Korean) and Written Opinion of the ISA (in Korean) issued in PCT/KR2019/013993, mailed Feb. 7, 2020; ISA/KR.

* cited by examiner

COMPOUND FOR ORGANIC ELECTRIC ELEMENT, ORGANIC ELECTRIC ELEMENT USING SAME, AND ELECTRONIC DEVICE THEREOF

CROSS-REFERENCE TO RELATED APPLICATIONS

This application is a U.S. National Phase Application under 35 U.S.C. 371 of International Application No. PCT/KR2019/013993, filed on Oct. 23, 2019, which claims the benefit of Korean Patent Application No. 10-2018-0126915, filed on Oct. 23, 2018. The entire disclosures of the above applications are hereby incorporated by reference for all purposes as if fully set forth herein.

TECHNICAL FIELD

The present disclosure relates to a compound for an organic electric element, an organic electric element using the same compound, and an electronic device including the same element.

BACKGROUND ART

In general, an organic light emitting phenomenon refers to a phenomenon where electrical energy is converted into light energy using an organic material. An organic electric element using the organic light emitting phenomenon has a structure including an anode, a cathode, and an organic material layer disposed between the cathode and the anode. Here, in a number of cases, the organic material layer has a multi-layer structure made of different materials in order to improve the efficiency and stability of an organic electric element. For example, the organic material layer may include a hole injection layer, a hole transport layer, an emissive layer, an electron transport layer, an electron injection layer, and the like.

The materials used in the organic material layer may be categorized as emissive materials and charge transport materials, such as a hole injection material, a hole transport material, an electron transport material, and an electron injection material, depending on the function.

In addition, the emissive materials may be categorized as high-molecular weight types and low-molecular weight types depending on the molecular weight, and may be categorized as fluorescent materials based on singlet excitation of electrons and phosphorescent materials based on triplet excitation of electrons depending on the emission mechanism. In addition, the emissive materials may be categorized as blue, green, and red emissive materials depending on the color of emitted light, as well as yellow and orange emissive materials necessary for realizing more natural colors.

When a single material is used as an emissive material, a maximum emission wavelength may be shifted to a long wavelength and color purity may decrease because of interactions between molecules, or device efficiency may decrease because of an emission quenching effect. Thus, a host-dopant system may be used as an emissive material in order to increase color purity and increase luminous efficiency through energy transfer. According to the principle, when a small amount of dopant having a smaller energy band gap than the host of the emissive layer is added to the emissive layer, excitons generated in the emissive layer are transferred to the dopant to generate light with high efficiency. At this time, since the wavelength of the host is shifted to the wavelength band of the dopant, light having an intended wavelength may be obtained depending on the type of the dopant used.

Currently, in the portable display market, displays are increasing in size into large-area displays. Since portable displays are provided with a battery serving as a power supply, portable displays require more efficient consumption power than existing consumption power. In addition, in this situation, not only the challenge for efficient consumption power but also challenges for luminous efficiency and lifetime must be solved.

Efficiency, lifetime, a driving voltage and the like are related to each other. An increase in the efficiency leads to a relative decrease in the driving voltage, by which the crystallization of the organic material due to Joule heating during driving is reduced, thereby increasing the lifetime. However, simply improving the organic material layer may not maximize the efficiency. This is because, when the optimal combination of the energy level and T1 value between each organic material layer and the intrinsic properties (mobility, interfacial properties, etc.) of the material are achieved, both increased life and high efficiency may be achieved. Therefore, it is necessary to develop a light-emitting material that may efficiently achieve charge balance in the emitting layer while having high thermal stability.

That is, in order to sufficiently exhibit the excellent characteristics of the organic electric element, materials for forming the organic material layer in the element, such as a hole injection material, a hole transport material, a light-emitting material, an electron transport material, an electron injection material, and an emitting-auxiliary layer material, should be supported by stable and efficient materials. However, such a stable and efficient organic material layer material for an organic electric element has not been sufficiently developed yet.

DISCLOSURE

Technical Problem

The present disclosure is intended to provide a compound able to provide high luminous efficiency, a low driving voltage, high heat resistance, high color purity, and increased lifetime to an element, an organic electric element using the same compound, and an electronic device including the same element.

Technical Solution

According to an aspect, the present disclosure provides a compound represented by the following formula:

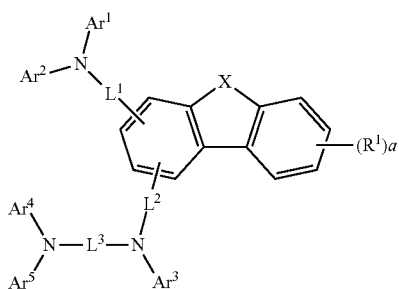

According to another aspect, the present disclosure provides an organic electric element using the compound represented by the above formula and an electronic device including the same element.

Advantageous Effects

As set forth above, it is possible to realize high luminous efficiency, a low driving voltage, and high heat resistance of the element, improve the color purity of the element, and increase the lifetime of the element using the compound according to the present disclosure.

MODE FOR INVENTION

Figure 1:
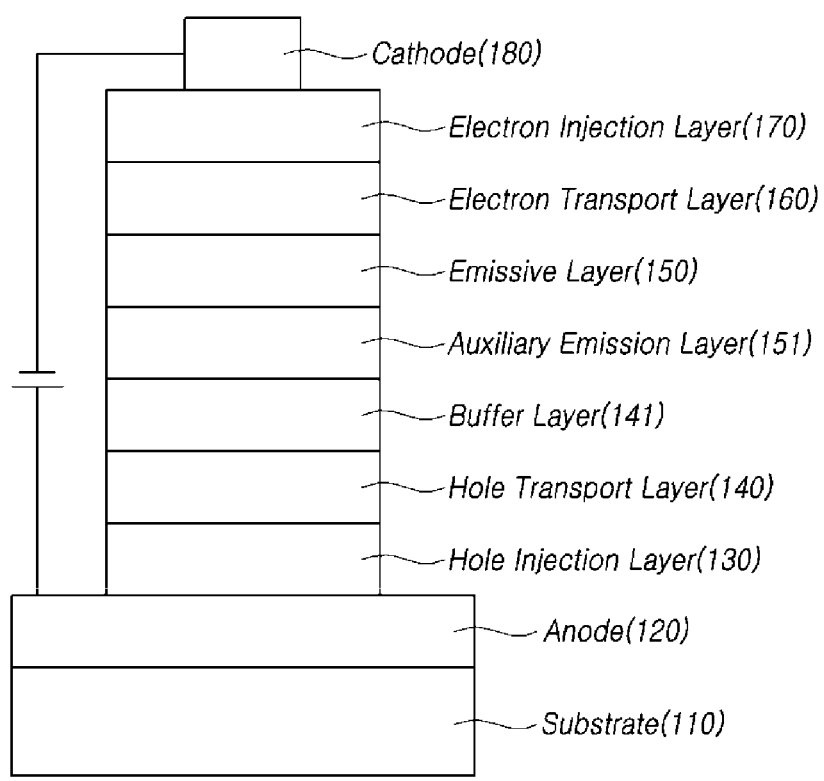
FIG. 1 is a cross-sectional view illustrating an organic light-emitting element according to an embodiment of the present disclosure.

Hereinafter, embodiments of the present disclosure will be described in detail with reference to the accompanying drawings.

In designating components of the drawings by reference numerals, the same components will be designated by the same reference numerals if possible although they are shown in different drawings. Further, in the following description of the present disclosure, a detailed description of known functions and configurations incorporated herein will be omitted in the situation in which the subject matter of the present disclosure may be rendered unclear thereby.

In addition, terms, such as first, second, A, B, (a), or (b), may be used herein when describing components of the present disclosure. Each of these terminologies is not used to define an essence, order, or sequence of a corresponding component but used merely to distinguish the corresponding component from other components. In the case that it is described that a certain component is "connected", "coupled", or "joined" to another component, it should be understood that another component may be "connected", "coupled", or "joined" to the component not only directly but also indirectly through an intervening component.

In addition, in the case that it is described that a certain component, such as a layer, a film, an area, or a plate, is "above" or "over" another component, it should be understood that the component may be above another component not only "directly" but also indirectly through an intervening component. In contrast, in the case that it is described that a certain component is "directly above" another component, it should be understood that there is no intervening element.

Terms used in this specification and the accompanying Claims will be defined as follows, unless otherwise stated.

Unless otherwise stated, the term "halo" or "halogen", as used herein, includes fluorine (F), chlorine (Cl), bromine (Br), or iodine (I).

Unless otherwise stated, the term "alkyl" or "alkyl group", as used herein, has a single bond of 1 to 60 carbon atoms, and refers to saturated aliphatic functional radicals including a straight chain alkyl group, a branched chain alkyl group, a cycloalkyl (alicyclic) group, an alkyl-substituted cycloalkyl group, or a cycloalkyl-substituted alkyl group.

Unless otherwise stated, the term "haloalkyl" or "halogen alkyl", as used herein, includes a halogen-substituted alkyl group.

Unless otherwise stated, the term "alkenyl" or "alkynyl", as used herein, has a double or triple bond of 2 to 60 carbon atoms and includes a straight chain group or a branched chain group, but is not limited thereto.

Unless otherwise stated, the term "cycloalkyl" as used herein refers to, but is not limited to, alkyl forming a ring having 3 to 60 carbon atoms.

The term "alkoxy group" or "alkyloxy group", as used herein, refers to an alkyl group to which an oxygen radical is attached and, unless otherwise stated, has, but is not limited to, 1 to 60 carbon atoms.

The term "alkenoxyl group", "alkenoxy group", "alkenyloxyl group", or "alkenyloxy group" refers to an alkenyl group to which an oxygen radical is attached, and unless otherwise stated, has, but is not limited to, 2 to 60 carbon atoms.

Unless otherwise stated, the term "aryl group" or "arylene group", as used herein, has, but is not limited thereto, 6 to 60 carbon atoms. In this specification, the aryl group or the arylene group includes a monocyclic compound, a ring assembly, fused polycyclic systems, a compound, or the like. For example, the aryl group may refer to a phenyl group, a monovalent functional group of biphenyl, a monovalent functional group of naphthalene, a fluorenyl group, or a substituted fluorenyl group.

Unless stated otherwise, the term "fluorenyl group" or "fluorenylene group", as used herein, refers to a monovalent or divalent functional group of fluorene. The term "substituted fluorenyl group" or "substituted fluorenylene group", as used herein, refers to a monovalent or divalent functional group of substituted fluorene. The term "substituted fluorene" refers to a compound in which at least one of substituent R, R', R", or R''' below is a functional group other than hydrogen, and includes a case in which R and R' are bonded to form a spiro compound together with carbon atoms attached thereto.

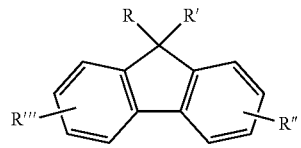

In addition, R, R', R", and R''' may independently be an alkyl group having 1 to 20 carbon atoms, an alkenyl group having 1 to 20 carbon atoms, an aryl group having 6 to 30 carbon atoms, or a heterocyclic group having 3 to 30 carbon atoms. For example, the aryl group may be phenyl, biphenyl, naphthalene, anthracene, or phenanthrene. The heterocyclic group may be pyrrole, furan, thiophene, pyrazole, imidazole, triazole, pyridine, pyrimidine, pyridazine, pyrazine, triazine, indole, benzofuran, quinazoline, or quinoxaline. For example, each of the substituted fluorenyl group and the substituted fluorenylene group may be a monovalent or divalent functional group of 9,9-dimethylfluorene, 9,9-diphenylfluorene, or 9,9'-spirobi[9H-fluorene].

The term "ring assembly", as used herein, refers to a compound in which two or more rings (single rings or fused ring systems) are joined directly by single or double bonds and in which the number of such direct ring junctions is one less than the total number of ring systems in the compound.

In ring assemblies, the same or different ring systems may be joined directly by single or double bonds.

Herein, the aryl group includes the ring assembly. Thus, the aryl group includes biphenyl and terphenyl in which benzene rings, i.e. mono-aromatic rings, are joined by single bonds. In addition, the aryl group includes compounds in which a single aromatic ring and a fused aromatic ring system are joined by a single bond. For example, the aryl group also includes compounds in which a benzene ring, i.e. an example of the single aromatic ring, and fluorene, i.e. an example of the fused aromatic ring system, are joined by a single bond to form a conjugated pi electron system.

The term "fused polycyclic system", as used herein, refers to a form of fused rings sharing at least two atoms. The fused polycyclic system includes a form in which two or more hydrocarbon ring systems are fused, a form in which at least one hetero ring system including at least one heteroatom is fused, and the like. The fused polycyclic system may be an aromatic ring, a heteroaromatic ring, an aliphatic ring, or combinations thereof.

The term "spiro compound", as used herein, has "a spiro union", which refers to a union of two rings sharing only one atom. In this case, the atom shared by the two rings is referred to as a "spiro atom". Such spiro compounds are referred to as, for example, "monospiro", "dispiro", and "trispiro" compound depending on the number of spiro atoms included in the compound.

The term "heterocyclic group", as used herein, includes not only aromatic rings, such as a "heteroaryl group" or a "heteroarylene group", but also non-aromatic rings. Unless stated otherwise, the heterocyclic group refers to, but is not limited to, rings each having 2 to 60 carbon atoms and including one or more heteroatoms. The term "heteroatom", as used herein, refers to N, O, S, P, or Si, unless stated otherwise. The "heterocyclic group" refers to monocyclic compounds, ring assemblies, fused polycyclic systems, spiro compounds, or the like.

In addition, the "heterocyclic group", as used herein, may include rings having $SO_2$ in place of a ring-forming carbon atom. For example, the "heterocyclic group" includes the following compound:

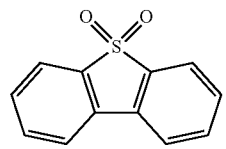 [SMILES: O=S1(=O)c2ccccc2-c2ccccc21]

The term "ring", as used herein, refers to monocyclic rings and polycyclic rings, includes not only hydrocarbon rings but also hetero rings including at least one heteroatom, and includes aromatic rings and non-aromatic rings.

The term "polycyclic ring", as used herein, includes ring assemblies, such as biphenyl or terphenyl, fused polycyclic systems, and spiro compounds. The polycyclic ring includes not only aromatic compounds but also non-aromatic compounds, and includes not only hydrocarbon rings but also hetero rings including at least one heteroatom.

In addition, in the case that prefixes are named consecutively, it means that substituents are listed in the order of the prefixes. For example, an aryl alkoxy group refers to an alkoxy group substituted with an aryl group, an alkoxy carbonyl group refers to a carbonyl group substituted with an alkoxy group, and an aryl carbonyl alkenyl group refers to an alkenyl group substituted with an arylcarbonyl group, with the arylcarbonyl group being a carbonyl group substituted with an aryl group.

Unless clearly stated otherwise, the term "substituted" in the term "substituted or non-substituted", as used herein, refers to substitution with one or more substituents selected from the group consisting of, but not limited to, deuterium, a halogen, an amino group, a nitrile group, a nitro group, a $C_1$-$C_{20}$ alkyl group, a $C_1$-$C_{20}$ alkoxy group, a $C_1$-$C_{20}$ alkyl amine group, a $C_1$-$C_{20}$ alkylthiophene group, a $C_6$-$C_{20}$ arylthiophene group, a $C_2$-$C_{20}$ alkenyl group, a $C_2$-$C_{20}$ alkynyl group, a $C_3$-$C_{20}$ cycloalkyl group, a $C_6$-$C_{20}$ aryl group, a $C_6$-$C_{20}$ aryl group substituted with deuterium, a $C_8$-$C_{20}$ aryl alkenyl group, a silane group, a boron group, a germanium group, and a $C_2$-$C_{20}$ heterocyclic group including at least one heteroatom selected from the group consisting of O, N, S, Si, and P.

Herein, "the name of a functional group" corresponding to the aryl group, the arylene group, the heterocyclic group, or the like illustrated as each symbol and a substituent thereof may be written in "the name of the functional group on which the valence thereof is reflected" or may be written in "the name of the parent compound thereof". For example, phenanthrene, i.e., a type of aryl group, may be written in group names by distinguishing the valence. That is, a monovalent phenanthrene "group" may be written as "phenanthryl (group)," while a divalent phenanthrene "group" may be written as "phenanthrylene (group)". In contrast, phenanthrene groups may be written as "phenanthrene", i.e. the name of the parent compound, regardless of the valence. Similarly, pyrimidine may be written as "pyrimidine" regardless of the valence or may be written in group names each corresponding to the valence, in which a monovalent pyrimidine group is written as pyrimidinyl (group) and a divalent pyrimidine group is written as pyrimidinylene (group). Accordingly, when the type of a substituent is written in the name of the parent compound in this specification, the written name may refer to an n-valence "group" formed by the desorption of a carbon atom and/or a heteroatom-bonded hydrogen atom from the parent compound.

In addition, unless clearly stated otherwise, formulas used herein are applied in the same manner as the definition of the substituent based on the exponential definition of the following Formula:

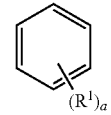

Here, when a is 0, there is no substituent $R^1$. When a is 1, a single substituent $R^1$ is attached to any one of the carbon atoms of the benzene ring. When a is 2 or 3, the substituent $R^1$ is attached in the following manner, where $R^1$ may be of the same or different values. When a is an integer between 4 and 6, the substituent $R^1$ is attached to a carbon atom of the benzene ring in a similar manner. Here, the illustration of hydrogen atoms attached to carbon atoms of the benzene ring will be omitted.

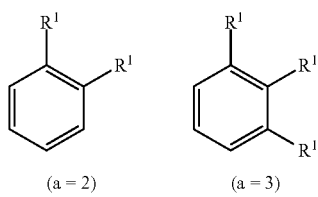

(a = 2)     (a = 3)

Herein, the expression "substituents bonded to form a ring" refers to a case that a plurality of substituents bonded to each other form a saturated or unsaturated ring by sharing a carbon atom and at least one heteroatom selected from among O, N, S, Si, or P. For example, naphthalene may be regarded as an unsaturated ring formed by a methyl group and a butadienyl group, which are substituted to one of benzene rings, are in vicinity of each other, and share one carbon atom, or an unsaturated ring formed by a vinyl group and a propylenyl group sharing one carbon atom. In addition, fluorine itself may be regarded to be an aryl group having 13 carbon atoms. In addition, fluorine may also be regarded to be a compound in which two methyl groups substituted to biphenyl groups are bonded while sharing one carbon atom so as to form a ring.

FIG. 1 is a view illustrating an example of an organic light-emitting element according to an embodiment of the present disclosure.

Referring to FIG. 1, an organic electric element 100 includes a first electrode 120 and a second electrode 180 provided on a substrate 110 and an organic material layer provided between the first electrode 120 and the second electrode 180 and containing a compound according to the present disclosure. Here, the first electrode 120 may be an anode (or a positively charged electrode), while the second electrode 180 may be a cathode (or a negatively charged electrode). In the case of an inverted type, the first electrode may be a cathode, while the second electrode may be an anode.

The organic material layer may include a hole injection layer 130, a hole transport layer 140, an emissive layer 150, an electron transport layer 160, and an electron injection layer 170 provided sequentially on the first electrode 120. One of these layers may be omitted, or a hole stop layer, an electron stop layer, an auxiliary emission layer 151, a buffer layer 141, or the like may be further included. The electron transport layer 160 or the like may serve as the hole stop layer.

In addition, although not shown, the organic electric element according to the present disclosure may further include a passivation layer or a light efficiency improvement layer (or a capping layer) provided on one surface, from among at least one surface of the first electrode the second electrode, opposite the organic material layer.

The compound according to the present disclosure applied to the organic material layer may be used as a material for the hole injection layer 130, the hole transport layer 140, the electron transport layer 160, the electron injection layer 170, the emissive layer 150, the light efficiency improvement layer, the auxiliary emission layer, or the like.

In addition, even with the same core, the band gap, electrical properties, interfacial properties, and the like may vary depending on which substituents are attached at which positions, regardless of the same core. The selection of the core and a combination of the core and a sub-substituent bonded thereto are significantly important. In particular, when the energy levels, $T_1$ values, inherent material properties (e.g. mobility or interfacial properties), and the like among the respective layers of the organic material layer are optimally combined, both increased lifetime and high efficiency may be achieved.

As described above, recently, in organic electroluminescent elements, the auxiliary emission layer may be provided between the hole transport layer and the emissive layer in order to overcome the problem of light emission in the hole transport layer. It is necessary to form different auxiliary emission layers corresponding to red (R), green (G), and blue (B) emissive layers, respectively. In other words, the auxiliary emission layer includes a red auxiliary emission layer from among the red auxiliary emission layer, a green auxiliary emission layer, or a blue auxiliary emission layer corresponding to the red emissive layer, the green emissive layer, the blue emissive layer. In addition, the correlation of the auxiliary emission layer with the hole transport layer and the emissive layer (i.e. the host) must be determined. Even though a similar core is used, when the organic material layer is changed, it may be difficult to analogize the characteristics of the auxiliary emission layer.

Thus, the energy levels, $T_1$ values, intrinsic properties of materials (e.g. mobility or interfacial properties), or the like of the respective organic material layers may be optimized by forming at least one of the emissive layer, the hole transport layer, or the auxiliary emission layer by using the compound represented by Formula 1 according to the present disclosure, thereby increasing the lifetime of the organic electric element while improving the efficiency of the organic electric element.

An organic electroluminescent element according to an embodiment of the present disclosure may be fabricated using a variety of deposition methods. The organic electroluminescent element may be fabricated using a deposition method, such as physical vapor deposition (PVD) or chemical vapor deposition (CVD). For example, the organic electroluminescent element may be fabricated by: forming the positively charged electrode 120 by depositing a metal, a conductive metal oxide, or an alloy thereof on a substrate; forming the organic material layer including the hole injection layer 130, the hole transport layer 140, the emissive layer 150, the electron transport layer 160, and the electron injection layer 170 on the positively charged electrode 120; and depositing a material usable as the negatively charged electrode 180 on the organic material layer. In addition, the auxiliary emission layer 151 may be further provided between the hole transport layer 140 and the emissive layer 150.

In addition, the organic material layer may be fabricated into a smaller number of layers by a solution process or a solvent process, such as a spin coating process, a nozzle printing process, an inkjet printing process, a slot coating process, a dip coating process, a roll-to-roll process, a doctor blading process, a screen printing process, or a thermal transfer process, using a variety of polymer materials. Since the organic material layer according to the present disclosure may be formed by a variety of methods, the scope of the right of the present disclosure is not limited by the method forming the organic material layer.

The organic electric element according to the present disclosure may be a top emission type, a bottom emission type, or a dual emission type depending on the material used therein.

The white organic light-emitting device (WOLED) has merits, such as the ease of realization of high resolution, superior processability, and the ability thereof to be fabricated using existing color filter technologies for liquid crystal displays (LCDs). For the WOLED mainly used in a backlight unit, a variety of structures have been proposed and patented. Representative are a planar side-by-side arrangement of red (R), green (G), and blue (B) light-emitting structures, a vertical stack arrangement of RGB light-emitting structures, and a color conversion material (CCM) structure in which electroluminescence from a blue (B) organic emissive layer and photo-luminescence from an inorganic luminescent material using the electroluminescence are used. The present disclosure may be applied to the WOLED.

In addition, the organic electric element according to the present disclosure may be one of an organic electroluminescent element (OLED), an organic photovoltaic cell, an organic photo conductor (OPC), an organic transistor (e.g. an organic thin-film transistor (TFT)), or a monochromatic or white lighting element.

Figure 2:
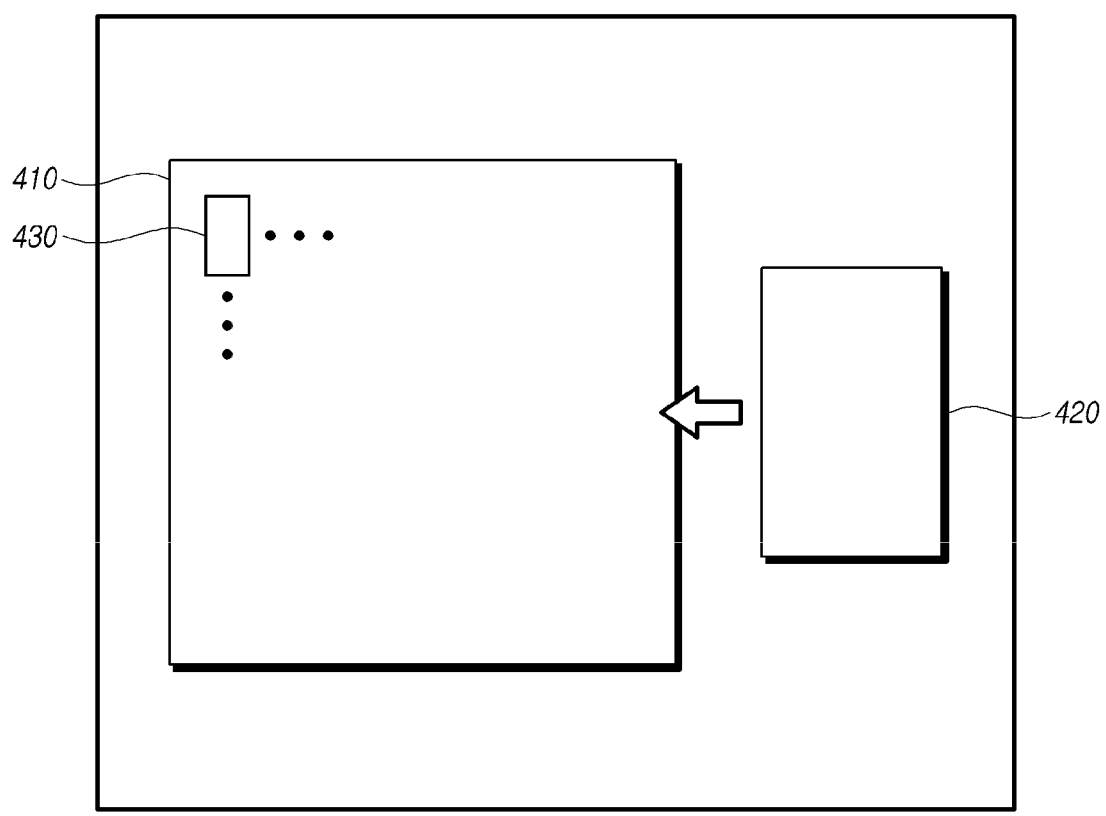
FIG. 2 is a view illustrating an example of an electronic device according to an embodiment of the present disclosure.

FIG. 2 is a view illustrating an example of an electronic device according to an embodiment of the present disclosure.

The electronic device 200 may comprise an electronic device including a display device 210 including an organic electric element 230 according to the present disclosure, as described above, and a controller 220 controlling the display device. Here, the electronic device may be a present or future wired/wireless communication terminal, and refers to all types of electronic devices including a mobile communication terminal, such as a mobile device, a personal digital assistant (PDA), an electronic dictionary, a portable multimedia player (PMP), a remote control, a navigation device, a game device, a variety of televisions (TVs), a variety of computers, and the like.

The controller 220 may be a controller applying at least one of a driving voltage or a signal to the organic electric element. For example, the controller 220 may comprise a plurality of gate lines, a gate driver circuit driving the gate lines, a plurality of data lines, a data driver circuit driving the data lines, and a controller controlling the gate driver circuit and the data driver circuit.

The controller controls the data driver circuit and the gate driver circuit by supplying a variety of control signals to the data driver circuit and the gate driver circuit.

Hereinafter, a compound according to an aspect of the present disclosure will be described. The compound according to the aspect of the present disclosure is represented by Formula 1 below.

<Formula 1>

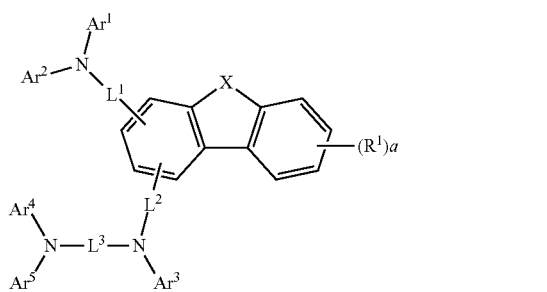

Here, X, $Ar^1$ to $Ar^5$, $R^1$, a, and $L^1$ to $L^3$ used in Formula 1 will be now described.

X is O or S.

Due to the use of the above-described element as X in Formula 1, the compound according to Formula 1 may provide an element that achieves high luminous efficiency, a low driving voltage, high heat resistance, high color purity, and increased lifetime.

$Ar^1$ to $Ar^5$ are the same or different and are respectively and independently selected from the group consisting of a $C_6$-$C_{60}$ aryl group; a $C_2$-$C_{60}$ heterocyclic group including at least one heteroatom selected from among O, N, S, Si, or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$).

When $Ar^1$ to $Ar^5$ are respectively an aryl group, each of $Ar^1$ to $Ar^5$ may be independently a $C_6$-$C_{40}$ aryl group, a $C_6$-$C_{30}$ aryl group, $C_6$-$C_{25}$ aryl group, or a $C_6$-$C_{20}$ aryl group. For example, each of $Ar^1$ to $Ar^5$ may be independently selected from the group consisting of benzene, naphthalene, anthracene, phenanthrene, tetracene, benzo anthracene, triphenylene, biphenyl, terphenyl, and substituted or unsubstituted fluorene. When $Ar^1$ to $Ar^5$ are as above, the compound of Formula 1 may provide an element that achieves high luminous efficiency, a low driving voltage, high heat resistance, high color purity, and increased lifetime.

When $Ar^1$ to $Ar^5$ are respectively a heterocyclic group, each of $Ar^1$ to $Ar^5$ may be a $C_2$-$C_{30}$ heterocyclic group or a $C_2$-$C_{15}$ heterocyclic group. For example, each of $Ar^1$ to $Ar^5$ may be independently selected from the group consisting of pyrrole, pyrazole, imidazole, triazole, furan, thiophene, pyridine, pyridazine, pyrimidine, pyrazine, triazine, indole, quinazoline, quinoxaline, dibenzothiophene, and dibenzofuran. When $Ar^1$ to $Ar^5$ are as above, the compound of Formula 1 may provide an element that achieves high luminous efficiency, a low driving voltage, high heat resistance, high color purity, and increased lifetime.

$R^1$ is selected from the group consisting of deuterium; tritium; halogen; a cyano group; a nitro group; a $C_6$-$C_{60}$ aryl group; a $C_2$-$C_{60}$ heterocyclic group including at least one heteroatom selected from among O, N, S, Si, or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$). When a is two or more, $R^1$ may be the same or different, and a plurality of $R^1$s may be bonded to form a ring.

When $R^1$ is an alkyl group, $R^1$ may be a $C_1$-$C_{30}$ alkyl group, a $C_1$-$C_{20}$ alkyl group, or a $C_1$-$C_{10}$ alkyl group. For example, the alkyl group may be a $C_1$-$C_{10}$ straight chain alkyl group, a branched alkyl group, a cycloalkyl group, an alkyl-substituted cycloalkyl group, or a cycloalkyl-substituted alkyl group. When $R^1$ is as above, the compound of Formula 1 may provide an element that achieves high luminous efficiency, a low driving voltage, high heat resistance, high color purity, and increased lifetime.

When $R^1$ is an aryl group, $R^1$ may be a $C_6$-$C_{40}$ aryl group, a $C_6$-$C_{30}$ aryl group, $C_6$-$C_{25}$ aryl group, or a $C_6$-$C_{20}$ aryl group. For example, $R^1$ may be selected from the group consisting of benzene, naphthalene, anthracene, phenanthrene, tetracene, benzo anthracene, triphenylene, biphenyl, terphenyl, and substituted and unsubstituted fluorine. When $R^1$ is as above, the compound of Formula 1 may provide an element that achieves high luminous efficiency, a low driving voltage, high heat resistance, high color purity, and increased lifetime.

When $R^1$ is an alkoxy group, $R^1$ may be a $C_1$-$C_{30}$ alkoxy group, a $C_1$-$C_{20}$ alkoxy group, or a $C_1$-$C_{10}$ alkoxy group. For example, the alkyl group may be a $C_1$-$C_9$ straight chain alkyl group, a branched alkyl group, a cycloalkyl group, an alkyl-substituted cycloalkyl group, or a cycloalkyl-substituted alkyl group to which an oxygen radical is attached. When $R^1$ is as above, the compound of Formula 1 may provide an element that achieves high luminous efficiency, a low driving voltage, high heat resistance, high color purity, and increased lifetime.

a is an integer of 0 to 4. Since a is a coefficient of $R^1$ substituted to the condensed benzene ring of Formula 1, when a is 0, it is to be understood that hydrogen in the condensed benzene ring is not substituted with $R^1$. When a is an integer of 0 to 4, it is to be understood that $R^1$ is substituted to the condensed benzene ring by the number corresponding to a. When two or more $R^1$s are present, one or more $R^1$s in the plurality of $R^1$s may be the same or different.

$L^1$ to $L^3$ are the same or different. Each of $L^1$ to $L^3$ is independently selected from the group consisting of a single bond; a $C_6$-$C_{60}$ aryl group; a $C_3$-$C_{60}$ aliphatic ring group; a $C_2$-$C_{60}$ heterocyclic group including at least one heteroatom selected from among O, N, S, Si, or P; or combinations thereof.

When $L^1$ to $L^3$ are respectively an aryl group, each of $L^1$ to $L^3$ may be independently a $C_6$-$C_{40}$ aryl group, a $C_6$-$C_{30}$ aryl group, $C_6$-$C_{25}$ aryl group, or a $C_6$-$C_{20}$ aryl group. For example, each of $L^1$ to $L^3$ may be independently selected from the group consisting of benzene, naphthalene, anthracene, phenanthrene, tetracene, benzo anthracene, triphenylene, biphenyl, terphenyl, and substituted and unsubstituted fluorine. When L' to $L^3$ are as above, the compound of Formula 1 may provide an element that achieves high luminous efficiency, a low driving voltage, high heat resistance, high color purity, and increased lifetime.

When $L^1$ to $L^3$ are respectively a heterocyclic group, each of $L^1$ to $L^3$ may be a $C_2$-$C_{30}$ heterocyclic group or a $C_2$-$C_{15}$ heterocyclic group. For example, each of $L^1$ to $L^3$ may be selected from the group consisting of pyrrole, pyrazole, imidazole, triazole, furan, thiophene, pyridine, pyridazine, pyrimidine, pyrazine, triazine, indole, quinazoline, quinoxaline, dibenzothiophene, and dibenzofuran. When $L^1$ to $L^3$ are as above, the compound of Formula 1 may provide an element that achieves high luminous efficiency, a low driving voltage, high heat resistance, high color purity, and increased lifetime.

L' is selected from the group consisting of a single bond; a $C_6$-$C_{60}$ aryl group; a $C_3$-$C_{60}$ aliphatic ring group; a $C_2$-$C_{60}$ heterocyclic group including at least one heteroatom selected from among O, N, S, Si, or P; or combinations thereof.

When L' is an aryl group, L' may be a $C_6$-$C_{40}$ aryl group, a $C_6$-$C_{30}$ aryl group, $C_6$-$C_{25}$ aryl group, or a $C_6$-$C_{20}$ aryl group. For example, L' may be selected from the group consisting of benzene, naphthalene, anthracene, phenanthrene, tetracene, benzo anthracene, triphenylene, biphenyl, terphenyl, and substituted and unsubstituted fluorine. When L' is as above, the compound of Formula 1 may provide an element that achieves high luminous efficiency, a low driving voltage, high heat resistance, high color purity, and increased lifetime.

Each of $R_a$ and $R_b$ is independently selected from the group consisting of a $C_6$-$C_{60}$ aryl group; a fluorenyl group; a $C_3$-$C_{60}$ aliphatic ring group; a $C_2$-$C_{60}$ heterocyclic group including at least one heteroatom selected from among O, N, S, Si, or P; or combinations thereof.

When each of $R_a$ and $R_b$ is an aryl group, each of $R_a$ and $R_b$ may be independently a $C_6$-$C_{40}$ aryl group, a $C_6$-$C_{30}$ aryl group, $C_6$-$C_{25}$ aryl group, or a $C_6$-$C_{20}$ aryl group. For example, each of $R_a$ and $R_b$ may be selected from the group consisting of benzene, naphthalene, anthracene, phenanthrene, tetracene, benzo anthracene, triphenylene, biphenyl, terphenyl, and substituted and unsubstituted fluorine. When $R_a$ and $R_b$ are as above, the compound of Formula 1 may provide an element that achieves high luminous efficiency, a low driving voltage, high heat resistance, high color purity, and increased lifetime.

In $Ar^1$ to $Ar^5$ and $R^1$ described above, each of an aliphatic hydrocarbon group, the aryl group, the heterocyclic group, the fused ring group, the alkyl group, the alkenyl group, the alkynyl group, the alkoxy group, the aryloxy group, and the silane group may be further substituted with one or more substituents selected from the group consisting of deuterium; a nitro group; a nitrile group; a halogen group; an amino group; a silane group substituted and unsubstituted with a $C_1$-$C_{20}$ alkyl group or a $C_6$-$C_{20}$ aryl group; a siloxane group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a $C_2$-$C_{20}$ heterocyclic group; a $C_3$-$C_{20}$ cycloalkyl group; a $C_7$-$C_{20}$ aryl alkyl group; and a $C_8$-$C_{20}$ aryl alkenyl group. In addition, these substituents may be bonded to form a ring. Here, "ring" refers to a fused ring including a saturated ring or an unsaturated ring and comprised of a $C_3$-$C_{60}$ aliphatic ring, a $C_6$-$C_{60}$ aromatic ring, a $C_2$-$C_{60}$ hetero ring, or combinations thereof.

When the compound of Formula 1 is used in the organic material layer of the organic electric element, the organic electric element having high luminous efficiency and increased lifetime may be fabricated.

The compound represented by Formula 1 may be represented by Formula 2 or Formula 3.

<Formula 2>

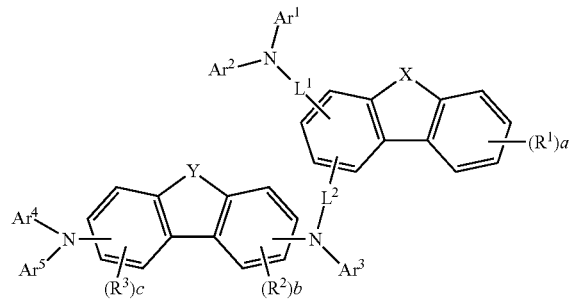

<Formula 3>

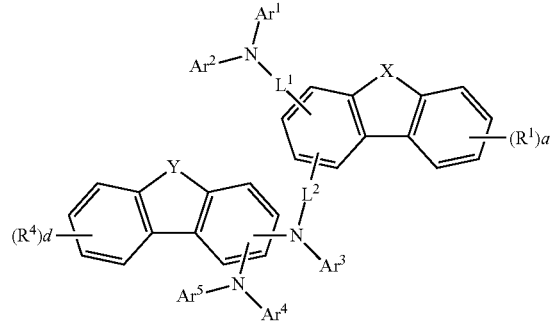

In Formula 2 and Formula 3, Y is O or S, $R^2$ to $R^4$ are the same or different, $R^2$ to $R^4$ are respectively the same as $R^1$ defined in the above description regarding Formula 1, each of b and c is independently an integer of 0 to 3, d is an integer of 0 to 4, and $Ar^1$ to $Ar^5$, $R^1$, $L^1$ to $L^2$, X, and a are the same those defined in the above description regarding Formula 1. When the compound of Formula 1 has a structure including at least two of dibenzothiophene and/or dibenzofuran as in Formula 2 and Formula 3, an element that achieves high luminous efficiency, a low driving voltage, high heat resistance, high color purity, and increased lifetime may be provided.

The compound represented by Formula 1 may be represented by one of Formula 4 to Formula 15.

<Formula 4>
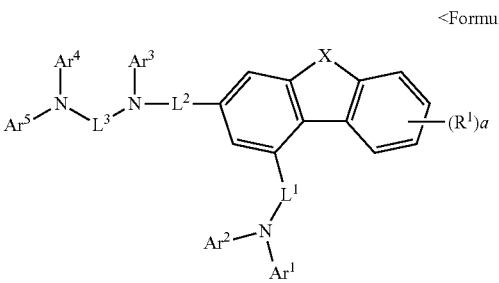

<Formula 5>
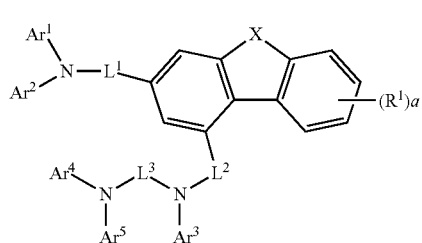

<Formula 6>
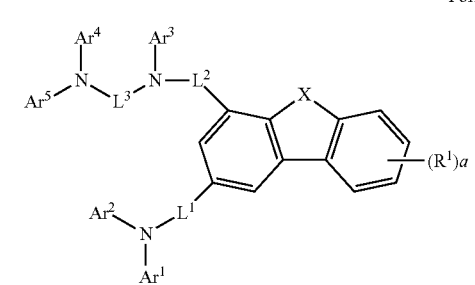

<Formula 7>
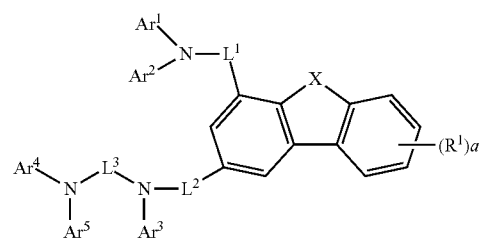

<Formula 8>
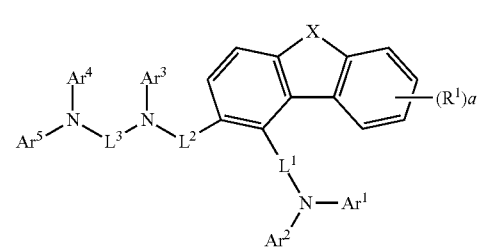

<Formula 9>
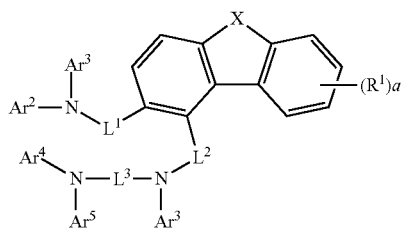

<Formula 10>
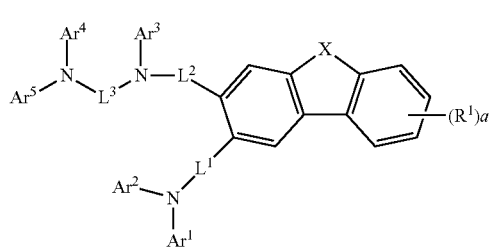

<Formula 11>
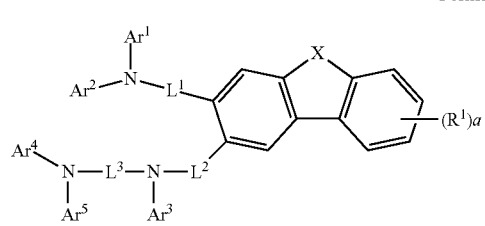

<Formula 12>
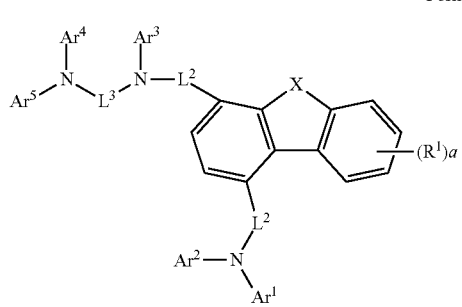

<Formula 13>
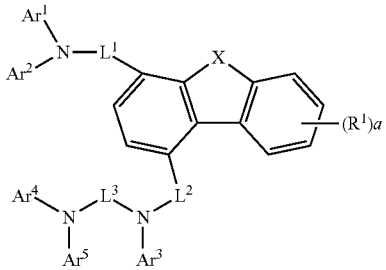

<Formula 14>
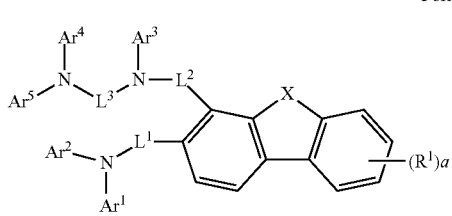

<Formula 15>

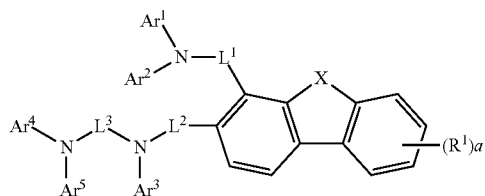

In Formulas 4 to 15 above, $Ar^1$ to $Ar^5$, $R^1$, $L^1$ to $L^3$, X and a are the same as those defined in the above description regarding Formula 1.

The compound represented by Formula 1 may be, for example, a compound represented by one of Formulas 4 to 7 above. When the compound represented by one of Formulas 4 to 7 is used, an element that achieves higher luminous efficiency and longer increased lifetime may be provided.

Specifically, the compound represented by Formula 1 may be, but is not limited to, one of the following compounds.

P-1

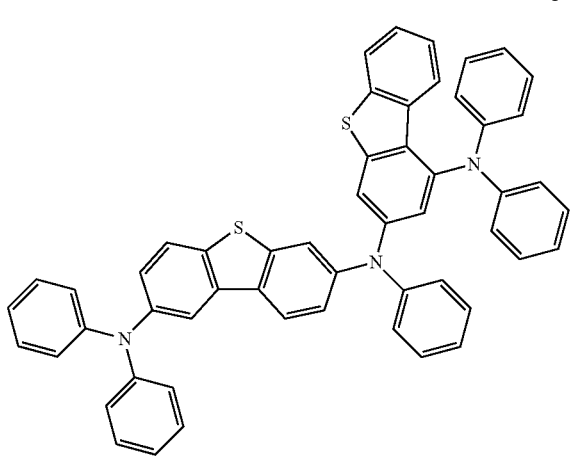

P-2

P-3

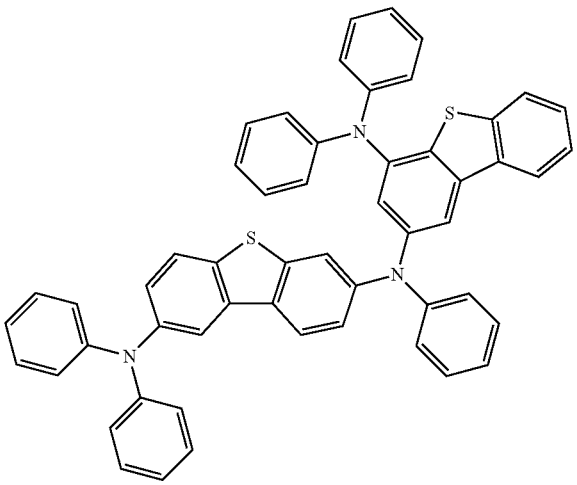

P-4

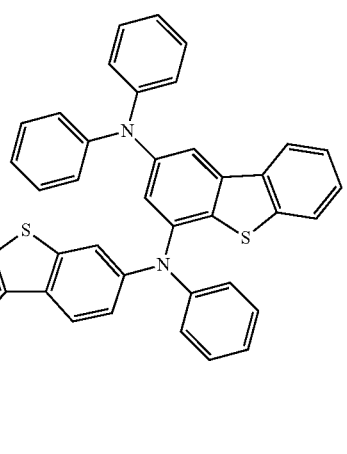

P-5

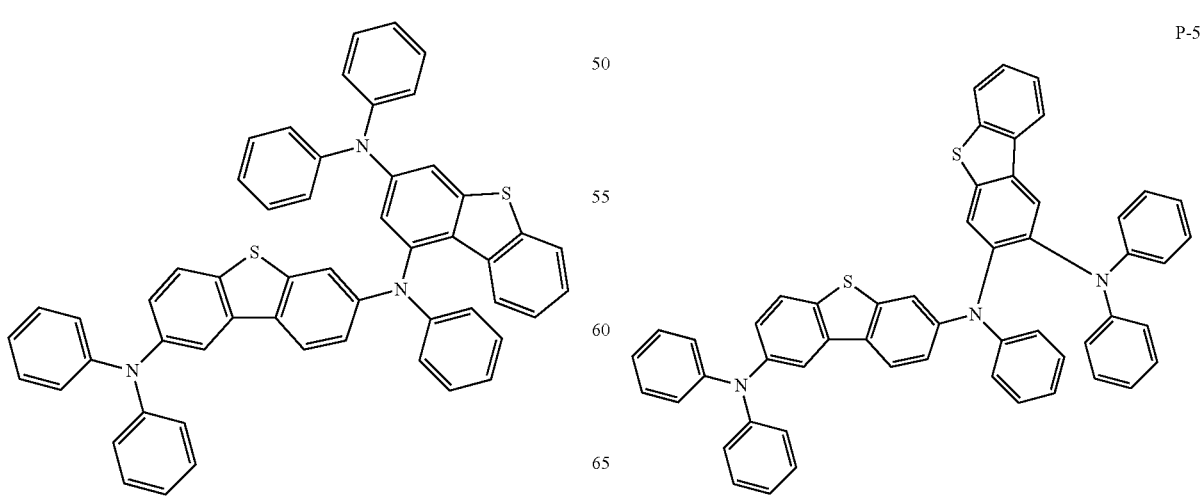

P-6
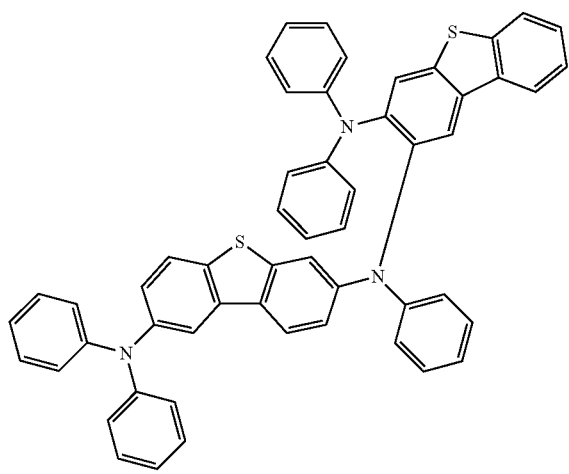
P-9
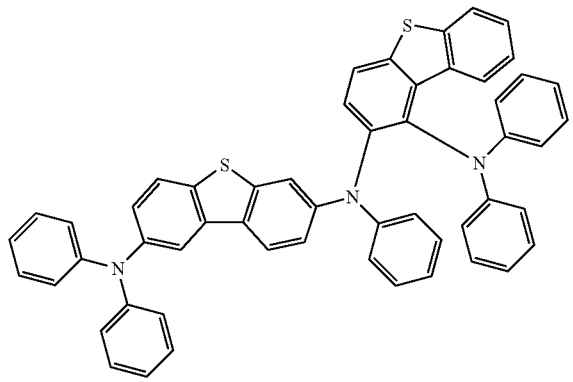
P-7
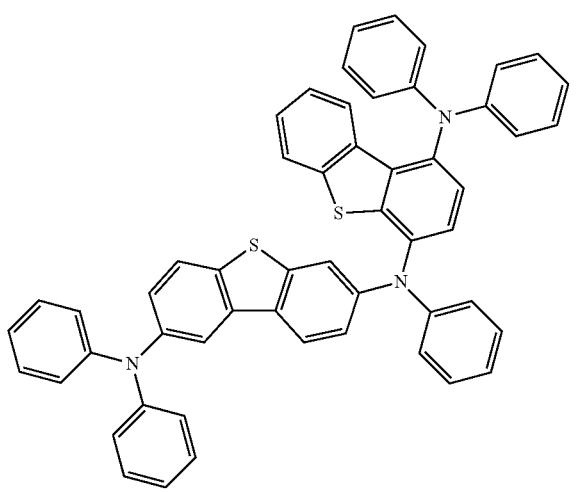
P-10
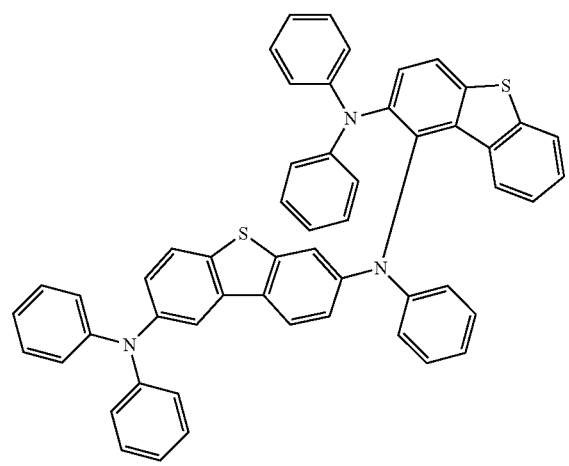
P-8
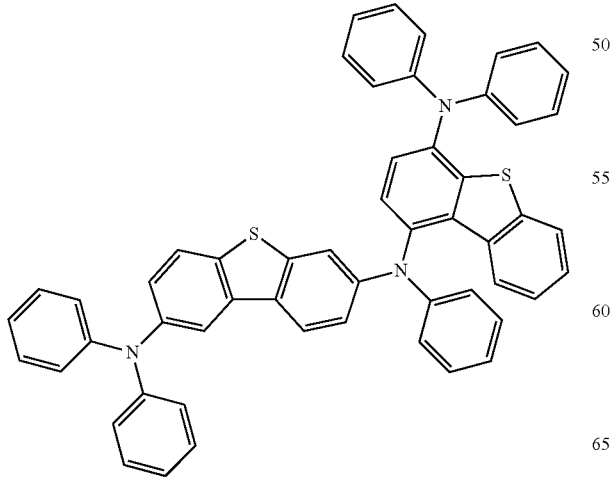
P-11
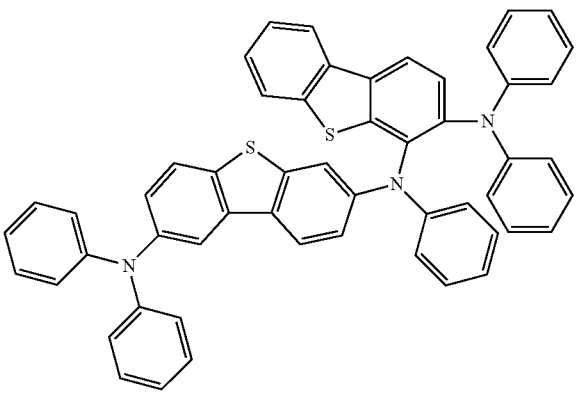

-continued
P-12
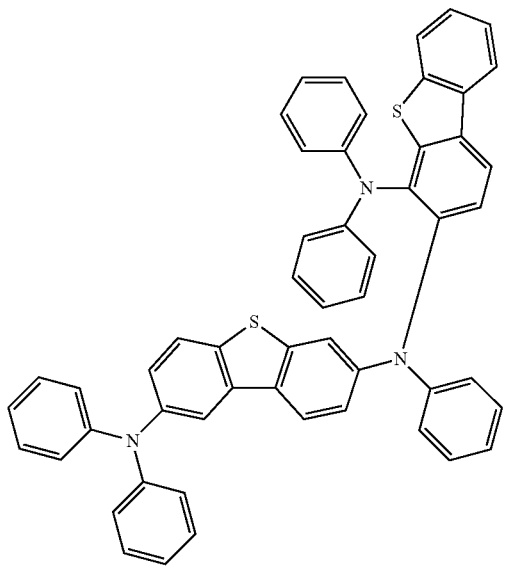
P-13
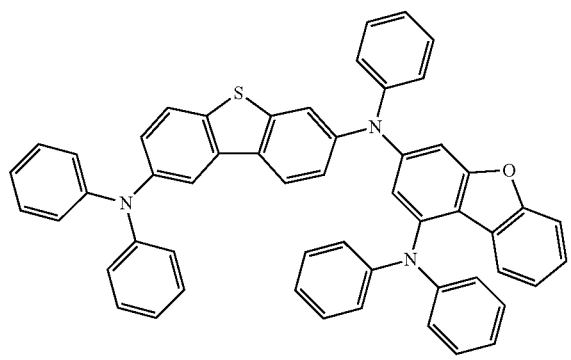
P-14
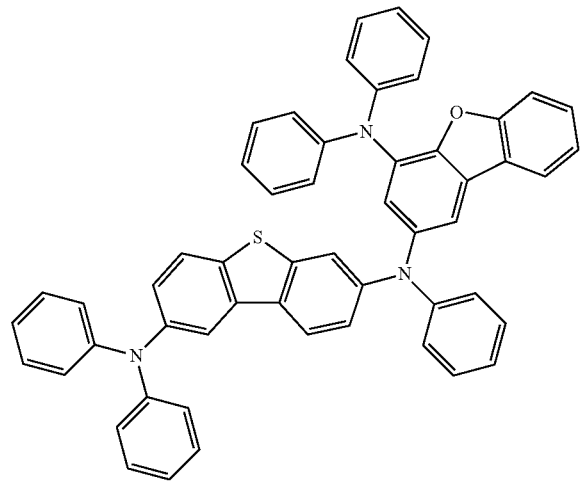
-continued
P-15
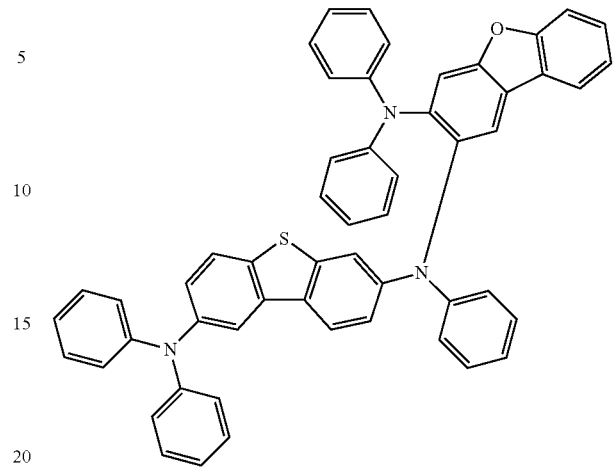
P-16
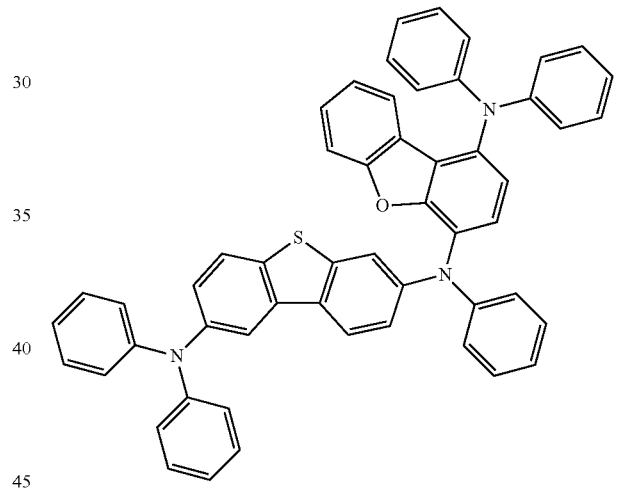
P-17
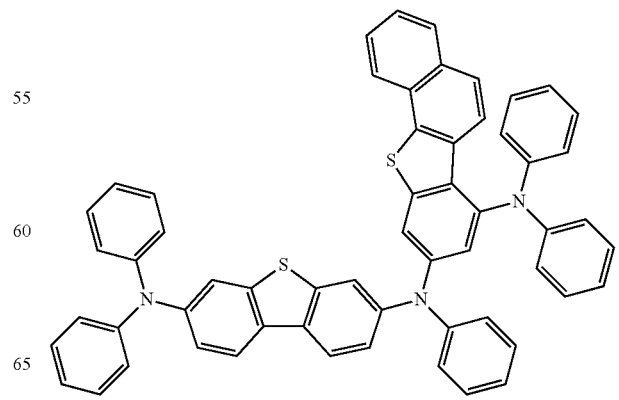

-continued
P-18
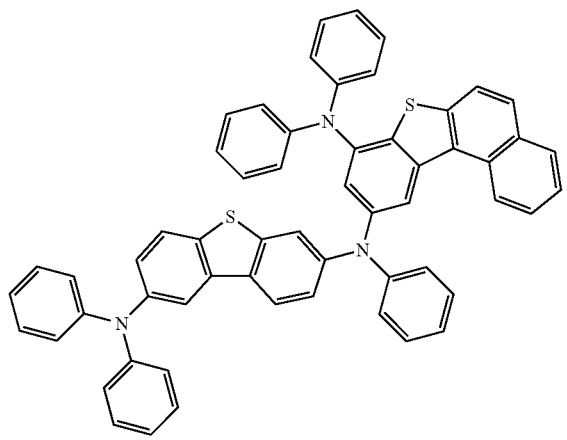
P-19
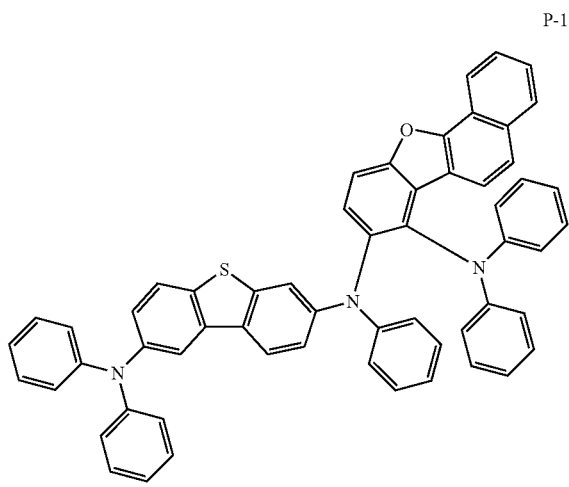
P-20
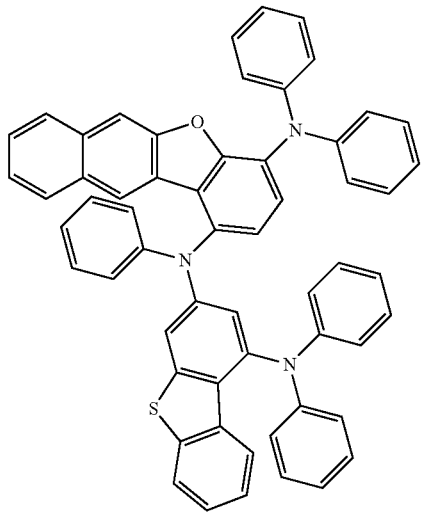
-continued
P-21
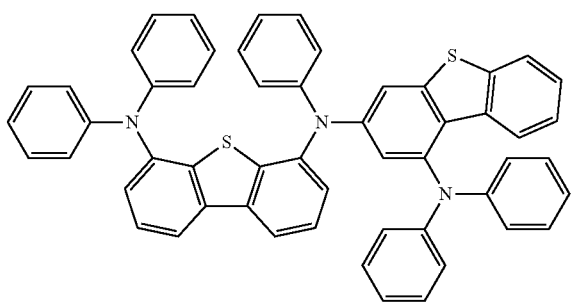
P-22
P-23
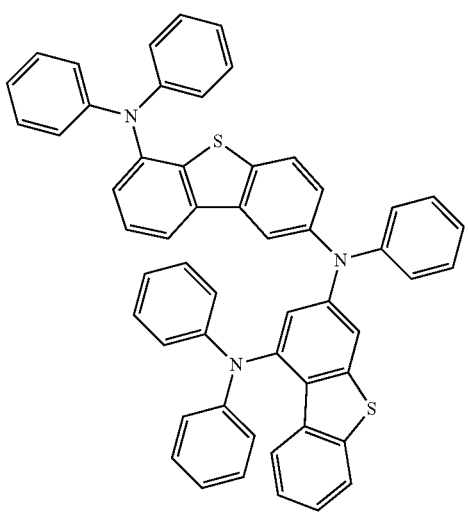

P-24
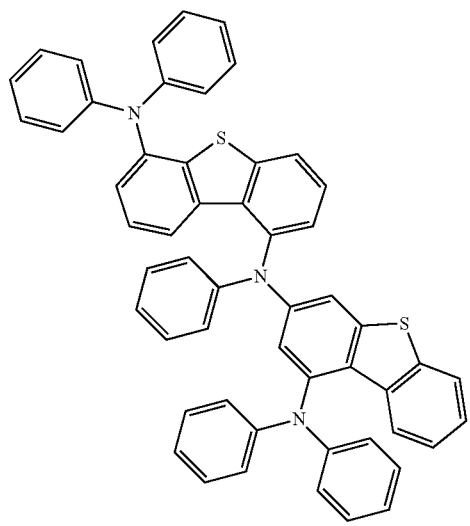
P-27
P-28
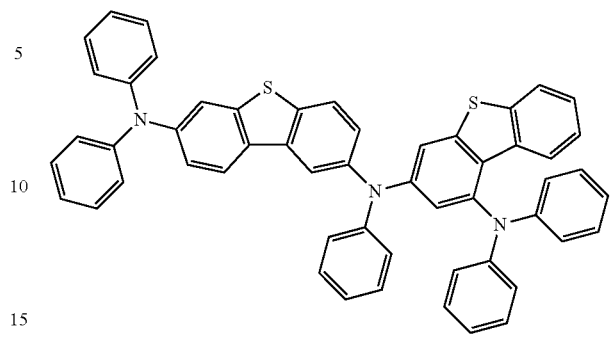
P-25
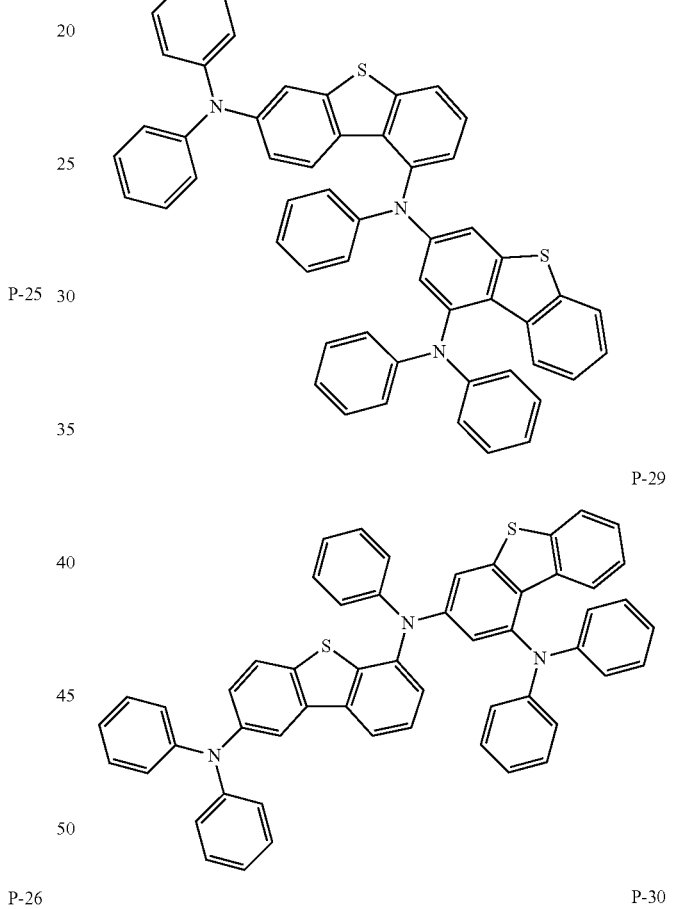
P-29
P-26
P-30
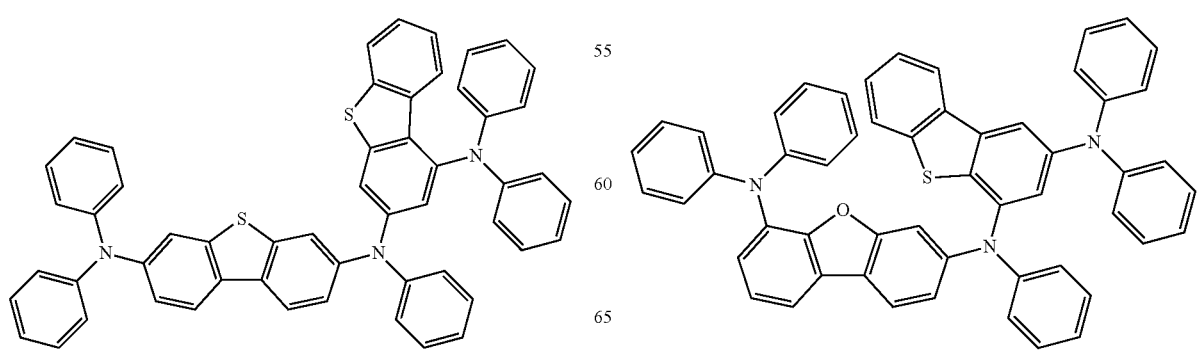

-continued
P-31
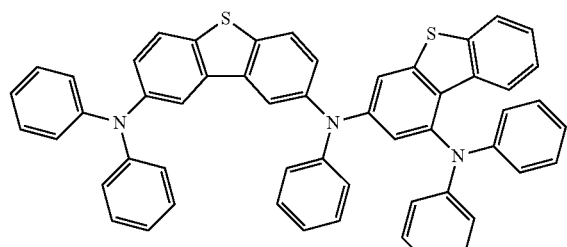
P-32
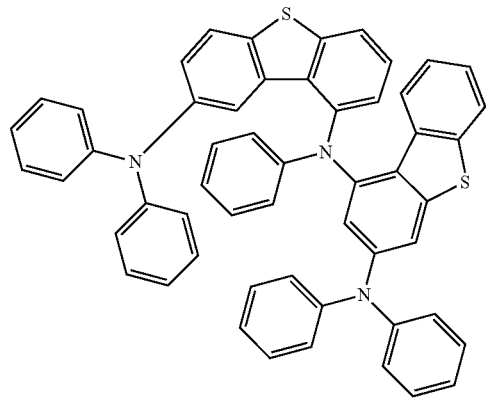
P-33
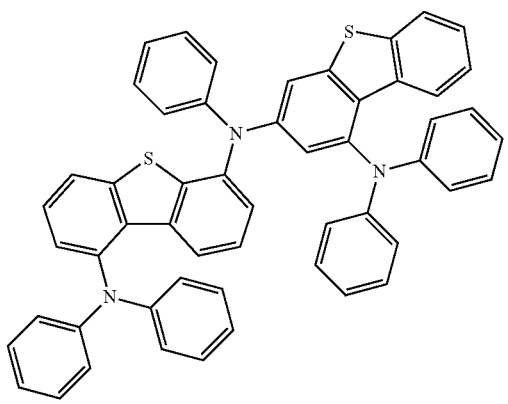
P-34
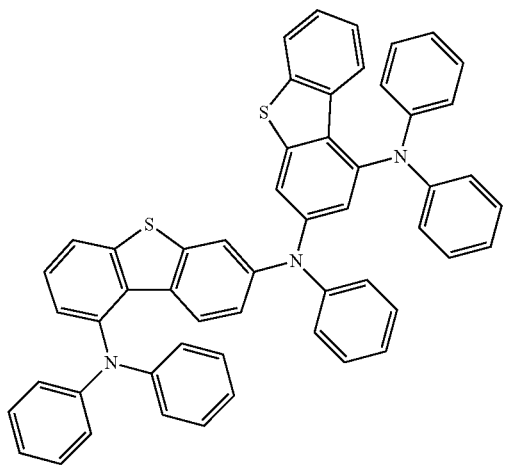
-continued
P-35
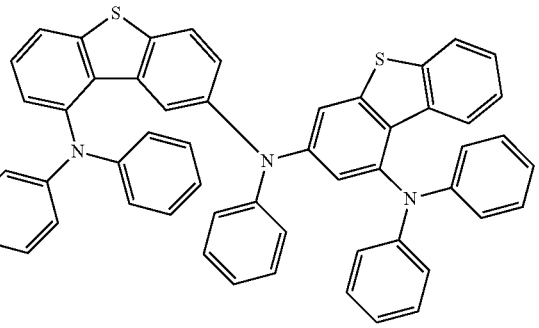
P-36
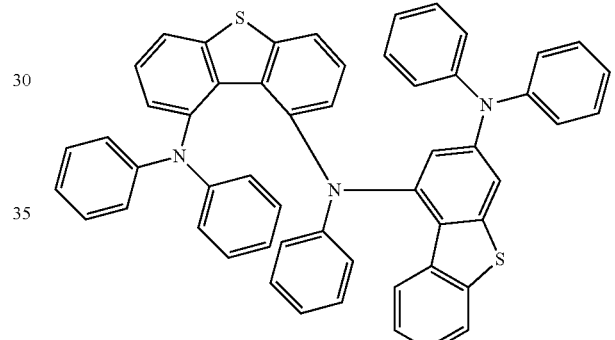
P-37
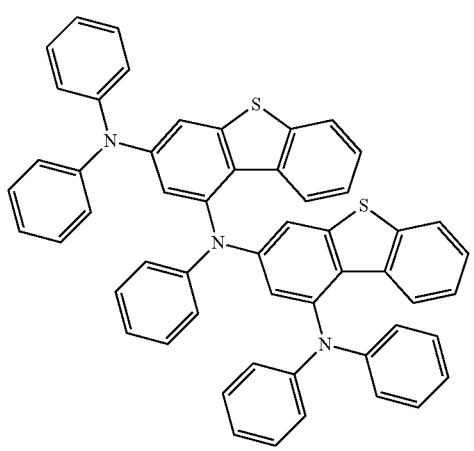

P-38
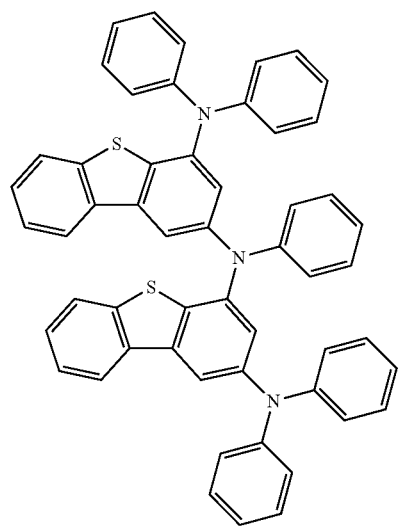
P-39
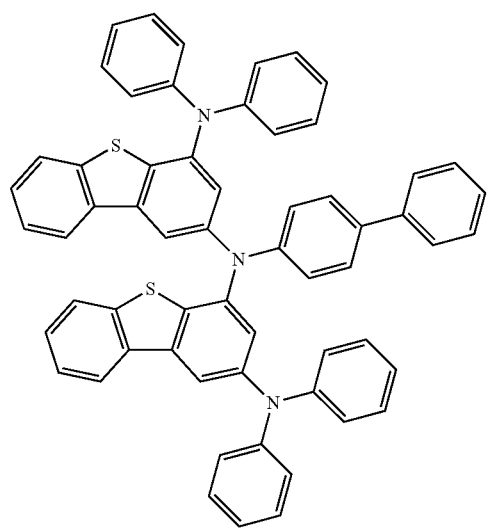
P-40
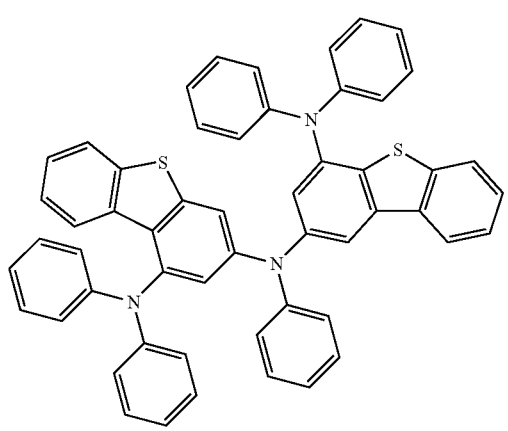
P-41
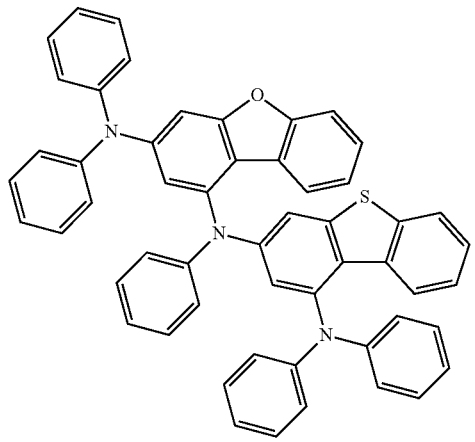
P-42
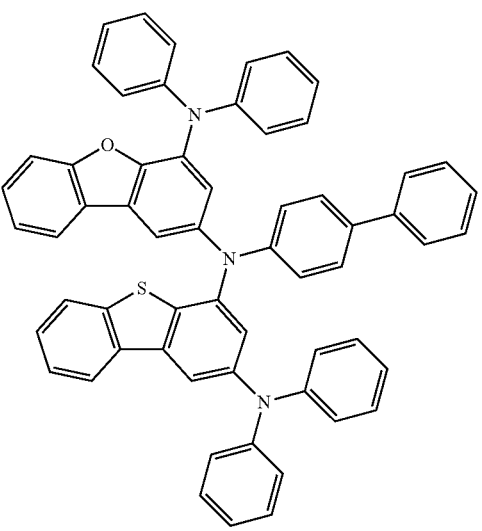
P-43
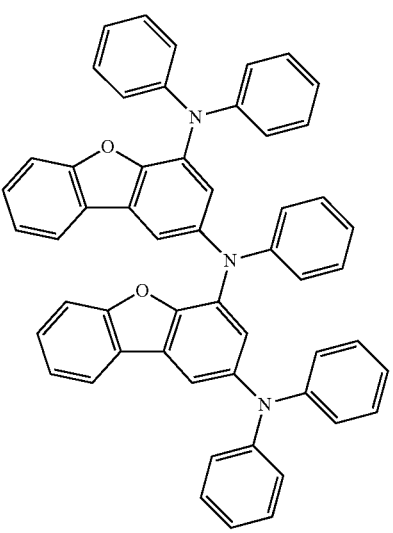

P-44
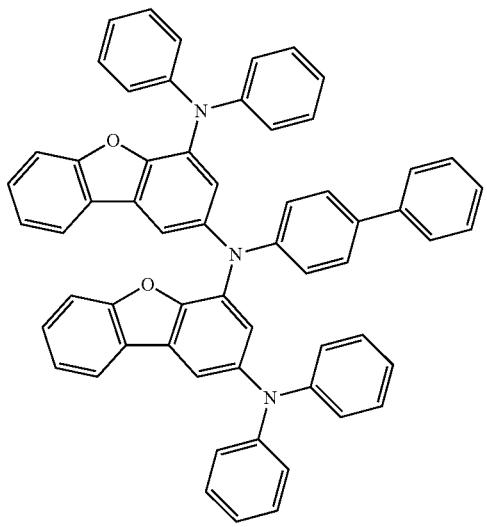
P-45
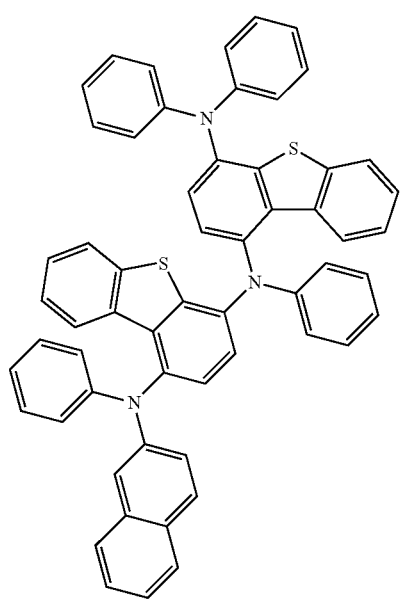
P-46
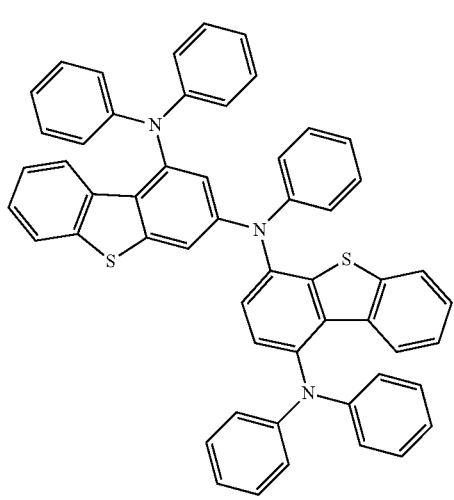
P-47
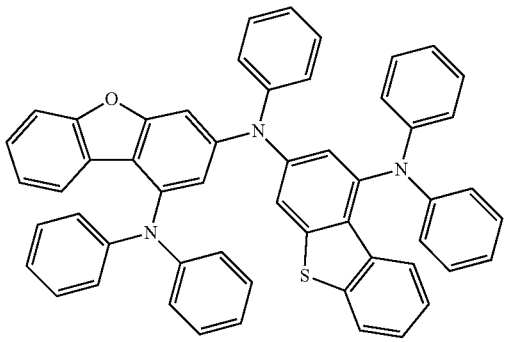
P-48
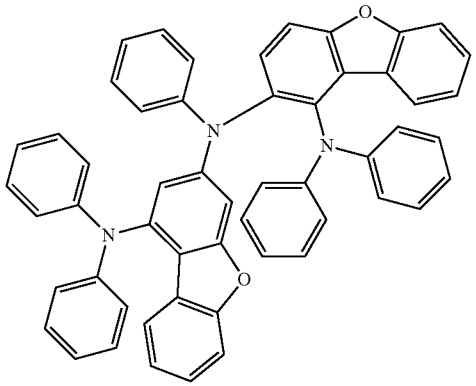
P-49, P-50
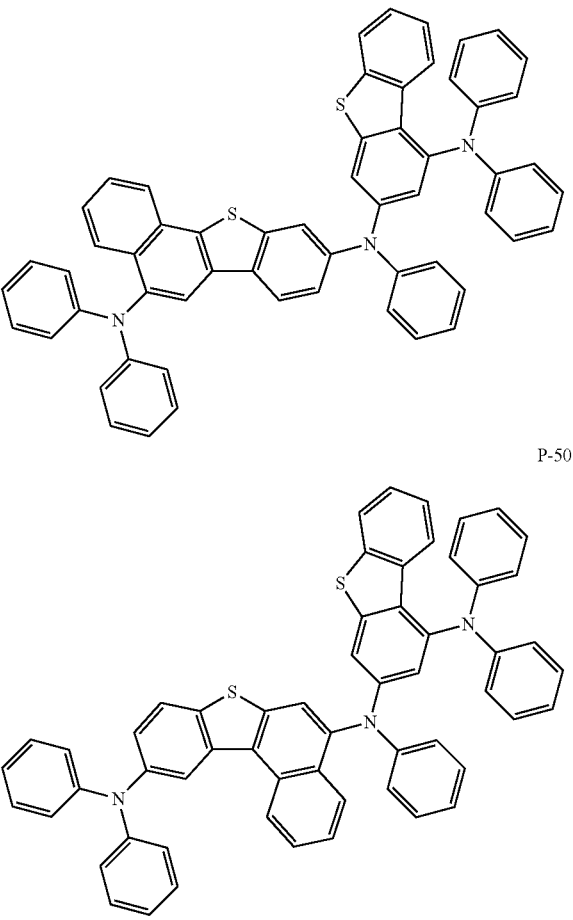

P-51
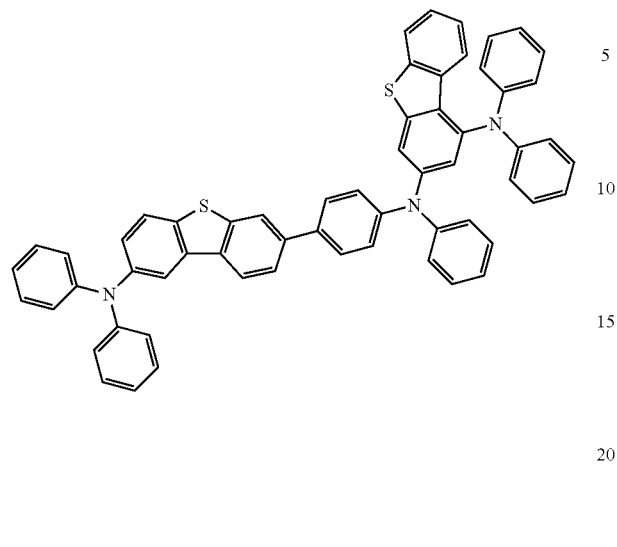
P-54
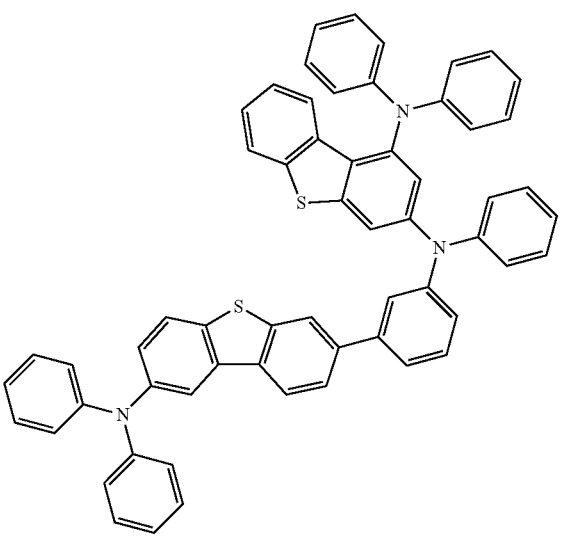
P-52
P-55
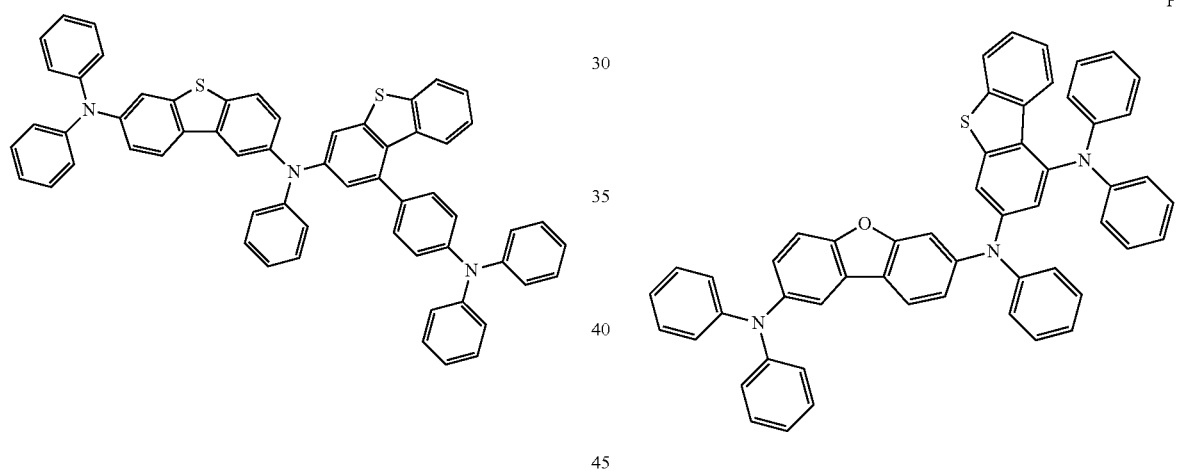
P-53
P-56
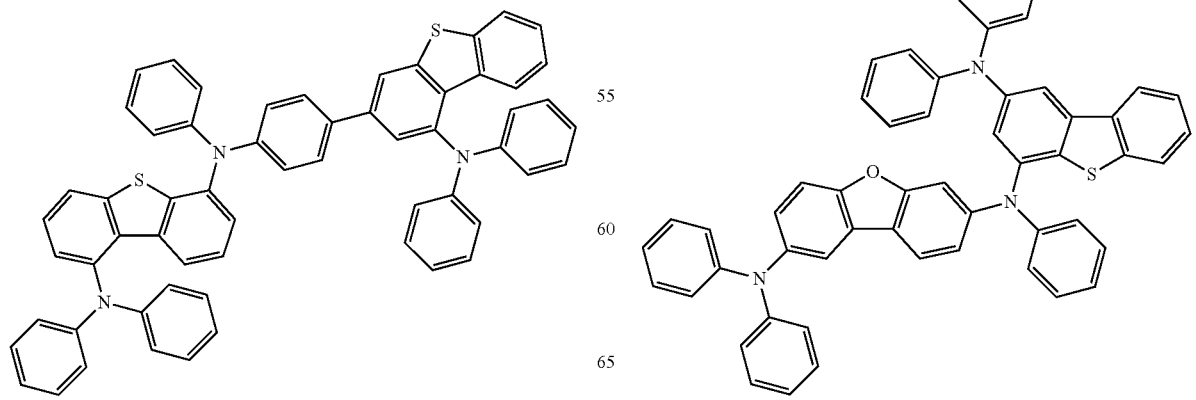

P-57
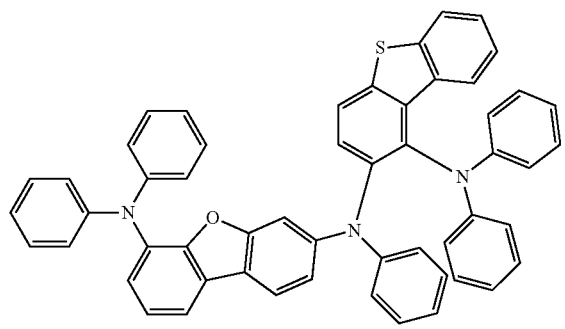
P-58
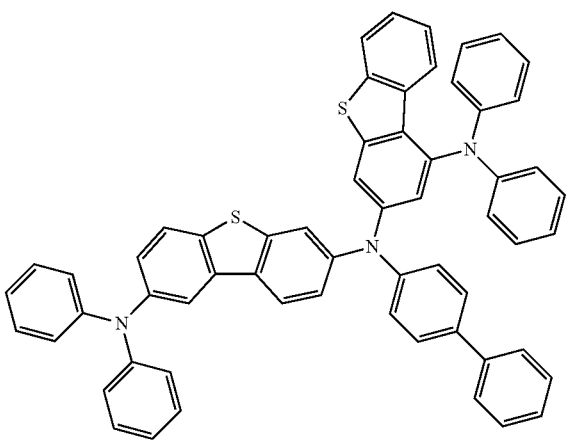
P-59
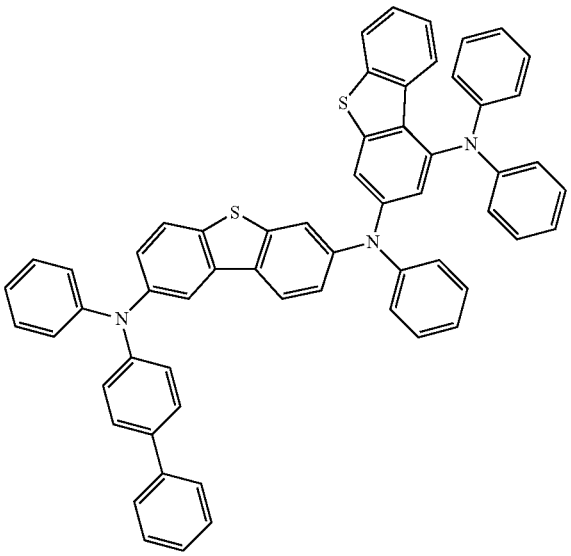
P-60
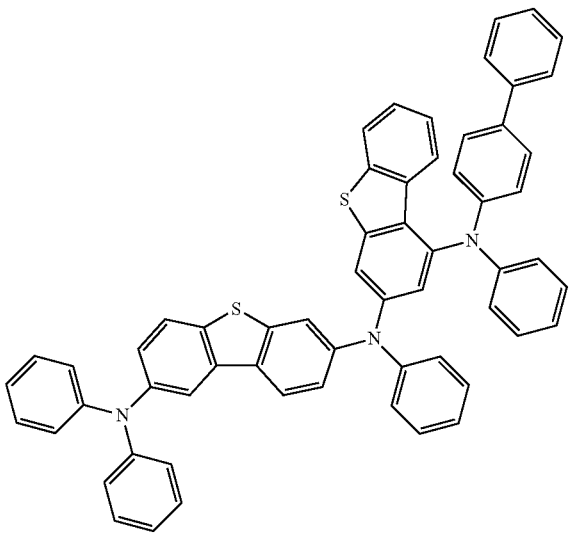
P-61
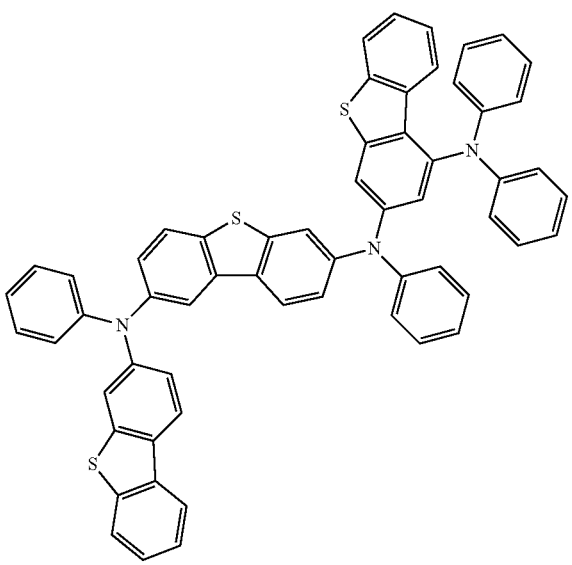
P-62
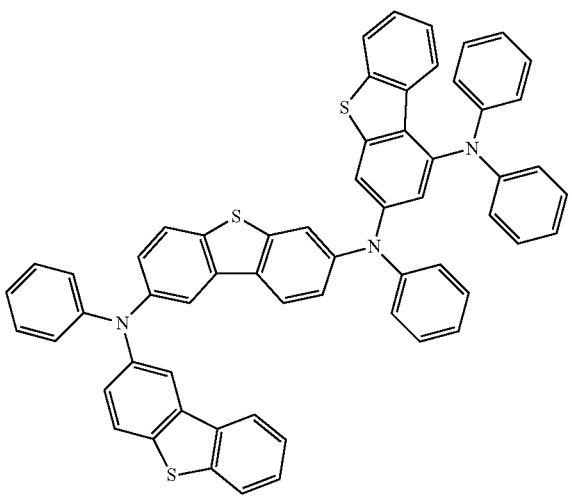

P-63
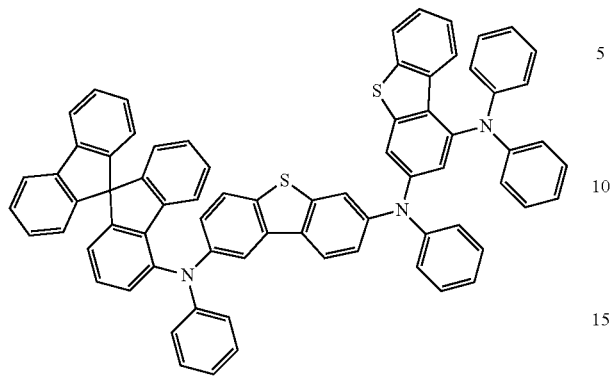
P-64
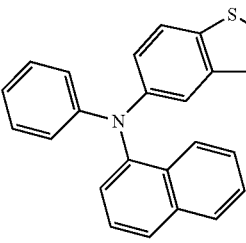
P-65
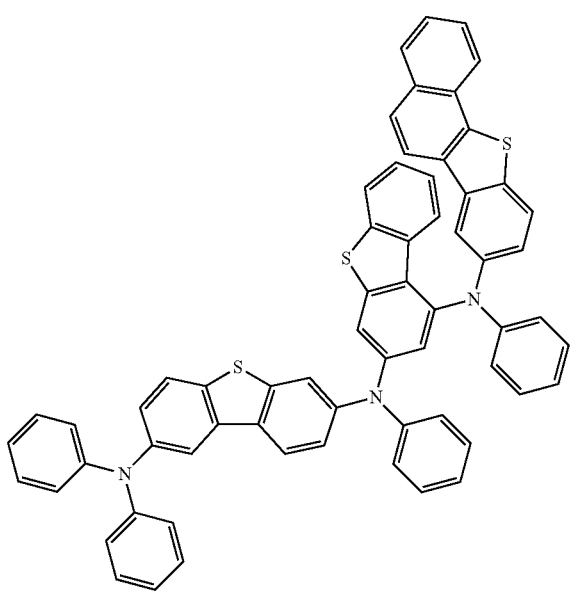
P-66
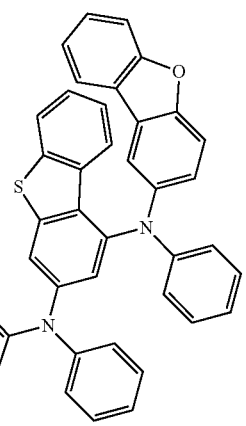
P-67
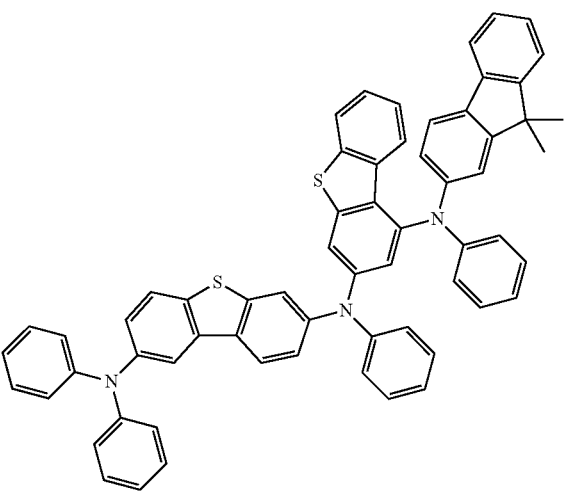
P-68
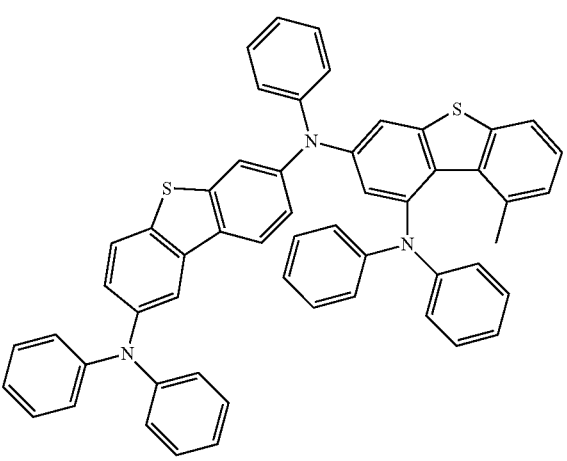

P-69
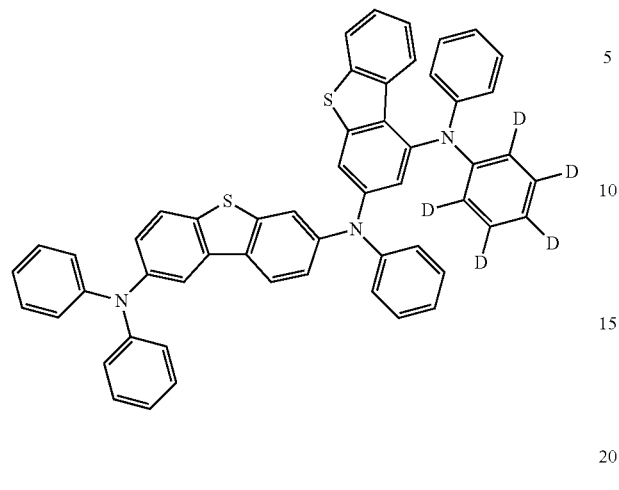
P-70
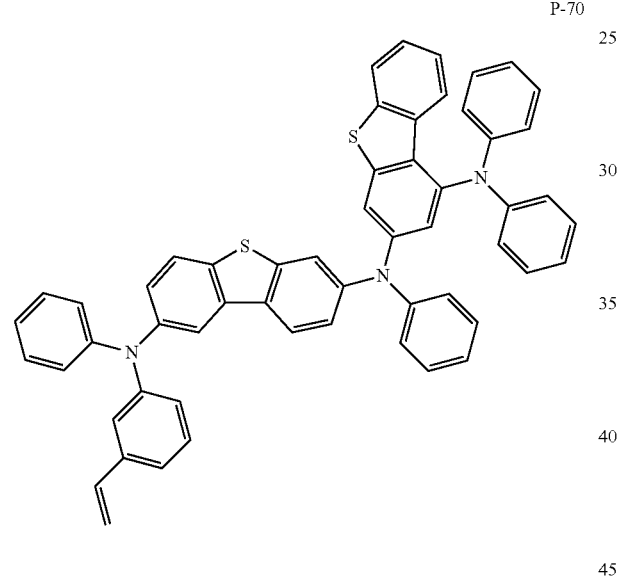
P-71
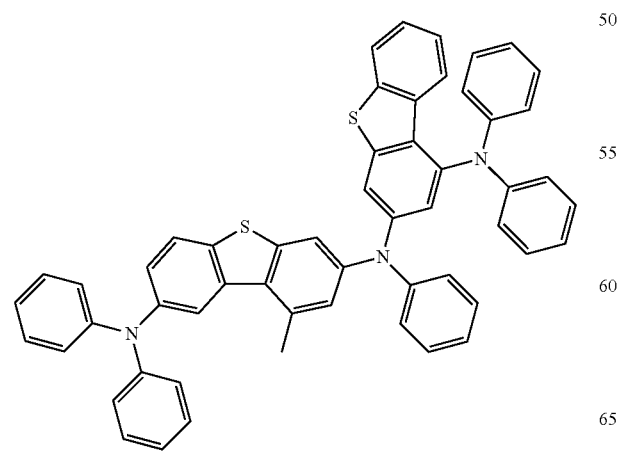
P-72
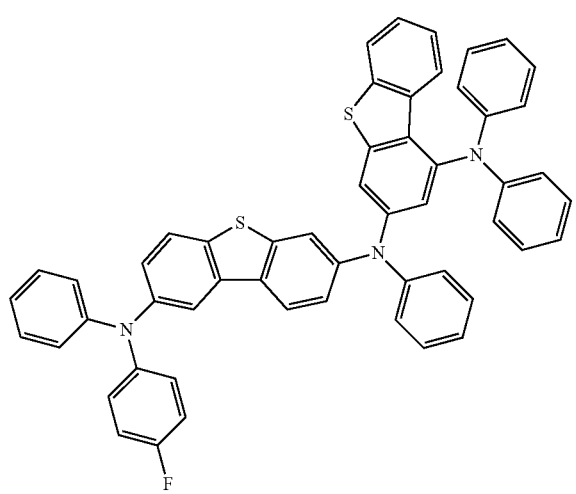
P-73
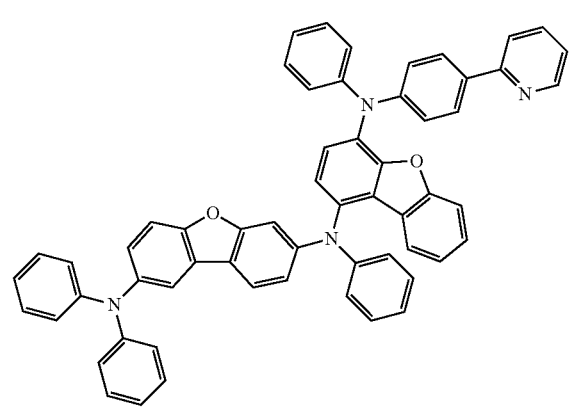
P-74
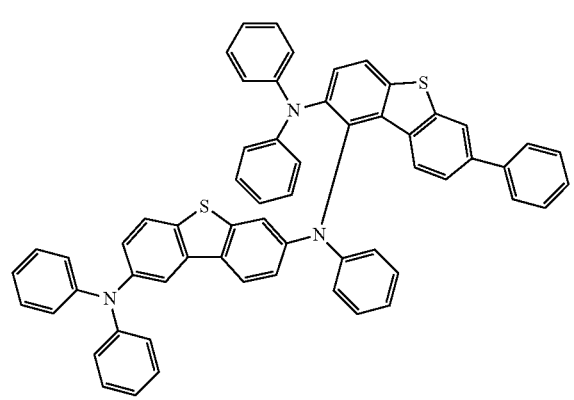

P-75
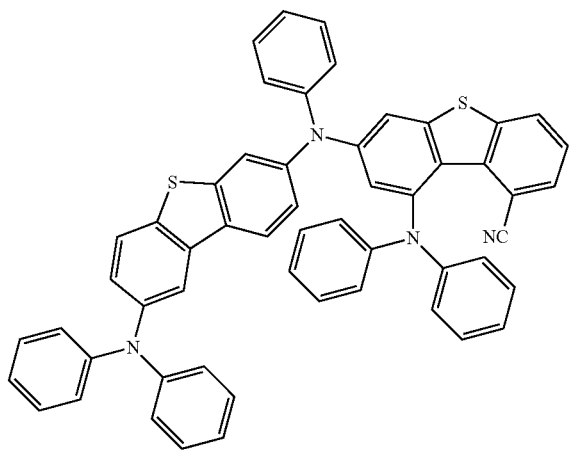
P-76
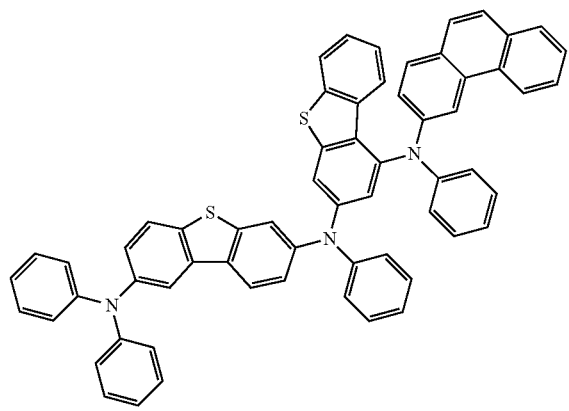
P-77
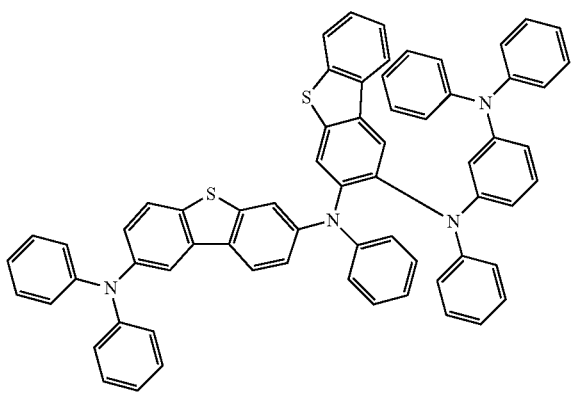
P-78
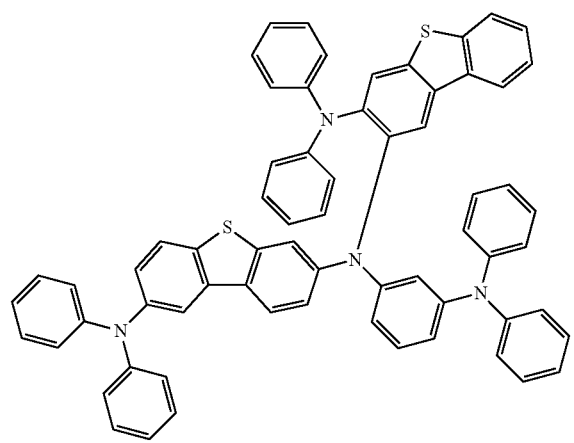
P-79
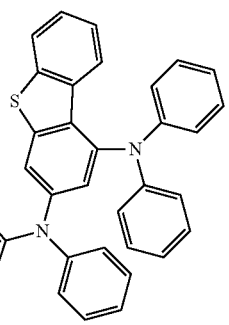
P-80
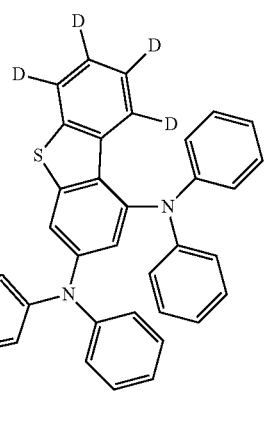

-continued
P-81
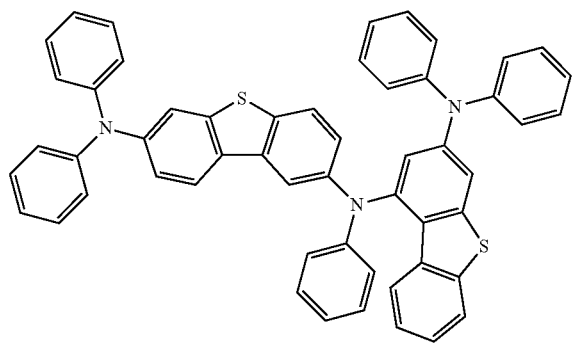
P-84
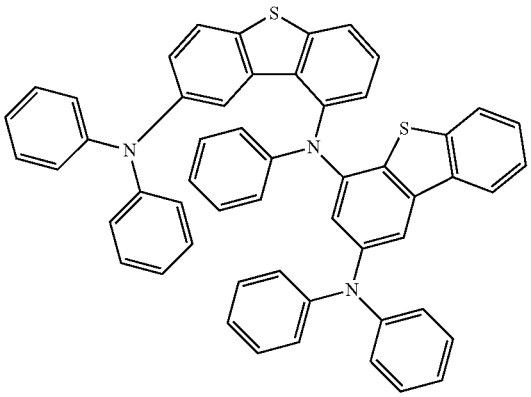
P-82
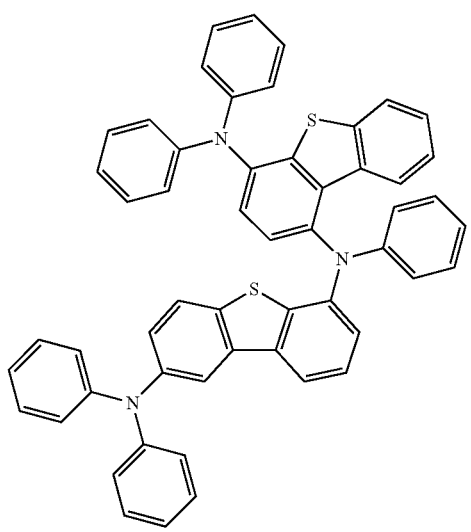
P-85
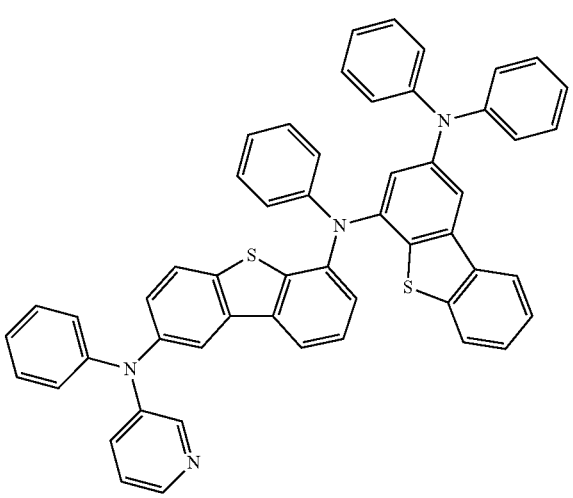
P-83
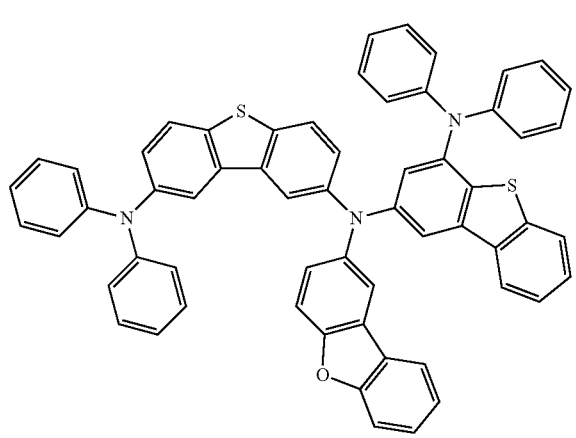
P-86
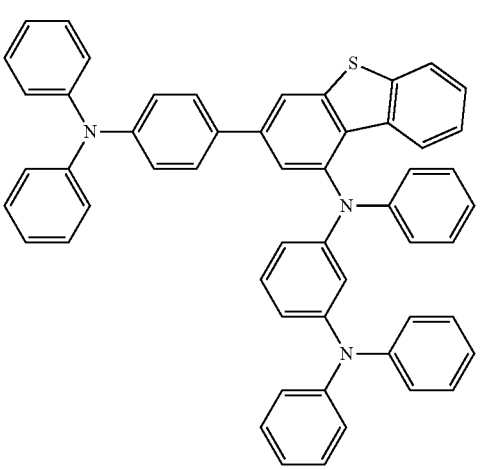

P-87
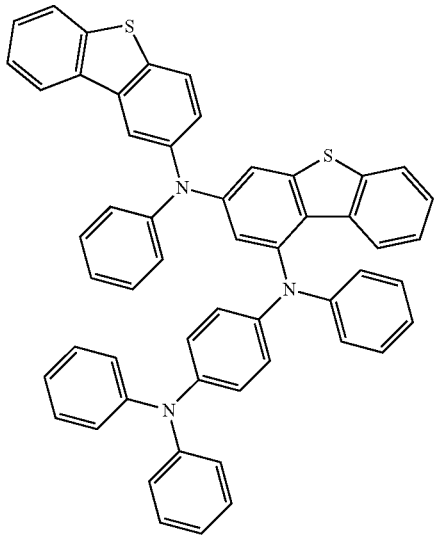
P-88
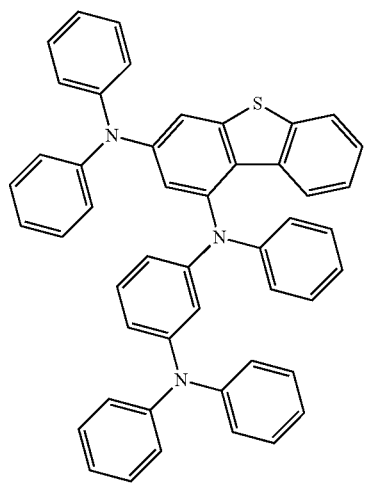
P-89
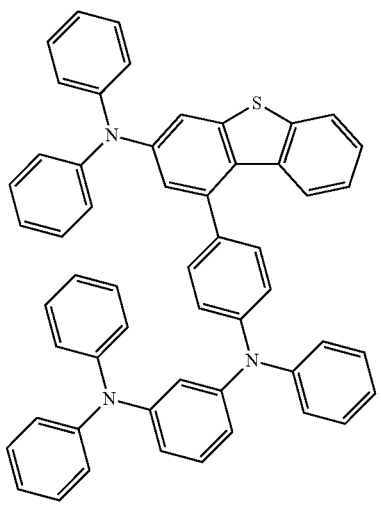
P-90
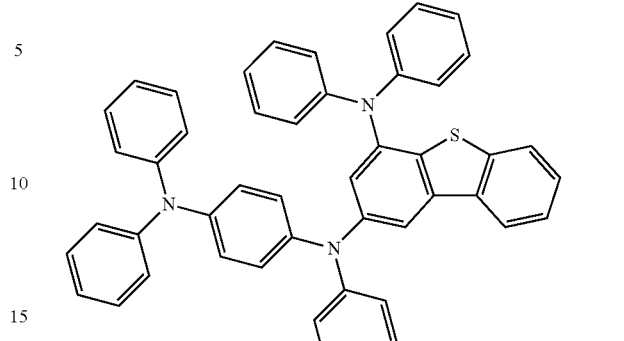
P-91
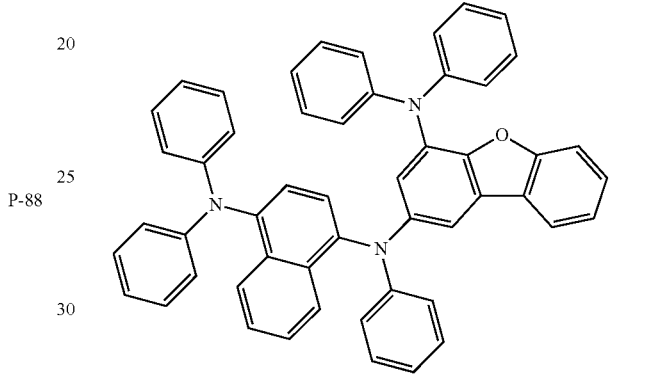
P-92
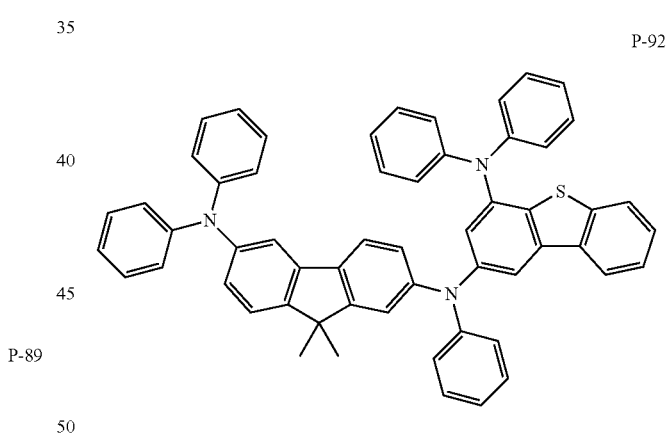
P-93
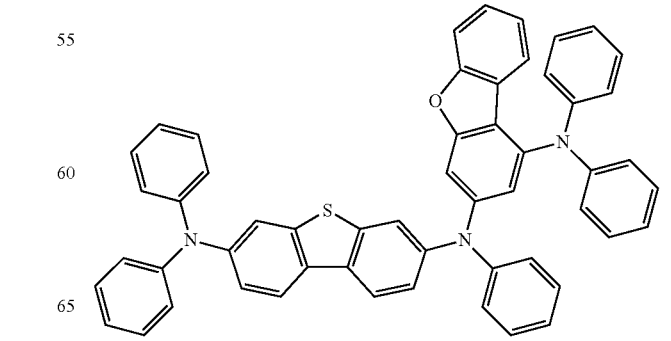

P-94
P-95
P-96
P-97
P-98
P-99
P-100
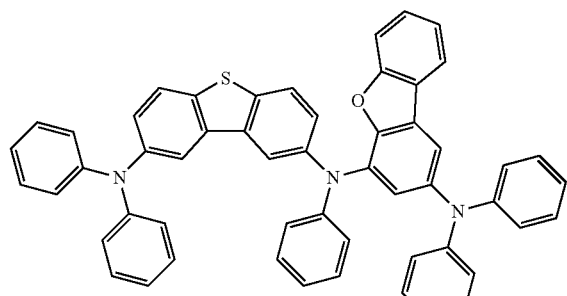
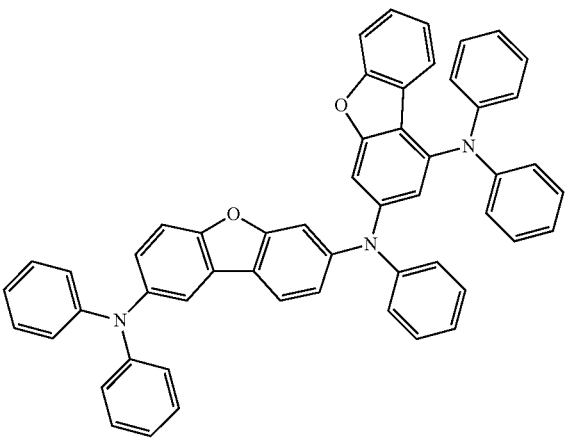
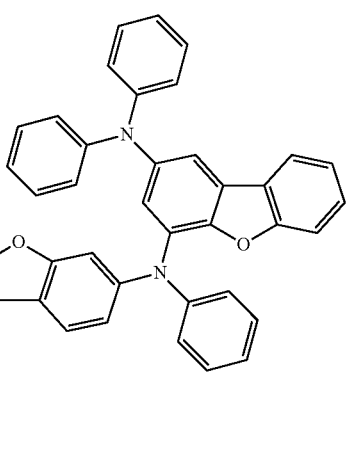
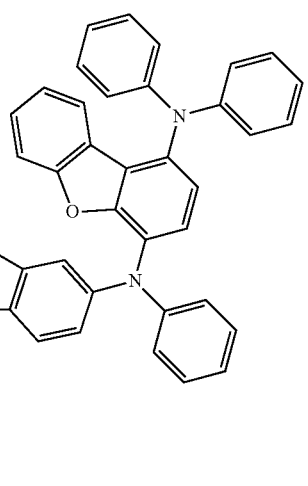

P-101
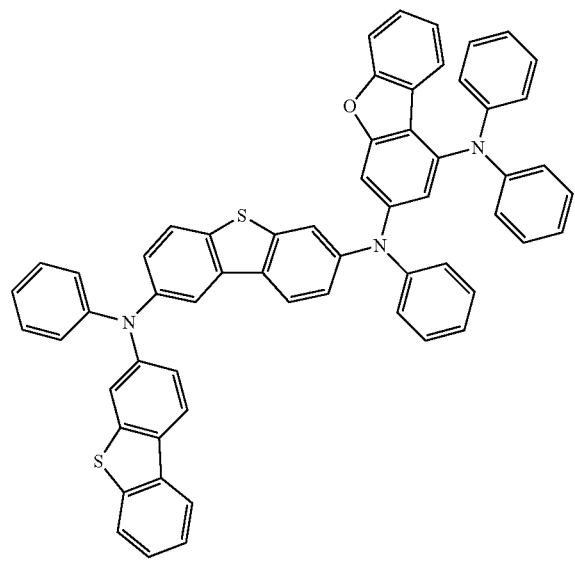
P-102
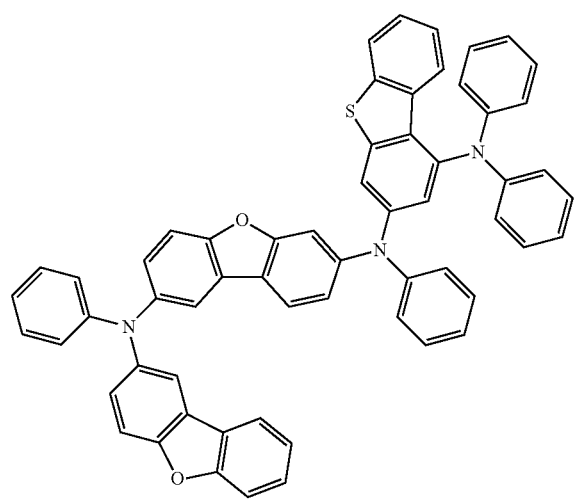
P-103
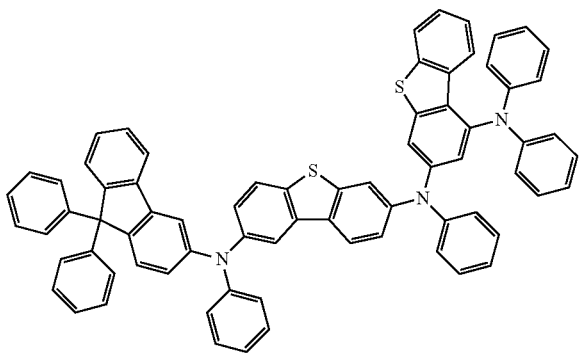
P-104
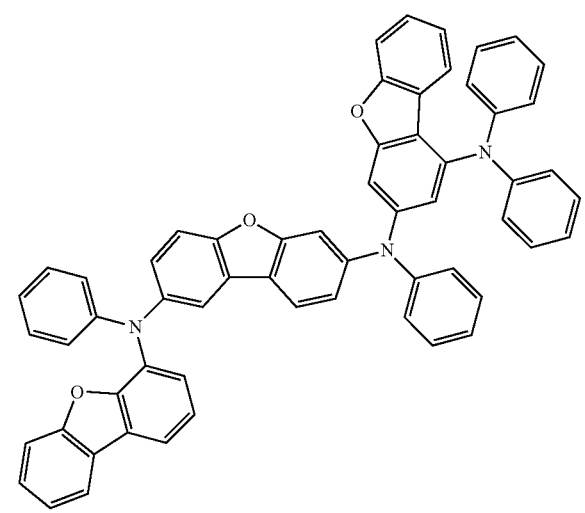
P-105
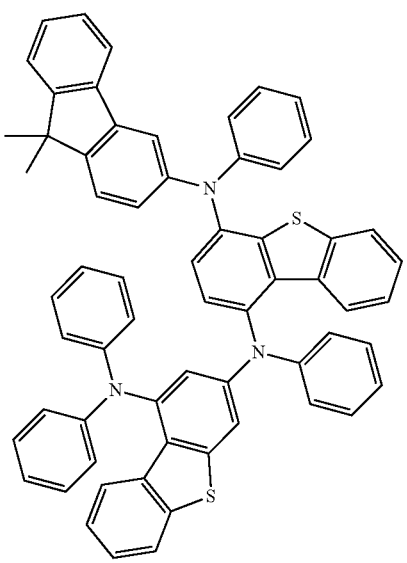
P-106
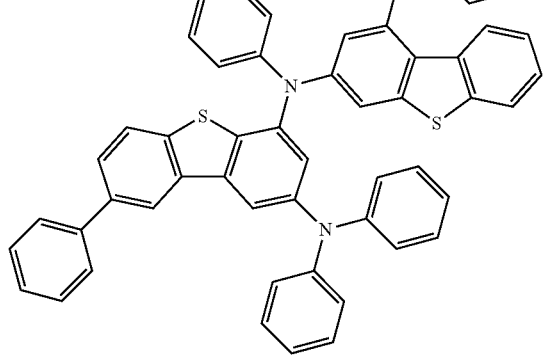

P-107
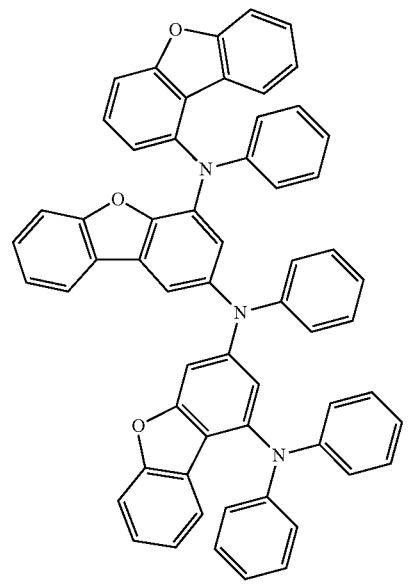

P-108
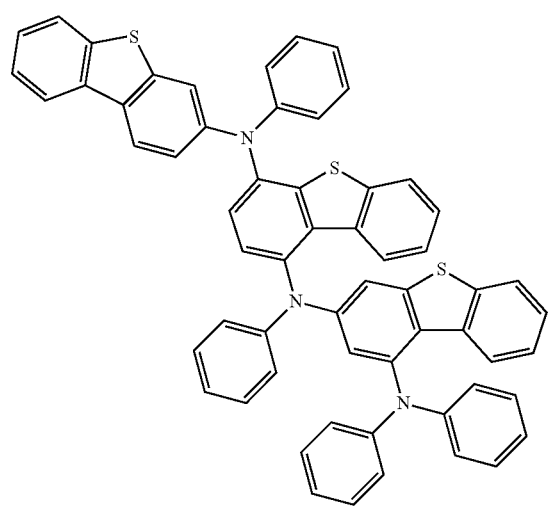

P-109
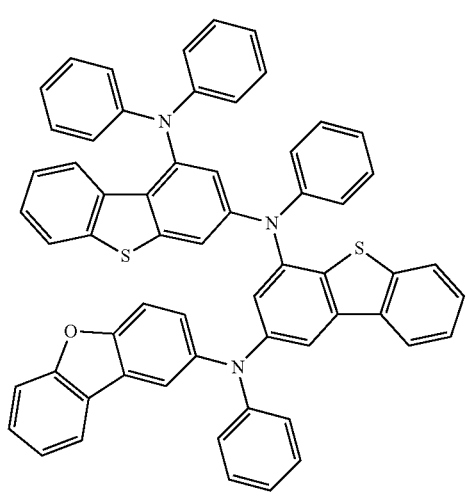

P-110
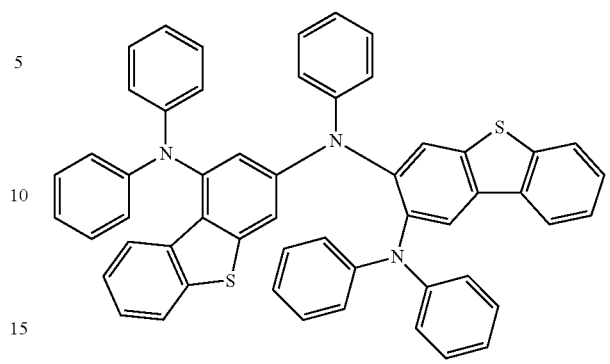

P-111
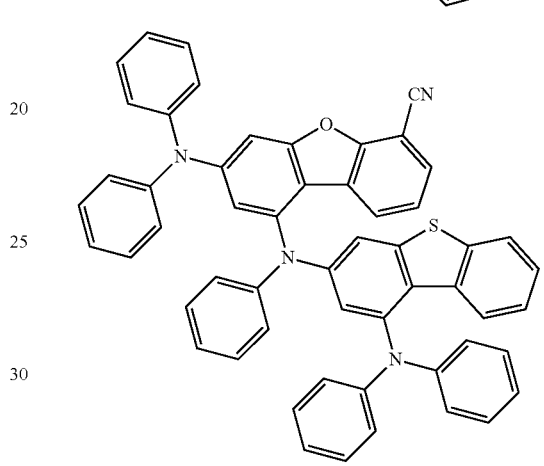

P-112
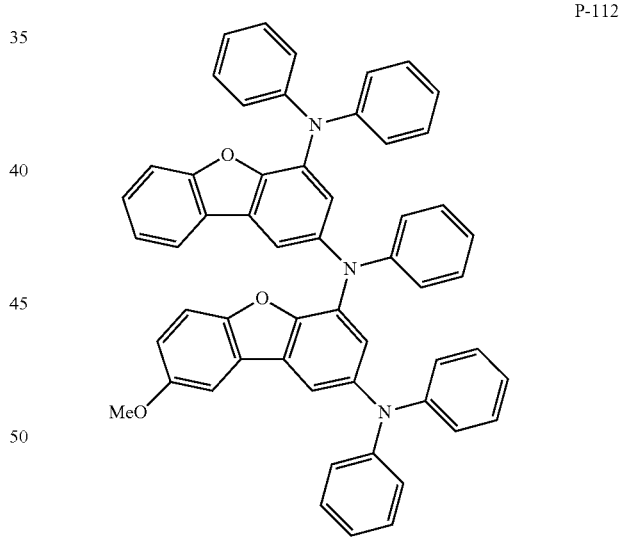

According to another embodiment, the present disclosure provides an organic electric element containing the compound represented by Formula 1.

The organic electric element may include a first electrode, a second electrode, and an organic material layer located between the first electrode and the second electrode. The organic material layer may include the compound represented by Formula 1. The compound represented by Formula 1 may be contained in at least one layer from among the hole injection layer, the hole transport layer, the auxiliary emission layer, the emissive layer, the electron transport layer, or the electron injection layer of the organic material layer. In particular, the compound represented by Formula 1 may be included in the auxiliary emission layer or the hole transport layer.

That is, the compound represented by Formula 1 may be used as a material for the hole injection layer, the hole transport layer, the auxiliary emission layer, the emissive layer, the electron transport layer, or the electron injection layer. In particular, the compound represented by Formula 1 may be used as a material for the auxiliary emission layer or the hole transport layer. Specifically, the organic electric element including one of the compound represented by Formula 1 is provided to the organic material layer. More specifically, the organic electric element containing a compound represented by each of respective Formulas 1-1 to 1-112 is provided to the organic material layer.

According to another embodiment, provided is an organic electric element characterized in that a single compound of the above-described compounds, a combination of two or more different compounds of the above-described compounds, or two or more compounds of the above-described compounds combined with a different compound are contained in at least one layer from among the hole injection layer, the hole transport layer, the auxiliary emission layer, the emissive layer, the electron transport layer, or the electron injection layer of the organic material layer.

According to another embodiment, the layer in which the single compound is contained, the combination of two or more different compounds is contained, the two or more compounds combined with a different compound are contained may be at least one layer from among the auxiliary emission layer or the hole transport layer.

In other words, a single compound corresponding to Formula 1, a combination of two or more different compounds corresponding to Formula 1, or a mixture of two or more compounds corresponding to Formula 1 and a compound not corresponding to the present disclosure may be included in each of the layers. Here, any compound not corresponding to the present disclosure may be a single compound or two or more types of compounds. When a combination of two or more types including the compound and another compound is contained, the other compound may be an already known compound, a compound to be developed in the future, or the like. Here, the compounds contained in the organic material layer may be compounds of the same type or be a mixture in which two or more different types of compounds represented by Formula 1 are mixed.

For example, in the organic material layer, two types of compounds having different structures from among the above-described compounds may be mixed at a mole ratio of from 99:1 to 1:99.

According to another embodiment, the present disclosure provides an organic electric element further including a light efficiency improvement layer formed on at least one of one surface of the first electrode opposite the organic material layer or one surface of the second electrode opposite the organic material layer.

Synthesis examples of the compound represented by Formula 1 and fabrication examples of the organic electric element according to embodiments of the present disclosure will be described in detail hereinafter, but the present disclosure is not limited thereto.

SYNTHESIS EXAMPLES

The compound (or final products) represented by Formula 1 according to the present disclosure is synthesized by reacting Sub 1 and Sub 2 as in Reaction Formula 1 below but is not limited thereto.

In Reaction Formula 1 below, X, $R^1$, $Ar^1$ to $Ar^5$, $L^1$ to $L^3$, and a are the same as those described above regarding Formula 1, and $Pd_2(dba)_3$ described in Synthesis Examples of this specification is tris(dibenzylideneacetone)dipalladium(0).

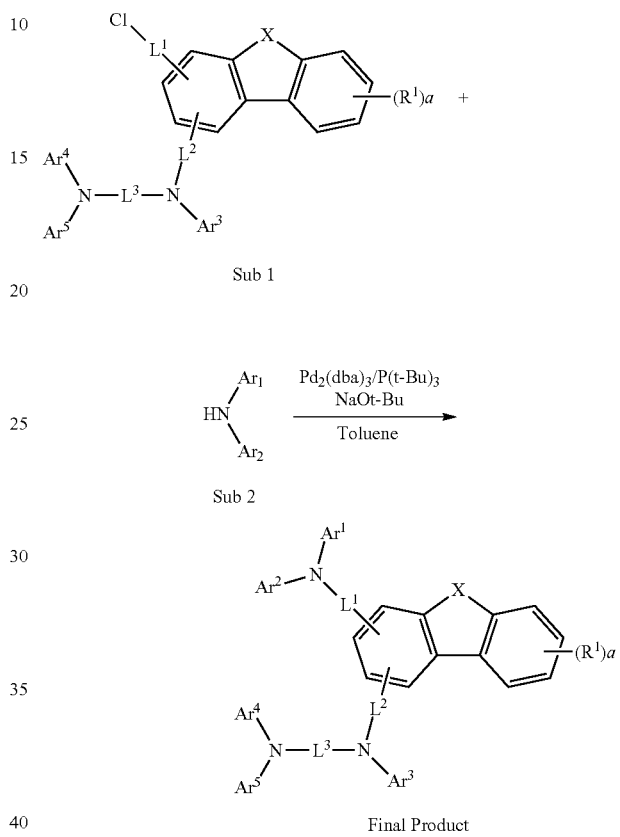

<Reaction Formula 1>

I. Synthesis Example of Sub 1

Sub 1 of Reaction Formula 1 may be synthesized by a reaction path of Reaction Formula 2 below but is not limited thereto.

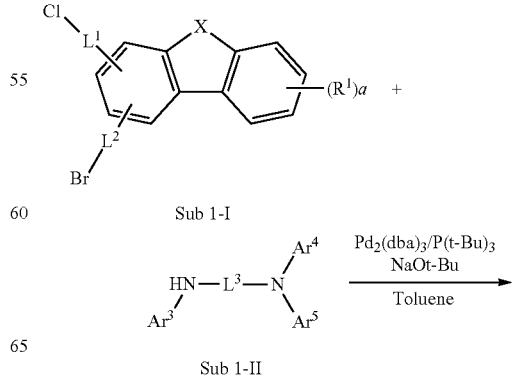

<Reaction Formula 2>

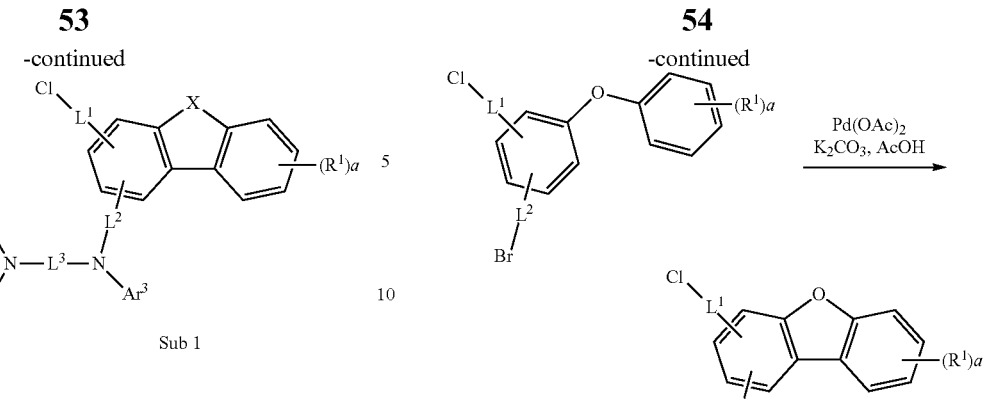

Sub 1

Sub 1-I of Reaction Formula 2 may be synthesized by reaction paths of Reaction Formulas 2 to 4 below but is not limited thereto.

<Reaction Formula 3>

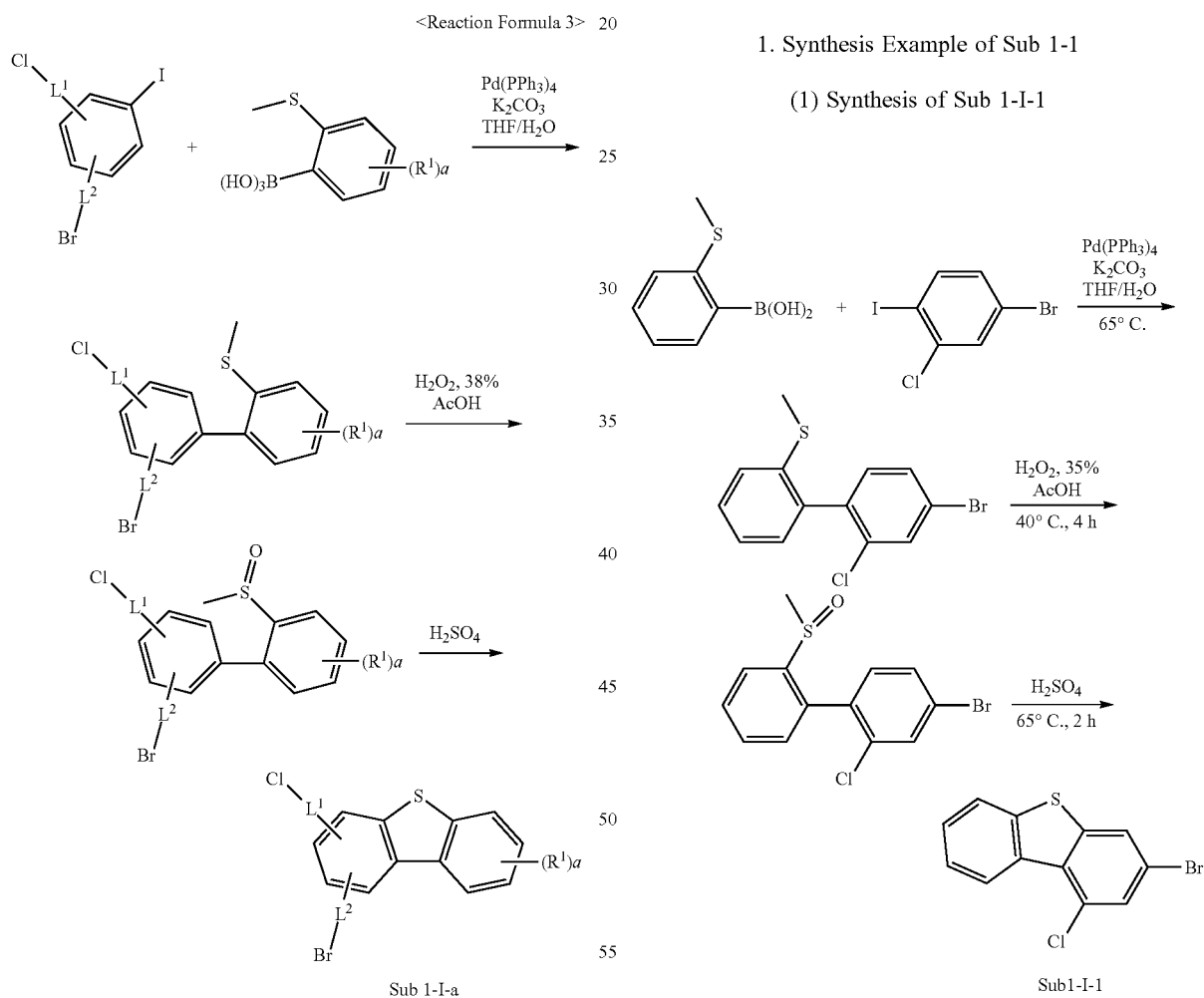

Sub 1-I-a

<Reaction Formula 4>

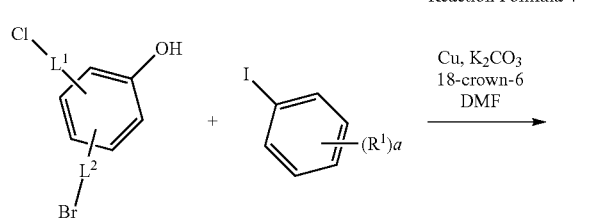

1. Synthesis Example of Sub 1-1

(1) Synthesis of Sub 1-I-1

1) After (2-(methylthio)phenyl) boronic acid (31.5 g, 187.6 mmol) was dissolved with tetrahydrofuran (THF) 600 mL in a round bottom flask, 4-bromo-2-chloroiodobenzene (62 g, 187.6 mmol), Pd(PPh$_3$)$_4$ (6.5 g, 5.6 mmol), K$_2$CO$_3$ (51.8 g, 375.2 mmol), and water 200 mL were added, followed by stirring at 80° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing (4'-bromo-2'-chloro-[1,1'-biphenyl]-2-yl)(methyl)sulfane 50 g (yield: 85%).

2) After (4'-bromo-2'-chloro-[1,1'-biphenyl]-2-yl)(methyl)sulfane (50 g, 159.4 mmol) was dissolved with AcOH 700 mL in a round bottom flask, $H_2O_2$ (13.7 mL, 159.4 mmol) was added, followed by stirring at room temperature. At the completion of the reaction, the solvent was removed, and then the reaction solution was neutralized with 1M NaOH. Afterwards, extraction was performed using ethyl acetate (EA) and then recrystallization was performed, thereby producing 4'-bromo-2'-chloro-2-(methylsulfinyl)-1,1'-biphenyl 48.3 g (yield: 92%).

3) 4'-bromo-2'-chloro-2-(methylsulfinyl)-1,1'-biphenyl (48.3 g, 146.4 mmol) was input to $H_2SO_4$ 500 g, followed by stirring at 65° C. At the completion of the reaction, the reaction solution was neutralized using a NaOH water solution. Afterwards, a silica gel column method and recrystallization were performed to a produced compound, thereby producing Sub 1-I-1 40.1 g (yield: 92%).

Synthesis of Sub 1-1

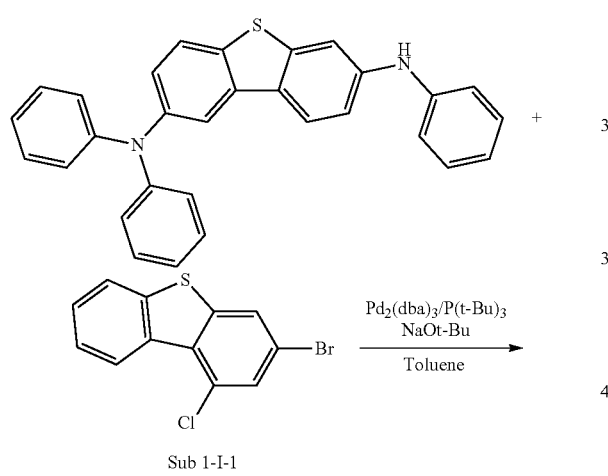

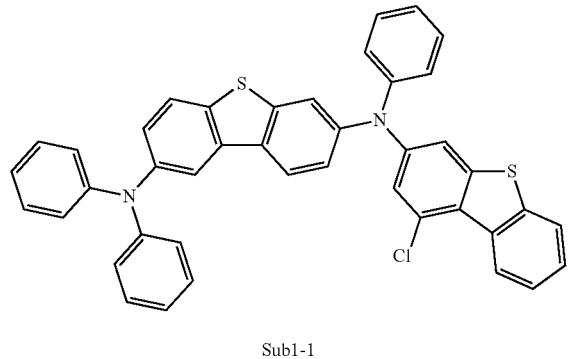

Sub1-1

After Sub 1-I-1 (4.7 g, 15.8 mmol) was dissolved with toluene (60 ml) in a round bottom flask, $N^2,N^2,N^7$-triphenyldibenzo[b,d]thiophene-2,7-diamine (7 g, 15.8 mmol), $Pd_2(dba)_3$ (0.43 g, 0.5 mmol), 50% P(t-Bu)$_3$ (0.9 ml, 0.4 mmol), and NaOt-Bu (2.3 g, 47.4 mmol) were added, followed by stirring at 65° C. At the completion of the reaction, the reaction solution was extracted with $CH_2Cl_2$ and water, and then an organic layer was dried with $MgSO_4$ and concentrated. Afterwards, a silica gel column method and recrystallization were performed to a produced compound, thereby producing a product Sub 1-1 7.8 g (yield: 75%).

2. Synthesis Example of Sub 1-4

(1) Synthesis of Sub 1-I-2

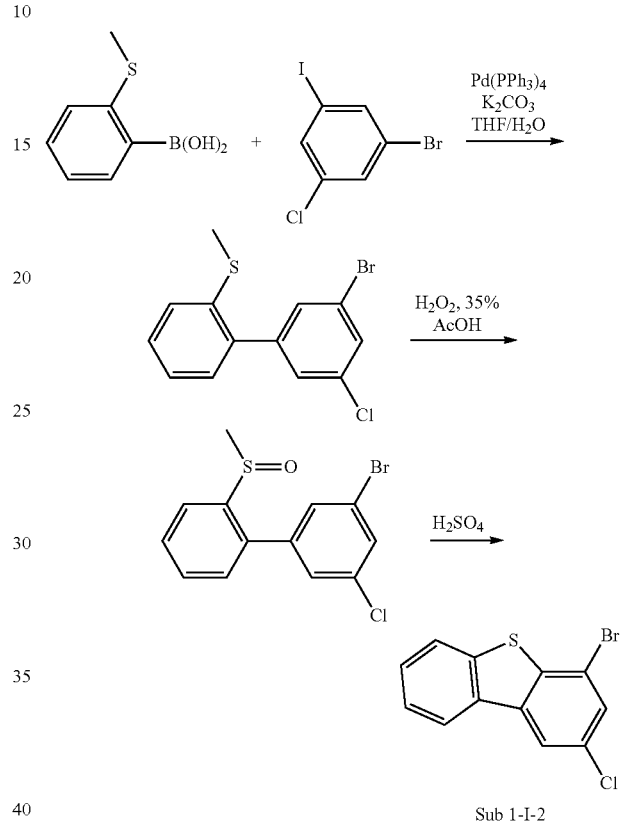

Sub 1-I-2

1) After (2-(methylthio)phenyl) boronic acid (37.8 g, 225.1 mmol) was dissolved with tetrahydrofuran (THF) 900 mL in a round bottom flask, 3-bromo-5-chloroiodobenzene (75 g, 236.3 mmol), Pd(PPh$_3$)$_4$ (7.8 g, 6.75 mmol), $K_2CO_3$ (62.2 g, 450.2 mmol), and water 300 mL were added, followed by stirring at 80° C. At the completion of the reaction, the reaction solution was extracted with $CH_2Cl_2$ and water, and then an organic layer was dried with $MgSO_4$ and concentrated. Afterwards, a silica gel column method and recrystallization were performed to a produced compound, thereby producing (3'-bromo-5'-chloro-[1,1'-biphenyl]-2-yl)(methyl)sulfane 58 g (yield: 82%).

2) After (3'-bromo-5'-chloro-[1,1'-biphenyl]-2-yl)(methyl)sulfane (58 g, 184.9 mmol) was dissolved with AcOH 1000 mL in a round bottom flask, $H_2O_2$ (15.9 mL, 184.9 mmol) was added, followed by stirring at room temperature. At the completion of the reaction, the solvent was removed, and then the reaction solution was neutralized with 1M NaOH. Afterwards, extraction was performed using ethyl acetate (EA) and then recrystallization was performed, thereby producing 3'-bromo-5'-chloro-2-(methylsulfinyl)-1,1'-biphenyl 57.9 g (yield: 95%).

3) 3'-bromo-5'-chloro-2-(methylsulfinyl)-1,1'-biphenyl (57.9 g, 175.6 mmol) was input to $H_2SO_4$ 600 g followed by stirring at 65° C. At the completion of the reaction, the reaction solution was neutralized using a NaOH water solution. Afterwards, a silica gel column method and recrystallization were performed to a produced compound, thereby producing Sub 1-I-2 45 g (yield: 87%).

(2) Synthesis of Sub 1-4

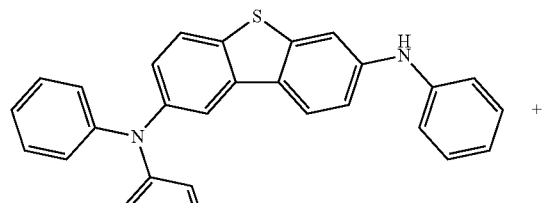

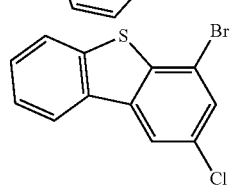

Sub 1-I-2

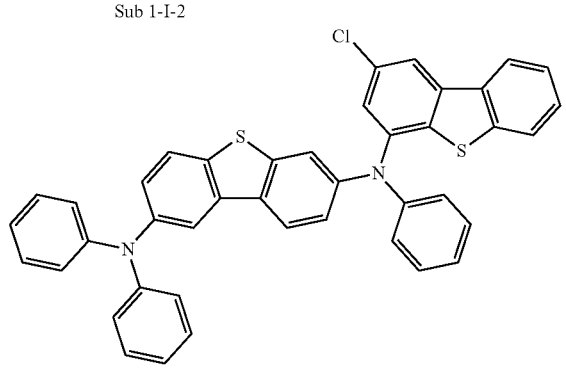

Sub1-4

After Sub 1-I-2 (9.4 g, 31.6 mmol) was dissolved with toluene (100 ml) in a round bottom flask, $N^2,N^2,N^7$-triphenyldibenzo[b,d]thiophene-2,7-diamine (14 g, 31.65 mmol), Pd$_2$(dba)$_3$ (0.87 g, 0.9 mmol), 50% P(t-Bu)$_3$ (0.8 ml, 1.9 mmol), and NaOt-Bu (9.12 g, 94.9 mmol) were added, followed by stirring at 65° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product Sub 1-4 15.1 g (yield: 72%).

3. Synthesis Example of Sub 1-14

(1) Synthesis of Sub 1-I-4

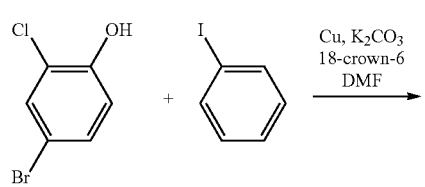

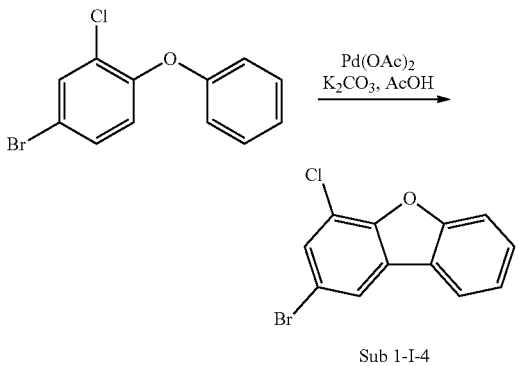

Sub 1-I-4

1) After 4-bromo-2-chlorophenol (15 g, 73.5 mmole) was dissolved with DMF 400 mL in a round bottom flask, iodobenzene (16.8 g, 80.9 mmol), K$_2$CO$_3$ (20.3 g 147.1 mmol), Cu (2.3 g, 36.8 mmol), and Dibenzo-18-crown-6 (1.6 g, 4.4 mmole) were added, followed by stirring at 120° C. At the completion of the reaction, the solvent was removed, the reaction solution was extracted with CH$_2$Cl$_2$ and water, and then an organic layer was dried with MgSO$_4$ and concentrated. Afterwards, a silica gel column method was performed to a produced compound, thereby producing a product 4-bromo-2-chloro-1-phenoxybenzene 16.5 g (yield: 79%).

2) Acetic acid 400 mL was input to 4-bromo-2-chloro-1-phenoxybenzene (16 g, 56.4 mmol)$^{oll}$ Pd(OAc)$_2$ (0.63 g, 2.8 mol), and K$_2$CO$_3$ (7.8 g, 56.4 mol), followed by stirring at 120° C. for 48 hours. At the completion of the reaction, the reaction solution was extracted with ethyl acetate (EA) and water, and then an organic layer was dried with MgSO$_4$ and concentrated. Afterwards, a silica gel column method was performed to a produced compound, thereby producing a product Sub 1-I-4 6.7 g (yield: 42%).

(2) Synthesis of Sub 1-14

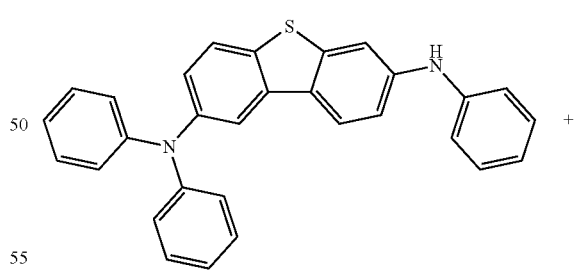

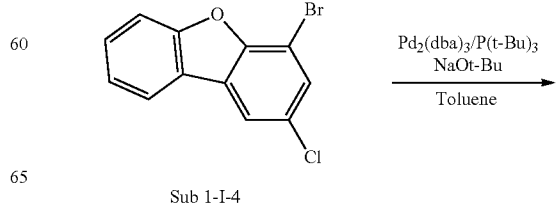

Sub 1-I-4

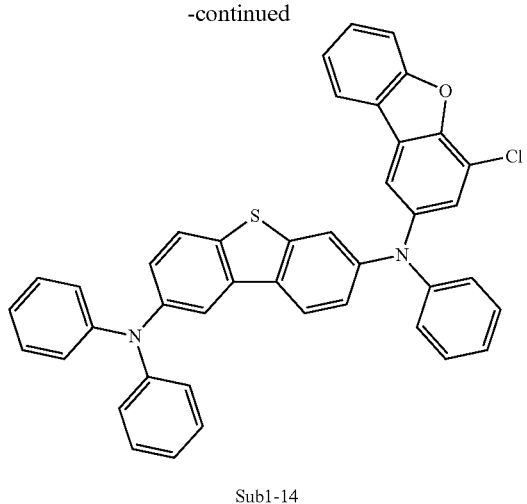

Sub1-14

After Sub 1-I-4 (6.4 g, 22.6 mmol) was dissolved with toluene (60 ml) in a round bottom flask, N²,N²,N⁷-triphenyldibenzo[b,d]thiophene-2,7-diamine (10 g, 22.6 mmol), Pd₂(dba)₃ (0.6 g, 0.7 mmol), 50% P(t-Bu)₃ (0.6 ml, 1.4 mmol), and NaOt-Bu (4.4 g, 45.2 mmol) were added, followed by stirring at 65° C. At the completion of the reaction, the reaction solution was extracted with CH₂Cl₂ and water, and then an organic layer was dried with MgSO₄ and concentrated. Afterwards, a silica gel column method and recrystallization were performed to a produced compound, thereby producing a product Sub 1-14 10.2 g (yield: 70%).

4. Synthesis Example of Sub 1-17

(1) Synthesis of Sub 1-I-3

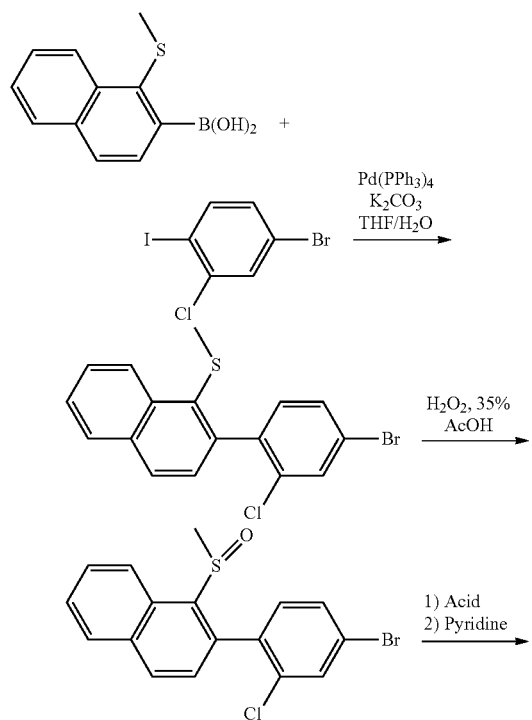

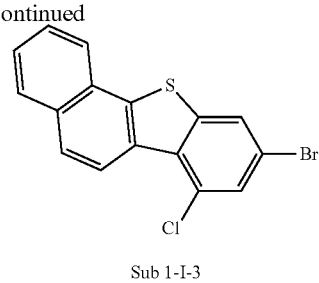

Sub 1-I-3

1) After (2-(methylthio)phenyl) boronic acid (30 g, 137.6 mmol) was dissolved with tetrahydrofuran (THF) 300 mL in a round bottom flask, 4-bromo-2-chloroiodobenzene (43.7 g, 137.6 mmol), Pd(PPh₃)₄ (4.8 g, 4.1 mmol), K₂CO₃ (57 g, 412.7 mmol), and water 100 mL were added, followed by stirring at 80° C. At the completion of the reaction, the reaction solution was extracted with CH₂Cl₂ and water, and then an organic layer was dried with MgSO₄ and concentrated. Afterwards, a silica gel column method and recrystallization were performed to a produced compound, thereby producing a product (2-(4-bromo-2-chlorophenyl)naphthalen-1-yl)(methyl)sulfane 37.5 g (yield: 75%).

2) After (2-(4-bromo-2-chlorophenyl) naphthalen-1-yl) (methyl)sulfane (37 g, 101.7 mmol) was dissolved with AcOH 300 mL in a round bottom flask, H₂O₂ (8.7 mL, 101.7 mmol) was added, followed by stirring at room temperature. At the completion of the reaction, the solvent was removed, and then the reaction solution was neutralized with 1M NaOH. Afterwards, extraction was performed using ethyl acetate (EA) and then recrystallization was performed, thereby producing 2-(4-bromo-2-chlorophenyl)-1-(methylsulfinyl)naphthalene 35.5 g (yield: 92%).

3) 2-(4-bromo-2-chlorophenyl)-1-(methylsulfinyl)naphthalene (35 g, 92.2 mmol) was input to trifluloromethanesulfonic acid 300 g, followed by stirring at 65° C. At the completion of the reaction, pyridine was input and then refluxing was performed for 30 minutes. Afterwards, a silica gel column method and recrystallization were performed to a produced compound, thereby producing Sub 1-I-3 26 g (yield: 81%).

(2) Synthesis of Sub 1-17

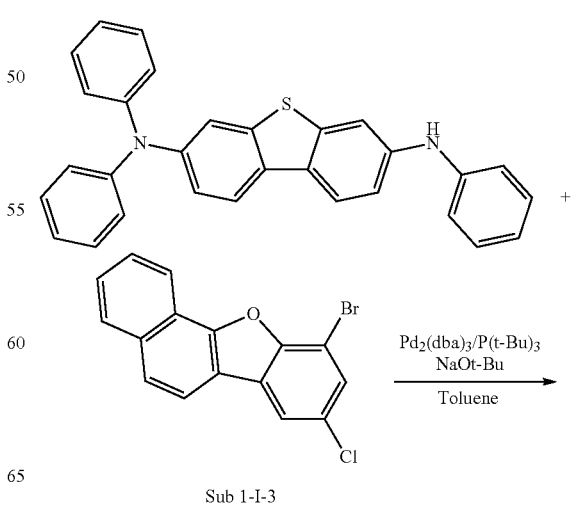

Sub 1-I-3

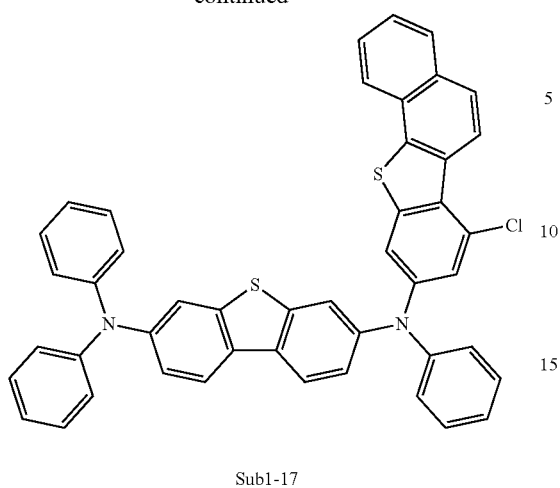

Sub1-17

After Sub 1-I-3 (10 g, 28.9 mmol) was dissolved with toluene (100 ml) in a round bottom flask, $N^3,N^3,N^7$-triphenyldibenzo[b,d]thiophene-3,7-diamine (12.8 g, 28.9 mmol), $Pd_2(dba)_3$ (0.79 g, 0.9 mmol), 50% $P(t-Bu)_3$ (0.7 ml, 1.7 mmol), and NaOt-Bu (8.3 g, 86.8 mmol), followed by stirring at 65° C. At the completion of the reaction, the reaction solution was extracted with $CH_2Cl_2$ and water, and then an organic layer was dried with $MgSO_4$ and concentrated. Afterwards, a silica gel column method and recrystallization were performed to a produced compound, thereby producing a product Sub 1-17 16 g (yield: 78%).

5. Synthesis Example of Sub 1-48

(1) Synthesis of Sub 1-I-5

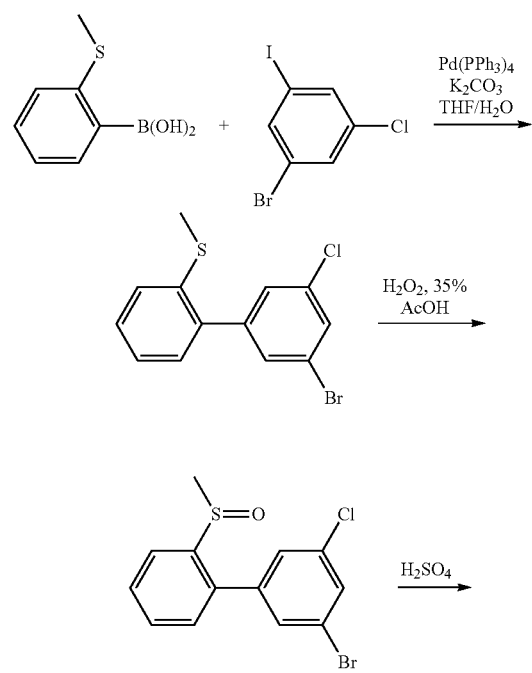

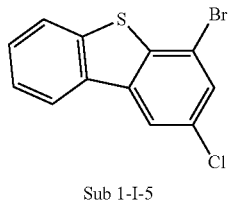

Sub 1-I-5

After (2-(methylthio)phenyl) boronic acid (50 g, 297.6 mmol) was dissolved with tetrahydrofuran (THF) 1000 mL in a round bottom flask, 5-bromo-3-chloroiodobenzene (94.4 g, 297.6 mmol), $Pd(PPh_3)_4$ (10.3 g, 8.9 mmol), $K_2CO_3$ (123.44 g, 892.8 mmol), and water 300 mL were added, followed by stirring at 80° C. At the completion of the reaction, the reaction solution was extracted with $CH_2Cl_2$ and water, and then an organic layer was dried with $MgSO_4$ and concentrated. Afterwards, a silica gel column method and recrystallization were performed to a produced compound, thereby producing (5'-bromo-3'-chloro-[1,1'-biphenyl]-2-yl)(methyl)sulfane 74 g (yield: 79%).

(5'-bromo-3'-chloro-[1,1'-biphenyl]-2-yl)(methyl)sulfane (74 g, 235.9 mmol) was dissolved with AcOH 1000 mL in a round bottom flask, $H_2O_2$ (20.3 mL, 235.9 mmol) was added, followed by stirring at room temperature. At the completion of the reaction, the solvent was removed, and then the reaction solution was neutralized with 1M NaOH. Afterwards, extraction was performed using ethyl acetate (EA) and then recrystallization was performed, thereby producing 5'-bromo-3'-chloro-2-(methylsulfinyl)-1,1'-biphenyl 71.5 g (yield: 92%).

3) 5'-bromo-3'-chloro-2-(methylsulfinyl)-1,1'-biphenyl (71.5 g, 217.0 mmol) was input to $H_2SO_4$ 800 g, followed by stirring at 65° C. At the completion of the reaction, the reaction solution was neutralized using a NaOH water solution. Afterwards, a silica gel column method and recrystallization were performed to a produced compound, thereby producing Sub 1-I-5 64.5 g (yield: 83%).

(2) Synthesis of Sub 1-I-6

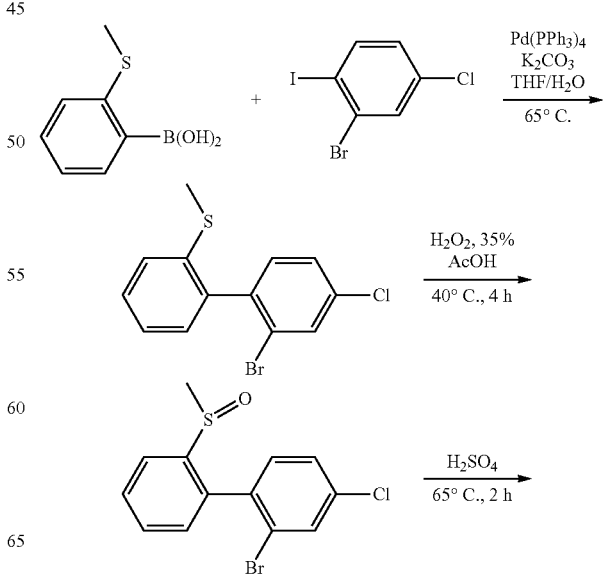

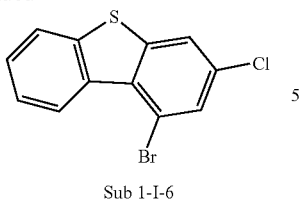

Sub 1-I-6

After (2-(methylthio)phenyl) boronic acid (50 g, 297.6 mmol) was dissolved with tetrahydrofuran (THF) 1000 mL in a round bottom flask, 2-bromo-4-chloroiodobenzene (94.4 g, 297.6 mmol), Pd(PPh$_3$)$_4$ (10.3 g, 8.9 mmol), K$_2$CO$_3$ (123.44 g, 892.8 mmol), and water 300 mL were added, followed by stirring at 80° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing (2'-bromo-4'-chloro-[1,1'-biphenyl]-2-yl)(methyl)sulfane 79.6 g (yield: 85%).

2) After (2'-bromo-4'-chloro-[1,1'-biphenyl]-2-yl)(methyl)sulfane (79.6 g, 253.8 mmol) was dissolved with AcOH 1000 mL in a round bottom flask, H$_2$O$_2$ (21.8 mL, 253.8 mmol) was input, followed by stirring at room temperature. At the completion of the reaction, the solvent was removed, and then the reaction solution was neutralized with 1M NaOH. Afterwards, extraction was performed using ethyl acetate (EA) and then recrystallization was performed, thereby producing 2'-bromo-4'-chloro-2-(methylsulfinyl)-1,1'-biphenyl 74.4 g (yield: 89%).

3) 2'-bromo-4'-chloro-2-(methylsulfinyl)-1,1'-biphenyl (74.4 g, 225.8 mmol) was input to H$_2$SO$_4$ 800 g, followed by stirring at 65° C. At the completion of the reaction, the reaction solution was neutralized using a NaOH water solution. Afterwards, a silica gel column method and recrystallization were performed to a produced compound, thereby producing Sub 1-I-6 63.2 g (yield: 94%).

(3) Synthesis of Sub 1-48

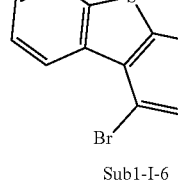 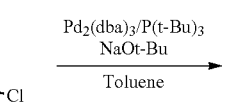

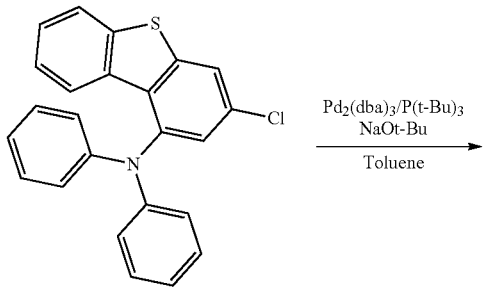

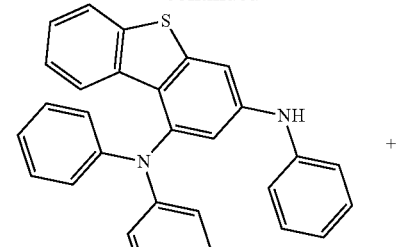

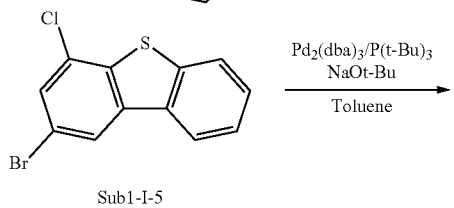

Sub1-I-5

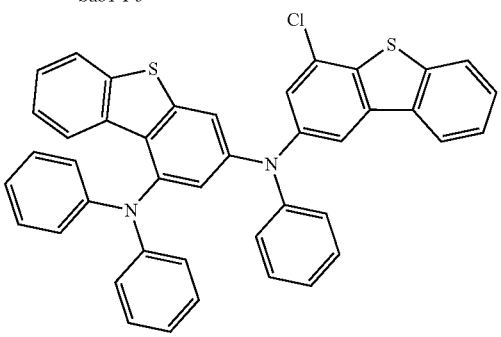

Sub1-48

After Sub 1-I-6 (10.0 g, 33.6 mmol) was dissolved with toluene (90 ml) in a round bottom flask, diphenylamine (5.7 g, 33.6 mmol), Pd$_2$(dba)$_3$ (0.9 g, 1.0 mmol), 50% P(t-Bu)$_3$ (0.8 ml, 2.0 mmol), and NaOt-Bu (6.5 g, 67.2 mmol) were added, followed by stirring at 65° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product 3-chloro-N,N-diphenyldibenzo[b,d]thiophen-1-amine 10.5 g (yield: 81%).

2) After 3-chloro-N,N-diphenyldibenzo[b,d]thiophen-1-amine (10.0 g, 27.2 mmol) was dissolved with toluene (90 ml) in a round bottom flask, aniline (2.5 g, 27.2 mmol), Pd$_2$(dba)$_3$ (0.75 g, 0.8 mmol), 50% P(t-Bu)$_3$ (0.7 ml, 1.6 mmol), and NaOt-Bu (5.2 g, 54.4 mmol) were added, followed by stirring at 120° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product N1,N1,N$^3$-triphenyldibenzo[b,d]thiophene-1,3-diamine 8.8 g (yield: 73%).

3) After N$^1$,N$^1$,N$^3$-triphenyldibenzo[b,d]thiophene-1,3-diamine (8.8 g, 19.9 mmol) was dissolved with toluene (60 ml) in a round bottom flask, Sub 1-I-5 (5.9 g, 19.9 mmol), Pd$_2$(dba)$_3$ (0.55 g, 0.6 mmol), 50% P(t-Bu)$_3$ (0.5 ml, 1.2 mmol), and NaOt-Bu (3.8 g, 39.8 mmol) were added, followed by stirring at 65° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product Sub 1-48 11.3 g (yield: 86%).

6. Synthesis Example of Sub 1-55

(1) Synthesis of Sub 1-I-7

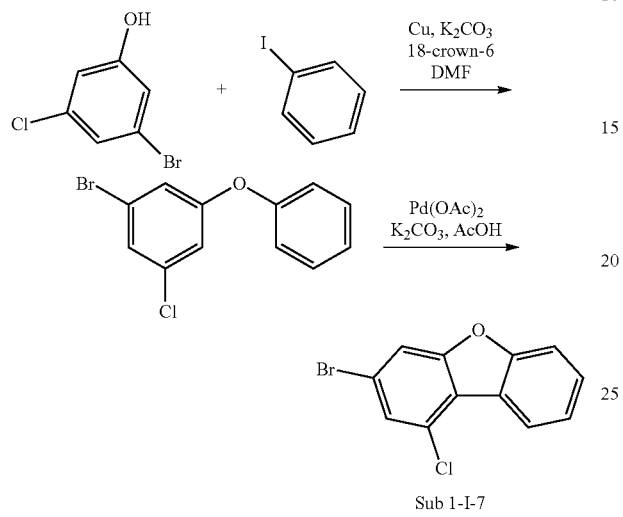

Sub 1-I-7

After 3-bromo-5-chlorophenol (10 g, 49 mmol) was dissolved with DMF 300 mL in a round bottom flask, iodobenzene (11.2 g, 53.9 mmol), $K_2CO_3$ (13.5 g 98.1 mmol), Cu (1.5 g, 24.5 mmol), and Dibenzo-18-crown-6 (1.06 g, 2.9 mmole) were added, followed by stirring at 120° C. At the completion of the reaction, the solvent was removed, the reaction solution was extracted with $CH_2Cl_2$ and water, and then an organic layer was dried with $MgSO_4$ and concentrated. Afterwards, a silica gel column method was performed to a produced compound, thereby producing a product 3-bromo-5-chloro-1-phenoxybenzene 11.3 g (yield: 81%).

Acetic acid 300 mL was input to 3-bromo-5-chloro-1-phenoxybenzene (10 g, 35.2 mmol), $Pd(OAc)_2$ (0.39 g, 1.8 mol), and $K_2CO_3$ (4.9 g, 35.25 mol), followed by stirring at 120° C. for 48 hours. At the completion of the reaction, the reaction solution was extracted with ethyl acetate (EA) and water, and then an organic layer was dried with $MgSO_4$ and concentrated. Afterwards, a silica gel column method was performed to a produced compound, thereby producing a product Sub 1-I-7 2.5 g (yield: 45%).

(2) Synthesis of Sub 1-55

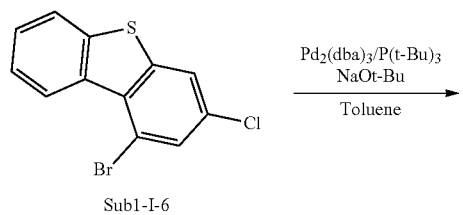

Sub1-I-6

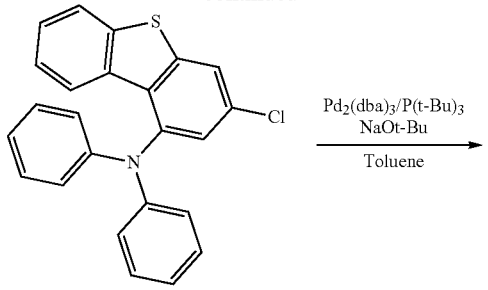

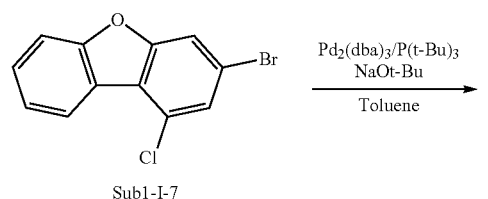

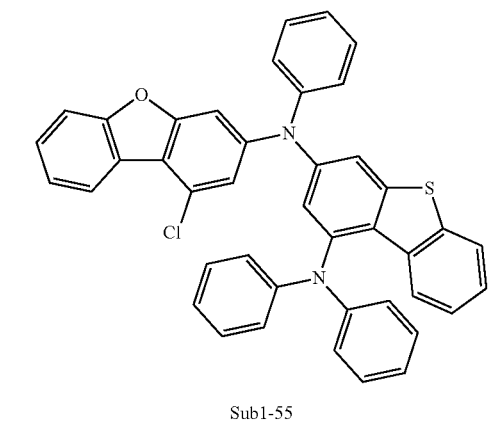

Sub1-55

After $N^1,N^1,N^3$-triphenyldibenzo[b,d]thiophene-1,3-diamine (6.0 g, 13.6 mmol) was dissolved with toluene (50 ml) in a round bottom flask, Sub 1-I-7 (3.8 g, 13.6 mmol), $Pd_2(dba)_3$ (0.37 g, 0.4 mmol), 50% $P(t-Bu)_3$ (0.3 ml, 0.8 mmol), and NaOt-Bu (2.6 g, 27.1 mmol) were added, followed by stirring at 110° C. At the completion of the reaction, the reaction solution was extracted with $CH_2Cl_2$ and water, and then an organic layer was dried with $MgSO_4$ and concentrated. Afterwards, a silica gel column method and recrystallization were performed to a produced compound, thereby producing a product Sub 1-55 6.2 g (yield: 71%).

7. Synthesis Example of Sub 1-77

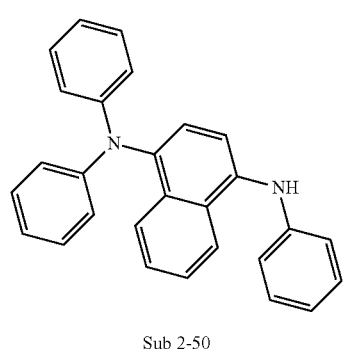

Sub 2-50

+

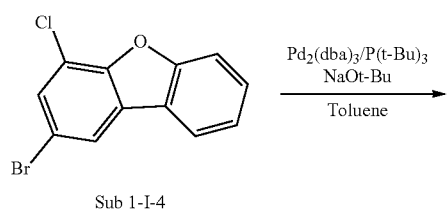

Sub 1-I-4

$\xrightarrow{\text{Pd}_2(\text{dba})_3/\text{P(t-Bu)}_3 \atop \text{NaOt-Bu}}$ Toluene

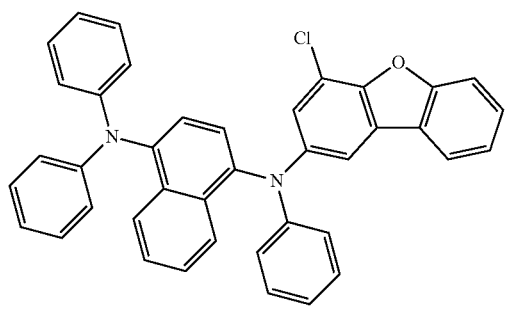

Sub1-77

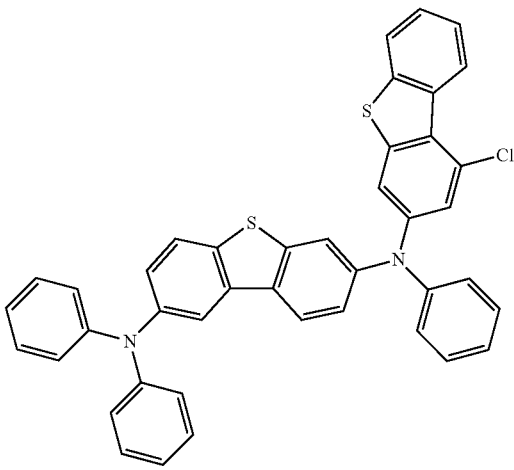

Sub1-1

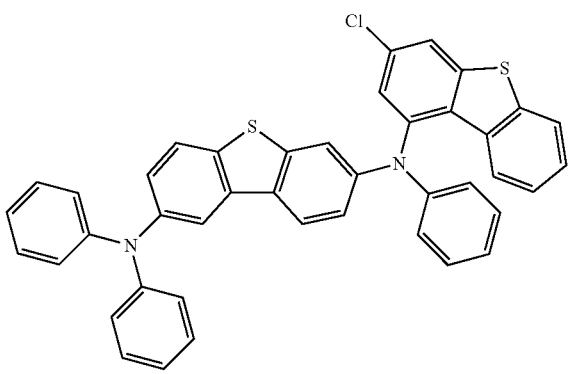

Sub1-2

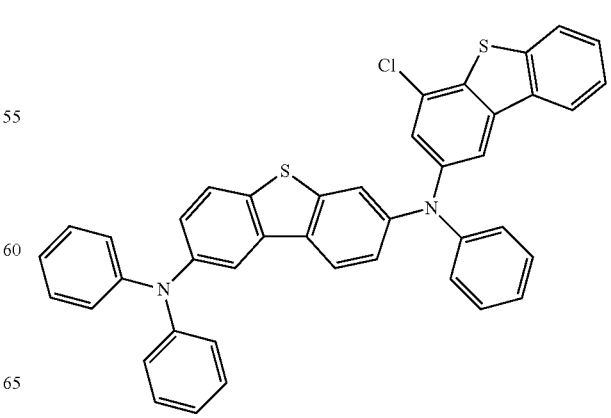

Sub1-3

After Sub 2-50 (7.0 g, 18.1 mmol) was dissolved with toluene (80 ml) in a round bottom flask, Sub 1-I-4 (5.1 g, 18.1 mmol), Pd$_2$(dba)$_3$ (0.5 g, 0.5 mmol), 50% P(t-Bu)$_3$ (0.44 ml, 1.1 mmol), and NaOt-Bu (3.5 g, 36.2 mmol) were added, followed by stirring at 65° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product Sub 1-77 7.8 g (yield: 73%).

In addition, compounds belonging to Sub 1 may be, but are not limited to, the following compounds. Table 1 represents field desorption-mass spectrometry (FD-MS) values of the compounds belonging to Sub 1.

-continued
Sub1-4
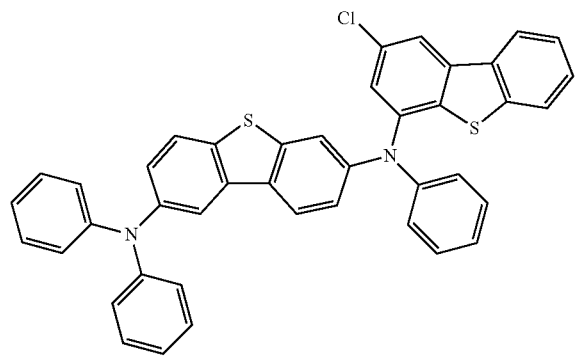
Sub1-5
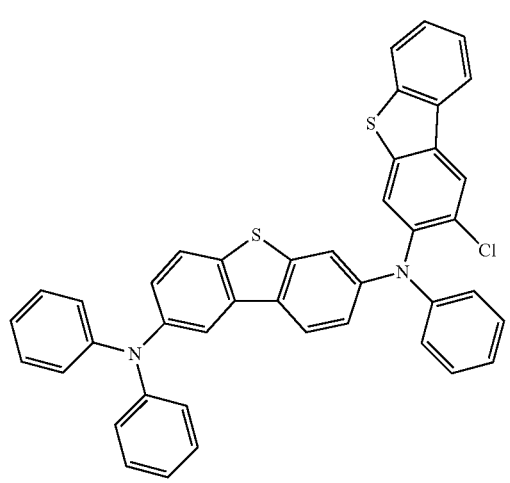
Sub1-6
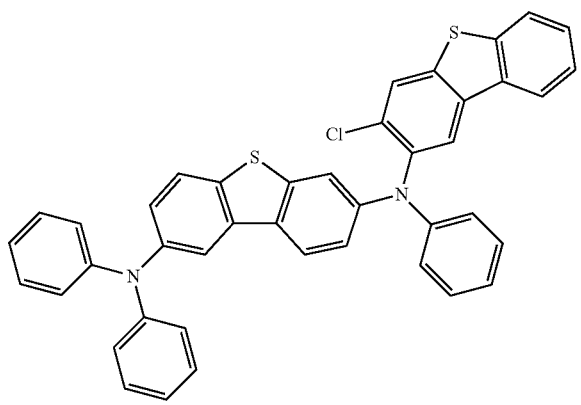
-continued
Sub1-7
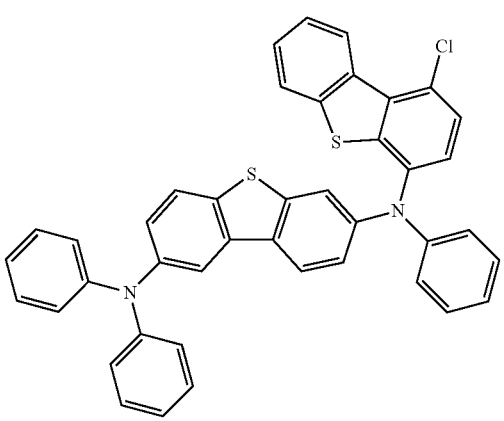
Sub1-8
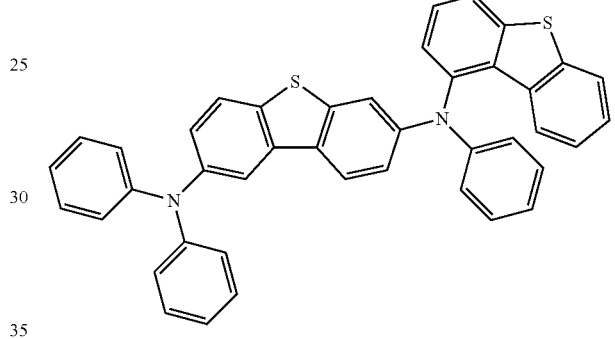
Sub1-9
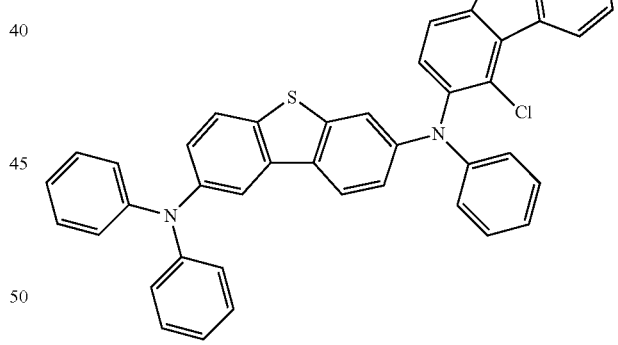
Sub1-10
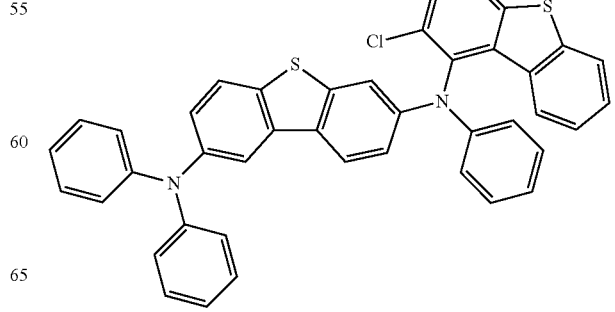

-continued
Sub1-11
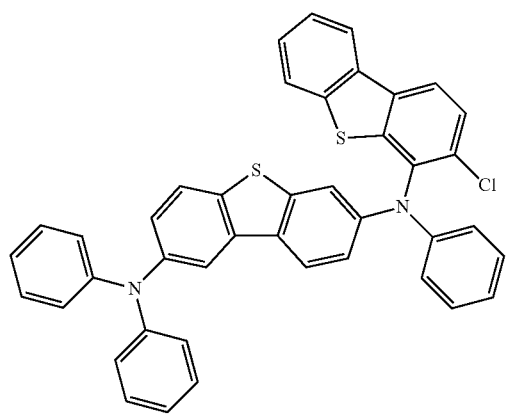
Sub1-12
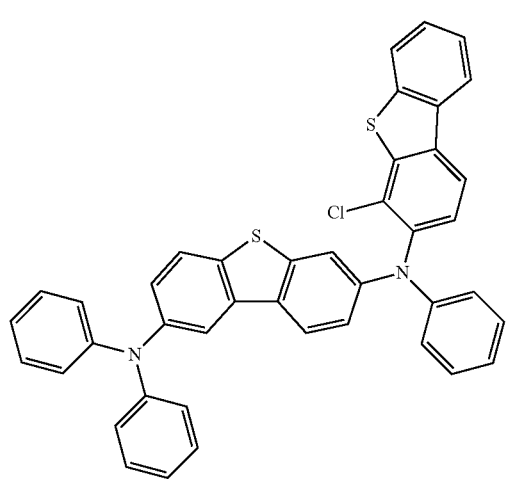
Sub1-13
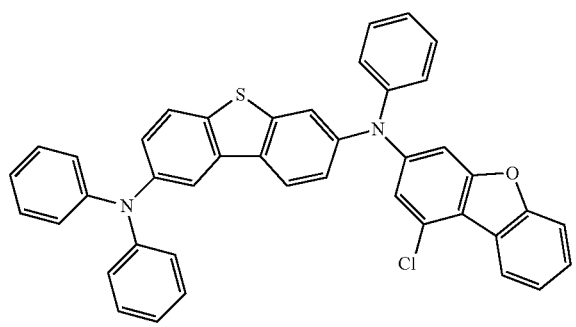
Sub1-14
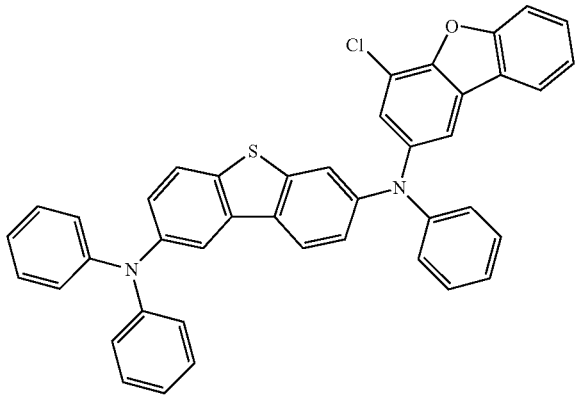
Sub1-15
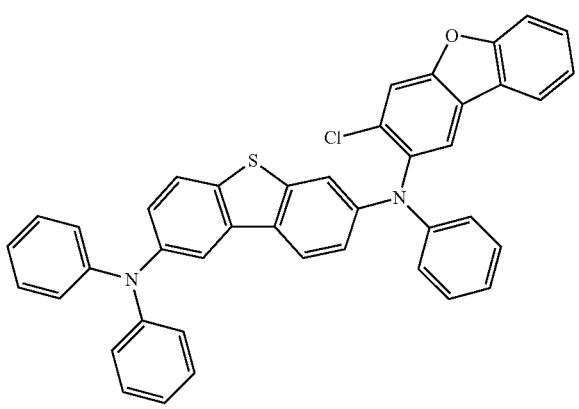
Sub1-16
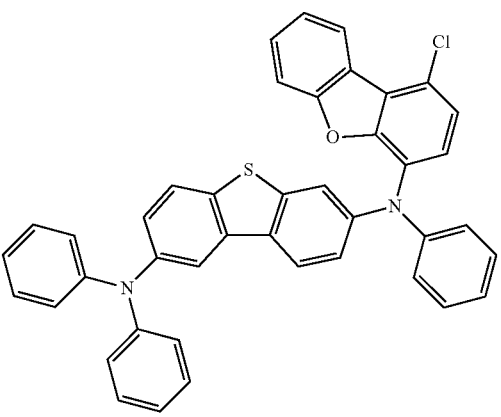

Sub1-17
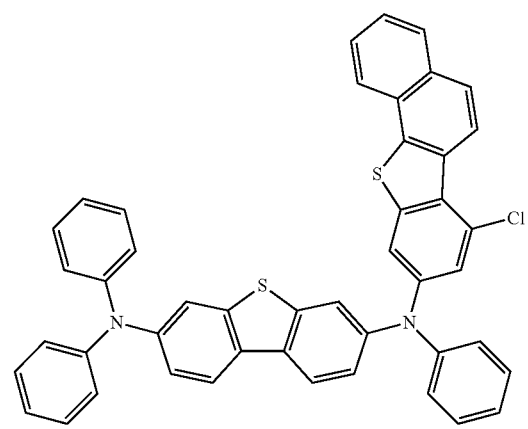
Sub1-20
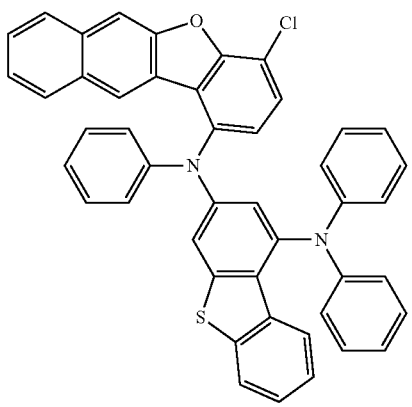
Sub1-21
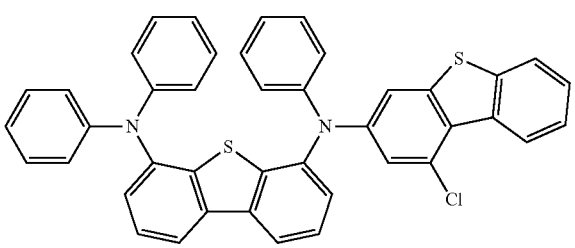
Sub1-18
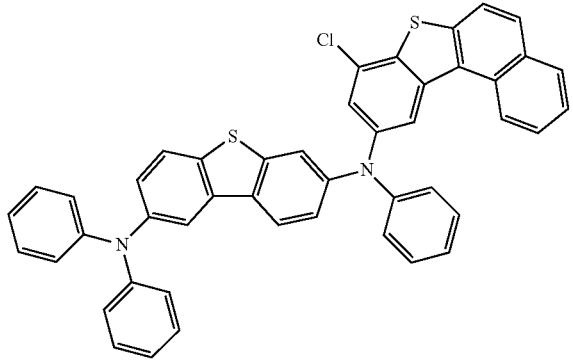
Sub1-22
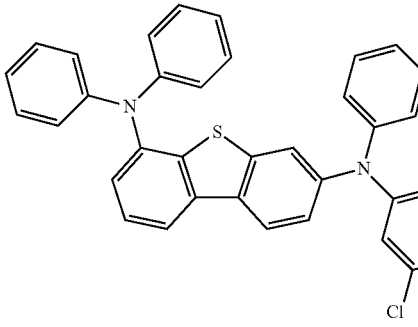
Sub1-19
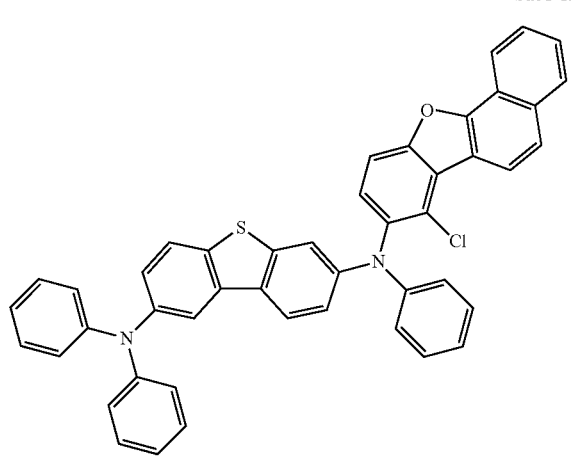
Sub1-23
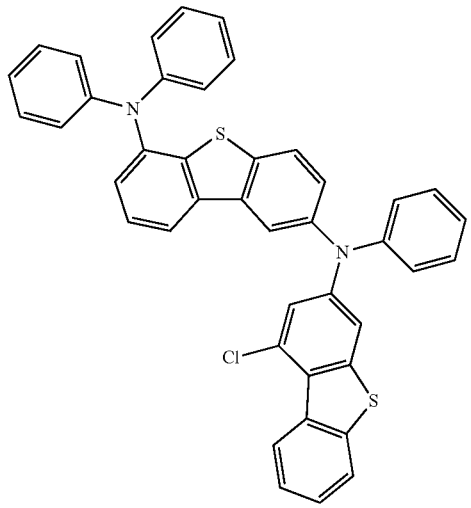

-continued
Sub1-24
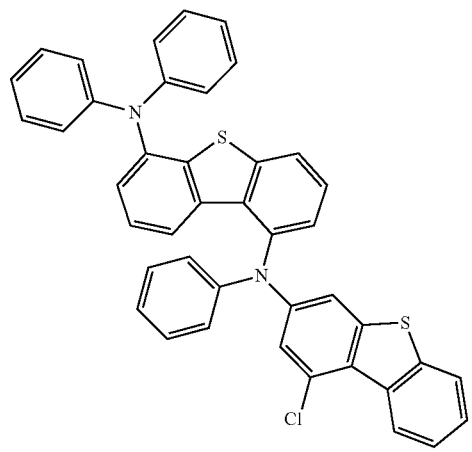
Sub1-25
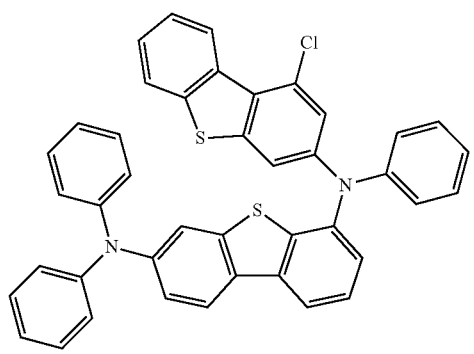
Sub1-26
Sub1-27
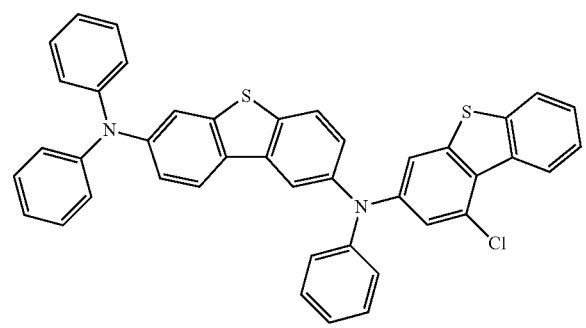
-continued
Sub1-28
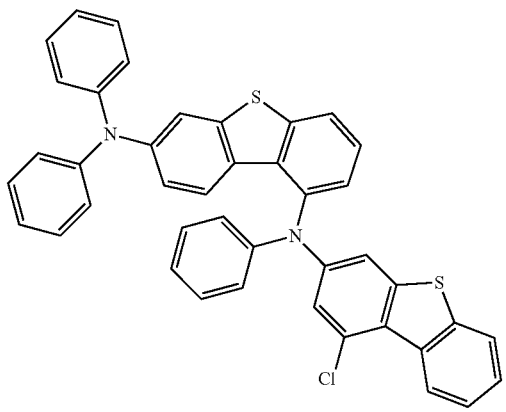
Sub1-29
Sub1-30
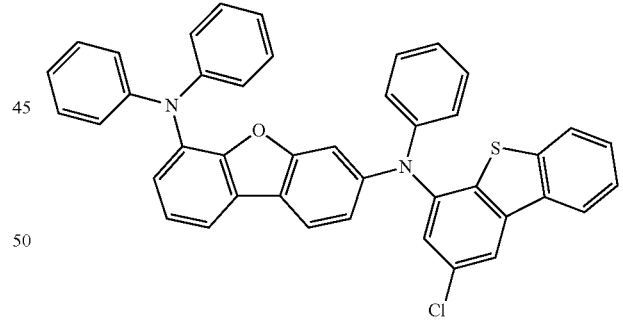
Sub1-31
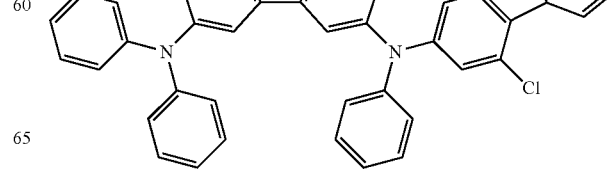

Sub1-32
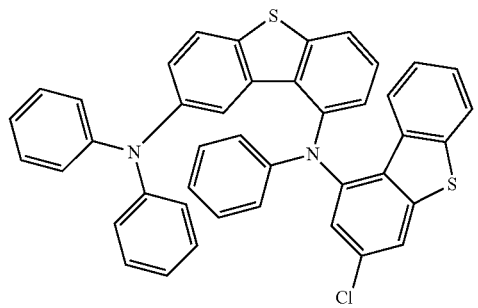
Sub1-33
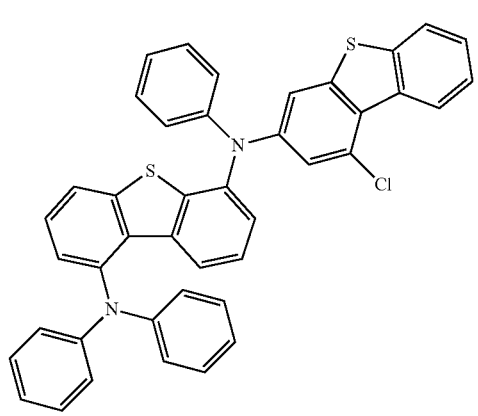
Sub1-34
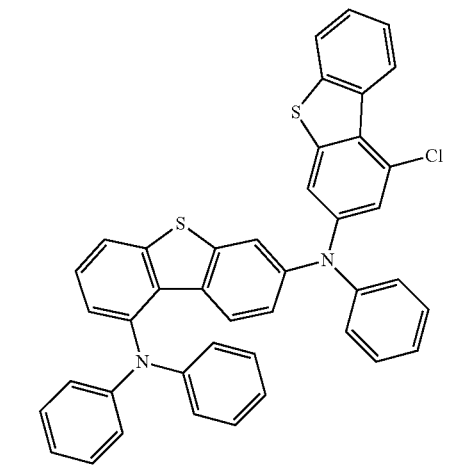
Sub1-35
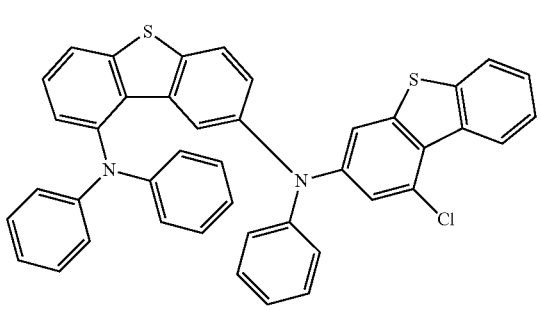
Sub1-36
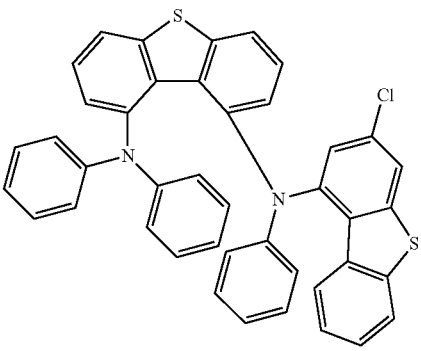
Sub1-37
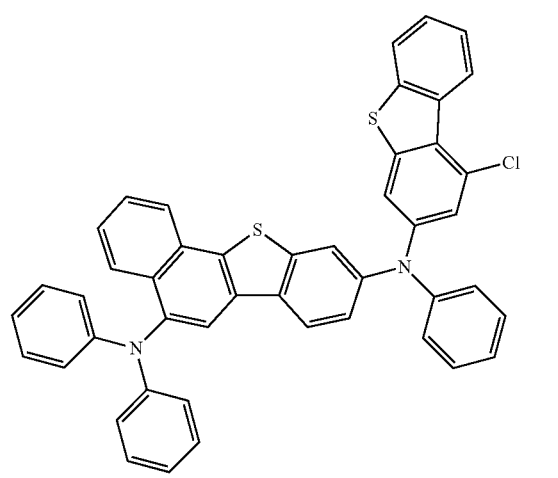
Sub1-38
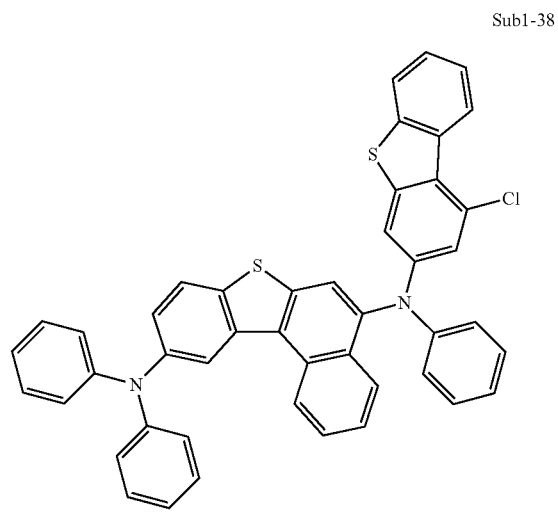
Sub1-39
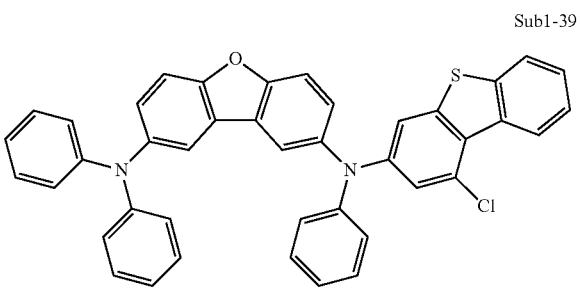

Sub1-40
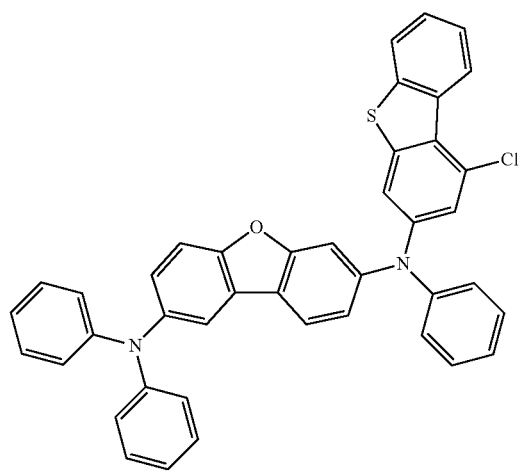
Sub1-41
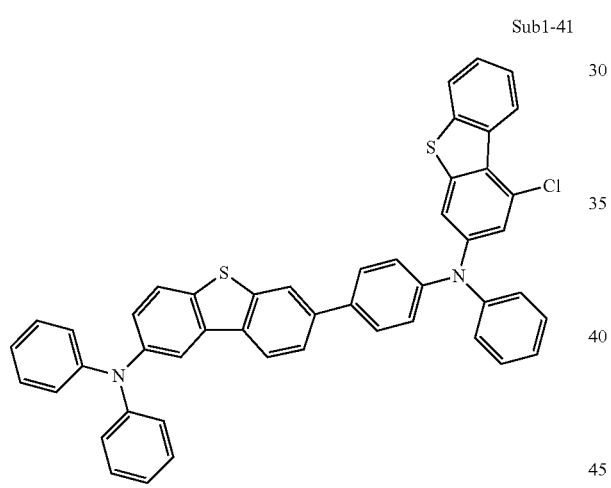
Sub1-42
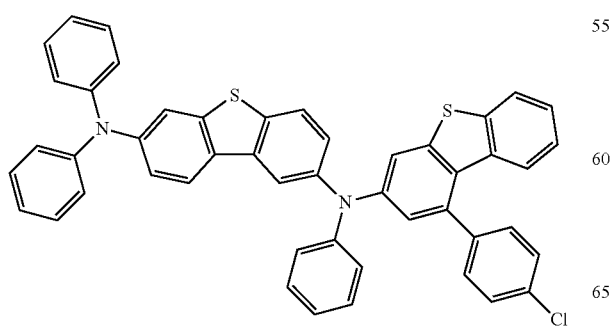
Sub1-43
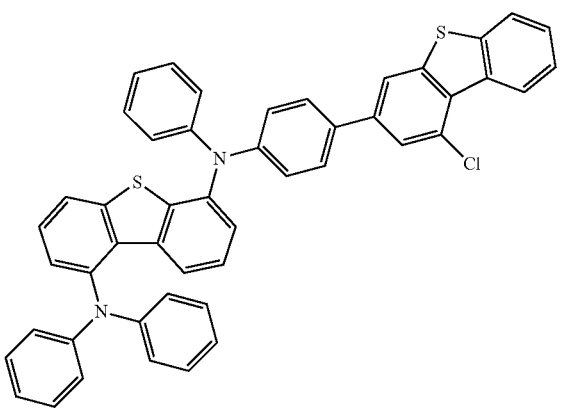
Sub1-44
Sub1-45
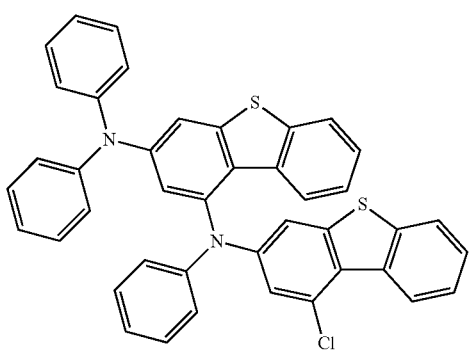

Sub1-46
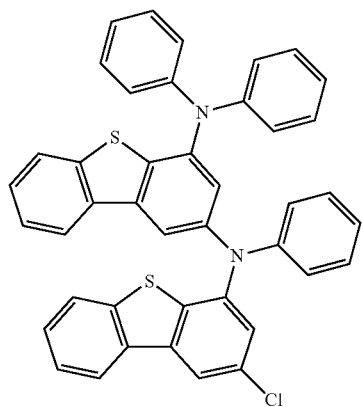
Sub1-47
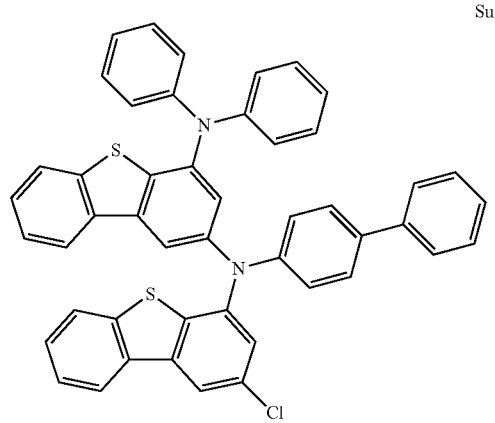
Sub1-48
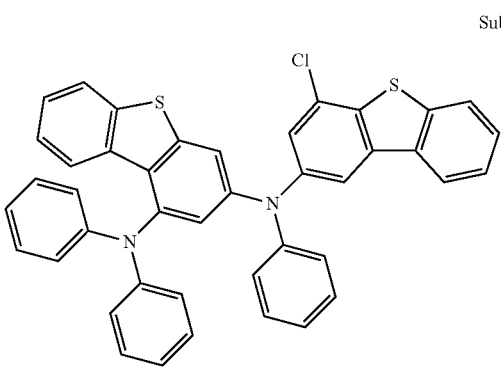
Sub1-49
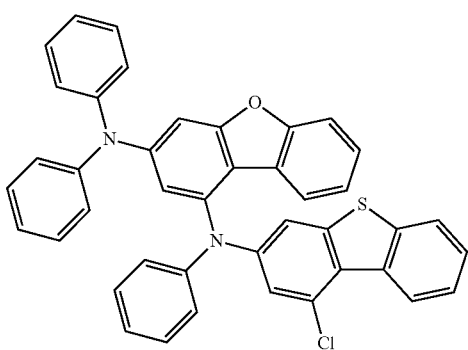
Sub1-50
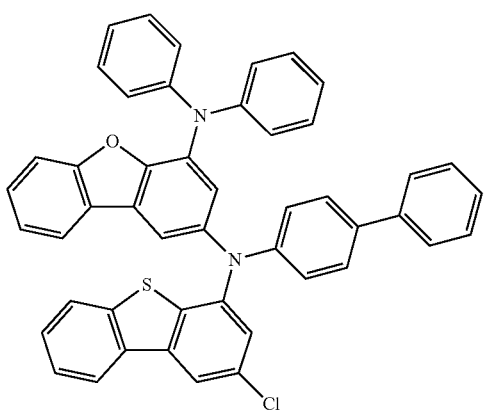
Sub1-51
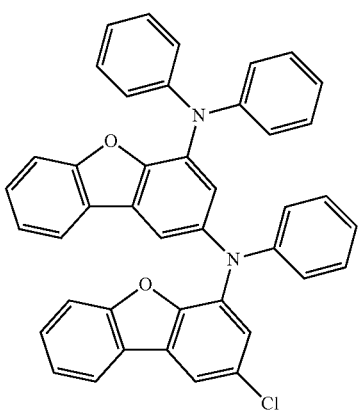
Sub1-52
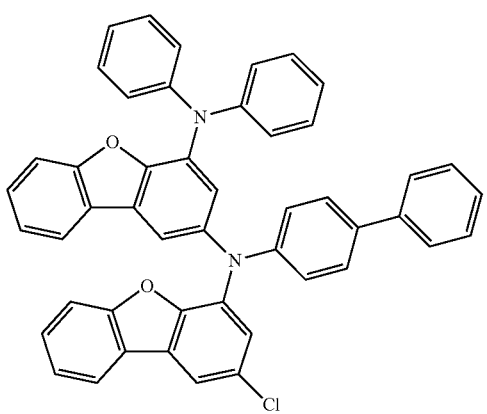

Sub1-53
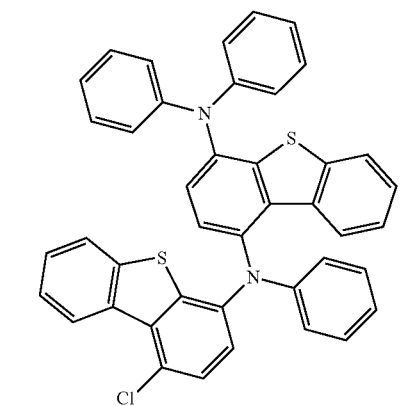
Sub1-54
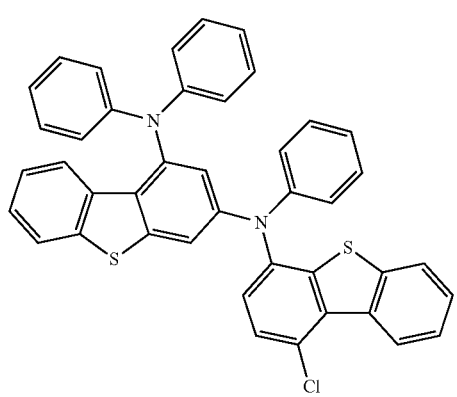
Sub1-55
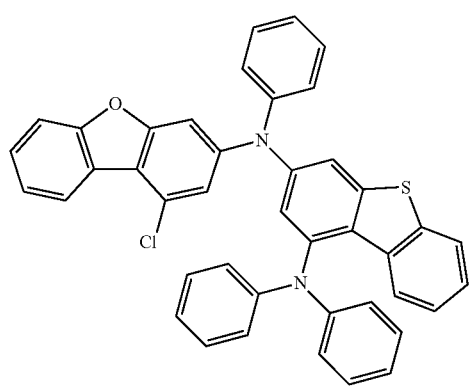
Sub1-56
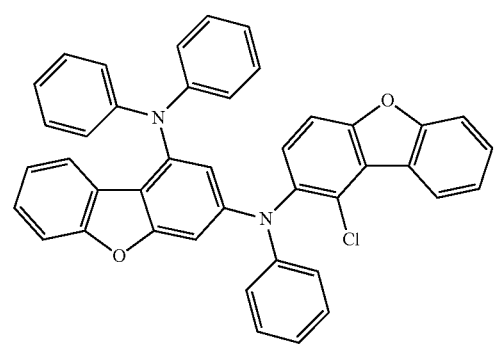
Sub1-57
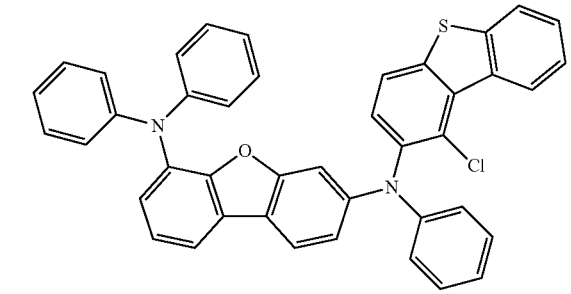
Sub1-58
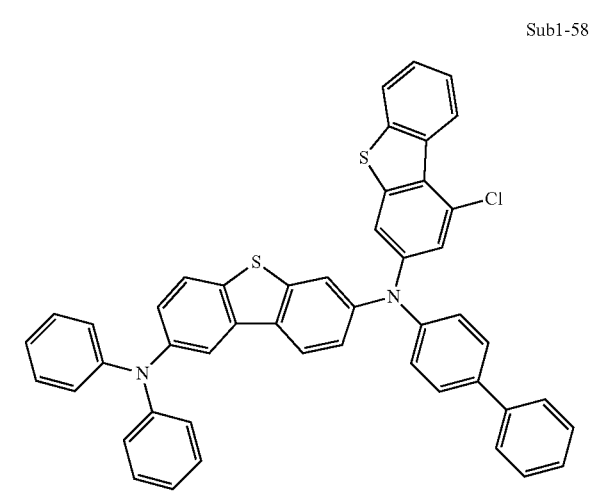
Sub1-59
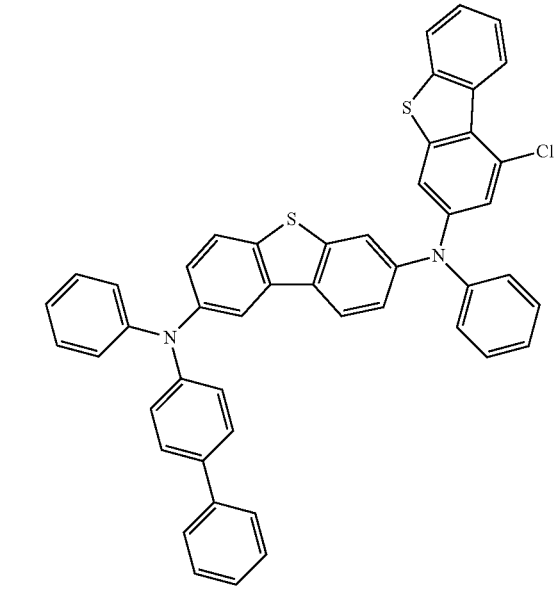

Sub1-60
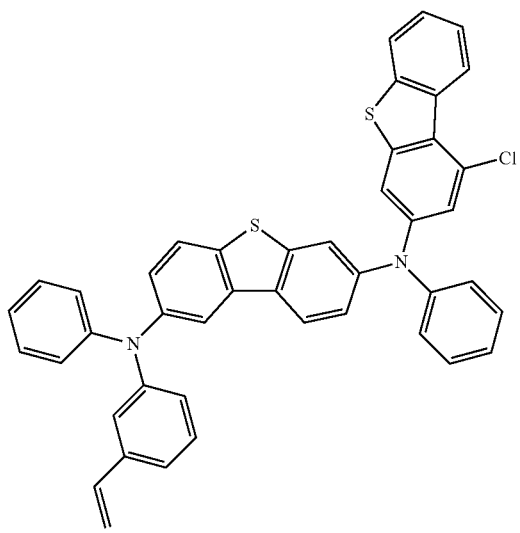
Sub1-61
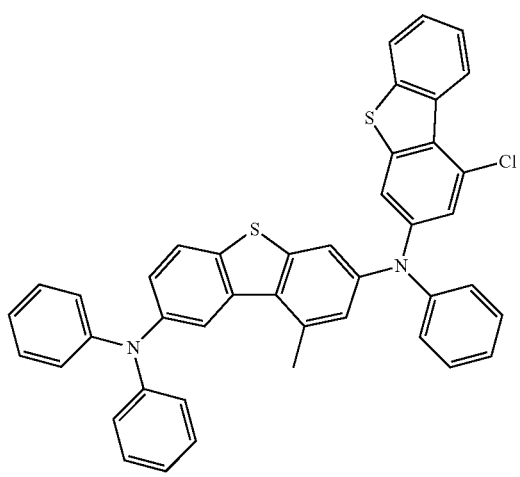
Sub1-62
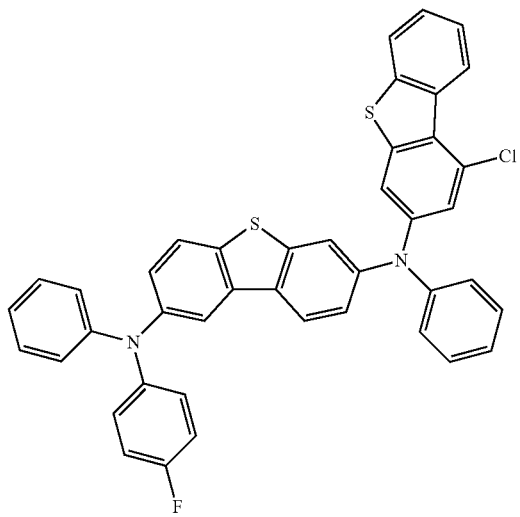
Sub1-63
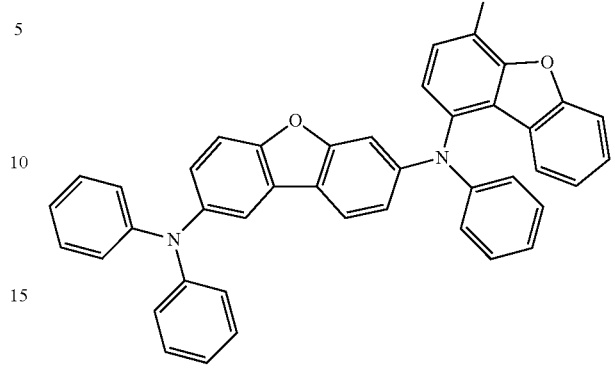
Sub1-64
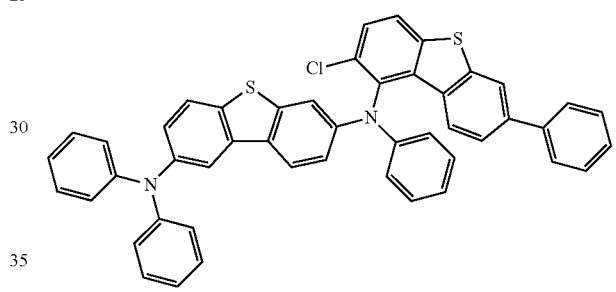
Sub1-65
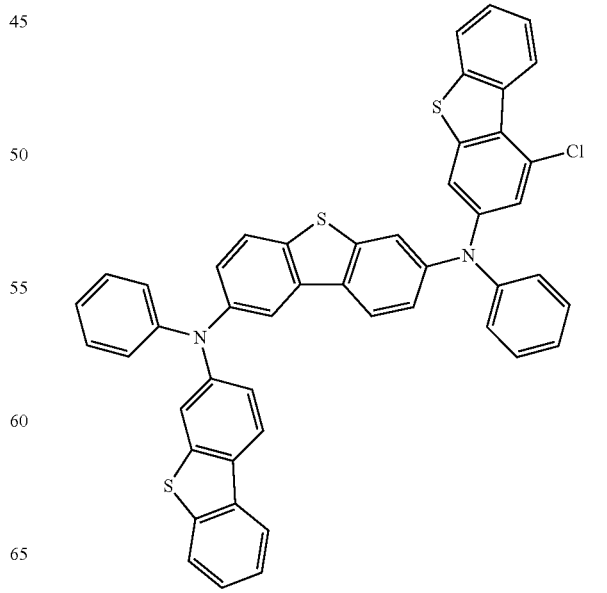

Sub1-66
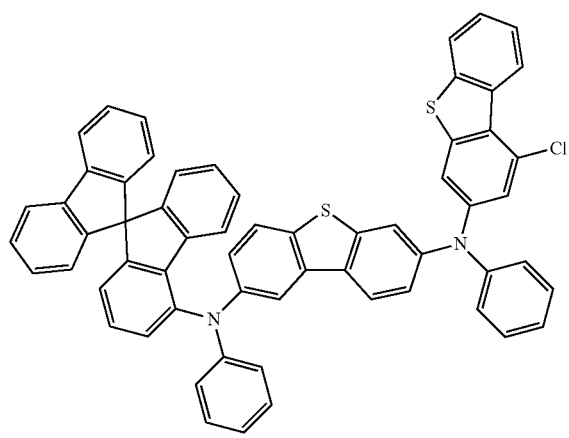
Sub1-67
Sub1-68
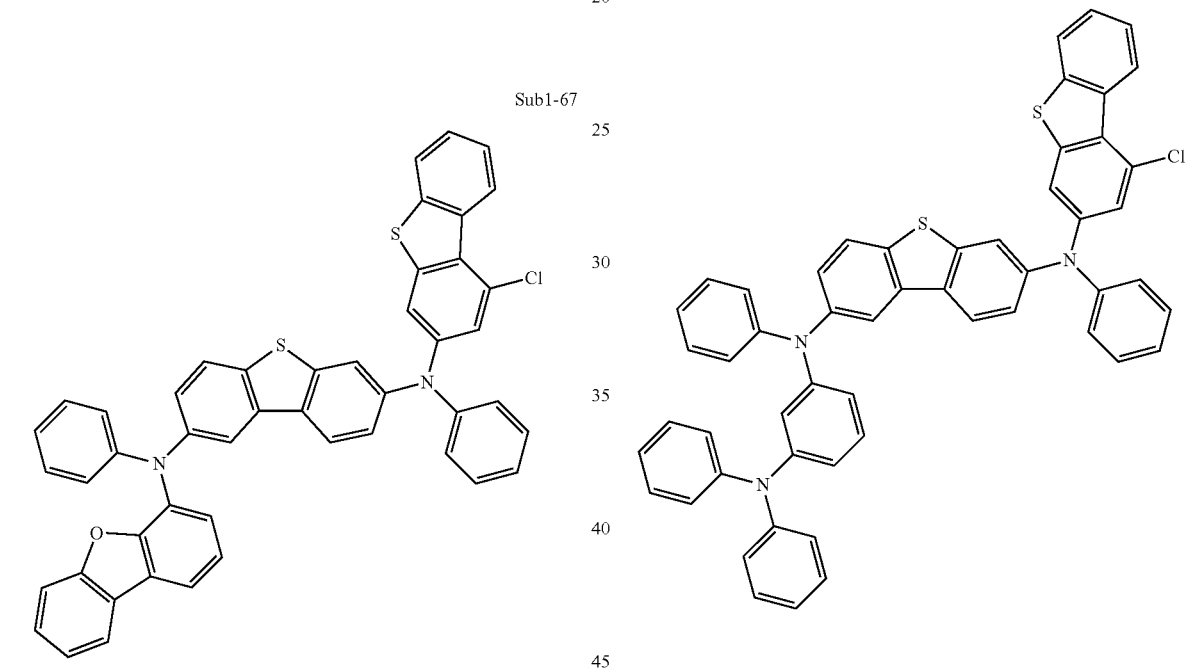
Sub1-69
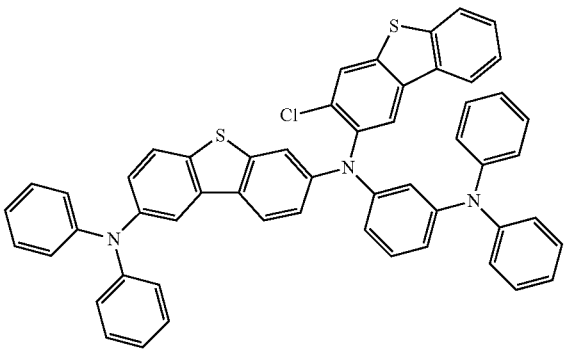
Sub1-70
Sub1-71
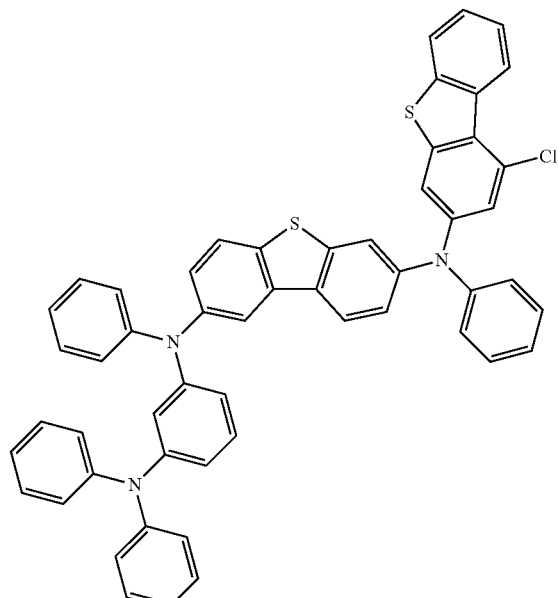

Sub1-72
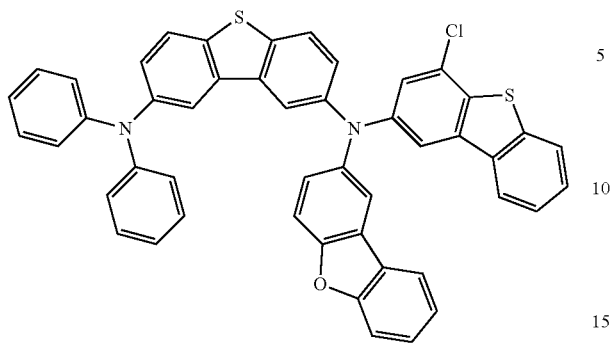
Sub1-76
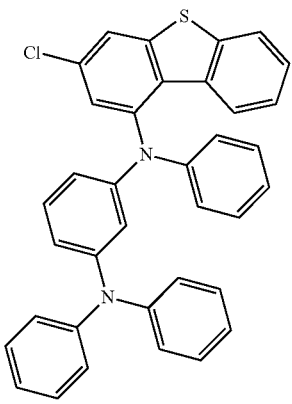
Sub1-73
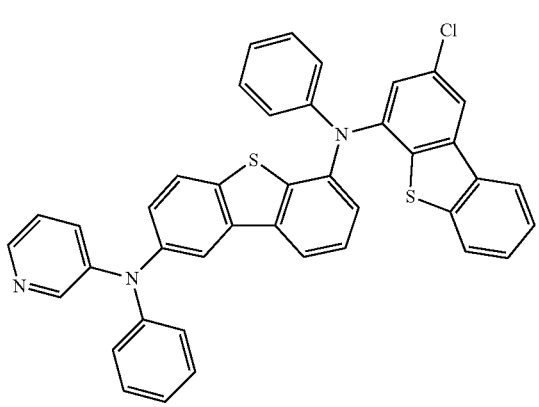
Sub1-77
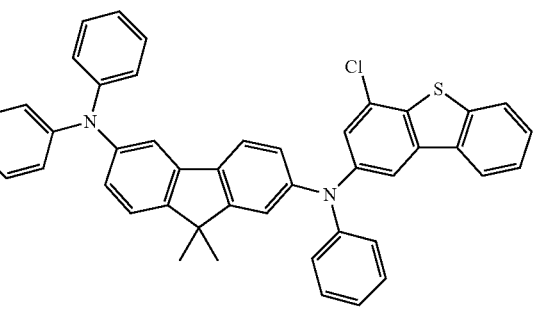
Sub1-74
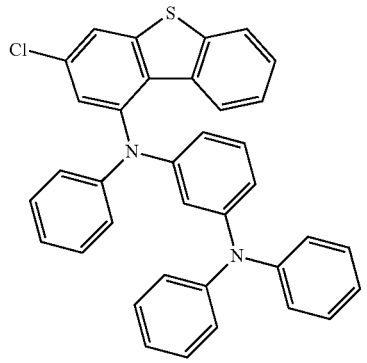
Sub1-78
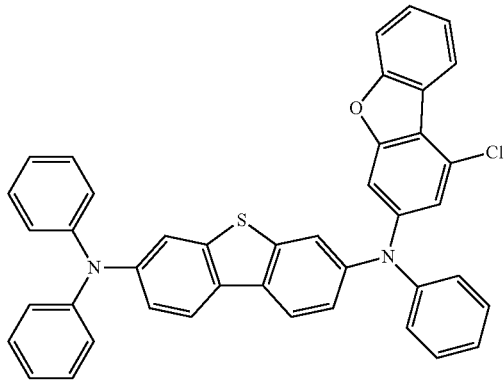
Sub1-75
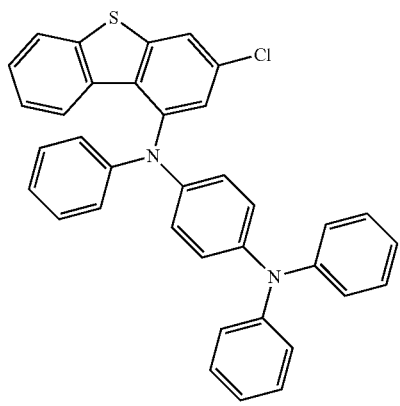
Sub1-79

-continued
Sub1-80
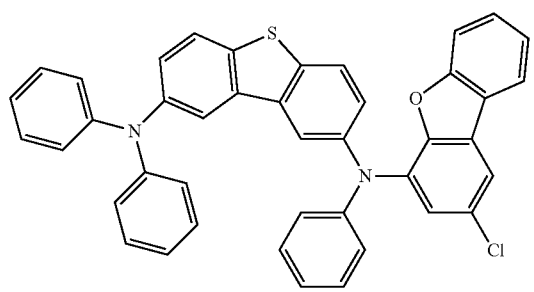
Sub1-81
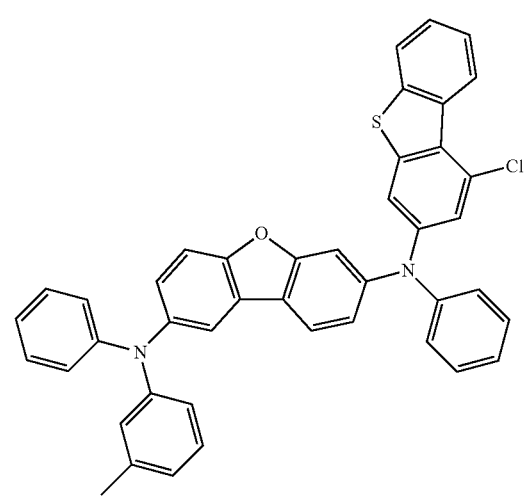
Sub1-82
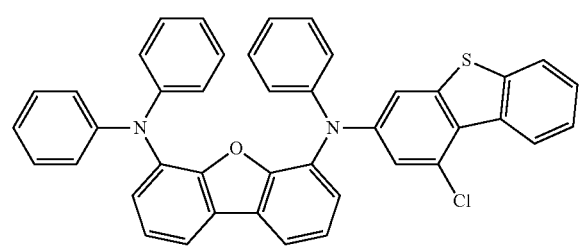
Sub1-83
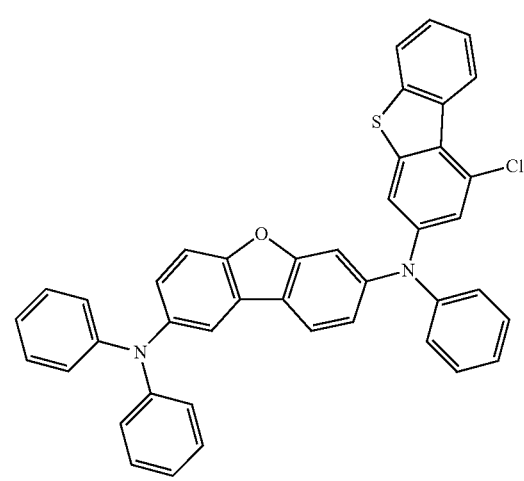
-continued
Sub1-84
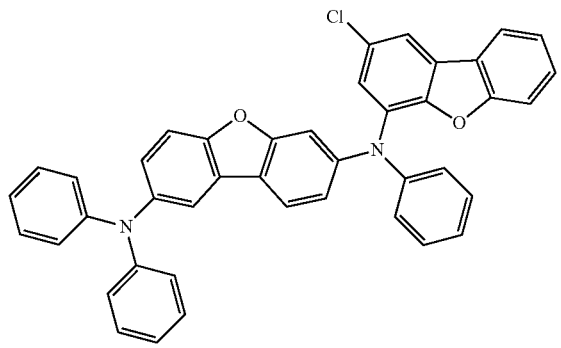
Sub1-85
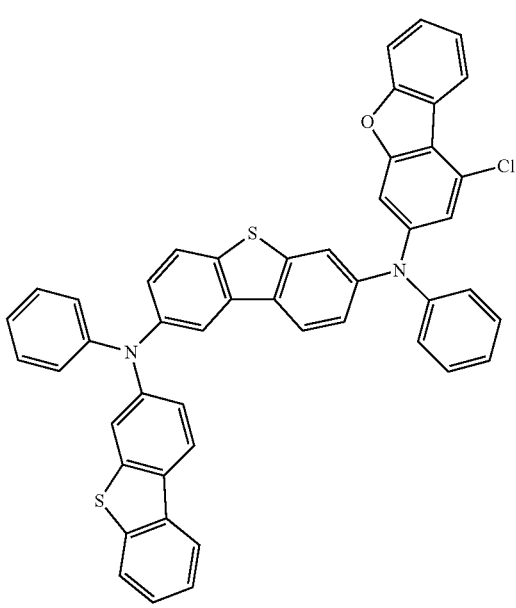
Sub1-86
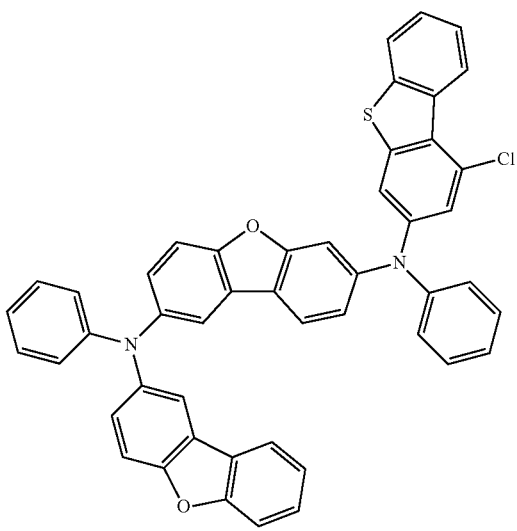

Sub1-87
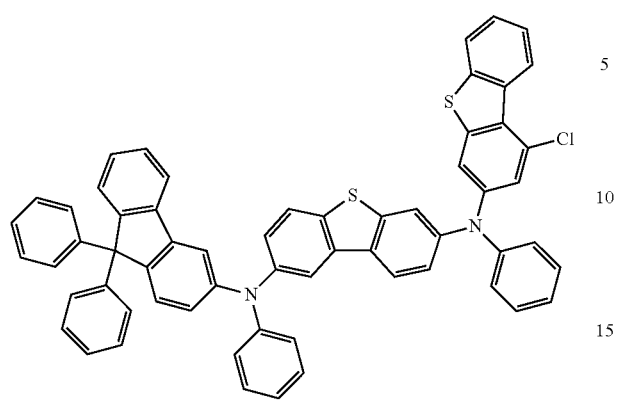
Sub1-90
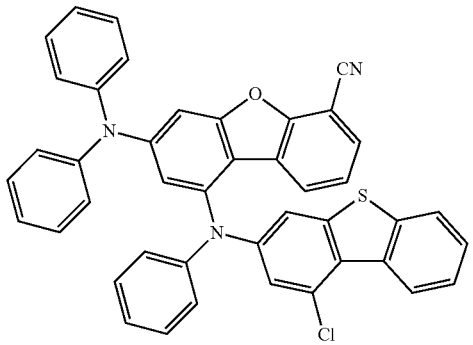
Sub1-88
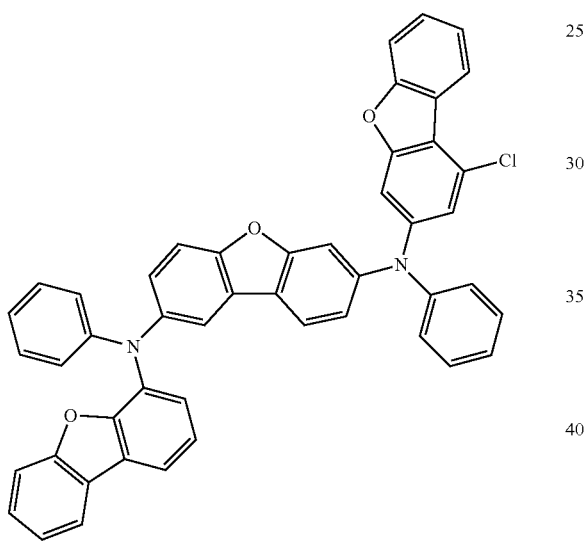
Sub1-91
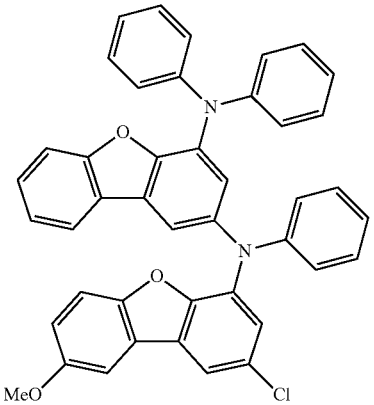
Sub1-92
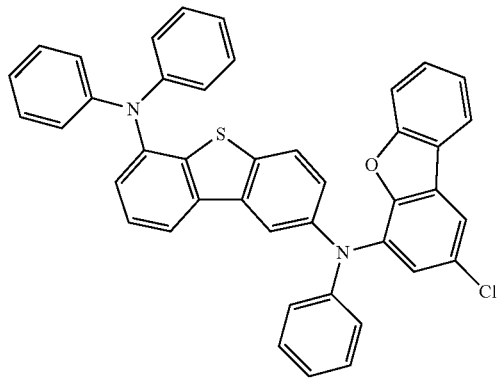
Sub1-89
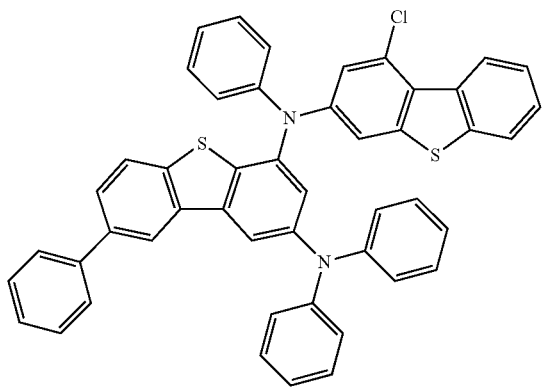
Sub1-93
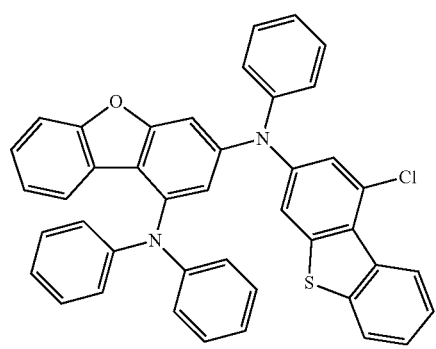

Sub1-94
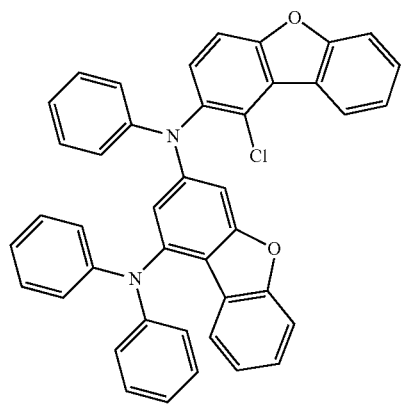
Sub1-95
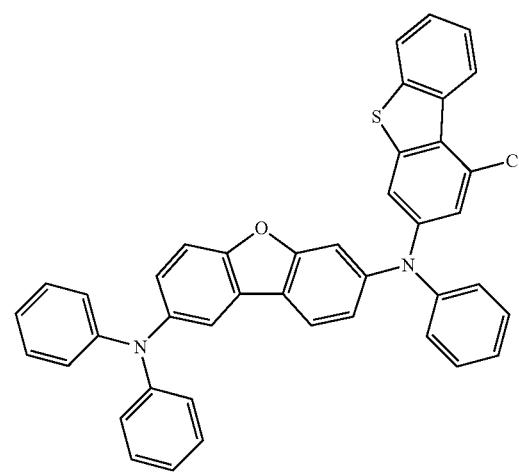
Sub1-96
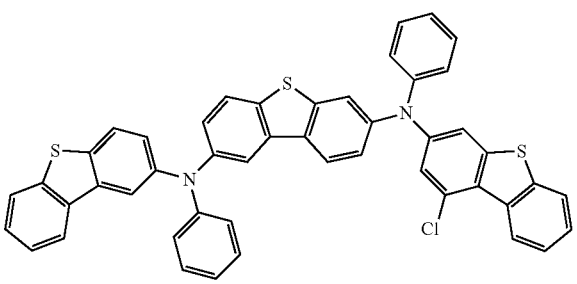
Sub1-97
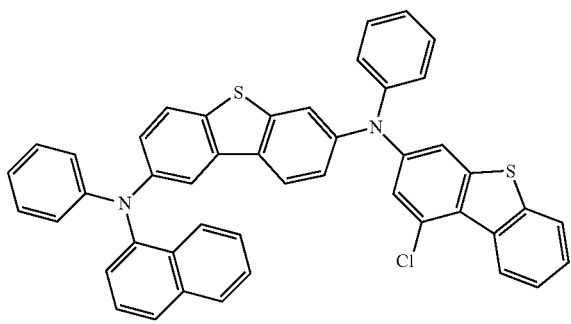
Sub1-98
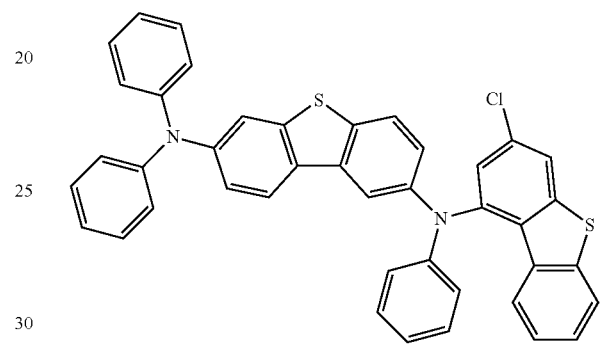
Sub1-99
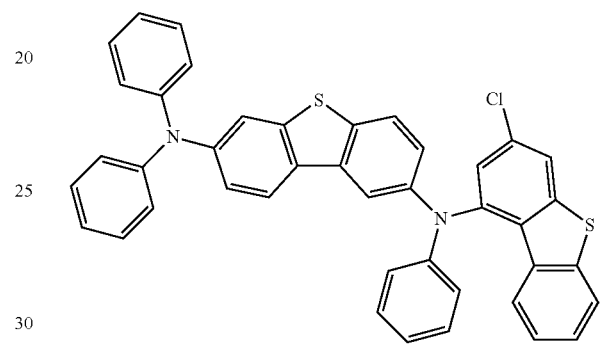
Sub1-100
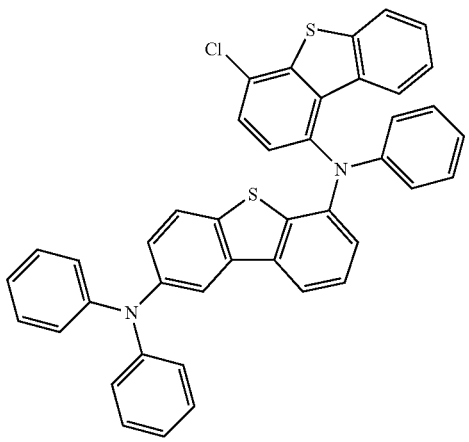
Sub1-101
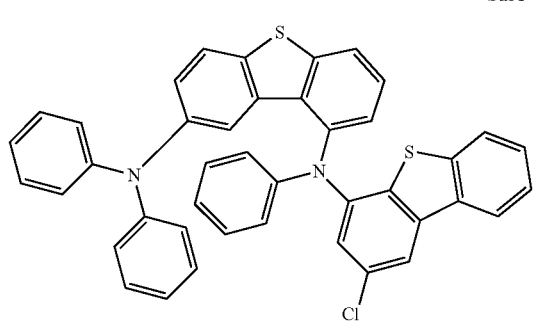

-continued
Sub1-102
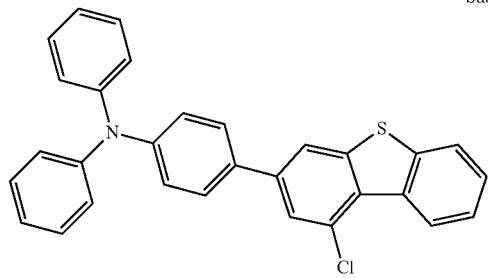
Sub1-103
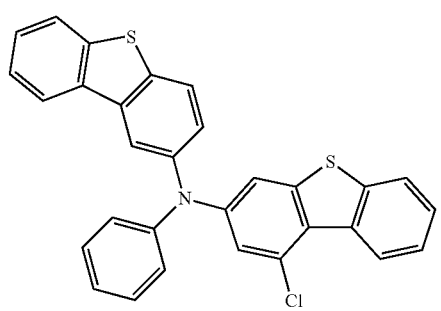
Sub1-104
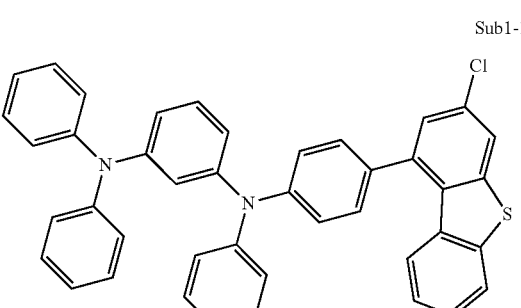
Sub1-105
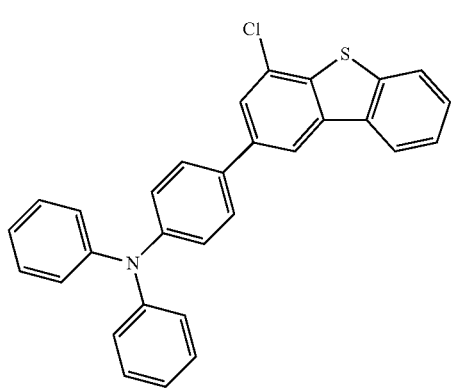
Sub1-106
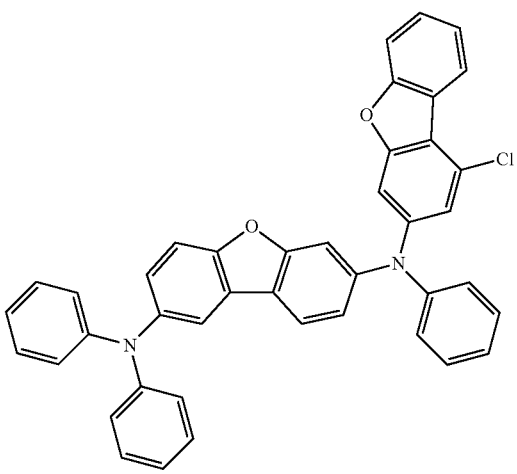
Sub1-107
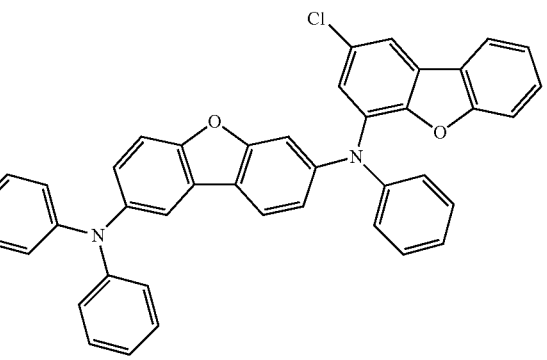
Sub1-108
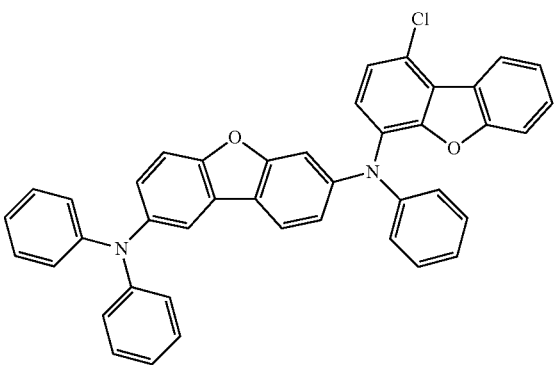
Sub1-109
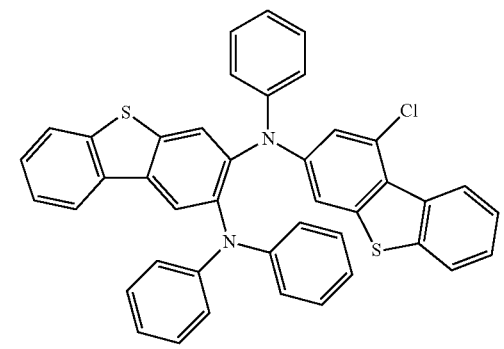

-continued

Sub1-110

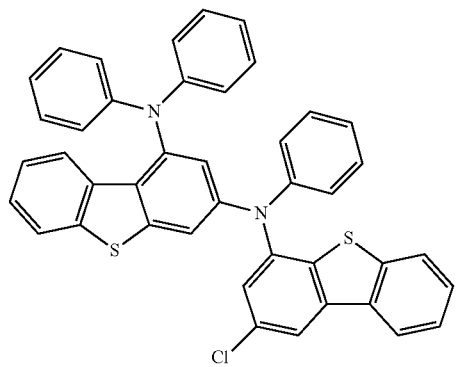

TABLE 1

| Compound | FD-MS | Compound | FD-MS |
|---|---|---|---|
| Sub 1-1 | m/z = 658.13 ($C_{42}H_{27}ClN_2S_2$ = 659.26) | Sub 1-2 | m/z = 658.13 ($C_{42}H_{27}ClN_2S_2$ = 659.26) |
| Sub 1-3 | m/z = 658.13 ($C_{42}H_{27}ClN_2S_2$ = 659.26) | Sub 1-4 | m/z = 658.13 ($C_{42}H_{27}ClN_2S_2$ = 659.26) |
| Sub 1-5 | m/z = 658.13 ($C_{42}H_{27}ClN_2S_2$ = 659.26) | Sub 1-6 | m/z = 658.13 ($C_{42}H_{27}ClN_2S_2$ = 659.26) |
| Sub 1-7 | m/z = 658.13 ($C_{42}H_{27}ClN_2S_2$ = 659.26) | Sub 1-8 | m/z = 658.13 ($C_{42}H_{27}ClN_2S_2$ = 659.26) |
| Sub 1-9 | m/z = 658.13 ($C_{42}H_{27}ClN_2S_2$ = 659.26) | Sub 1-10 | m/z = 658.13 ($C_{42}H_{27}ClN_2S_2$ = 659.26) |
| Sub 1-11 | m/z = 658.13 ($C_{42}H_{27}ClN_2S_2$ = 659.26) | Sub 1-12 | m/z = 658.13 ($C_{42}H_{27}ClN_2S_2$ = 659.26) |
| Sub 1-13 | m/z = 642.15 ($C_{42}H_{27}ClN_2OS$ = 643.26) | Sub 1-14 | m/z = 642.15 ($C_{42}H_{27}ClN_2OS$ = 643.26) |
| Sub 1-15 | m/z = 642.15 ($C_{42}H_{27}ClN_2OS$ = 643.26) | Sub 1-16 | m/z = 642.15 ($C_{42}H_{27}ClN_2OS$ = 643.26) |
| Sub 1-17 | m/z = 708.15 ($C_{46}H_{29}ClN_2S_2$ = 709.32) | Sub 1-18 | m/z = 708.15 ($C_{46}H_{29}ClN_2S_2$ = 709.32) |
| Sub 1-19 | m/z = 692.17 ($C_{46}H_{29}ClN_2OS$ = 693.26) | Sub 1-20 | m/z = 692.17 ($C_{46}H_{29}ClN_2OS$ = 693.26) |
| Sub 1-21 | m/z = 658.13 ($C_{42}H_{27}ClN_2S_2$ = 659.26) | Sub 1-22 | m/z = 658.13 ($C_{42}H_{27}ClN_2S_2$ = 659.26) |
| Sub 1-23 | m/z = 658.13 ($C_{42}H_{27}ClN_2S_2$ = 659.26) | Sub 1-24 | m/z = 658.13 ($C_{42}H_{27}ClN_2S_2$ = 659.26) |
| Sub 1-25 | m/z = 658.13 ($C_{42}H_{27}ClN_2S_2$ = 659.26) | Sub 1-26 | m/z = 658.13 ($C_{42}H_{27}ClN_2S_2$ = 659.26) |
| Sub 1-27 | m/z = 658.13 ($C_{42}H_{27}ClN_2S_2$ = 659.26) | Sub 1-28 | m/z = 658.13 ($C_{42}H_{27}ClN_2S_2$ = 659.26) |
| Sub 1-29 | m/z = 658.13 ($C_{42}H_{27}ClN_2S_2$ = 659.26) | Sub 1-30 | m/z = 642.15 ($C_{42}H_{27}ClN_2OS$ = 643.20) |
| Sub 1-31 | m/z = 658.13 ($C_{42}H_{27}ClN_2S_2$ = 659.26) | Sub 1-32 | m/z = 658.13 ($C_{42}H_{27}ClN_2S_2$ = 659.26) |
| Sub 1-33 | m/z = 658.13 ($C_{42}H_{27}ClN_2S_2$ = 659.26) | Sub 1-34 | m/z = 658.13 ($C_{42}H_{27}ClN_2S_2$ = 659.26) |
| Sub 1-35 | m/z = 658.13 ($C_{42}H_{27}ClN_2S_2$ = 659.26) | Sub 1-36 | m/z = 658.13 ($C_{42}H_{27}ClN_2S_2$ = 659.26) |
| Sub 1-37 | m/z = 708.15 ($C_{46}H_{29}ClN_2S_2$ = 709.32) | Sub 1-38 | m/z = 708.15 ($C_{46}H_{29}ClN_2S_2$ = 709.32) |
| Sub 1-39 | m/z = 642.15 ($C_{42}H_{27}ClN_2OS$ = 643.26) | Sub 1-40 | m/z = 642.15 ($C_{42}H_{27}ClN_2OS$ = 643.26) |
| Sub 1-41 | m/z = 734.16 ($C_{48}H_{31}ClN_2S_2$ = 735.36) | Sub 1-42 | m/z = 734.16 ($C_{48}H_{31}ClN_2S_2$ = 735.36) |
| Sub 1-43 | m/z = 734.16 ($C_{48}H_{31}ClN_2S_2$ = 735.36) | Sub 1-44 | m/z = 734.16 ($C_{48}H_{31}ClN_2S_2$ = 735.36) |
| Sub 1-45 | m/z = 658.13 ($C_{42}H_{27}ClN_2S_2$ = 659.26) | Sub 1-46 | m/z = 658.13 ($C_{42}H_{27}ClN_2S_2$ = 659.26) |
| Sub 1-47 | m/z = 734.16 ($C_{48}H_{31}ClN_2S_2$ = 735.36) | Sub 1-48 | m/z = 658.13 ($C_{42}H_{27}ClN_2S_2$ = 659.26) |
| Sub 1-49 | m/z = 642.15 ($C_{42}H_{27}ClN_2OS$ = 643.2) | Sub 1-50 | m/z = 718.18 ($C_{48}H_{31}ClN_2OS$ = 719.30) |
| Sub 1-51 | m/z = 626.18 ($C_{42}H_{27}ClN_2O_2$ = 627.14) | Sub 1-52 | m/z = 702.21 ($C_{48}H_{31}ClN_2O_2$ = 703.24) |
| Sub 1-53 | m/z = 658.13 ($C_{42}H_{27}ClN_2S_2$ = 659.26) | Sub 1-54 | m/z = 658.13 ($C_{42}H_{27}ClN_2S_2$ = 659.26) |
| Sub 1-55 | m/z = 642.15 ($C_{42}H_{27}ClN_2OS$ = 643.20) | Sub 1-56 | m/z = 626.18 ($C_{42}H_{27}ClN_2O_2$ = 627.14) |
| Sub 1-57 | m/z = 642.15 ($C_{42}H_{27}ClN_2OS$ = 643.20) | Sub 1-58 | m/z = 734.16 ($C_{48}H_{31}ClN_2S_2$ = 735.36) |
| Sub 1-59 | m/z = 734.16 ($C_{48}H_{31}ClN_2S_2$ = 735.36) | Sub 1-60 | m/z = 684.15 ($C_{44}H_{29}ClN_2S_2$ = 685.30) |
| Sub 1-61 | m/z = 672.15 ($C_{43}H_{29}ClN_2S_2$ = 673.29) | Sub 1-62 | m/z = 676.12 ($C_{42}H_{28}ClFN_2S_2$ = 677.25) |
| Sub 1-63 | m/z = 626.18 ($C_{42}H_{27}ClN_2O_2$ = 627.14) | Sub 1-64 | m/z = 734.16 ($C_{48}H_{31}ClN_2S_2$ = 735.36) |
| Sub 1-65 | m/z = 764.12 ($C_{48}H_{29}ClN_2S_3$ = 765.40) | Sub 1-66 | m/z = 896.21 ($C_{61}H_{37}ClN_2S_2$ = 897.55) |
| Sub 1-67 | m/z = 748.14 ($C_{48}H_{29}ClN_2OS_2$ = 749.34) | Sub 1-68 | m/z = 683.13 ($C_{43}H_{26}ClN_3S_2$ = 684.27) |
| Sub 1-69 | m/z = 825.20 ($C_{54}H_{36}ClN_3S_2$ = 826.47) | Sub 1-70 | m/z = 825.20 ($C_{54}H_{36}ClN_3S_2$ = 826.47) |
| Sub 1-71 | m/z = 662.16 ($C_{42}H_{23}D_4ClN_2S_2$ = 663.29) | Sub 1-72 | m/z = 748.14 ($C_{48}H_{29}ClN_2OS_2$ = 749.34) |
| Sub 1-73 | m/z = 659.13 ($C_{41}H_{26}ClN_3S_2$ = 660.25) | Sub 1-74 | m/z = 552.14 ($C_{36}H_{25}ClN_2S$ = 553.12) |
| Sub 1-75 | m/z = 552.14 ($C_{36}H_{25}ClN_2S$ = 553.12) | Sub 1-76 | m/z = 552.14 ($C_{36}H_{25}ClN_2S$ = 553.12) |
| Sub 1-77 | m/z = 586.18 ($C_{40}H_{27}ClN_2O$ = 587.12) | Sub 1-78 | m/z = 668.21 ($C_{45}H_{33}ClN_2S$ = 669.28) |
| Sub 1-79 | m/z = 642.15 ($C_{42}H_{27}ClN_2OS$ = 643.20) | Sub 1-80 | m/z = 642.15 ($C_{42}H_{27}ClN_2OS$ = 643.20) |
| Sub 1-81 | m/z = 656.17 ($C_{43}H_{29}ClN_2OS$ = 657.23) | Sub 1-82 | m/z = 642.15 ($C_{42}H_{27}ClN_2OS$ = 643.20) |
| Sub 1-83 | m/z = 626.18 ($C_{42}H_{27}ClN_2O_2$ = 627.14) | Sub 1-84 | m/z = 626.18 ($C_{42}H_{27}ClN_2O_2$ = 627.14) |
| Sub 1-85 | m/z = 748.14 ($C_{48}H_{29}ClN_2OS_2$ = 749.34) | Sub 1-86 | m/z = 732.16 ($C_{48}H_{29}ClN_2O_2S$ = 733.28) |
| Sub 1-87 | m/z = 898.22 ($C_{61}H_{39}ClN_2S_2$ = 899.57) | Sub 1-88 | m/z = 716.19 ($C_{48}H_{29}ClN_2O_3$ = 717.22) |
| Sub 1-89 | m/z = 734.16 ($C_{48}H_{31}ClN_2S_2$ = 735.36) | Sub 1-90 | m/z = 667.15 ($C_{43}H_{26}ClN_3OS$ = 668.21) |
| Sub 1-91 | m/z = 656.19 ($C_{43}H_{29}ClN_2O_3$ = 657.17) | Sub 1-92 | m/z = 642.15 ($C_{42}H_{27}ClN_2OS$ = 643.20) |
| Sub 1-93 | m/z = 642.15 ($C_{42}H_{27}ClN_2OS$ = 643.20) | Sub 1-94 | m/z = 626.18 ($C_{42}H_{27}ClN_2O_2$ = 627.14) |
| Sub 1-95 | m/z = 642.15 ($C_{42}H_{27}ClN_2OS$ = 643.20) | Sub 1-96 | m/z = 764.12 ($C_{48}H_{29}ClN_2S_3$ = 765.40) |
| Sub 1-97 | m/z = 708.15 ($C_{46}H_{29}ClN_2S_2$ = 709.32) | Sub 1-98 | m/z = 672.15 ($C_{43}H_{29}ClN_2S_2$ = 673.29) |
| Sub 1-99 | m/z = 658.13 ($C_{42}H_{27}ClN_2S_2$ = 659.26) | Sub 1-100 | m/z = 658.13 ($C_{42}H_{27}ClN_2S_2$ = 659.26) |
| Sub 1-101 | m/z = 658.13 ($C_{42}H_{27}ClN_2S_2$ = 659.26) | Sub 1-102 | m/z = 461.10 ($C_{30}H_{20}ClNS$ = 462.01) |
| Sub 1-103 | m/z = 491.06 ($C_{30}H_{18}ClNS_2$ = 492.05) | Sub 1-104 | m/z = 628.17 ($C_{42}H_{29}ClN_2S$ = 629.22) |
| Sub 1-105 | m/z = 461.10 ($C_{30}H_{20}ClNS$ = 462.01) | Sub 1-106 | m/z = 626.18 ($C_{42}H_{27}ClN_2O_2$ = 627.14) |
| Sub 1-107 | m/z = 626.18 ($C_{42}H_{27}ClN_2O_2$ = 627.14) | Sub 1-108 | m/z = 626.18 ($C_{42}H_{27}ClN_2O_2$ = 627.14) |
| Sub 1-109 | m/z = 658.13 ($C_{42}H_{27}ClN_2S_2$ = 659.26) | Sub 1-110 | m/z = 658.13 ($C_{42}H_{27}ClN_2S_2$ = 659.26) |

II. Synthesis of Sub 2

Sub 2 of Reaction Formula 1 may be synthesized according to, but not limited to, Reaction Formula 5 below.

<Reaction Formula 5>

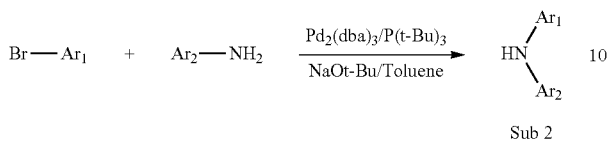

Synthesis examples of specific compounds belong to Sub 2 are as follows.

1. Synthesis Example of Sub 2-1

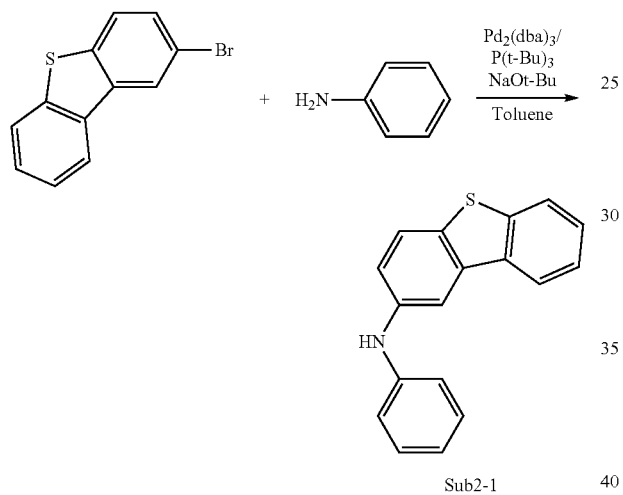

Aniline (14.84 g, 159.30 mmol), Pd$_2$(dba)$_3$ (3.98 g, 4.34 mmol), 50% P(t-Bu)$_3$ (5.6 ml, 11.59 mmol), NaOt-Bu (41.76 g, 434.47 mmol), and toluene (760 ml) were added to a starting material 2-bromodibenzo[b,d]thiophene (38.11 g, 144.82 mmol), followed by stirring at 80° C. At the completion of the reaction, the reaction solution was extracted with CH$_2$Cl$_2$ and water, and then an organic layer was dried with MgSO$_4$ and concentrated. Afterwards, a silica gel column method and recrystallization were performed to a produced compound, thereby producing a product Sub2-1 30.7 g (yield: 77%).

2. Synthesis Example of Sub 2-29

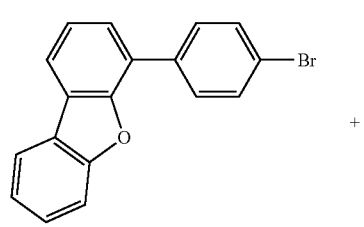

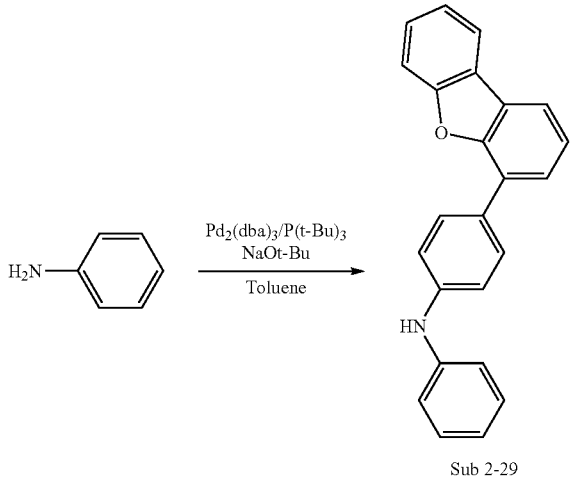

Aniline (5.8 g, 61.8 mmol), Pd$_2$(dba)$_3$ (1.7 g, 1.85 mmol), 50% P(t-Bu)$_3$ (1.5 ml, 3.71 mmol), NaOt-Bu (17.8 g, 185.6 mmol), and toluene (200 ml) were added to a starting material 4-(4-bromophenyl)dibenzo[b,d]furan (20 g, 61.8 mmol), and a product Sub2-29 17 g (yield: 82%) was produced by the above-described Sub 2-1 synthesis method.

3. Synthesis Example of Sub 2-34

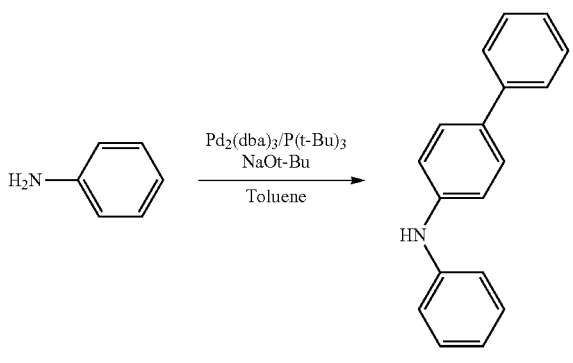

Aniline (10.39 g, 111.60 mmol), Pd$_2$(dba)$_3$ (2.79 g, 3.04 mmol), 50% P(t-Bu)$_3$ (4.0 ml, 8.12 mmol), NaOt-Bu (29.25 g, 304.38 mmol), and toluene (710 ml) were added to a starting material 4-bromo-1,1'-biphenyl (23.65 g, 101.46 mmol), and a product Sub 2-34 20.66 g (yield: 83%) was produced by the above-described Sub 2-1 synthesis method.

Compounds belonging to Sub 2 may be, but are not limited to, the following compounds. Table 2 represents FD-MS values of the compounds belonging to Sub 2.

Sub2-1
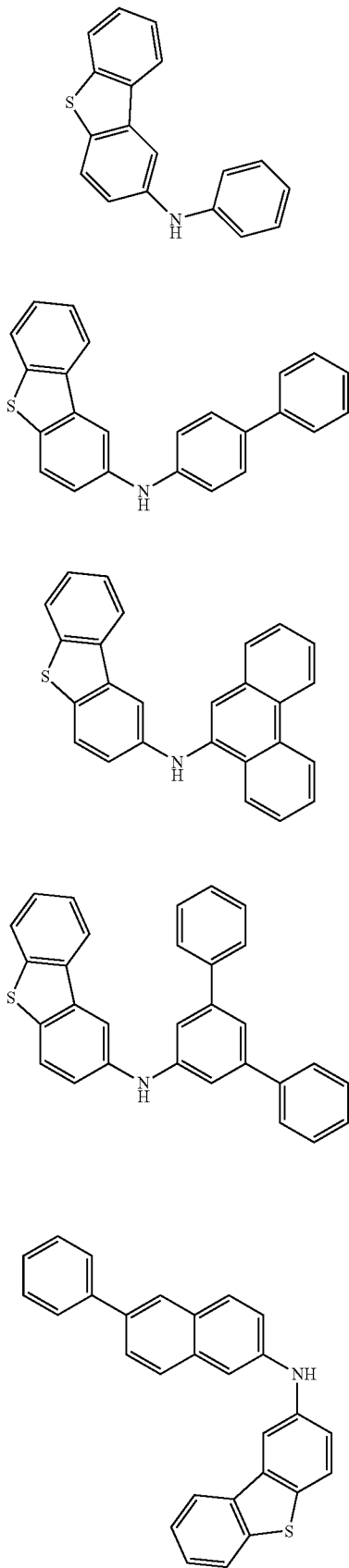
Sub2-6
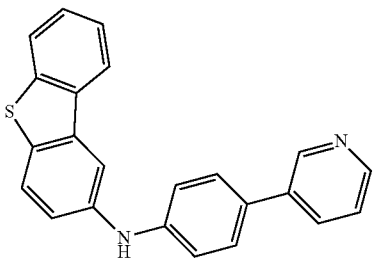
Sub2-7
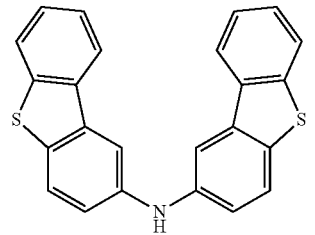
Sub2-8
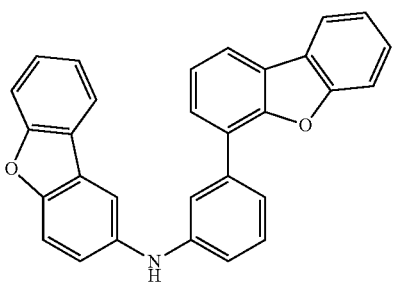
Sub2-9
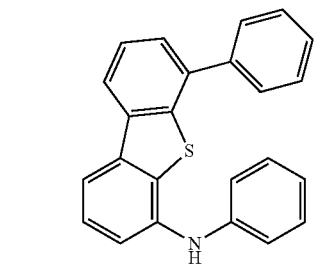
Sub2-10
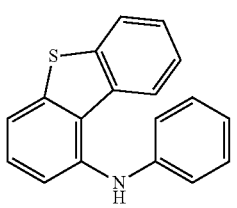
Sub2-11
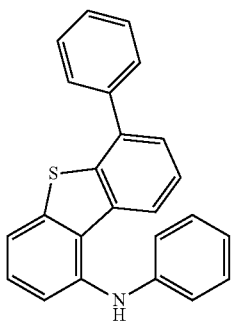

Sub2-12
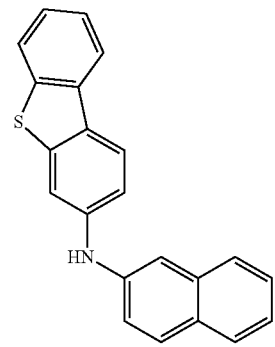
Sub2-13
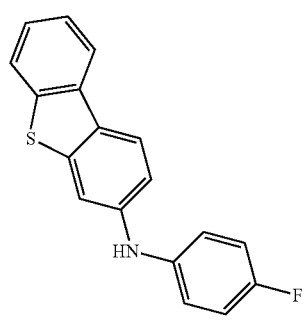
Sub2-14
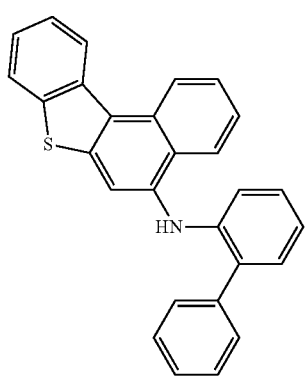
Sub2-15
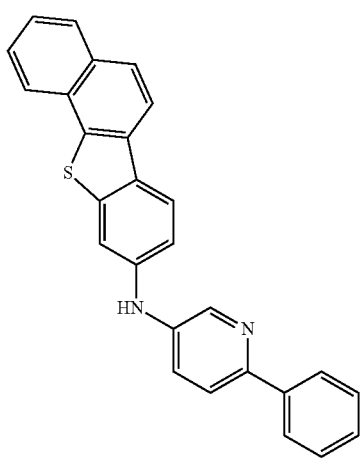
Sub2-16
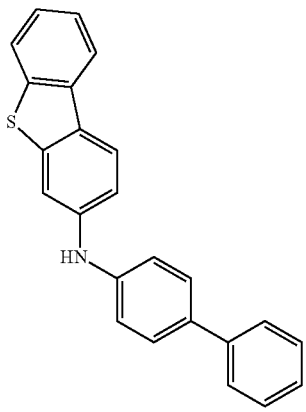
Sub2-17
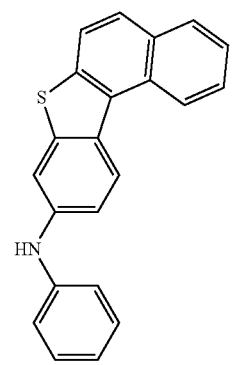
Sub2-18
Sub2-19

Sub2-20
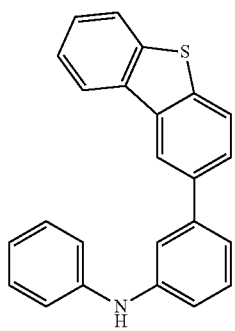
Sub2-21
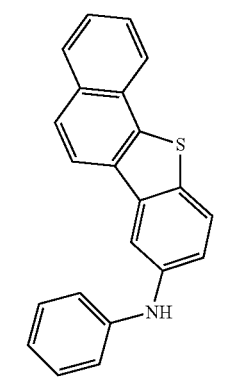
Sub2-22
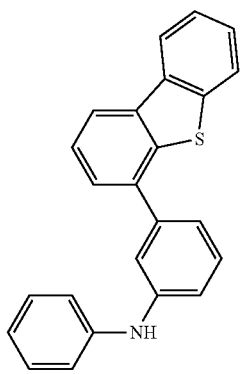
Sub2-23
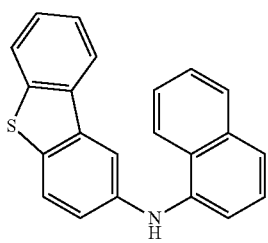
Sub2-24
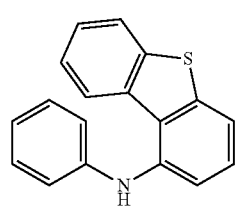
Sub2-25
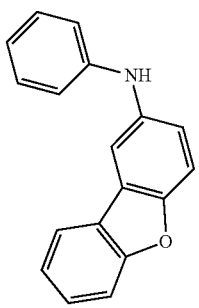
Sub2-26
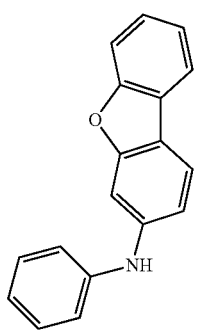
Sub2-27
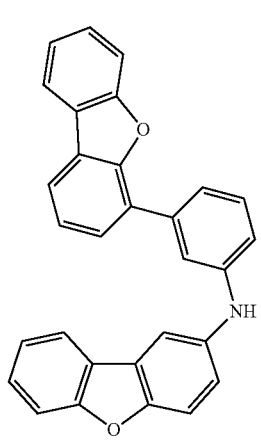
Sub2-28
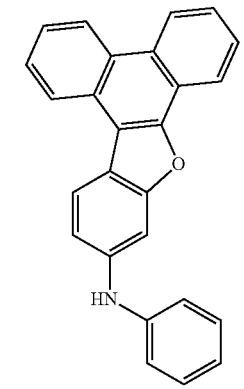

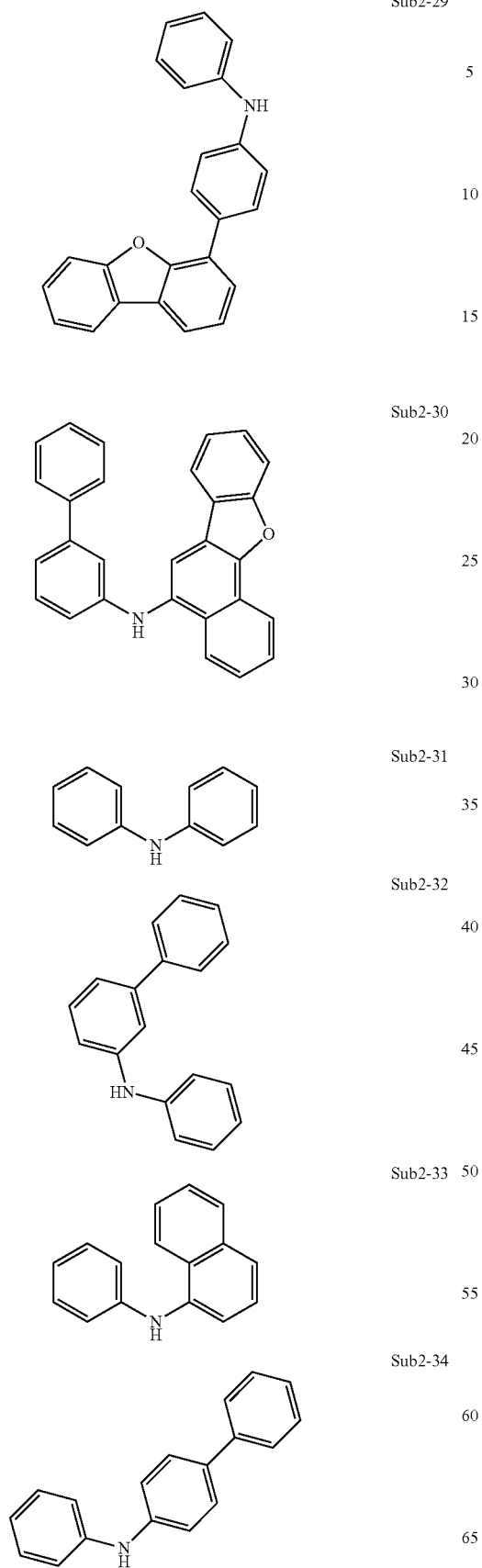
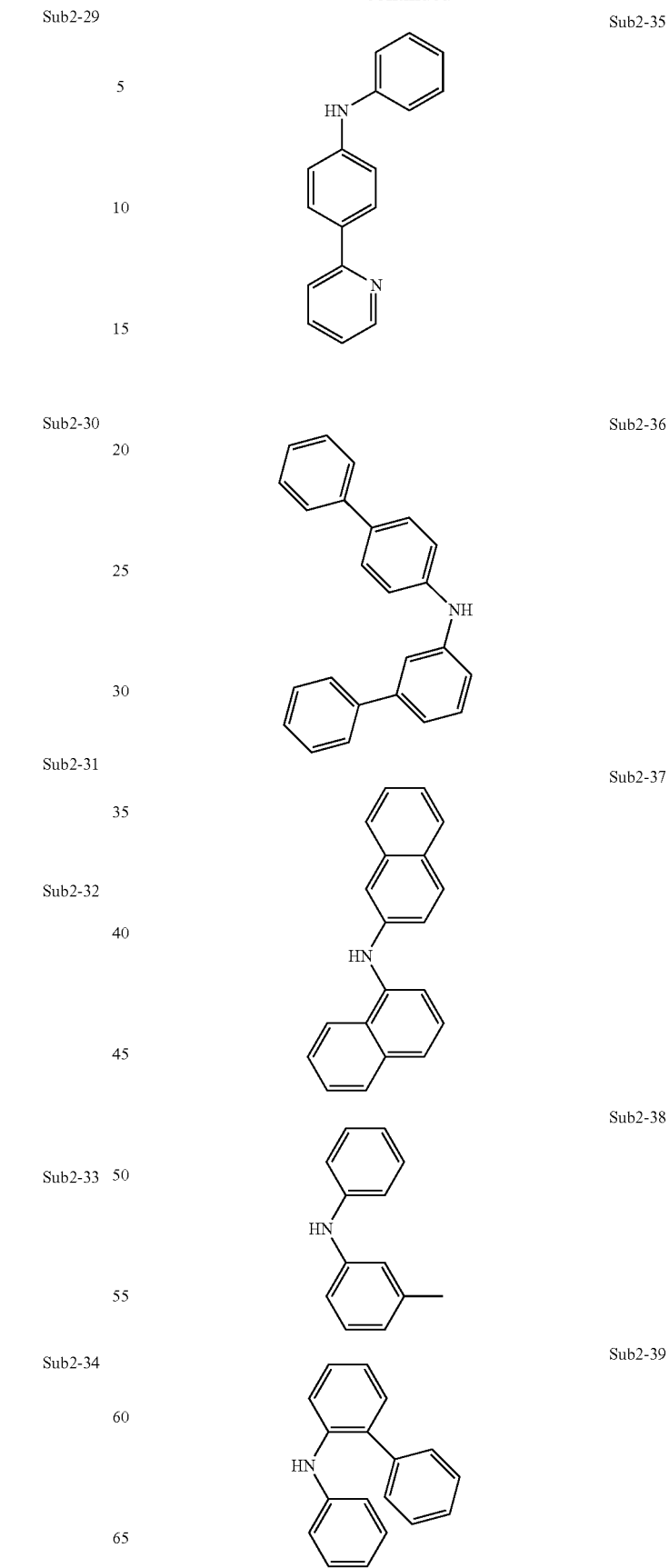

Sub2-40
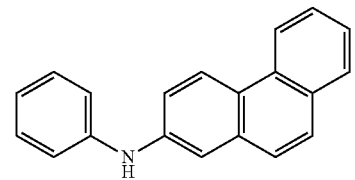
Sub2-41
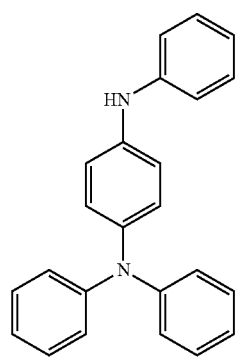
Sub2-42
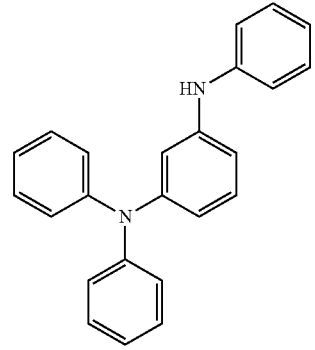
Sub2-43
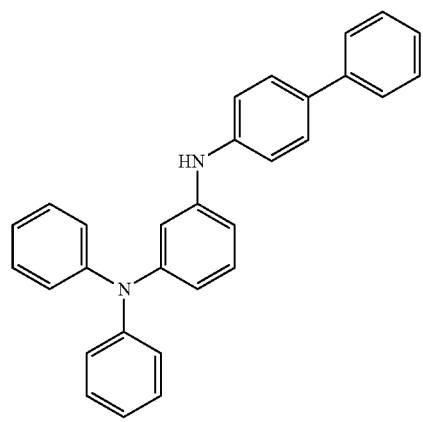
Sub2-44
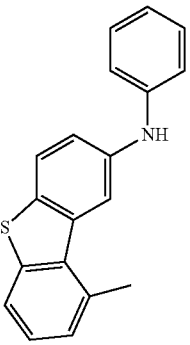
Sub2-45
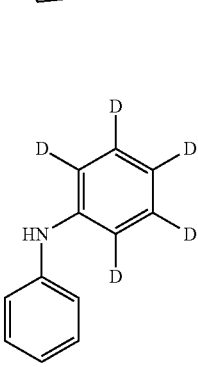
Sub2-46
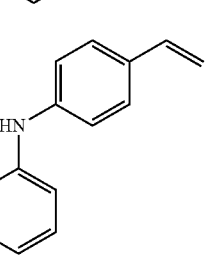
Sub2-47
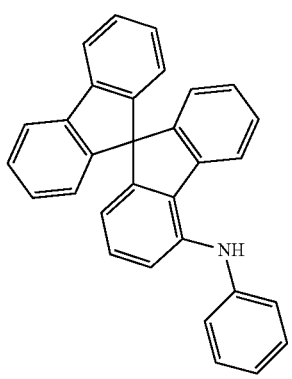
Sub2-48
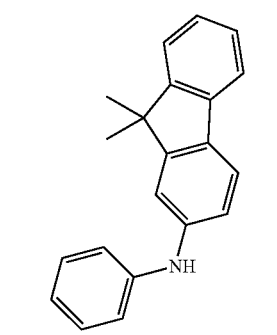

Sub2-49

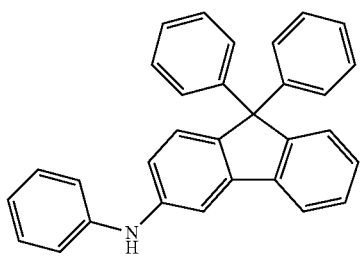

Sub2-51

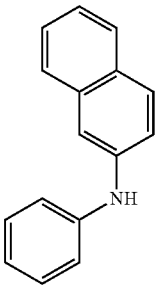

Sub2-50

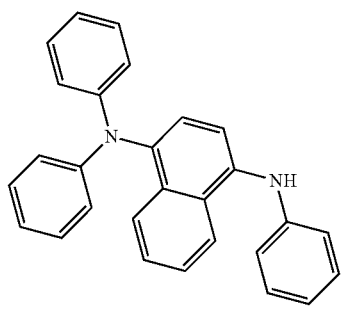

Sub2-52

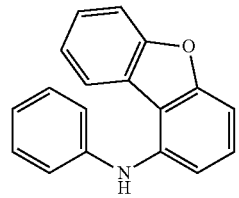

TABLE 2

| Compound | FD-MS | Compound | FD-MS |
| --- | --- | --- | --- |
| Sub 2-1 | m/z = 275.08 ($C_{18}H_{13}NS$ = 275.37) | Sub 2-2 | m/z = 351.11 ($C_{24}H_{17}NS$ = 351.47) |
| Sub 2-3 | m/z = 375.11 ($C_{26}H_{17}NS$ = 375.49) | Sub 2-4 | m/z = 427.14 ($C_{30}H_{21}NS$ = 427.57) |
| Sub 2-5 | m/z = 401.12 ($C_{28}H_{19}NS$ = 401.53) | Sub 2-6 | m/z = 352.10 ($C_{23}H_{16}N_2S$ = 352.46) |
| Sub 2-7 | m/z = 381.06 ($C_{24}H_{15}NS_2$ = 381.51) | Sub 2-8 | m/z = 457.10 ($C_{30}H_{19}N_2S$ = 457.61) |
| Sub 2-9 | m/z = 351.11 ($C_{24}H_{17}NS$ = 351.47) | Sub 2-10 | m/z = 275.08 ($C_{18}H_{13}NS$ = 275.37) |
| Sub 2-11 | m/z = 351.11 ($C_{24}H_{17}NS$ = 351.47) | Sub 2-12 | m/z = 325.09 ($C_{22}H_{15}NS$ = 325.43) |
| Sub 2-13 | m/z = 293.07 ($C_{18}H_{12}FNS$ = 293.36) | Sub 2-14 | m/z = 401.12 ($C_{28}H_{19}NS$ = 401.53) |
| Sub 2-15 | m/z = 402.12 ($C_{27}H_{18}N_2S$ = 402.52) | Sub 2-16 | m/z = 351.11 ($C_{24}H_{17}NS$ = 351.47) |
| Sub 2-17 | m/z = 275.08 ($C_{18}H_{13}NS$ = 275.37) | Sub 2-18 | m/z = 289.09 ($C_{19}H_{15}NS$ = 289.40) |
| Sub 2-19 | m/z = 325.09 ($C_{22}H_{15}NS$ = 325.43) | Sub 2-20 | m/z = 351.11 ($C_{24}H_{17}NS$ = 351.47) |
| Sub 2-21 | m/z = 325.09 ($C_{22}H_{15}NS$ = 325.43) | Sub 2-22 | m/z = 351.11 ($C_{24}H_{17}NS$ = 351.47) |
| Sub 2-23 | m/z = 325.09 ($C_{22}H_{15}NS$ = 325.43) | Sub 2-24 | m/z = 275.08 ($C_{18}H_{13}NS$ = 275.37) |
| Sub 2-25 | m/z = 259.10 ($C_{18}H_{13}NO$ = 259.31) | Sub 2-26 | m/z = 259.10 ($C_{18}H_{13}NO$ = 259.31) |
| Sub 2-27 | m/z = 425.14 ($C_{30}H_{19}NO_2$ = 425.49) | Sub 2-28 | m/z = 359.13 ($C_{26}H_{17}NO$ = 359.43) |
| Sub 2-29 | m/z = 335.13 ($C_{24}H_{17}NO$ = 335.41) | Sub 2-30 | m/z = 385.15 ($C_{28}H_{49}N_2O$ = 385.47) |
| Sub 2-31 | m/z = 169.09 ($C_{312}H_{11}N$ = 169.23) | Sub 2-32 | m/z = 245.12 ($C_{18}H_{15}N$ = 245.33) |
| Sub 2-33 | m/z = 219.10 ($C_{16}H_{13}N$ = 219.29) | Sub 2-34 | m/z = 245.12 ($C_{18}H_{15}N$ = 245.33) |
| Sub 2-35 | m/z = 246.12 ($C_{17}H_{14}N_2$ = 246.31) | Sub 2-36 | m/z = 321.15 ($C_{24}H_{19}N$ = 321.42) |
| Sub 2-37 | m/z = 269.12 ($C_{20}H_{15}N_3$ = 269.35) | Sub 2-38 | m/z = 183.10 ($C_{13}H_{13}N$ = 183.25) |
| Sub 2-39 | m/z = 245.12 ($C_{18}H_{15}N$ = 245.33) | Sub 2-40 | m/z = 269.12 ($C_{20}H_{15}N_2S$ = 269.35) |
| Sub 2-41 | m/z = 336.16 ($C_{24}H_{20}N_2$ = 336.44) | Sub 2-42 | m/z = 336.16 ($C_{24}H_{20}N_2$ = 336.44) |
| Sub 2-43 | m/z = 412.19 ($C_{30}H_{24}N_2$ = 412.54) | Sub 2-44 | m/z = 289.09 ($C_{19}H_{15}NS$ = 289.40) |
| Sub 2-45 | m/z = 174.12 ($C_{12}H_6D_5N$ = 174.26) | Sub 2-46 | m/z = 195.10 ($C_{14}H_{13}N$ = 195.27) |
| Sub 2-47 | m/z = 407.17 ($C_{31}H_{21}N$ = 407.52) | Sub 2-48 | m/z = 285.15 ($C_{24}H_{19}N$ = 285.39) |
| Sub 2-49 | m/z = 409.18 ($C_{31}H_{23}N$ = 409.53) | Sub 2-50 | m/z = 386.18 ($C_{28}H_{22}N_2$ = 386.50) |
| Sub 2-51 | m/z = 219.10 ($C_{16}H_{13}N$ = 219.29) | Sub 2-52 | m/z = 259.10 ($C_{18}H_{13}NO$ = 259.31) |

III. Synthesis Examples of Final Products

1. Synthesis Example of P-4

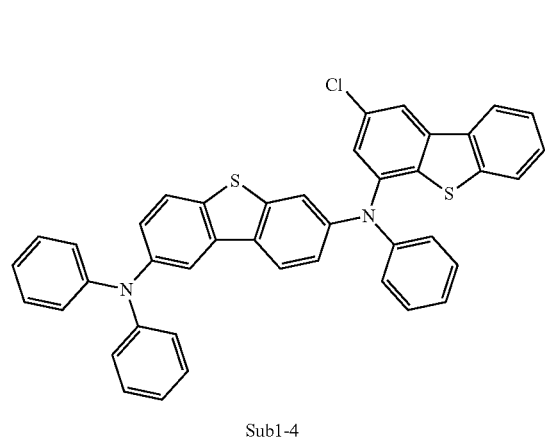
Sub1-4

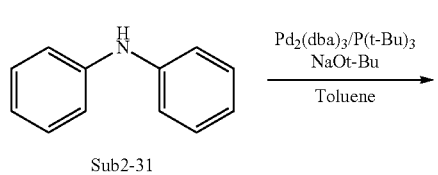
Sub2-31

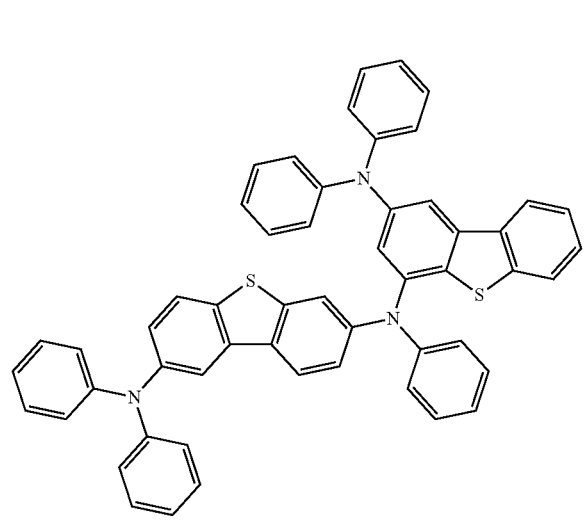
P-4

After Sub 1-4 (12.1 g, 18.4 mmol) was dissolved with toluene (40 ml) in a round bottom flask, Sub2-31 (3.1 g, 18.4 mmol), Pd$_2$(dba)$_3$ (0.5 g, 0.6 mmol), 50% P(t-Bu)$_3$ (0.45 ml, 1.1 mmol), and NaOt-Bu (3.53 g, 36.7 mmol) were added, followed by stirring at 110° C. At the completion of the reaction, the reaction solution was extracted with CH$_2$Cl$_2$ and water, and then an organic layer was dried with MgSO$_4$ and concentrated. A silica gel column method and sublimation purification were performed to a produced compound, thereby producing a product P-4 10.9 g (yield: 71%).

2. Synthesis Example of P-14

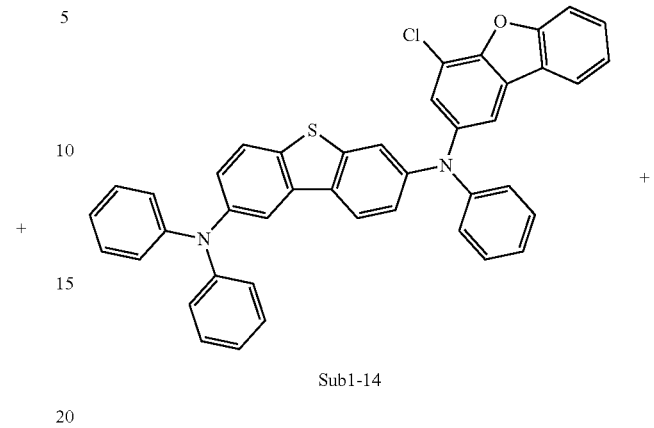
Sub1-14

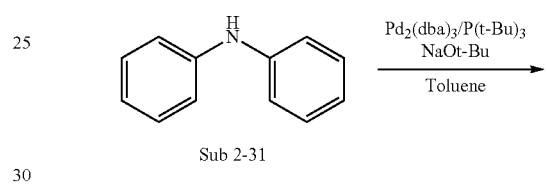
Sub 2-31

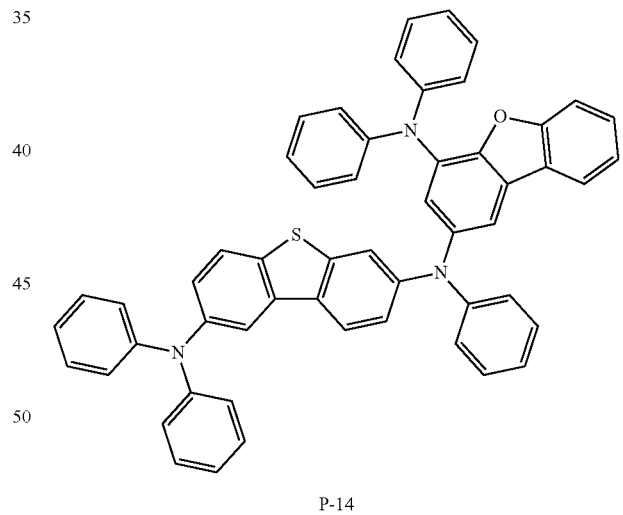
P-14

After Sub 1-14 (5.0 g, 7.8 mmol) was dissolved with toluene (20 ml) in a round bottom flask, Sub 2-31 (1.3 g, 7.8 mmol), Pd$_2$(dba)$_3$ (0.2 g, 0.2 mmol), 50% P(t-Bu)$_3$ (0.2 ml, 0.5 mmol), and NaOt-Bu (1.5 g, 15.5 mmol) were added, followed by stirring at 120° C. At the completion of the reaction, the reaction solution was extracted with CH$_2$Cl$_2$ and water, and then an organic layer was dried with MgSO$_4$ and concentrated. A silica gel column method and sublimation purification were performed to a produced compound, thereby producing a product P-14 4.5 g (yield: 75%).

3. Synthesis Example of P-40

4. Synthesis Example of P-65

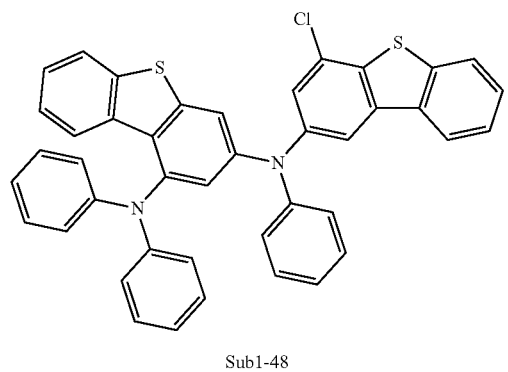
Sub1-48

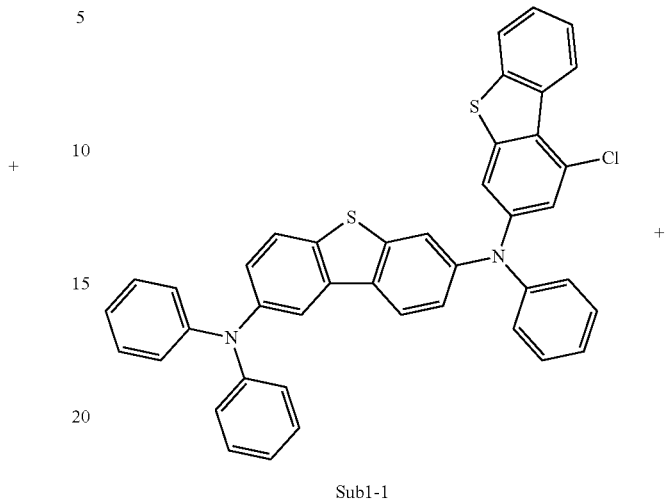
Sub1-1

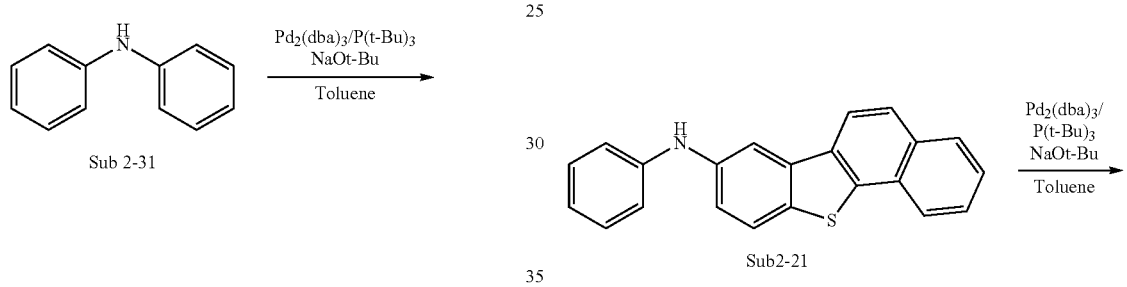
Sub 2-31 → Sub2-21

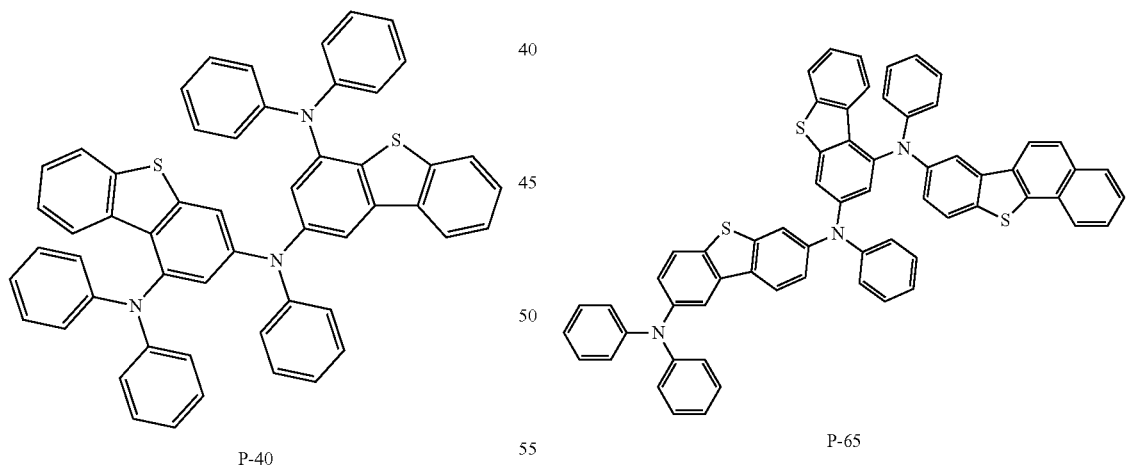
P-40 / P-65

After Sub 1-48 (10.0 g, 13.3 mmol) was dissolved with toluene (30 ml) in a round bottom flask, Sub 2-31 (2.3 g, 13.3 mmol), Pd$_2$(dba)$_3$ (0.37 g, 0.4 mmol), 50% P(t-Bu)$_3$ (0.3 ml, 0.8 mmol), and NaOt-Bu (2.6 g, 26.7 mmol) were added, followed by stirring at 110° C. At the completion of the reaction, the reaction solution was extracted with CH$_2$Cl$_2$ and water, and then an organic layer was dried with MgSO$_4$ and concentrated. A silica gel column method and sublimation purification were performed to a produced compound, thereby producing a product P-40 7.7 g (yield: 73%).

After Sub 1-1 (4.9 g, 15.2 mmol) was dissolved with toluene (30 ml) in a round bottom flask, Sub2-21 (10 g, 15.2 mmol), Pd$_2$(dba)$_3$ (0.4 g, 0.5 mmol), 50% P(t-Bu)$_3$ (0.37 ml, 0.9 mmol), and NaOt-Bu (2.2 g, 22.8 mmol) were added, followed by stirring at 110° C. At the completion of the reaction, the reaction solution was extracted with CH$_2$Cl$_2$ and water, and then an organic layer was dried with MgSO$_4$ and concentrated. A silica gel column method and sublimation purification were performed to a produced compound, thereby producing a product P-65 10.8 g (yield: 75%).

5. Synthesis Example of P-67

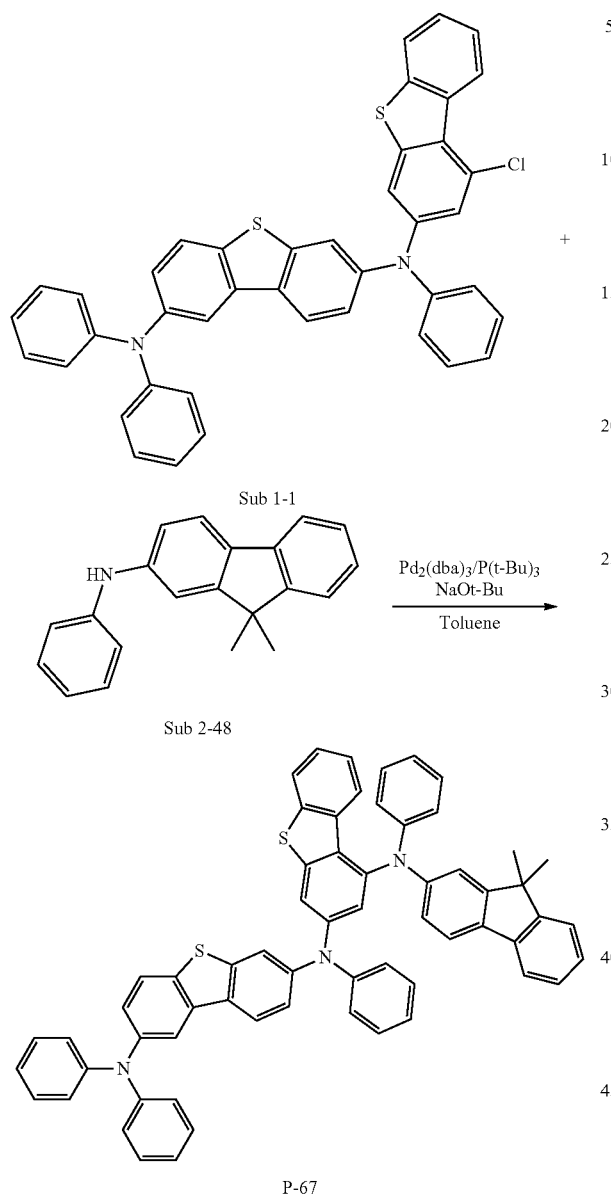

After Sub 1-1 (6.0 g, 9.1 mmol) was dissolved with toluene (20 ml) in a round bottom flask, Sub 2-48 (2.6 g, 9.1 mmol), $Pd_2(dba)_3$ (0.25 g, 0.3 mmol), 50% $P(t-Bu)_3$ (0.22 ml, 0.5 mmol), and NaOt-Bu (1.7 g, 18.2 mmol) were added, followed by stirring at 110° C. At the completion of the reaction, the reaction solution was extracted with $CH_2Cl_2$ and water, and then an organic layer was dried with $MgSO_4$ and concentrated. A silica gel column method and sublimation purification were performed to a produced compound, thereby producing a product P-67 5.9 g (yield: 71%).

6. Synthesis Example of P-91

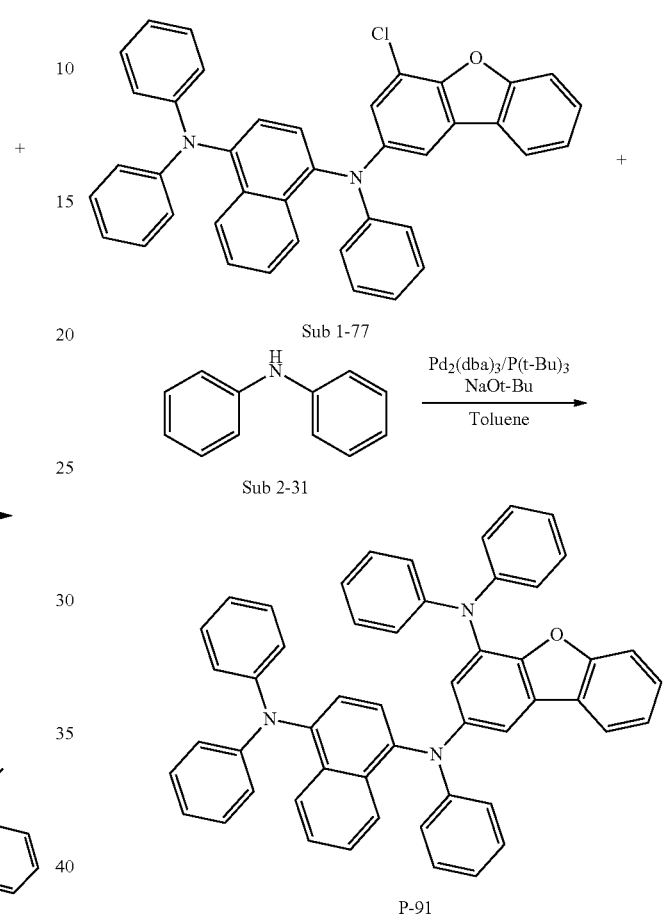

After Sub 1-77 (7.0 g, 11.9 mmol) was dissolved with toluene (30 ml) in a round bottom flask, Sub 2-31 (2.0 g, 11.9 mmol), $Pd_2(dba)_3$ (0.3 g, 0.4 mmol), 50% $P(t-Bu)_3$ (0.3 ml, 0.7 mmol), and NaOt-Bu (2.3 g, 23.8 mmol) were added, followed by stirring at 110° C. At the completion of the reaction, the reaction solution was extracted with $CH_2Cl_2$ and water, and then an organic layer was dried with $MgSO_4$ and concentrated. A silica gel column method and sublimation purification were performed to a produced compound, thereby producing a product P-91 11.9 g (yield: 70%).

In addition, the FD-MS values of the compounds P-1 to P-112 according to the present disclosure fabricated according to the above-described synthesis examples are represented in Table

TABLE 3

| Compound | FD-MS | Compound | FD-MS |
| --- | --- | --- | --- |
| P-1 | m/z = 791.24 ($C_{54}H_{37}N_3S_2$ = 792.03) | P-2 | m/z = 791.24 ($C_{54}H_{37}N_3S_2$ = 792.03) |
| P-3 | m/z = 791.24 ($C_{54}H_{37}N_3S_2$ = 792.03) | P-4 | m/z = 791.24 ($C_{54}H_{37}N_3S_2$ = 792.03) |
| P-5 | m/z = 791.24 ($C_{54}H_{37}N_3S_2$ = 792.03) | P-6 | m/z = 791.24 ($C_{54}H_{37}N_3S_2$ = 792.03) |
| P-7 | m/z = 791.24 ($C_{54}H_{37}N_3S_2$ = 792.03) | P-8 | m/z = 791.24 ($C_{54}H_{37}N_3S_2$ = 792.03) |
| P-9 | m/z = 791.24 ($C_{54}H_{37}N_3S_2$ = 792.03) | P-10 | m/z = 791.24 ($C_{54}H_{37}N_3S_2$ = 792.03) |
| P-11 | m/z = 791.24 ($C_{54}H_{37}N_3S_2$ = 792.03) | P-12 | m/z = 791.24 ($C_{54}H_{37}N_3S_2$ = 792.03) |

TABLE 3-continued

| Compound | FD-MS | Compound | FD-MS |
|---|---|---|---|
| P-13 | m/z = 775.27 ($C_{54}H_{37}N_3OS$ = 775.97) | P-14 | m/z = 775.27 ($C_{54}H_{37}N_3OS$ = 775.97) |
| P-15 | m/z = 775.27 ($C_{54}H_{37}N_3OS$ = 775.97) | P-16 | m/z = 775.27 ($C_{54}H_{37}N_3OS$ = 775.97) |
| P-17 | m/z = 841.26 ($C_{58}H_{39}N_3S_2$ = 842.09) | P-18 | m/z = 841.26 ($C_{58}H_{39}N_3S_2$ = 842.09) |
| P-19 | m/z = 825.28 ($C_{58}H_{39}N_3OS$ = 826.03) | P-20 | m/z = 825.28 ($C_{58}H_{39}N_3OS$ = 826.03) |
| P-21 | m/z = 791.24 ($C_{54}H_{37}N_3S_2$ = 792.03) | P-22 | m/z = 791.24 ($C_{54}H_{37}N_3S_2$ = 792.03) |
| P-23 | m/z = 791.24 ($C_{54}H_{37}N_3S_2$ = 792.03) | P-24 | m/z = 791.24 ($C_{54}H_{37}N_3S_2$ = 792.03) |
| P-25 | m/z = 791.24 ($C_{54}H_{37}N_3S_2$ = 792.03) | P-26 | m/z = 791.24 ($C_{54}H_{37}N_3S_2$ = 792.03) |
| P-27 | m/z = 791.24 ($C_{54}H_{37}N_3S_2$ = 792.03) | P-28 | m/z = 791.24 ($C_{54}H_{37}N_3S_2$ = 792.03) |
| P-29 | m/z = 791.24 ($C_{54}H_{37}N_3S_2$ = 792.03) | P-30 | m/z = 775.27 ($C_{54}H_{37}N_3OS$ = 775.97) |
| P-31 | m/z = 791.24 ($C_{54}H_{37}N_3S_2$ = 792.03) | P-32 | m/z = 791.24 ($C_{54}H_{37}N_3S_2$ = 792.03) |
| P-33 | m/z = 791.24 ($C_{54}H_{37}N_3S_2$ = 792.03) | P-34 | m/z = 791.24 ($C_{54}H_{37}N_3S_2$ = 792.03) |
| P-35 | m/z = 791.24 ($C_{54}H_{37}N_3S_2$ = 792.03) | P-36 | m/z = 791.24 ($C_{54}H_{37}N_3S_2$ = 792.03) |
| P-37 | m/z = 791.24 ($C_{54}H_{37}N_3S_2$ = 792.03) | P-38 | m/z = 791.24 ($C_{54}H_{37}N_3S_2$ = 792.03) |
| P-39 | m/z = 867.27 ($C_{60}H_{41}N_3S_2$ = 868.13) | P-40 | m/z = 791.24 ($C_{54}H_{37}N_3S_2$ = 792.03) |
| P-41 | m/z = 775.27 ($C_{54}H_{37}N_3OS$ = 775.97) | P-42 | m/z = 851.30 ($C_{60}H_{41}N_3OS$ = 852.07) |
| P-43 | m/z = 759.29 ($C_{54}H_{37}N_3O_2$ = 759.91) | P-44 | m/z = 835.32 ($C_{60}H_{41}N_3O_2$ = 836.01) |
| P-45 | m/z = 841.26 ($C_{58}H_{39}N_3S_2$ = 842.09) | P-46 | m/z = 791.24 ($C_{54}H_{37}N_3S_2$ = 792.03) |
| P-47 | m/z = 775.27 ($C_{54}H_{37}N_3OS$ = 775.97) | P-48 | m/z = 759.29 ($C_{54}H_{37}N_3O_2$ = 759.91) |
| P-49 | m/z = 841.26 ($C_{58}H_{39}N_3S_2$ = 842.09) | P-50 | m/z = 841.26 ($C_{58}H_{39}N_3S_2$ = 842.09) |
| P-51 | m/z = 867.27 ($C_{60}H_{41}N_3S_2$ = 868.13) | P-52 | m/z = 867.27 ($C_{60}H_{41}N_3S_2$ = 868.13) |
| P-53 | m/z = 867.27 ($C_{60}H_{41}N_3S_2$ = 868.13) | P-54 | m/z = 867.27 ($C_{60}H_{41}N_3S_2$ = 868.13) |
| P-55 | m/z = 775.27 ($C_{54}H_{37}N_3OS$ = 775.97) | P-56 | m/z = 775.27 ($C_{54}H_{37}N_3OS$ = 775.97) |
| P-57 | m/z = 775.27 ($C_{54}H_{37}N_3OS$ = 775.97) | P-58 | m/z = 867.27 ($C_{60}H_{41}N_3S_2$ = 868.13) |
| P-59 | m/z = 867.27 ($C_{60}H_{41}N_3S_2$ = 868.13) | P-60 | m/z = 867.27 ($C_{60}H_{41}N_3S_2$ = 868.13) |
| P-61 | m/z = 897.23 ($C_{60}H_{39}N_3S_3$ = 898.17) | P-62 | m/z = 897.23 ($C_{60}H_{39}N_3S_3$ = 898.17) |
| P-63 | m/z = 1029.32 ($C_{73}H_{47}N_3S_2$ = 1030.32) | P-64 | m/z = 881.25 ($C_{60}H_{39}N_3OS_2$ = 882.11) |
| P-65 | m/z = 947.25 ($C_{64}H_{41}N_3S_3$ = 948.23) | P-66 | m/z = 931.27 ($C_{64}H_{41}N_3OS_2$ = 932.17) |
| P-67 | m/z = 907.31 ($C_{63}H_{45}N_3S_2$ = 908.19) | P-68 | m/z = 805.26 ($C_{55}H_{39}N_3S_2$ = 806.06) |
| P-69 | m/z = 796.27 ($C_{54}H_{32}D_5N_3S_2$ = 797.06) | P-70 | m/z = 817.26 ($C_{56}H_{39}N_3S_2$ = 818.07) |
| P-71 | m/z = 805.26 ($C_{55}H_{39}N_3S_2$ = 806.06) | P-72 | m/z = 809.23 ($C_{54}H_{36}FN_3S_2$ = 810.02) |
| P-73 | m/z = 836.32 ($C_{59}H_{40}N_4O_2$ = 837.00) | P-74 | m/z = 867.27 ($C_{60}H_{41}N_3S_2$ = 868.13) |
| P-75 | m/z = 816.24 ($C_{55}H_{36}N_4S_2$ = 817.04) | P-76 | m/z = 891.27 ($C_{62}H_{41}N_3S_2$ = 892.15) |
| P-77 | m/z = 958.32 ($C_{66}H_{46}N_4S_2$ = 959.24) | P-78 | m/z = 958.32 ($C_{66}H_{46}N_4S_2$ = 959.24) |
| P-79 | m/z = 958.32 ($C_{66}H_{46}N_4S_2$ = 959.24) | P-80 | m/z = 795.27 ($C_{54}H_{33}D_4N_3S_2$ = 796.06) |
| P-81 | m/z = 791.24 ($C_{54}H_{37}N_3S_2$ = 792.03) | P-82 | m/z = 791.24 ($C_{54}H_{37}N_3S_2$ = 792.03) |
| P-83 | m/z = 881.25 ($C_{60}H_{39}N_3OS_2$ = 882.11) | P-84 | m/z = 791.24 ($C_{54}H_{37}N_3S_2$ = 792.03) |
| P-85 | m/z = 792.24 ($C_{53}H_{36}N_4S_2$ = 793.02) | P-86 | m/z = 761.29 ($C_{54}H_{39}N_3S$ = 761.99) |
| P-87 | m/z = 791.24 ($C_{54}H_{37}N_3S_2$ = 792.03) | P-88 | m/z = 685.26 ($C_{48}H_{35}N_3S$ = 685.89) |
| P-89 | m/z = 761.29 ($C_{54}H_{39}N_3S$ = 761.99) | P-90 | m/z = 685.26 ($C_{48}H_{35}N_3S$ = 685.89) |
| P-91 | m/z = 719.29 ($C_{52}H_{37}N_3O$ = 719.89) | P-92 | m/z = 801.32 ($C_{57}H_{43}N_3S$ = 802.05) |
| P-93 | m/z = 775.27 ($C_{54}H_{37}N_3OS$ = 775.97) | P-94 | m/z = 775.27 ($C_{54}H_{37}N_3OS$ = 775.97) |
| P-95 | m/z = 789.28 ($C_{55}H_{39}N_3OS$ = 790.00) | P-96 | m/z = 775.27 ($C_{54}H_{37}N_3OS$ = 775.97) |
| P-97 | m/z = 775.27 ($C_{54}H_{37}N_3OS$ = 775.97) | P-98 | m/z = 759.29 ($C_{54}H_{37}N_3O_2$ = 759.91) |
| P-99 | m/z = 759.29 ($C_{54}H_{37}N_3O_2$ = 759.91) | P-100 | m/z = 759.29 ($C_{54}H_{37}N_3O_2$ = 759.91) |
| P-101 | m/z = 881.25 ($C_{60}H_{39}N_3OS_2$ = 882.11) | P-102 | m/z = 865.28 ($C_{60}H_{39}N_3O_2S$ = 866.05) |
| P-103 | m/z = 1031.34 ($C_{73}H_{49}N_3S_2$ = 1032.34) | P-104 | m/z = 849.30 ($C_{60}H_{39}N_3O_3$ = 849.99) |
| P-105 | m/z = 907.31 ($C_{63}H_{45}N_3S_2$ = 908.19) | P-106 | m/z = 867.27 ($C_{60}H_{41}N_3S_2$ = 868.13) |
| P-107 | m/z = 849.30 ($C_{60}H_{39}N_3O_3$ = 849.99) | P-108 | m/z = 897.23 ($C_{60}H_{39}N_3S_3$ = 898.17) |
| P-109 | m/z = 881.25 ($C_{60}H_{39}N_3OS_2$ = 882.11) | P-110 | m/z = 791.24 ($C_{54}H_{37}N_3S_2$ = 792.03) |
| P-111 | m/z = 800.26 ($C_{55}H_{36}N_4OS$ = 800.98) | P-112 | m/z = 789.30 ($C_{55}H_{39}N_3O_3$ = 789.94) |

In the compounds of P-1 to P-112, a specific synthesis example of some of the compounds has not been described. Such compounds may be synthesized using Sub 1 and Sub 2 compounds presented in Table 4 below, in a manner similar to the above-described synthesis methods. The compounds presented in product columns may be synthesized by reacting the compounds presented in Sub 1 columns of Table 4 below with the compounds presented in Sub 2 columns of Table 4, but the synthesis methods are not limited thereto.

TABLE 4

| Sub 1 | Sub 2 | Final Product |
|---|---|---|
| Sub 1-1 | Sub 2-31 | P-1 |
| Sub 1-2 | Sub 2-31 | P-2 |
| Sub 1-3 | Sub 2-31 | P-3 |
| Sub 1-4 | Sub 2-31 | P-4 |
| Sub 1-5 | Sub 2-31 | P-5 |
| Sub 1-6 | Sub 2-31 | P-6 |
| Sub 1-7 | Sub 2-31 | P-7 |
| Sub 1-8 | Sub 2-31 | P-8 |

TABLE 4-continued

| Sub 1 | Sub 2 | Final Product |
|---|---|---|
| Sub 1-9 | Sub 2-31 | P-9 |
| Sub 1-10 | Sub 2-31 | P-10 |
| Sub 1-11 | Sub 2-31 | P-11 |
| Sub 1-12 | Sub 2-31 | P-12 |
| Sub 1-13 | Sub 2-31 | P-13 |
| Sub 1-14 | Sub 2-31 | P-14 |
| Sub 1-15 | Sub 2-31 | P-15 |
| Sub 1-16 | Sub 2-31 | P-16 |
| Sub 1-17 | Sub 2-31 | P-17 |
| Sub 1-18 | Sub 2-31 | P-18 |
| Sub 1-19 | Sub 2-31 | P-19 |
| Sub 1-20 | Sub 2-31 | P-20 |
| Sub 1-21 | Sub 2-31 | P-21 |
| Sub 1-22 | Sub 2-31 | P-22 |
| Sub 1-23 | Sub 2-31 | P-23 |
| Sub 1-24 | Sub 2-31 | P-24 |
| Sub 1-25 | Sub 2-31 | P-25 |
| Sub 1-26 | Sub 2-31 | P-26 |
| Sub 1-27 | Sub 2-31 | P-27 |
| Sub 1-28 | Sub 2-31 | P-28 |

TABLE 4-continued

| Sub 1 | Sub 2 | Final Product |
|---|---|---|
| Sub 1-29 | Sub 2-31 | P-29 |
| Sub 1-30 | Sub 2-31 | P-30 |
| Sub 1-31 | Sub 2-31 | P-31 |
| Sub 1-32 | Sub 2-31 | P-32 |
| Sub 1-33 | Sub 2-31 | P-33 |
| Sub 1-34 | Sub 2-31 | P-34 |
| Sub 1-35 | Sub 2-31 | P-35 |
| Sub 1-36 | Sub 2-31 | P-36 |
| Sub 1-45 | Sub 2-31 | P-37 |
| Sub 1-46 | Sub 2-31 | P-38 |
| Sub 1-47 | Sub 2-31 | P-39 |
| Sub 1-48 | Sub 2-31 | P-40 |
| Sub 1-49 | Sub 2-31 | P-41 |
| Sub 1-50 | Sub 2-31 | P-42 |
| Sub 1-51 | Sub 2-31 | P-43 |
| Sub 1-52 | Sub 2-31 | P-44 |
| Sub 1-53 | Sub 2-51 | P-45 |
| Sub 1-54 | Sub 2-31 | P-46 |
| Sub 1-93 | Sub 2-31 | P-47 |
| Sub 1-94 | Sub 2-31 | P-48 |
| Sub 1-37 | Sub 2-31 | P-49 |
| Sub 1-38 | Sub 2-31 | P-50 |
| Sub 1-41 | Sub 2-31 | P-51 |
| Sub 1-42 | Sub 2-31 | P-52 |
| Sub 1-43 | Sub 2-31 | P-53 |
| Sub 1-44 | Sub 2-31 | P-54 |
| Sub 1-40 | Sub 2-31 | P-55 |
| Sub 1-95 | Sub 2-31 | P-56 |
| Sub 1-57 | Sub 2-31 | P-57 |
| Sub 1-58 | Sub 2-31 | P-58 |
| Sub 1-59 | Sub 2-34 | P-59 |
| Sub 1-1 | Sub 2-34 | P-60 |
| Sub 1-65 | Sub 2-31 | P-61 |
| Sub 1-96 | Sub 2-31 | P-62 |
| Sub 1-66 | Sub 2-31 | P-63 |
| Sub 1-67 | Sub 2-31 | P-64 |
| Sub 1-1 | Sub 2-21 | P-65 |
| Sub 1-97 | Sub 2-25 | P-66 |
| Sub 1-1 | Sub 2-48 | P-67 |
| Sub 1-98 | Sub 2-31 | P-68 |
| Sub 1-1 | Sub 2-45 | P-69 |
| Sub 1-60 | Sub 2-31 | P-70 |
| Sub 1-61 | Sub 2-31 | P-71 |
| Sub 1-62 | Sub 2-31 | P-72 |
| Sub 1-63 | Sub 2-35 | P-73 |
| Sub 1-64 | Sub 2-31 | P-74 |
| Sub 1-68 | Sub 2-31 | P-75 |
| Sub 1-1 | Sub 2-40 | P-76 |
| Sub 1-5 | Sub 2-42 | P-77 |
| Sub 1-6 | Sub 2-31 | P-78 |
| Sub 1-70 | Sub 2-31 | P-79 |
| Sub 1-71 | Sub 2-31 | P-80 |
| Sub 1-99 | Sub 2-31 | P-81 |
| Sub 1-100 | Sub 2-31 | P-82 |
| Sub 1-72 | Sub 2-31 | P-83 |
| Sub 1-101 | Sub 2-31 | P-84 |
| Sub 1-73 | Sub 2-31 | P-85 |
| Sub 1-102 | Sub 2-42 | P-86 |
| Sub 1-103 | Sub 2-41 | P-87 |
| Sub 1-76 | Sub 2-31 | P-88 |
| Sub 1-104 | Sub 2-31 | P-89 |
| Sub 1-105 | Sub 2-31 | P-90 |
| Sub 1-77 | Sub 2-31 | P-91 |
| Sub 1-78 | Sub 2-31 | P-92 |
| Sub 1-79 | Sub 2-31 | P-93 |
| Sub 1-80 | Sub 2-31 | P-94 |
| Sub 1-81 | Sub 2-31 | P-95 |
| Sub 1-82 | Sub 2-31 | P-96 |
| Sub 1-39 | Sub 2-31 | P-97 |
| Sub 1-106 | Sub 2-31 | P-98 |
| Sub 1-107 | Sub 2-31 | P-99 |
| Sub 1-108 | Sub 2-31 | P-100 |
| Sub 1-85 | Sub 2-31 | P-101 |
| Sub 1-86 | Sub 2-31 | P-102 |
| Sub 1-87 | Sub 2-31 | P-103 |
| Sub 1-88 | Sub 2-31 | P-104 |
| Sub 1-54 | Sub 2-48 | P-105 |
| Sub 1-89 | Sub 2-31 | P-106 |
| Sub 1-51 | Sub 2-52 | P-107 |
| Sub 1-54 | Sub 2-17 | P-108 |
| Sub 1-110 | Sub 2-31 | P-109 |
| Sub 1-109 | Sub 2-31 | P-110 |
| Sub 1-90 | Sub 2-31 | P-111 |
| Sub 1-91 | Sub 2-31 | P-112 |

The synthesis examples relate to examples compounds of some of the compounds represented by Formula 1. The above-described reactions are based on Buchwald-Hartwig cross coupling reaction, Suzuki cross-coupling reaction, Miyaura boration reaction, Suzuki cross-coupling reaction, Intramolecular acid-induced cyclization reaction (J. Mater. Chem. 1999, 9, 2095.), Pd (II)-catalyzed oxidative cyclization reaction (Org. Lett. 2011, 13, 5504), PPh3-mediated reductive cyclization reaction (J. Org. Chem. 2005, 70, 5014.), Grignard reaction, Cyclic Dehydration reaction, and the like. It will be clearly understood by those having ordinary knowledge in the art that the above-described reactions may be performed even when the other substituents (i.e. substituent such as X, $Ar^1$ to $Ar^5$, $R^1$, a, and $L^1$ to $L^3$) defined in Formula 1 are bonded, in addition to the substituents clearly represented in the specific synthesis examples.

Evaluation of the Fabrication of Organic Electric Element

[Example 1] Red Organic Electroluminescent Element (Auxiliary Emission Layer)

An organic electroluminescent element was fabricated by a common method using a compound of the present disclosure as an auxiliary emission layer. First, a hole injection layer was formed by vacuum-depositing 4,4',4"-Tris[2-naphthyl(phenyl)amino]triphenylamine (hereinafter, referred to as "2-TNATA") to a thickness of 60 nm on an indium tin oxide (ITO) layer (i.e. a positively charged electrode) formed on a glass substrate, and then a hole transport layer was formed by vacuum-depositing N,N'-bis(1-naphthalenyl)-N,N'-bis-phenyl-(1,1'-biphenyl)-4,4'-diamine (hereinafter, referred to as "NPB") to a thickness of 60 nm on the hole injection layer. Subsequently, an auxiliary emission layer was formed by vacuum-depositing the compound P-1 according to the present disclosure to a thickness of 20 nm on the hole transport layer, and then an emissive layer was formed by vacuum-depositing a host material to a thickness of 30 nm on the auxiliary emission layer, the host material being 4,4'-N,N'-dicarbazole-biphenyl (hereinafter, referred to as "CBP") doped with a dopant material bis-(1-phenylisoquinolyl) iridium(III) acetylacetonate (hereinafter, referred to as "$(piq)_2Ir(acac)$") at a weight ratio of 95:5. Afterwards, a hole blocking layer was formed by vacuum-depositing (1,1'-biphenyl-4-olato)bis(2-methyl-8-quinolinolato)aluminum (hereinafter, referred to as "BAlq") to a thickness of 10 nm on the emissive layer, and then an electron transport layer was formed by vacuum-depositing Bis(10-hydroxybenzo[h]quinolinato)beryllium (hereinafter, referred to as "$BeBq_2$") to a thickness of 50 nm on the hole blocking layer. Thereafter, an electron injection layer was formed by depositing an alkali-metal halide LiF to a thickness of 0.2 nm, and then a negatively charged electrode was formed by depositing Al to a thickness of 150 nm. Consequently, the organic electroluminescent element was fabricated.

[Examples 2 to 17] Red Organic Electroluminescent Element (Auxiliary Emission Layer)

Organic electroluminescent elements were fabricated in the same manner as in Example 1 except that the compounds P-3 to P-98 according to the present disclosure were used as the auxiliary emission layer material in place of the compound P-1 according to the present disclosure.

Comparative Examples 1 to 3

Organic electroluminescent elements were fabricated in the same manner as in Example 1 except that Comparative Compounds 1 to 3 presented in Table 5 below were used as the auxiliary emission layer material in place of the compound P-1 according to the present disclosure.

<Comparative Compound 1>

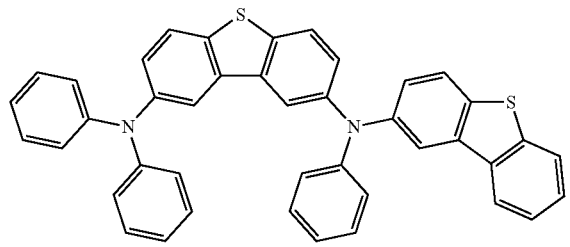

<Comparative Compound 2>

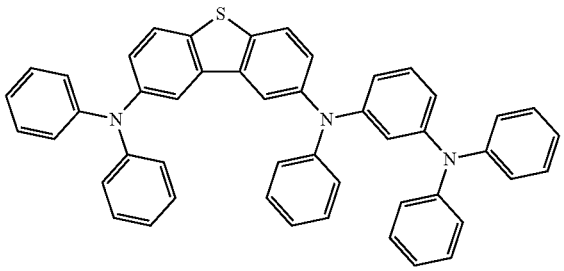

<Comparative Compound 3>

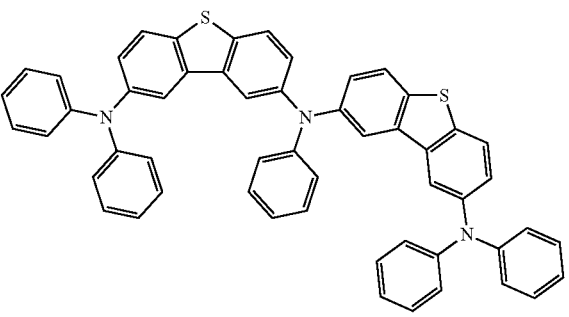

The electroluminescence (EL) properties of the organic electroluminescent elements, fabricated according to Examples 1 to 17 according to the present disclosure and Comparative Examples 1 to 3, were measured using PR-650 available from Photo Research by applying a forward-bias DC voltage to the organic electroluminescent elements. The T95 lifetimes of the organic electroluminescent elements fabricated were measured at a reference luminance of 2500 cd/m² using lifetime measuring equipment fabricated by McScience. The results of the measurement are illustrated in Table 5 below.

TABLE 5

| | | Voltage | Current Density | Brightness | Efficiency | Lifetime | CIE | |
|---|---|---|---|---|---|---|---|---|
| | Compound | (V) | (mA/cm²) | (cd/m²) | (cd/A) | T95 (hr) | x | y |
| Comp. Ex. (1) | Comp. Compound 1 | 6.9 | 37.3 | 2500.0 | 9.6 | 108.3 | 0.63 | 0.30 |
| Comp. Ex. (2) | Comp. Compound 2 | 6.6 | 18.1 | 2500.0 | 13.8 | 124.8 | 0.63 | 0.32 |
| Comp. Ex. (3) | Comp. Compound 3 | 6.4 | 12.4 | 2500.0 | 20.0 | 136.7 | 0.62 | 0.33 |
| Ex. (1) | Compound (P-1) | 5.9 | 8.5 | 2500.0 | 29.5 | 160.3 | 0.61 | 0.32 |
| Ex. (2) | Compound (P-3) | 5.9 | 8.6 | 2500.0 | 28.9 | 158.7 | 0.61 | 0.30 |
| Ex. (3) | Compound (P-7) | 6.0 | 9.4 | 2500.0 | 26.6 | 157.4 | 0.62 | 0.35 |
| Ex. (4) | Compound (P-13) | 6.1 | 9.0 | 2500.0 | 27.8 | 163.7 | 0.64 | 0.34 |
| Ex. (5) | Compound (P-31) | 6.2 | 9.3 | 2500.0 | 27.0 | 154.1 | 0.63 | 0.34 |
| Ex. (6) | Compound (P-37) | 6.1 | 10.0 | 2500.0 | 24.9 | 153.2 | 0.61 | 0.35 |
| Ex. (7) | Compound (P-40) | 6.2 | 10.1 | 2500.0 | 24.7 | 150.7 | 0.64 | 0.34 |
| Ex. (8) | Compound (P-45) | 6.2 | 10.8 | 2500.0 | 23.2 | 149.2 | 0.60 | 0.35 |
| Ex. (9) | Compound (P-46) | 6.3 | 10.4 | 2500.0 | 24.0 | 147.5 | 0.63 | 0.33 |

TABLE 5-continued

|  | Compound | Voltage (V) | Current Density (mA/cm$^2$) | Brightness (cd/m$^2$) | Efficiency (cd/A) | Lifetime T95 (hr) | CIE x | CIE y |
|---|---|---|---|---|---|---|---|---|
| Ex. (10) | Compound (P-47) | 6.3 | 11.2 | 2500.0 | 22.2 | 144.6 | 0.61 | 0.32 |
| Ex. (11) | Compound (P-49) | 6.1 | 9.5 | 2500.0 | 26.4 | 151.8 | 0.64 | 0.34 |
| Ex. (12) | Compound (P-51) | 6.1 | 9.8 | 2500.0 | 25.5 | 150.4 | 0.62 | 0.32 |
| Ex. (13) | Compound (P-55) | 6.0 | 9.1 | 2500.0 | 27.5 | 165.7 | 0.65 | 0.31 |
| Ex. (14) | Compound (P-56) | 6.0 | 9.3 | 2500.0 | 27.0 | 164.9 | 0.61 | 0.32 |
| Ex. (15) | Compound (P-72) | 6.2 | 11.6 | 2500.0 | 21.6 | 139.4 | 0.65 | 0.31 |
| Ex. (16) | Compound (P-88) | 6.3 | 12.2 | 2500.0 | 20.4 | 136.9 | 0.63 | 0.32 |
| Ex. (17) | Compound (P-98) | 6.2 | 10.3 | 2500.0 | 24.3 | 167.4 | 0.60 | 0.32 |

As seen from the results of Table 5, when the red organic light-emitting elements were fabricated using the materials for the organic electroluminescent element according to the present disclosure as the materials for the auxiliary emission layer, the electrical properties of the elements were improved compared to those of Comparative Examples fabricated using Comparative Compounds 1 to 3. First, it may be seen that the results of the elements of Comparative Examples 2 and 3 fabricated using Comparative Compounds 2 and 3 in which three amine groups are attached were superior to those fabricated using Comparative Compound 1 in which two amine groups are attached. In addition, the results of the elements of Examples 1 to 17 fabricated using the compound according to the present disclosure in which two amine groups are substituted to the same ring of dibenzothiophene or dibenzofuran were more superior, although the elements of Examples 1 to 17 are similar to those of the comparative compounds.

Described in more detail, it may be seen that Comparative Compounds 2 and 3 having a structure in which three amine groups are attached had more superior element characteristics than Comparative Compound 1 having a structure in which two amine groups are attached. It is determined that, due to the introduction of amine within a proper range without an excessive increase in the number of amines, the HOMO (highest occupied molecular orbital) energy level of the hole transport layer or the auxiliary emission layer was adjusted to have a most proper difference in the HOMO energy level from that of the emissive layer, and thus, light emission inside the emissive layer was facilitated due to an increase in charge balance.

In addition, when the compound according to the present disclosure was compared with Comparative Compound 3, it may be seen that the compound according to the present disclosure in which two amine groups are attached to the same ring of dibenzothiophene or dibenzofuran had far superior results, unlike the comparative compound.

These results may be explained on the basis of the HOMO values of Comparative Compound 3 and the compound according to the present disclosure. Referring to Table 6 below, it is apparent that each of the compounds P-1 and P-38 according to the present disclosure has a deeper HOMO value than Comparative Compound 3.

TABLE 6

|  | Comparative Compound 3 | P-1 | P-38 |
|---|---|---|---|
| HOMO (eV) | 4.784 | 4.890 | 4.871 |

It is determined that the compound according to the present disclosure may have stronger hole properties and increased stability not only for electrodes but also for holes due to deeper HOMO energy level, thereby more efficiency transferring holes in the auxiliary emission layer. Accordingly, it is regarded that the charge balance of holes and electrons in the emissive layer are increased, thereby improving the driving voltage, efficiency, and lifetime of the entirety of the element.

[Example 18] Green Organic Electroluminescent Element (Auxiliary Emission Layer)

After a hole injection layer was formed by vacuum-depositing 2-TNATA to a thickness of 60 nm on an ITO layer (i.e. a positively charged electrode) formed on a glass substrate, a hole transport layer was formed by vacuum-depositing NPB to a thickness of 60 nm on the hole injection layer. Subsequently, an auxiliary emission layer was formed by vacuum-depositing the compound P-5 according to the present disclosure to a thickness of 20 nm on the hole transport layer, and then an emissive layer was formed by vacuum-depositing a host material to a thickness of 30 nm on the auxiliary emission layer, the host material being CBP doped with a dopant material tris(2-phenylpyridine)-iridium (hereinafter, referred to as "Ir(ppy)$_3$") at a weight ratio of 95:5. Afterwards, a hole blocking layer was formed by vacuum-depositing BAlq to a thickness of 10 nm on the emissive layer, and then an electron transport layer was formed by vacuum-depositing BeBq$_2$ to a thickness of 50 nm on the blocking layer. Thereafter, an electron injection layer was formed by depositing an alkali-metal halide LiF to a thickness of 0.2 nm, and then a negatively charged electrode was formed by depositing Al to a thickness of 150 nm. Consequently, an organic electroluminescent element was fabricated.

[Examples 19 to 34] Green Organic Electroluminescent Element (Auxiliary Emission Layer)

Organic electroluminescent elements were fabricated in the same manner as in Example 18 except that the compounds P-15 to P-112 according to the present disclosure, described in Table 5 below, were used as the auxiliary emission layer material in place of the compound P-5 according to the present disclosure.

Comparative Examples 4 to 6

Organic electroluminescent elements were fabricated in the same manner as in Example 18 except that Comparative Compounds 1 to 3 presented in Table 5 below were used as the auxiliary emission layer material in place of the compound P-5 according to the present disclosure.

The electroluminescence (EL) properties of the organic electroluminescent elements, fabricated according to Examples 18 to 34 according to the present disclosure and Comparative Examples 4 to 6, were measured using PR-650 available from Photo Research by applying a forward-bias DC voltage to the organic electroluminescent elements. The T95 lifetimes of the organic electroluminescent elements fabricated were measured at a reference luminance of 5000 $cd/m^2$ using lifetime measuring equipment fabricated by McScience. The results of the measurement are illustrated in Table 7 below.

As seen from the results of Table 7, it may be seen that, when the green organic light-emitting elements were fabricated using the organic electroluminescent element materials according to the present disclosure as the auxiliary emission layer materials, the organic electroluminescent elements may have a lower driving voltage, improved luminous efficiency, and increased lifetime compared to the comparative examples using Comparative Compounds 1 to 3. This indicates that the compounds according to the present disclosure in which two amine groups are attached to the same ring of dibenzothiophene or dibenzofuran may have significantly different chemical and/or physical properties from those of the compounds of the comparative examples and thus improved results may be obtained from the device, like the illustration of Table 5.

In addition, it may be seen that the element characteristics of the red organic electroluminescent element and the green organic electroluminescent element using the compound according to the present disclosure as the material for the auxiliary emission layer vary depending on the position of the compound according to the present disclosure at which the amine group is attached, as illustrated in Table 8 below.

TABLE 7

|  | Compound | Voltage (V) | Current Density ($mA/cm^2$) | Brightness ($cd/m^2$) | Efficiency (cd/A) | Lifetime T95 (hr) | CIE x | CIE y |
| --- | --- | --- | --- | --- | --- | --- | --- | --- |
| Comp. Ex. (4) | Comp. Compound 1 | 5.9 | 15.7 | 5000.0 | 31.9 | 114.8 | 0.30 | 0.63 |
| Comp. Ex. (5) | Comp. Compound2 | 5.8 | 14.3 | 5000.0 | 34.9 | 119.5 | 0.33 | 0.65 |
| Comp. Ex. (6) | Comp. Compound3 | 5.7 | 13.1 | 5000.0 | 38.1 | 123.2 | 0.34 | 0.62 |
| Ex. (18) | Compound (P-5) | 4.8 | 7.9 | 5000.0 | 63.3 | 133.4 | 0.31 | 0.64 |
| Ex. (19) | Compound (P-15) | 4.9 | 7.8 | 5000.0 | 64.1 | 135.2 | 0.30 | 0.61 |
| Ex. (20) | Compound (P-16) | 4.9 | 7.7 | 5000.0 | 64.7 | 135.1 | 0.35 | 0.60 |
| Ex. (21) | Compound (P-20) | 5.2 | 7.6 | 5000.0 | 66.0 | 137.8 | 0.33 | 0.64 |
| Ex. (22) | Compound (P-37) | 5.1 | 7.5 | 5000.0 | 66.6 | 138.6 | 0.35 | 0.64 |
| Ex. (23) | Compound (P-38) | 5.1 | 7.3 | 5000.0 | 68.4 | 140.6 | 0.33 | 0.62 |
| Ex. (24) | Compound (P-39) | 5.2 | 7.4 | 5000.0 | 67.2 | 139.2 | 0.31 | 0.61 |
| Ex. (25) | Compound (P-41) | 5.2 | 7.1 | 5000.0 | 70.1 | 147.5 | 0.32 | 0.64 |
| Ex. (26) | Compound (P-42) | 5.3 | 7.2 | 5000.0 | 69.6 | 141.6 | 0.34 | 0.62 |
| Ex. (27) | Compound (P-43) | 5.4 | 6.8 | 5000.0 | 73.4 | 145.7 | 0.34 | 0.64 |
| Ex. (28) | Compound (P-44) | 5.4 | 7.0 | 5000.0 | 71.7 | 143.2 | 0.34 | 0.64 |
| Ex. (29) | Compound (P-63) | 5.0 | 7.9 | 5000.0 | 63.1 | 132.4 | 0.31 | 0.61 |
| Ex. (30) | Compound (P-92) | 5.1 | 8.0 | 5000.0 | 62.2 | 129.9 | 0.31 | 0.62 |
| Ex. (31) | Compound (P-100) | 5.0 | 7.6 | 5000.0 | 65.6 | 135.9 | 0.32 | 0.64 |
| Ex. (32) | Compound (P-106) | 5.4 | 7.7 | 5000.0 | 64.9 | 134.1 | 0.34 | 0.62 |
| Ex. (33) | Compound (P-107) | 5.4 | 7.0 | 5000.0 | 71.3 | 142.3 | 0.32 | 0.63 |
| Ex. (34) | Compound (P-112) | 5.3 | 6.9 | 5000.0 | 72.4 | 143.2 | 0.33 | 0.64 |

TABLE 8

A

Structure

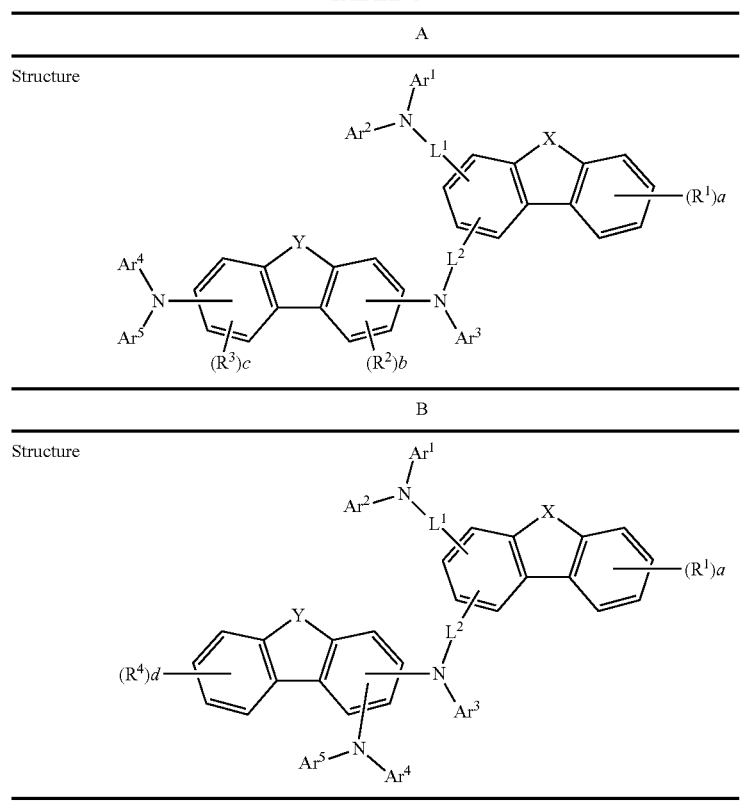

B

Structure

Referring to Tables 5 and 7 above, it may be seen that, in the red organic electroluminescent element, the compounds having an A type position at which the amine group is attached had more superior element characteristics. In contrast, in the green organic electroluminescent element, the compounds having a B type position at which the amine group is attached had more superior element characteristics than the A type. These results indicate that, even when the compounds have similar cores, the properties of the compounds, such as hole properties, luminous efficiency properties, energy levels (e.g. LUMO, HOMO level, and T1 level), hole injection and mobility properties, and electron blocking properties, may be changed depending on the position at which the substituent is attached, thereby deriving different element results.

[Example 35] Green Organic Electroluminescent Element (Hole Transport Layer)

After a hole injection layer was formed by vacuum-depositing 2-TNATA to a thickness of 60 nm on an ITO layer (i.e. a positively charged electrode) formed on a glass substrate, a hole transport layer was formed by vacuum-depositing the compound P-2 according to the present disclosure to a thickness of 60 nm on the hole injection layer. Subsequently, an emissive layer was formed by vacuum-depositing a host material to a thickness of 30 nm on the hole transport layer, the host material being CBP doped with a dopant material Ir(ppy)$_3$ at a weight ratio of 90:10. Afterwards, a hole blocking layer was formed by vacuum-depositing BAlq to a thickness of 10 nm on the emissive layer, and then an electron transport layer was formed by vacuum-depositing BeBq$_2$ to a thickness of 50 nm on the blocking layer. Thereafter, an electron injection layer was formed by depositing an alkali-metal halide LiF to a thickness of 0.2 nm, and then a negatively charged electrode was formed by depositing Al to a thickness of 150 nm. Consequently, an organic electroluminescent element was fabricated.

[Examples 36 to 46] Green Organic Electroluminescent Element (Hole Transport Layer)

Organic electroluminescent elements were fabricated in the same manner as in Example 35 except that the compounds P-4 to P-105 according to the present disclosure, described in Table 9 below, were used as the hole transport layer material in place of the compound P-2 according to the present disclosure.

[Comparative Examples 7 to 9] Green Organic Electroluminescent Element (Hole Transport Layer)

Organic electroluminescent elements were fabricated in the same manner as in Example 35 except that Comparative Compounds 1 to 3 presented in Table 9 below were used as the hole transport layer material in place of the compound P-2 according to the present disclosure.

The electroluminescence (EL) properties of the organic electroluminescent elements, fabricated according to Examples to 47 according to the present disclosure and Comparative Example 7 to 9, were measured using PR-650 available from Photo Research by applying a forward-bias DC voltage to the organic electroluminescent elements. The T95 lifetimes of the organic electroluminescent elements fabricated were measured at a reference luminance of 5000 cd/m$^2$ using lifetime measuring equipment fabricated by McScience. The results of the measurement are illustrated in Table 9 below.

TABLE 9

| | Compound | Voltage (V) | Current Density (mA/cm²) | Brightness (cd/m²) | Efficiency (cd/A) | Lifetime T95 (hr) | CIE x | CIE y |
|---|---|---|---|---|---|---|---|---|
| Comp. Ex. (7) | Comp. Compound 1 | 5.9 | 10.2 | 5000.0 | 24.4 | 79.1 | 0.31 | 0.64 |
| Comp. Ex. (8) | Comp. Compound 2 | 5.8 | 37.3 | 5000.0 | 27.9 | 82.8 | 0.34 | 0.63 |
| Comp. Ex. (9) | Comp. Compound 3 | 5.8 | 12.4 | 5000.0 | 35.6 | 120.9 | 0.32 | 0.61 |
| Ex. (35) | Compound (P-2) | 5.1 | 5.6 | 5000.0 | 44.7 | 142.2 | 0.30 | 0.60 |
| Ex. (36) | Compound (P-4) | 5.1 | 5.7 | 5000.0 | 43.7 | 139.6 | 0.33 | 0.64 |
| Ex. (37) | Compound (P-16) | 5.3 | 5.9 | 5000.0 | 42.6 | 148.6 | 0.30 | 0.62 |
| Ex. (38) | Compound (P-30) | 5.2 | 6.0 | 5000.0 | 41.4 | 152.1 | 0.33 | 0.63 |
| Ex. (39) | Compound (P-38) | 5.2 | 6.1 | 5000.0 | 40.9 | 142.4 | 0.31 | 0.61 |
| Ex. (40) | Compound (P-42) | 5.3 | 6.2 | 5000.0 | 40.1 | 144.3 | 0.31 | 0.64 |
| Ex. (41) | Compound (P-52) | 5.4 | 6.3 | 5000.0 | 39.6 | 136.4 | 0.32 | 0.64 |
| Ex. (42) | Compound (P-67) | 5.3 | 6.5 | 5000.0 | 38.4 | 140.0 | 0.33 | 0.62 |
| Ex. (43) | Compound (P-70) | 5.4 | 6.4 | 5000.0 | 38.9 | 138.6 | 0.34 | 0.64 |
| Ex. (44) | Compound (P-90) | 5.5 | 7.0 | 5000.0 | 35.5 | 126.3 | 0.34 | 0.64 |
| Ex. (45) | Compound (P-99) | 5.4 | 6.9 | 5000.0 | 36.2 | 156.8 | 0.31 | 0.61 |
| Ex. (46) | Compound (P-105) | 5.4 | 6.6 | 5000.0 | 37.8 | 132.1 | 0.35 | 0.63 |

As seen from the results of Table 9, it may be seen that, when the green organic light-emitting elements were fabricated using the organic electroluminescent element materials according to the present disclosure as the hole transport layer materials, the organic electroluminescent elements may have a lower driving voltage, improved luminous efficiency, and increased lifetime compared to the comparative examples using Comparative Compounds 1 to 3. First, it may be seen that the element characteristics of Comparative Compounds 2 to 3 in which three amine groups are attached are improved than those of Comparative Compound 1 in which two amine groups are attached. That is, a lower driving voltage, higher luminous efficiency, and increased lifetime were derived from Comparative Compounds 2 to 3.

In addition, this indicates that the compounds according to the present disclosure in which two amine groups are attached to the same ring of dibenzothiophene or dibenzofuran may have significantly different chemical and/or physical properties from those of the compounds of the comparative examples and thus improved results may be obtained from the device, like the illustration of Table 5.

In the case of the hole transport layer, the correlation thereof with the emissive layer (i.e. the host) must be determined. Even though a similar core is used, it may be difficult for those having ordinary knowledge in the art to analogize characteristics occurring in the hole transport layer in which the compound according to the present disclosure is used.

In the above results of the evaluation of the fabrication of the element in which the characteristics of the element are described, the compound according to the present disclosure was applied to one layer of the hole transport layer and the auxiliary emission layer. However, the compound according to the present disclosure may be used in both the hole transport layer and the auxiliary emission layer.

The above description provides examples of the present disclosure for illustrative purposes only. Those having ordinary knowledge in the technical field, to which the present disclosure pertains, will appreciate that various modifications are possible without departing from the essential features of the present disclosure. Therefore, the examples disclosed in the present disclosure are intended to illustrate the technical idea of the present disclosure, and the scope of the present disclosure is not limited by the examples.

The scope of the present disclosure shall be construed on the basis of the accompanying claims in such a manner that all of the technical ideas included within the scope equivalent to the claims belong to the present disclosure.

CROSS-REFERENCE TO RELATED APPLICATION

This application claims priority from Korean Patent Application No. 10-2018-0126915, filed in the Republic of Korea on Oct. 23, 2018, which is hereby incorporated by reference for all purposes as if fully set forth herein.

The invention claimed is:
1. A compound represented by following Formula 1:

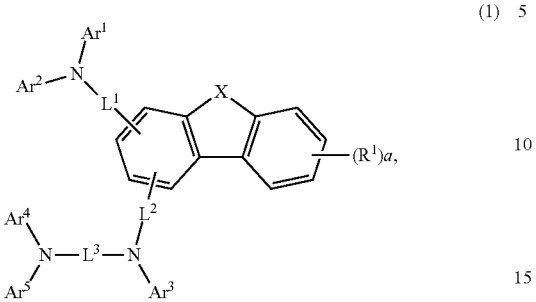

(1)

where
1) X is O or S,
2) $Ar^1$ to $Ar^5$ are the same or different, each of $Ar^1$ to $Ar^5$ being independently selected from a group consisting of a $C_6$-$C_{60}$ aryl group; a $C_2$-$C_{60}$ heterocyclic group including at least one heteroatom selected from among O, N, S, Si, or P; a fused ring group of a $C_3$-$C_{60}$ aliphatic ring and a $C_6$-$C_{60}$ aromatic ring; a $C_1$-$C_{60}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$),
3) $R^1$ is selected from the group consisting of deuterium; tritium; halogen; a cyano group; a nitro group; a $C_6$-$C_{60}$ aryl group; a $C_2$-$C_{60}$ heterocyclic group including at least one heteroatom selected from among O, N, S, Si, or P; a fused ring group of a $C_3$-$C_{60}$ aliphatic ring and a $C_6$-$C_{60}$ aromatic ring; a $C_1$-$C_{50}$ alkyl group; a $C_2$-$C_{20}$ alkenyl group; a $C_2$-$C_{20}$ alkynyl group; a $C_1$-$C_{30}$ alkoxy group; a $C_6$-$C_{30}$ aryloxy group; and -L'-N($R_a$)($R_b$), and when a is two or more, one or more $R^1$s are the same or different and a plurality of $R^1$s are bonded to form a ring,
4) A is an integer of 0 to 4,
5) $L^1$ and $L_2$ are the same or different, and each of $L^1$ and $L_2$ do not comprise any heteroatoms and are each independently selected from a group consisting of a single bond; a $C_6$-$C_{60}$ aryl group; a $C_5$-$C_{60}$ aliphatic ring group; or combinations thereof, and
6) $L^3$ is selected from a group consisting of a single bond; a $C_6$-$C_{60}$ aryl group; a $C_3$-$C_{60}$ aliphatic ring group; a $C_2$-$C_{60}$ heterocyclic group including at least one heteroatom selected from among O, S, Si, or P; or combinations thereof,
7) L' is selected from a group consisting of a single bond; a $C_6$-$C_{60}$ aryl group; a $C_3$-$C_{60}$ aliphatic ring group; a $C_2$-$C_{60}$ heterocyclic group including at least one heteroatom selected from among O, N, S, Si, or P; or combinations thereof, and each of $R_a$ and $R_b$ is independently selected from a group consisting of a $C_6$-$C_{60}$ aryl group; a fluorenyl group; a $C_3$-$C_{60}$ aliphatic ring group; a $C_2$-$C_{60}$ heterocyclic group including at least one heteroatom selected from among O, N, S, Si, or P; or combinations thereof,
8) in $Ar^1$ to $Ar^5$ and $R^1$, each of an aliphatic hydrocarbon group, the aryl group, the heterocyclic group, the fused ring group, the alkyl group, the alkenyl group, the alkynyl group, the alkoxy group, the aryloxy group, and the silane group is further substituted with one or more substituents selected from a group consisting of deuterium; a nitro group; a nitrile group; a halogen group; an amino group; a silane group substituted and unsubstituted with a $C_1$-$C_{20}$ alkyl group or a $C_6$-$C_{20}$ aryl group; a siloxane group; a $C_1$-$C_{20}$ alkylthio group; a $C_1$-$C_{20}$ alkoxy group; a $C_1$-$C_{20}$ alkyl group; a $C_2$-$C_{20}$ alkenyl group; a $C_2$-$C_{20}$ alkynyl group; a $C_6$-$C_{20}$ aryl group; a $C_6$-$C_{20}$ aryl group substituted with deuterium; a $C_2$-$C_{20}$ heterocyclic group; a $C_5$-$C_{20}$ cycloalkyl group; a $C_7$-$C_{20}$ aryl alkyl group; and a $C_8$-$C_{20}$ aryl alkenyl group, the substituents are allowed to be bonded to form a ring, and the ring refers to a fused ring including a saturated ring or an unsaturated ring and comprised of a $C_3$-$C_{60}$ aliphatic ring, a $C_6$-$C_{60}$ aromatic ring, a $C_2$-$C_{60}$ hetero ring, or combinations thereof.

2. The compound according to claim 1, wherein the compound represented by Formula 1 is represented by following Formula 2 or 3:

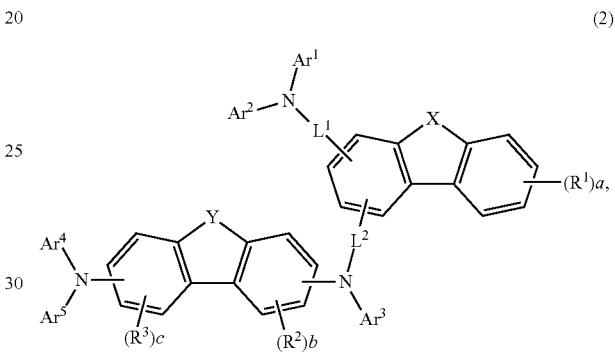

(2)

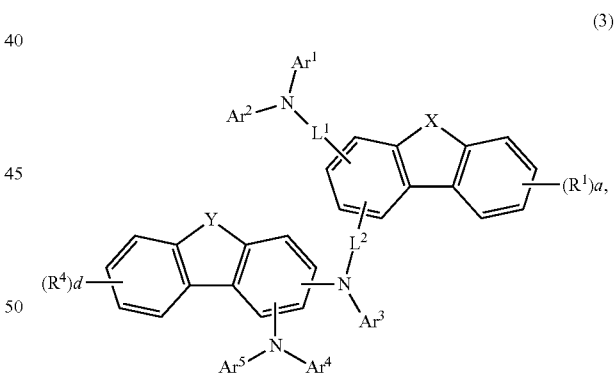

(3)

where
Y is O or S,
$R^2$ to $R^4$ are the same or different, each of $R^2$ to $R^4$ being the same as $R_1$ defined in claim 1,
each of b and c is independently an integer of 0 to 3, d is an integer of 0 to 4, and
$Ar^1$ to $Ar^5$, $R^1$, $L^1$ to $L^2$, X, and a are the same as defined in claim 1.

3. The compound according to claim 1, wherein the compound represented by Formula 1 is represented by one of following Formulas 4 to 7,

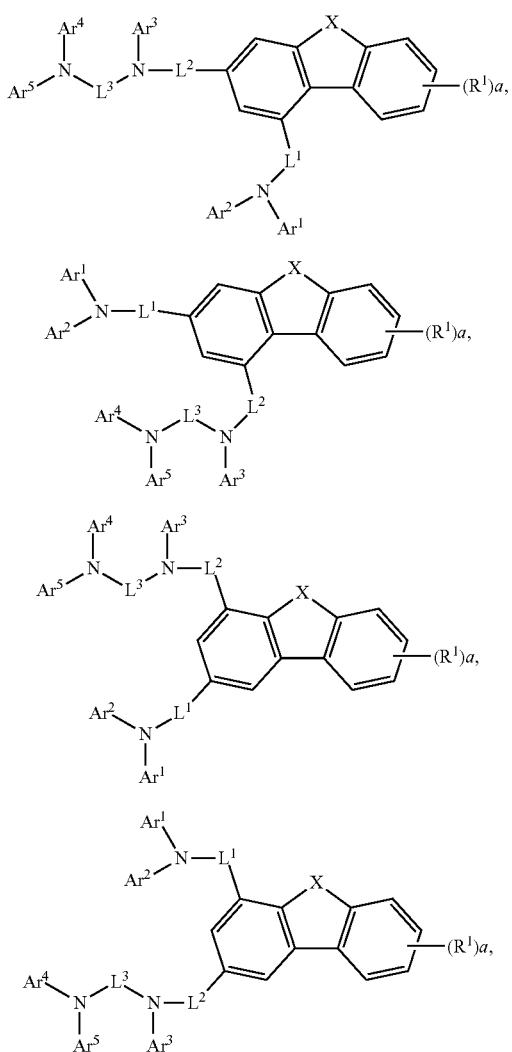

where Ar¹ to Ar⁵, R¹, L¹ to L³, X and a are the same as defined in claim 1.

4. An organic electric element comprising:

a first electrode;

a second electrode; and an organic material layer located between the first electrode and the second electrode, wherein the organic material layer contains the compound as claimed in claim 1.

5. The organic electric element according to claim 4, wherein the organic material layer comprises at least one layer from among a hole injection layer, a hole transport layer, an auxiliary emission layer, an emissive layer, an auxiliary electron transport layer, an electron transport layer, and an electron injection layer, and the compound comprises a mixture in which a single compound or two or more types of compounds represented by Formula 1 is mixed with at least one layer from among the hole injection layer, the hole transport layer, the auxiliary emission layer, the emissive layer, the auxiliary electron transport layer, the electron transport layer, and the electron injection layer.

6. The organic electric element according to claim 4, wherein the organic material layer comprises at least one layer of the auxiliary emission layer and the hole transport layer, and the compound comprises a mixture in which a single compound or two or more types of compounds represented by Formula 1 is mixed with at least one layer of the auxiliary emission layer and the hole transport layer.

7. The organic electric element according to claim 4, wherein the organic material layer is formed by at least one from among a spin coating process, a nozzle printing process, an inkjet printing process, a slot coating process, a dip coating process, or a roll-to-roll process.

8. An electronic device comprising:

a display device comprising the organic electric element as claimed in claim 5; and a controller controlling the display device.

9. The electronic device according to claim 8, wherein the electric element comprises one from among an organic electroluminescent element, an organic photovoltaic cell, an organic photo conductor, an organic transistor, or a monochromatic or white lighting element.

10. A compound represented by one of the following compounds:

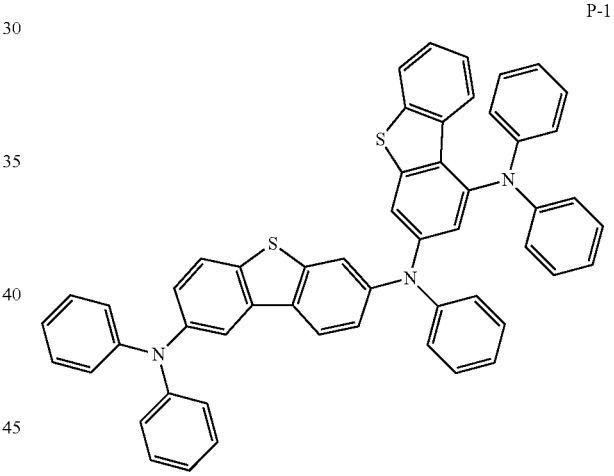

P-1

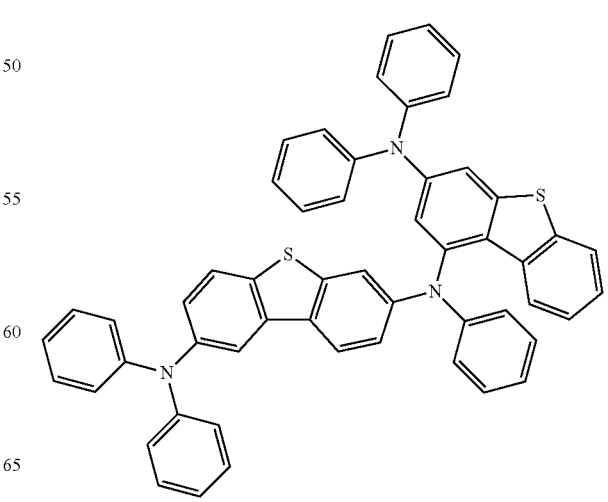

P-2

P-3
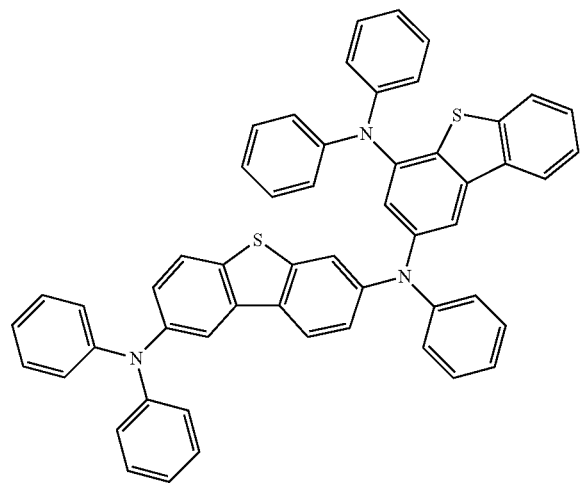
P-6
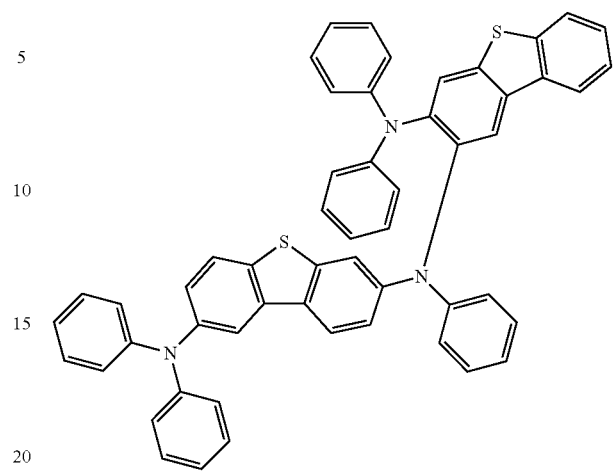
P-4
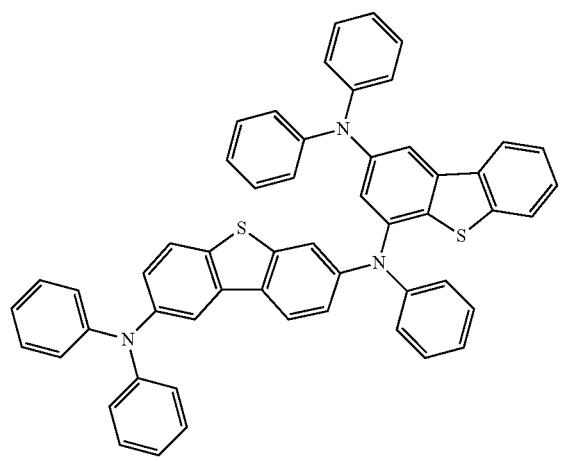
P-7
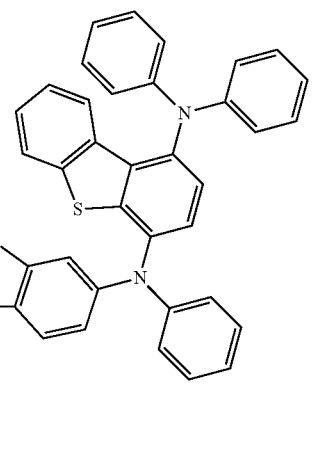
P-5
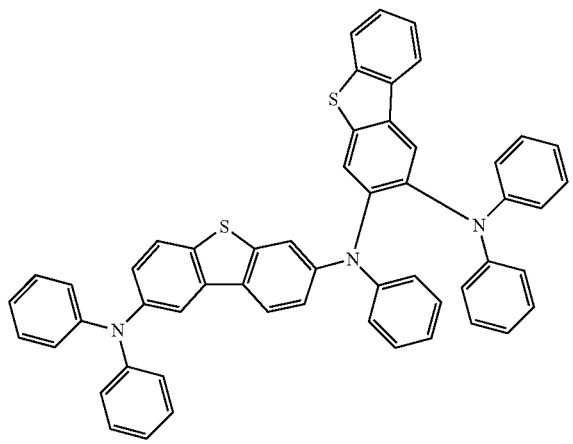
P-8
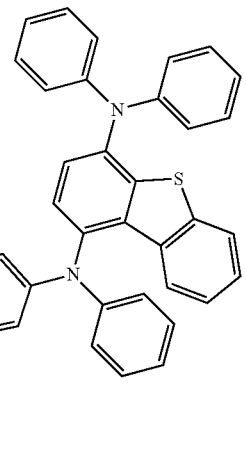

P-9
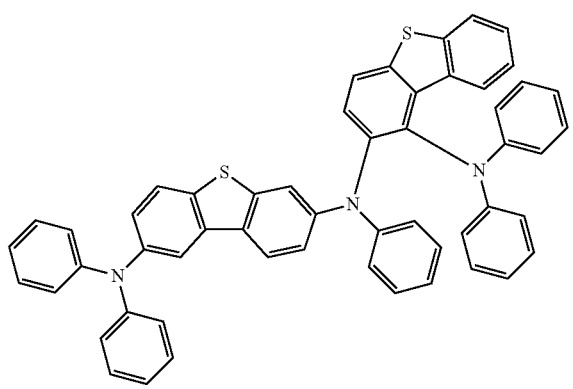
P-10
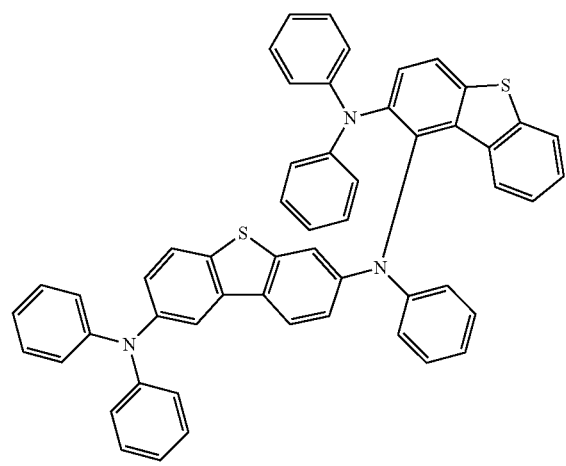
P-11
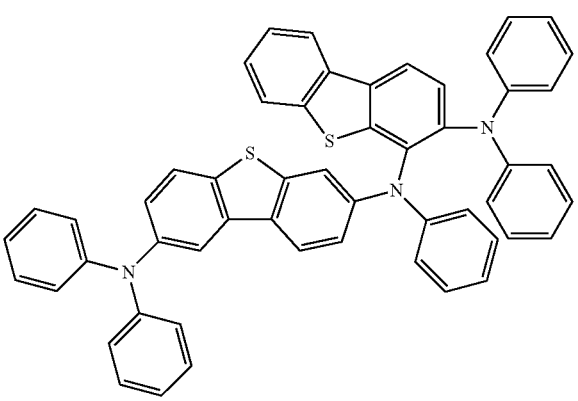
P-12
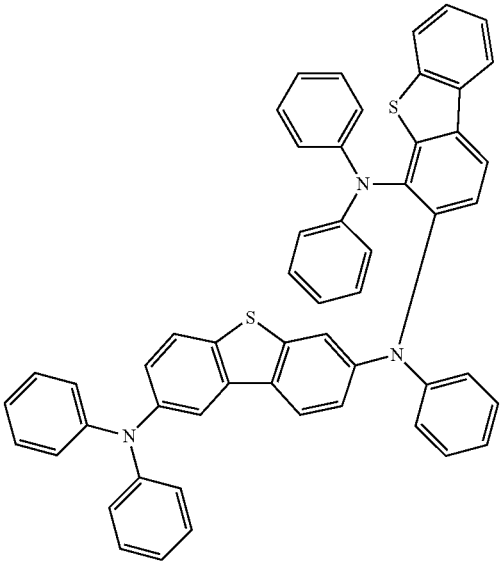
P-13
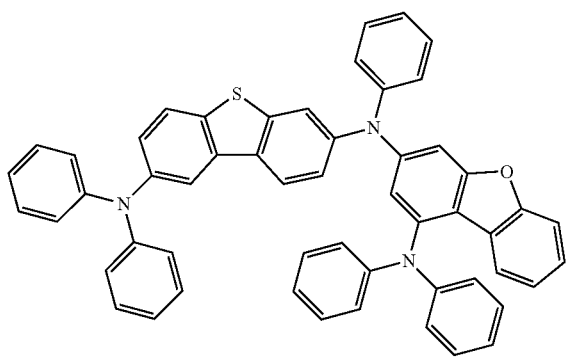
P-14
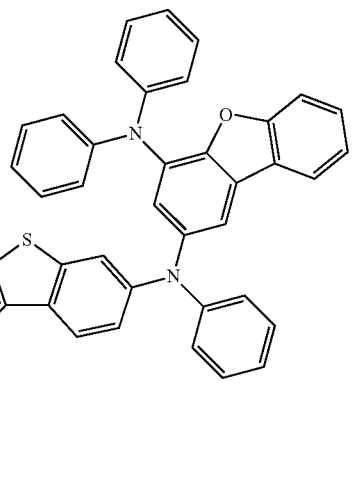

-continued
P-15
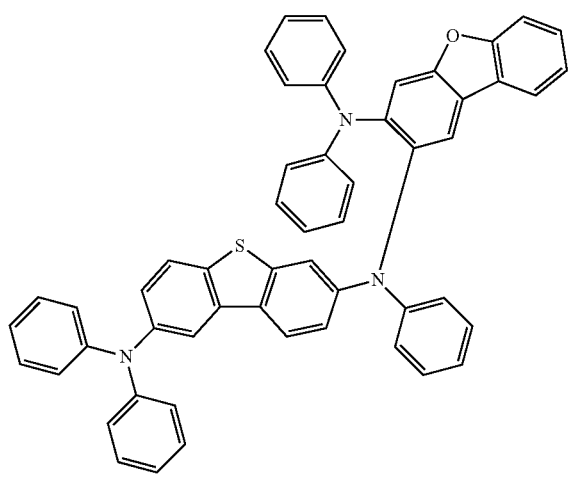
P-16
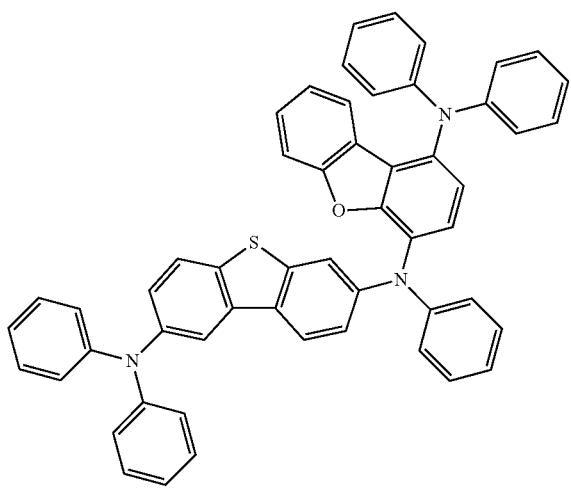
P-17
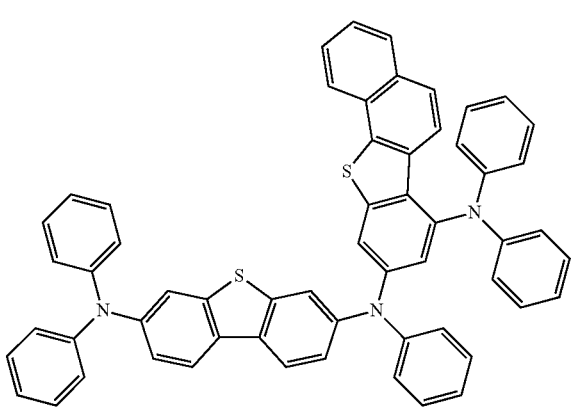
-continued
P-18
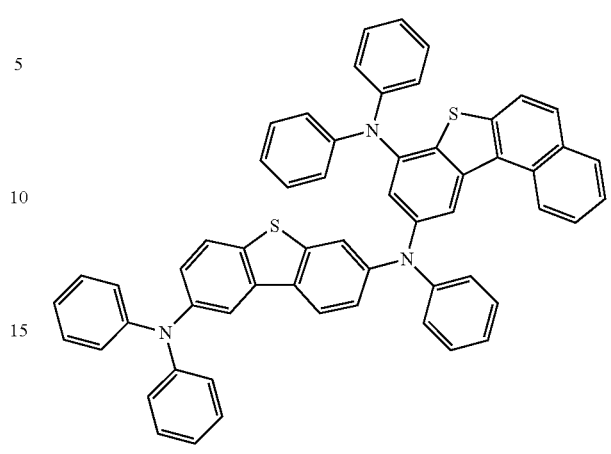
P-19
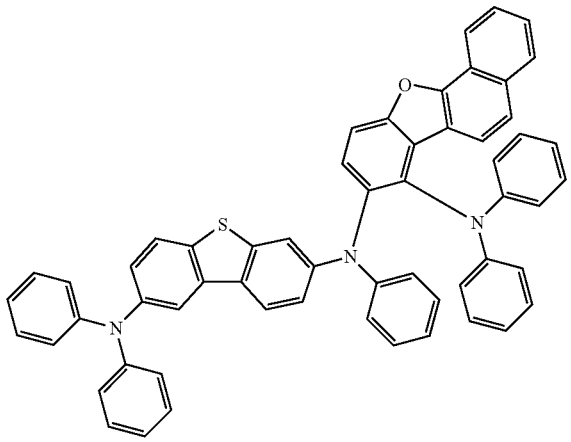
P-20
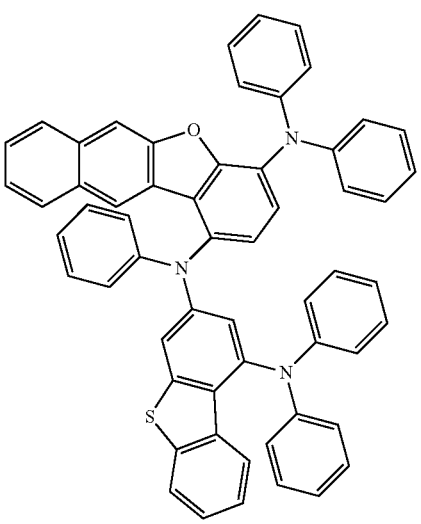

-continued
P-21
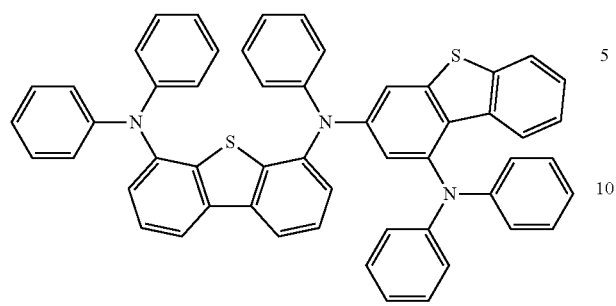
P-22
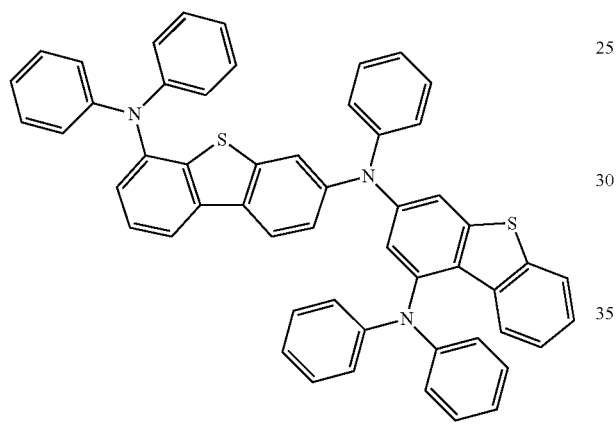
P-23
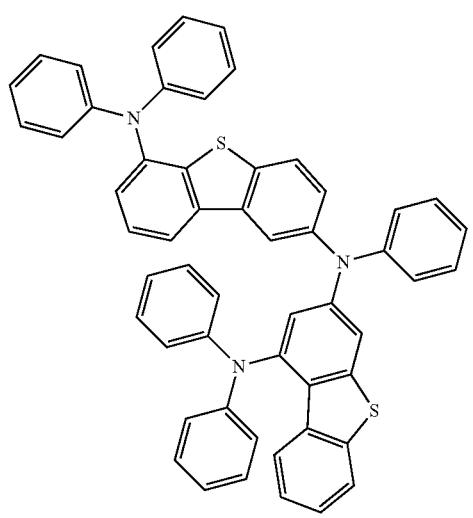
P-24
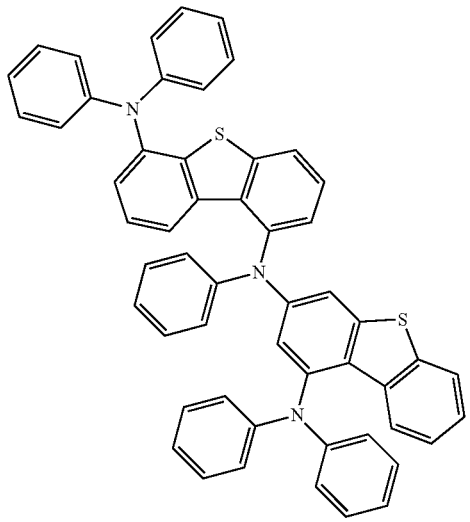
P-25
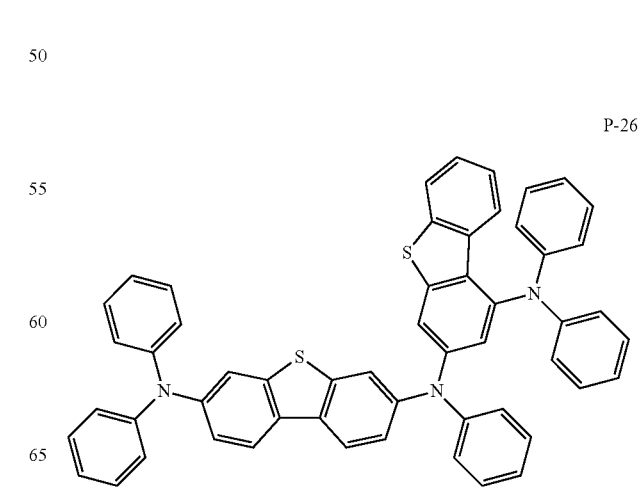
P-26
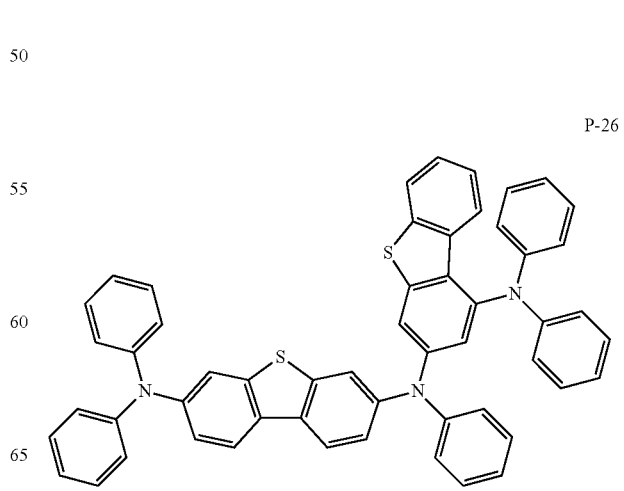

-continued
P-27
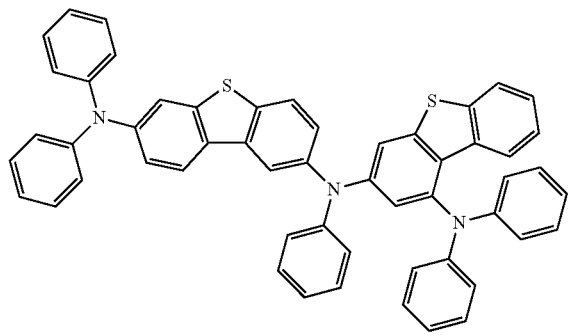
P-28
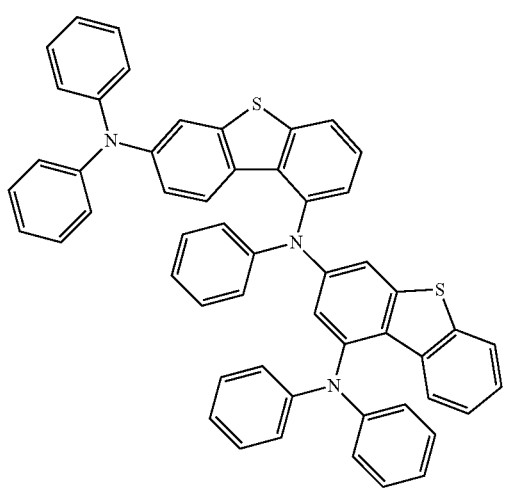
P-29
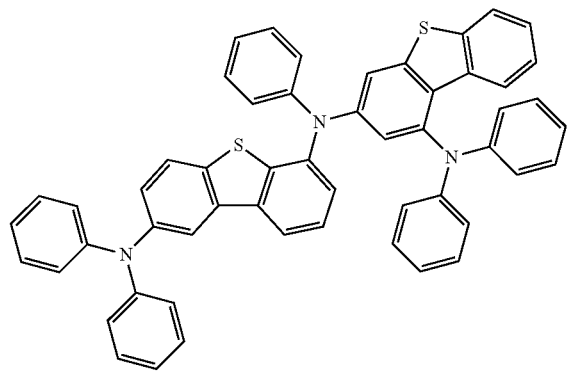
-continued
P-31
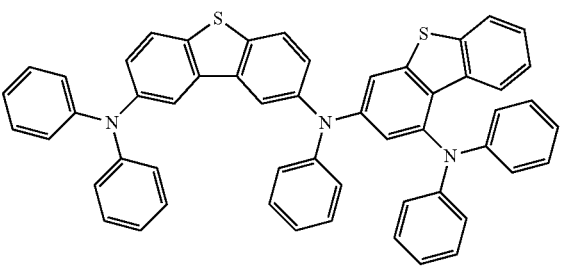
P-32
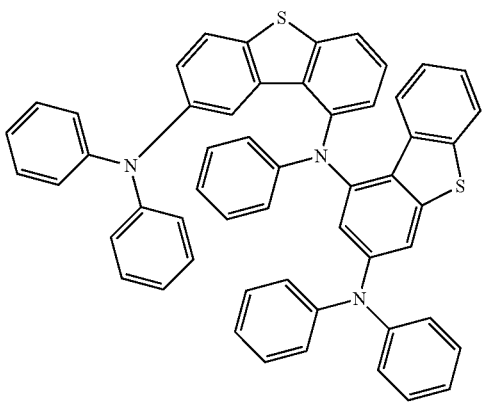
P-33
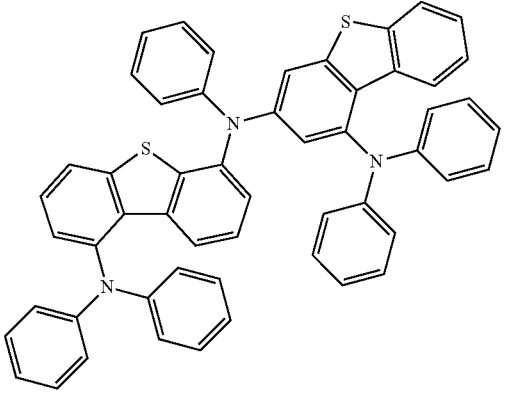
P-34
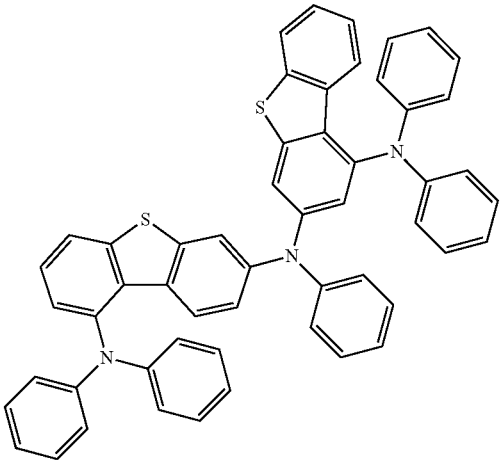
P-30

P-35
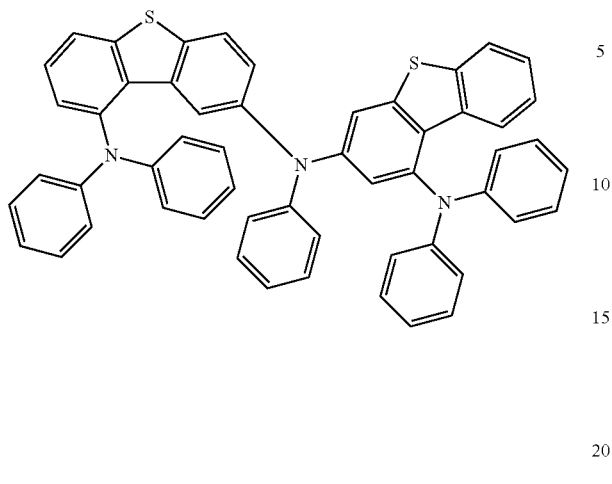
P-36
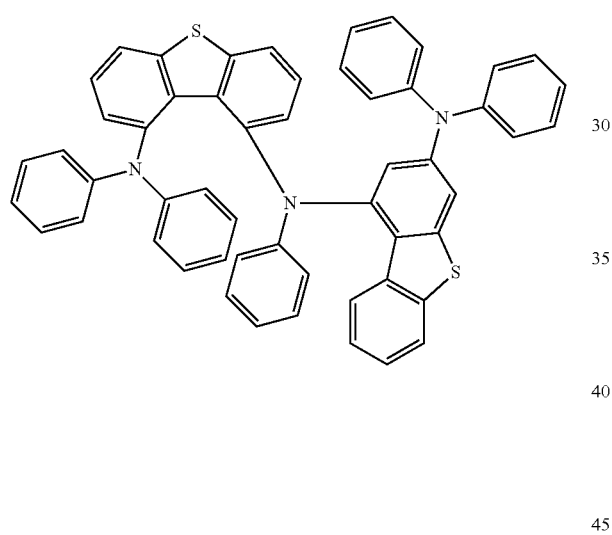
P-37
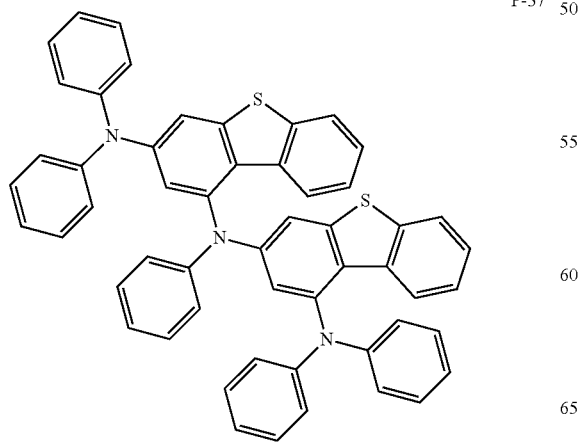
P-38
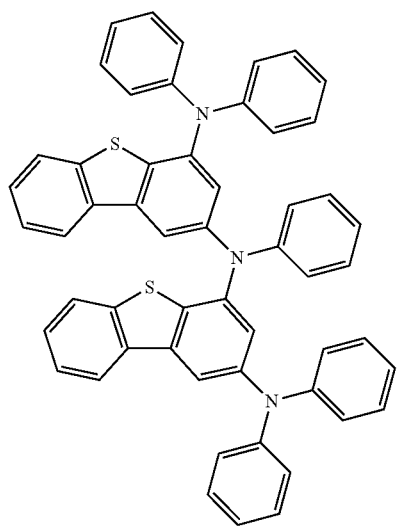
P-39
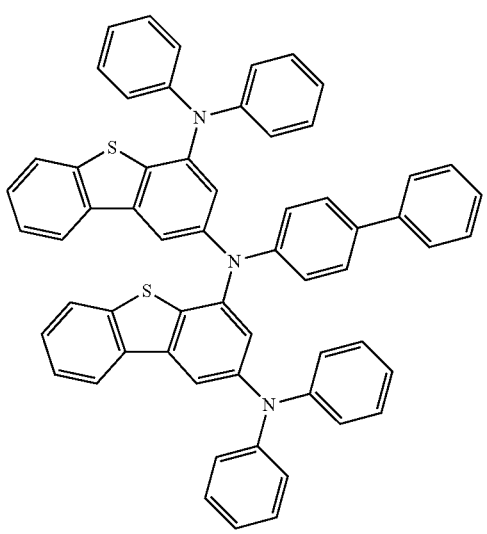
P-40
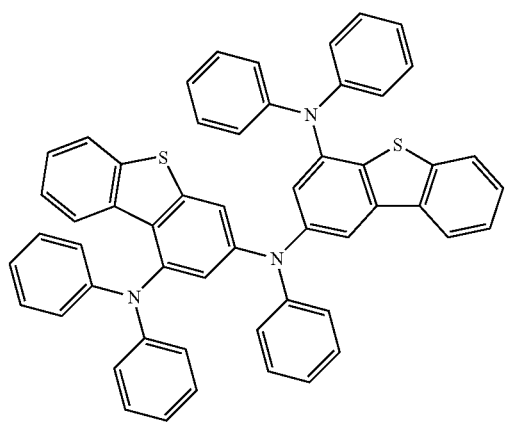

P-41
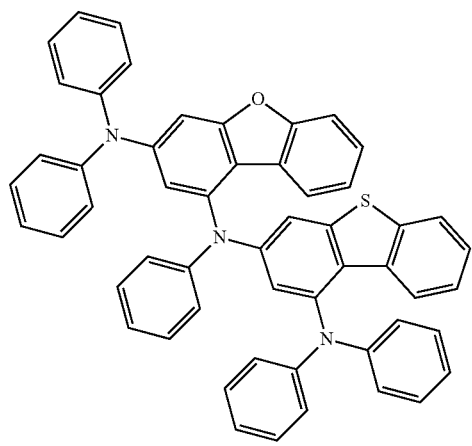
P-42
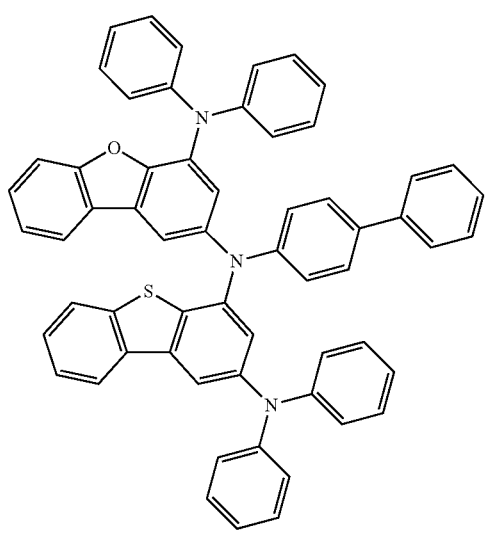
P-43
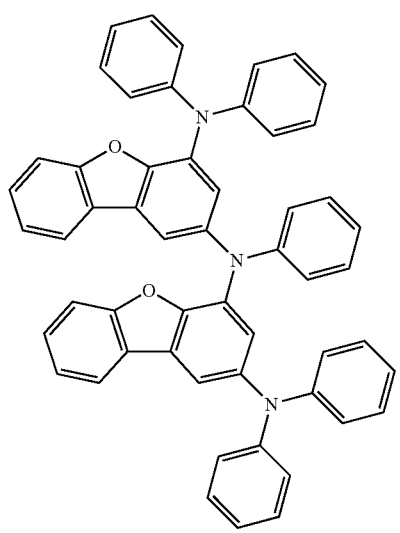
P-44
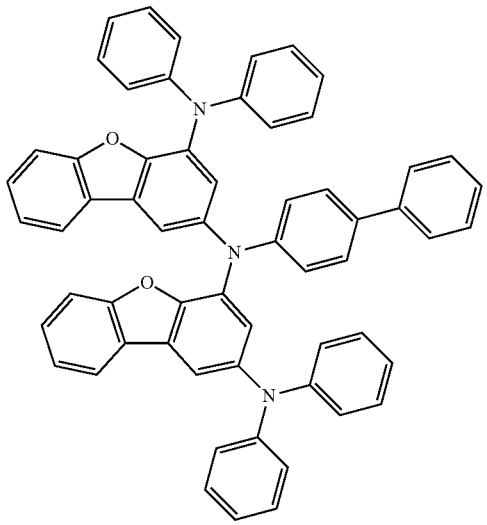
P-45
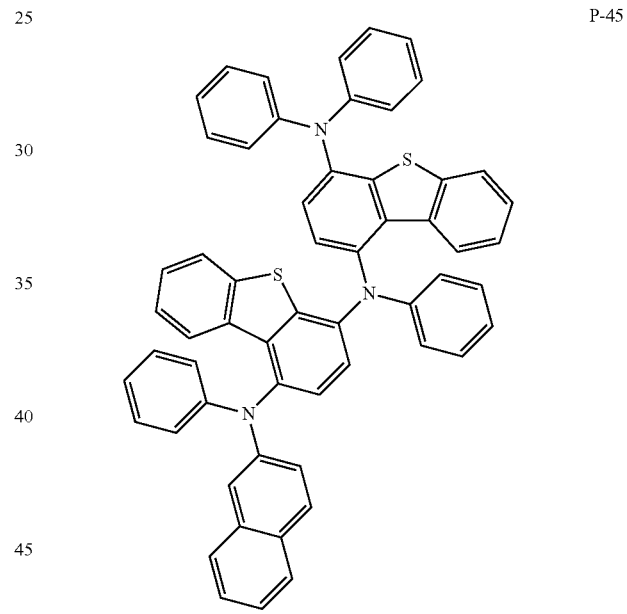
P-46
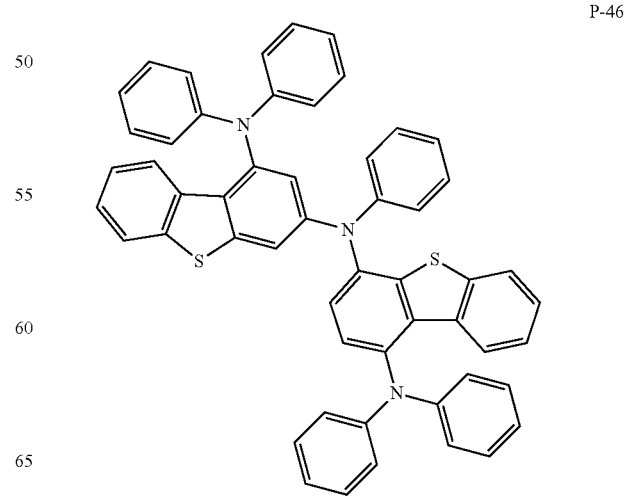

P-47
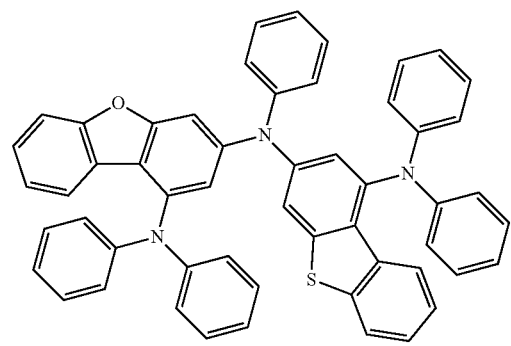
P-48
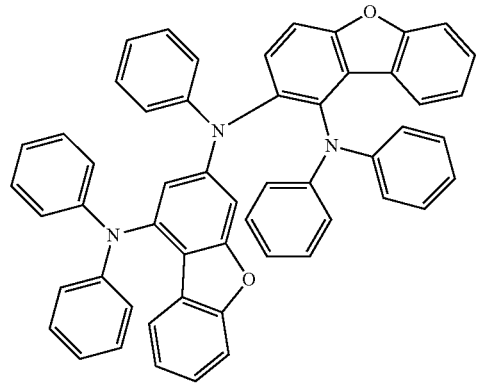
P-49
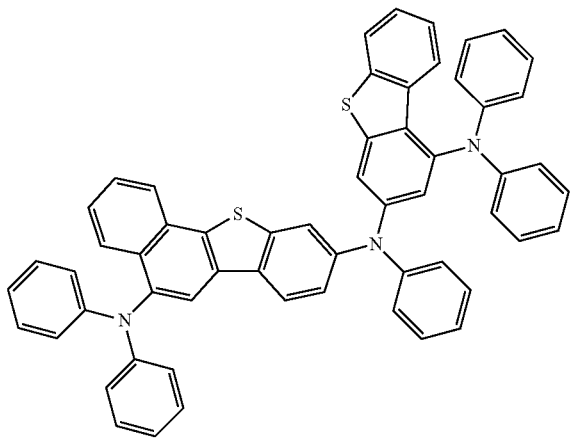
P-50
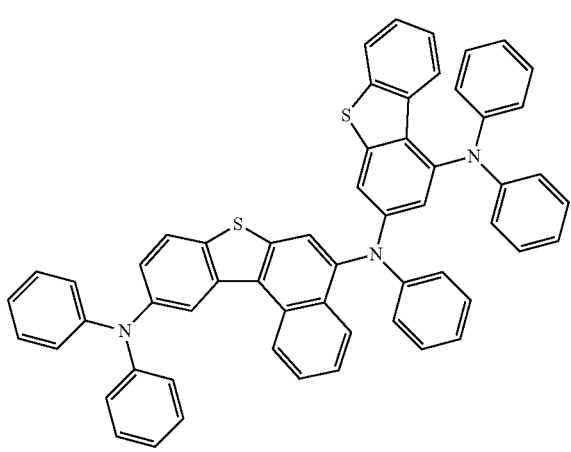
P-51
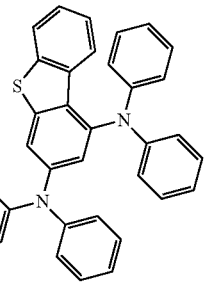
P-52
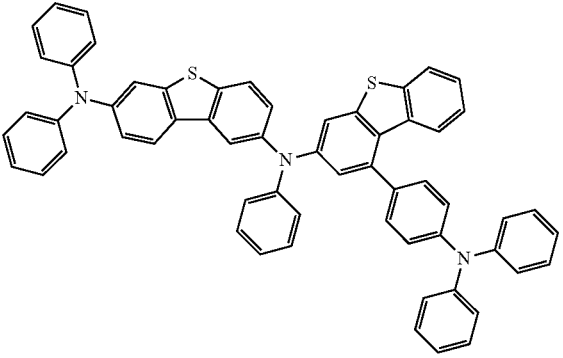
P-53
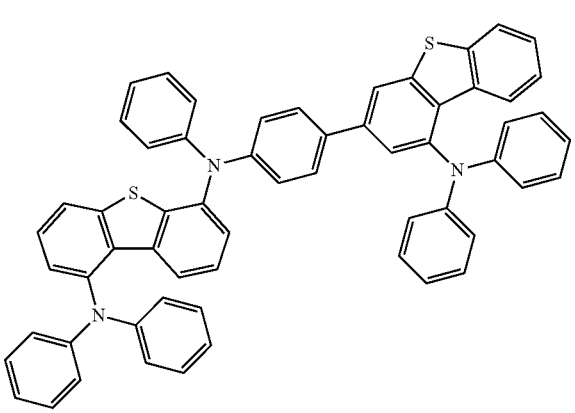

-continued
P-54
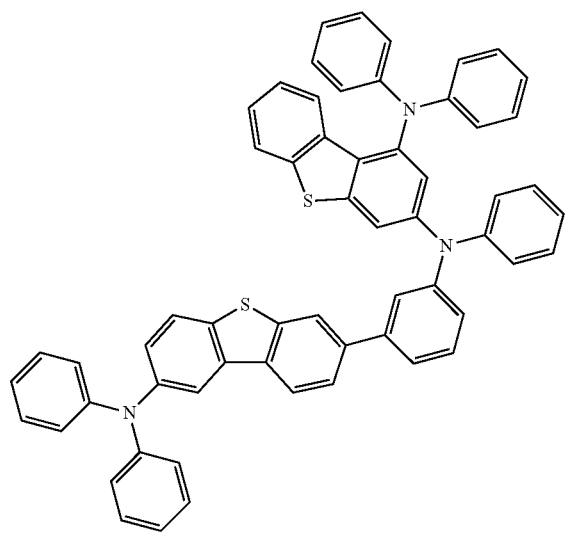
P-55
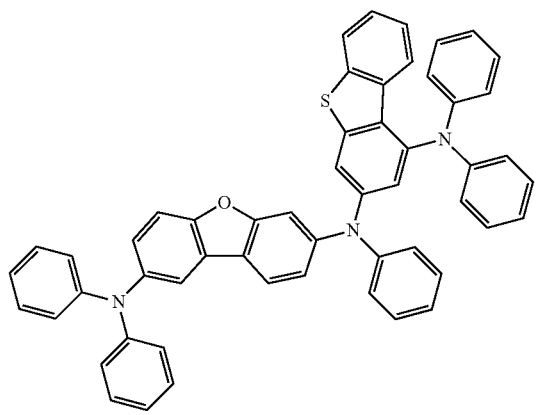
P-56
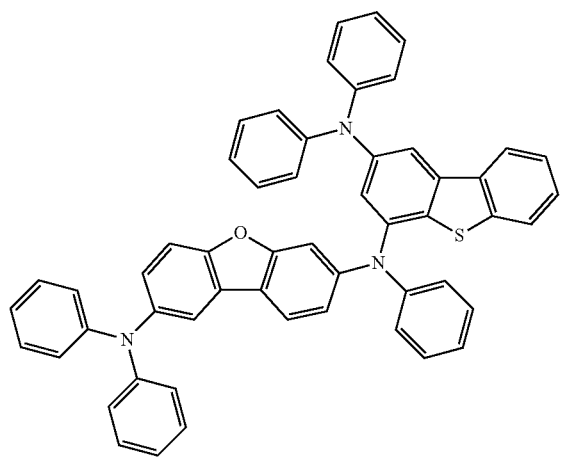
-continued
P-57
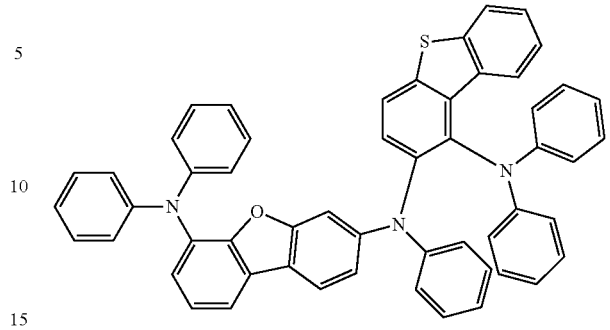
P-58
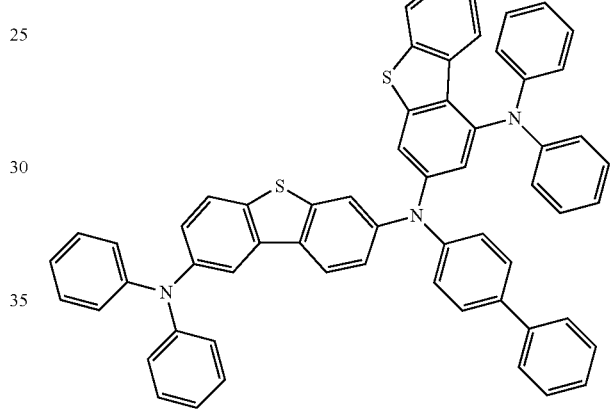
P-59
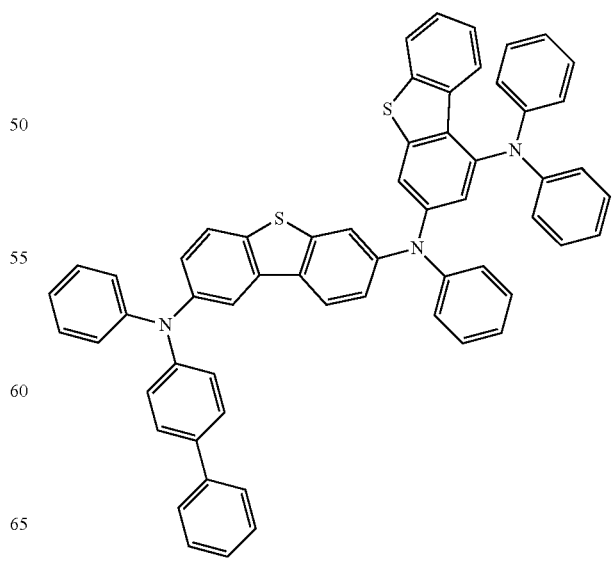

-continued
P-60
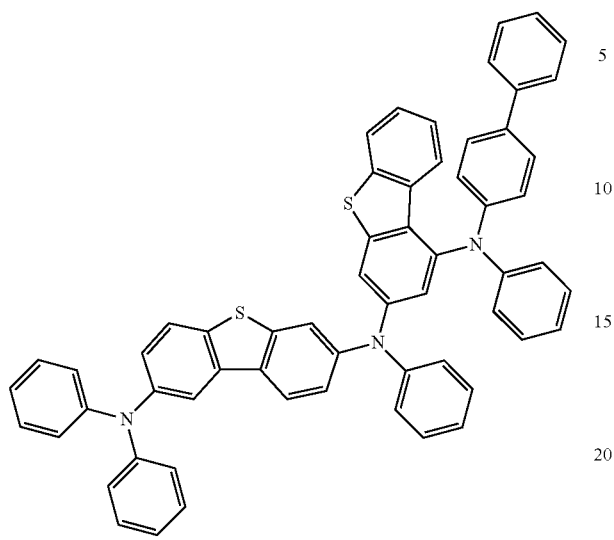
P-61
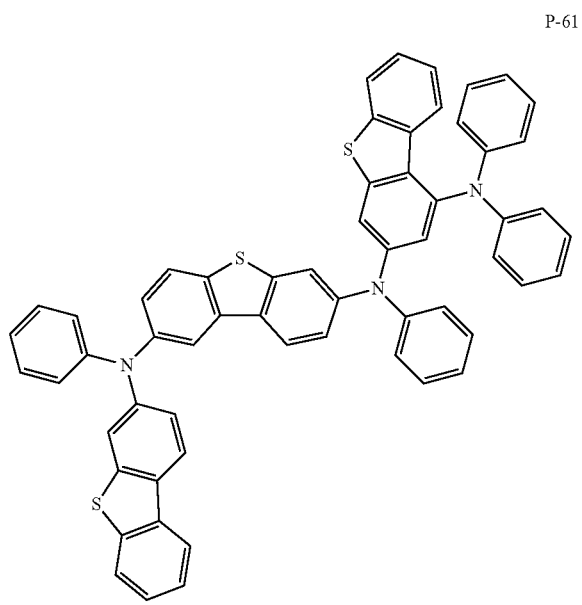
P-62
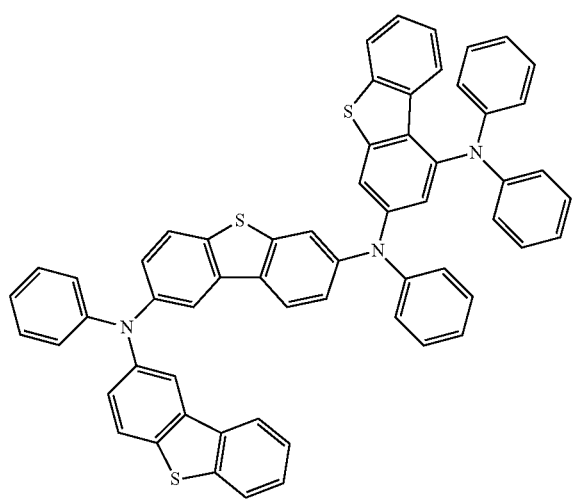
-continued
P-63
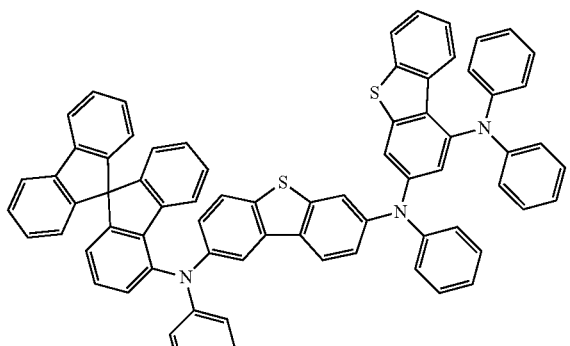
P-64
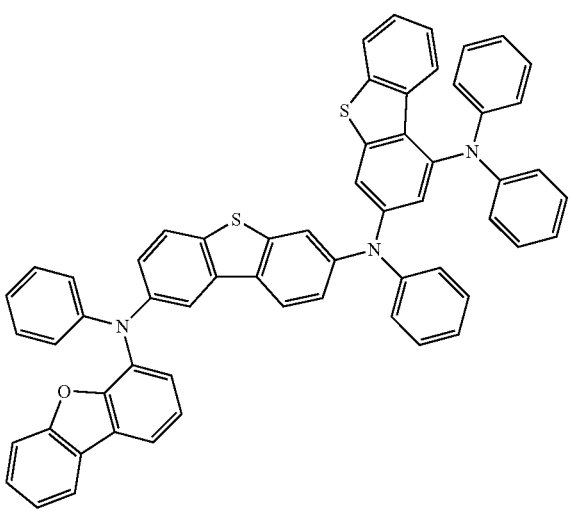
P-65
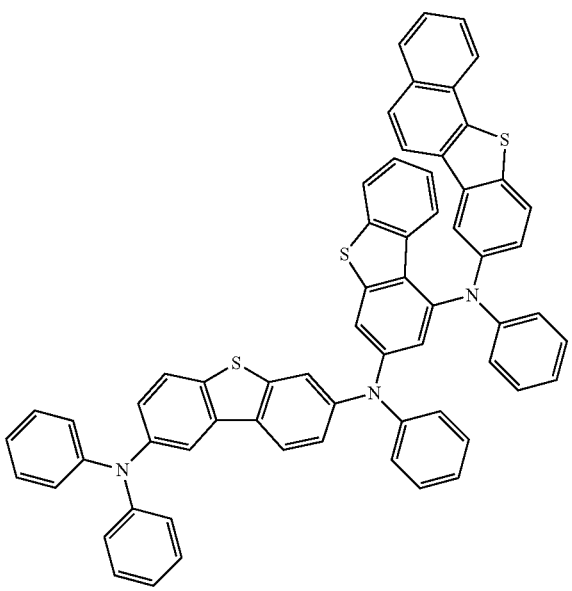

P-66
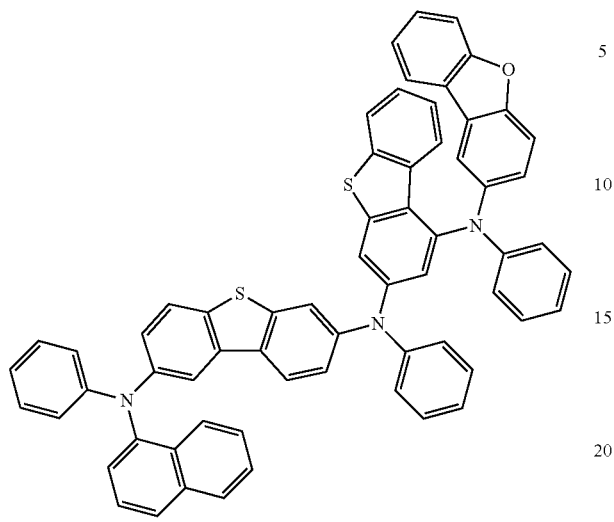
P-67
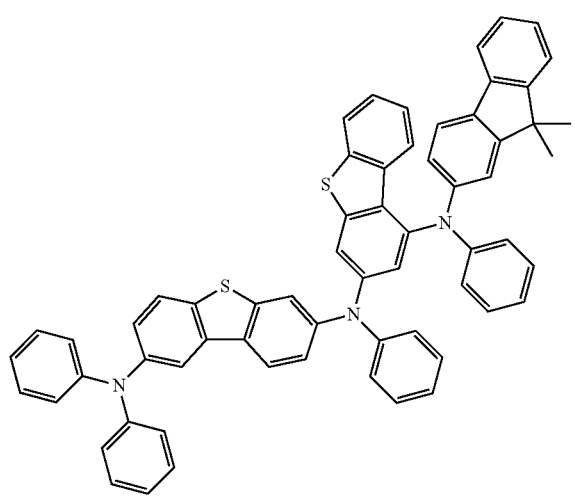
P-68
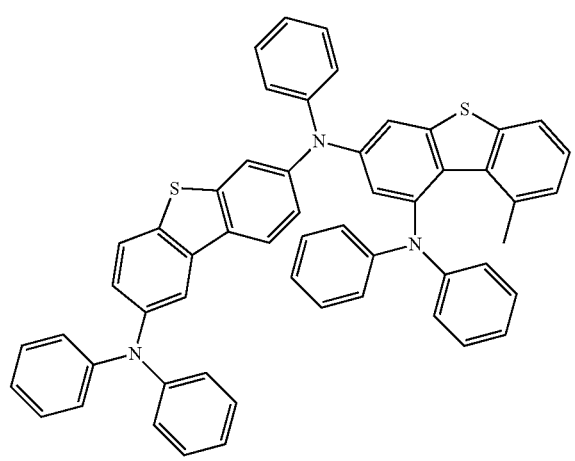
P-69
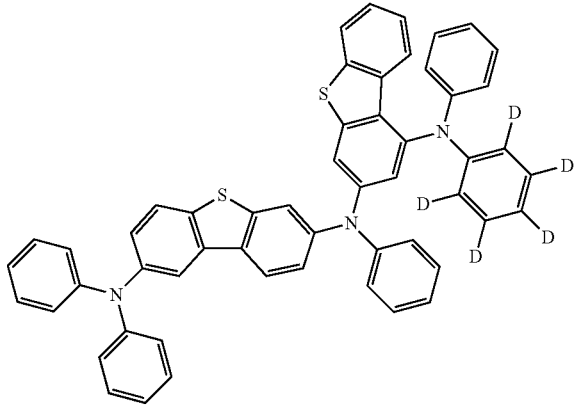
P-70
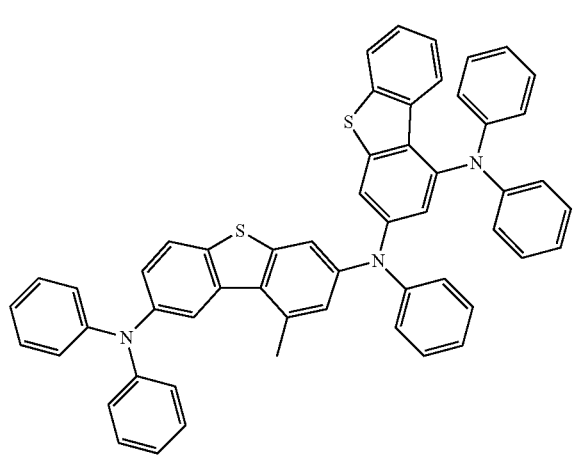
P-71

-continued
P-72
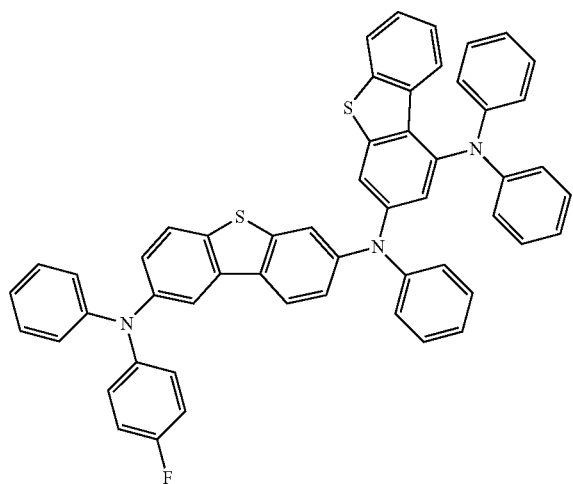
P-73
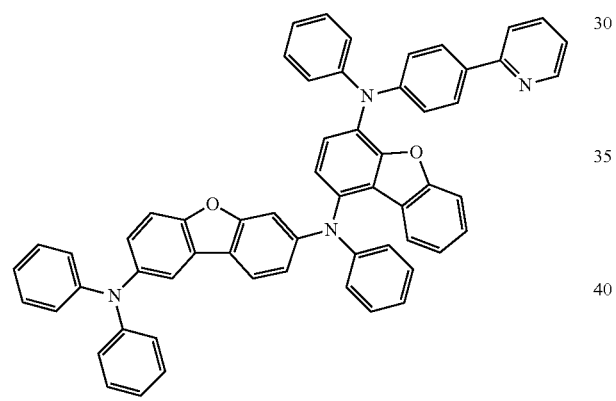
P-74
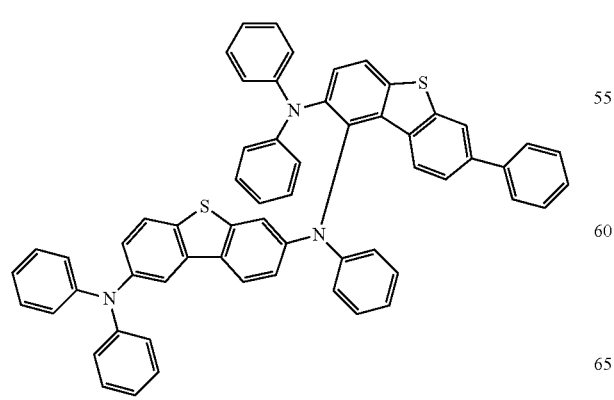
-continued
P-75
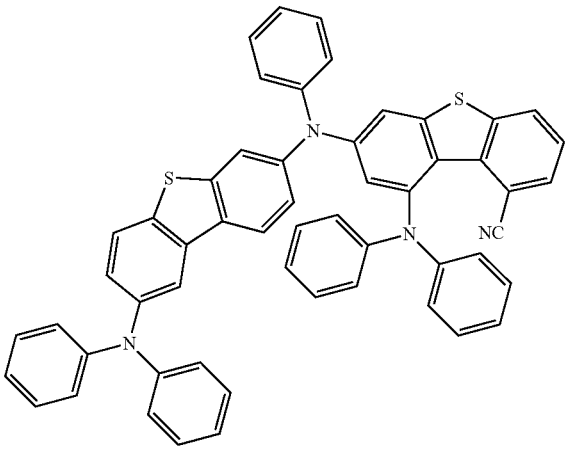
P-76
P-77
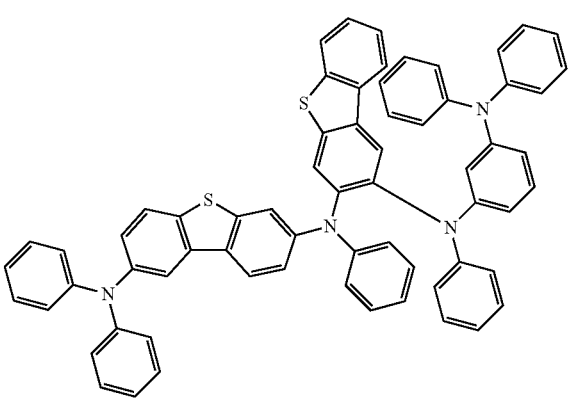

P-78
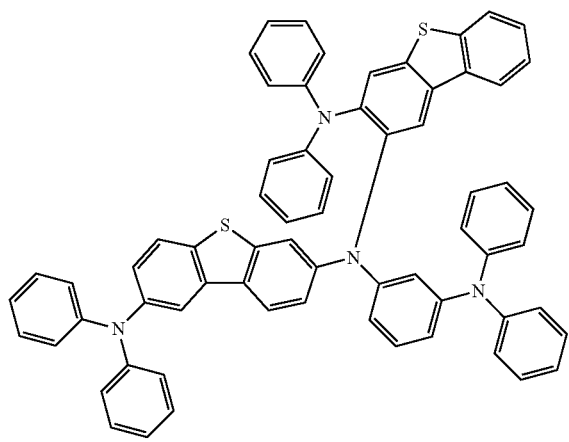
P-81
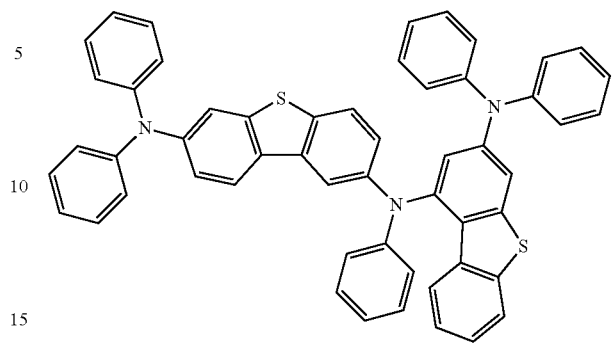
P-79
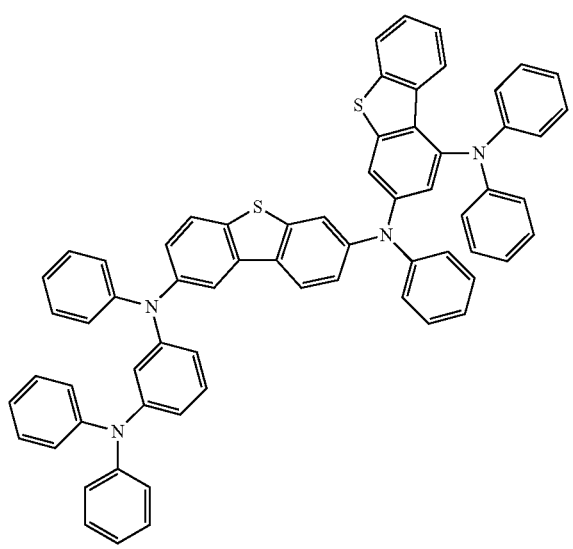
P-82
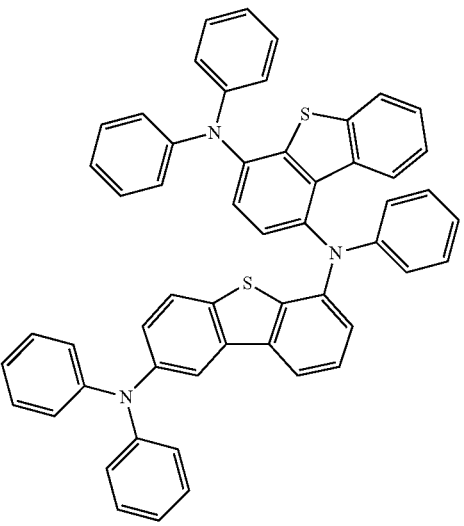
P-80
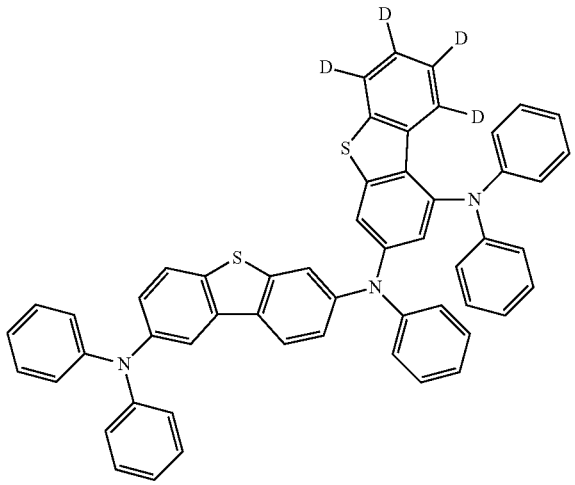
P-83
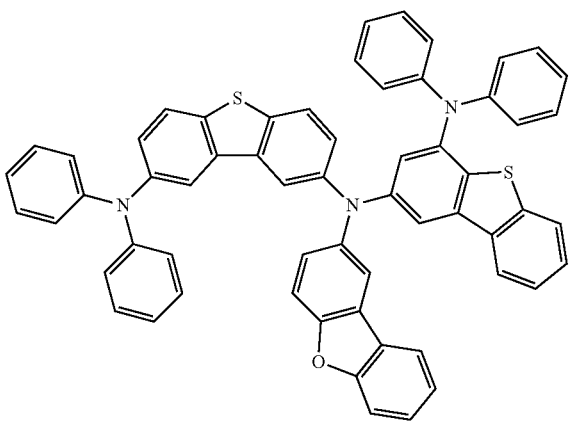

P-84
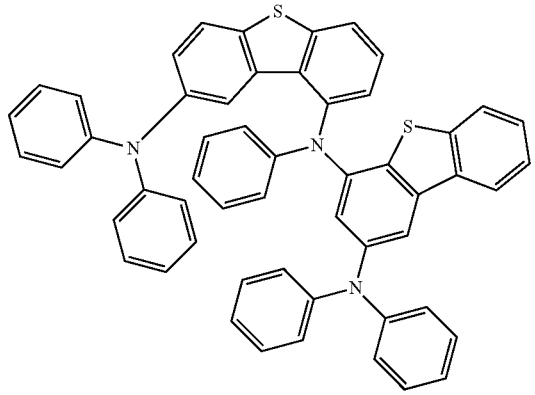
P-85
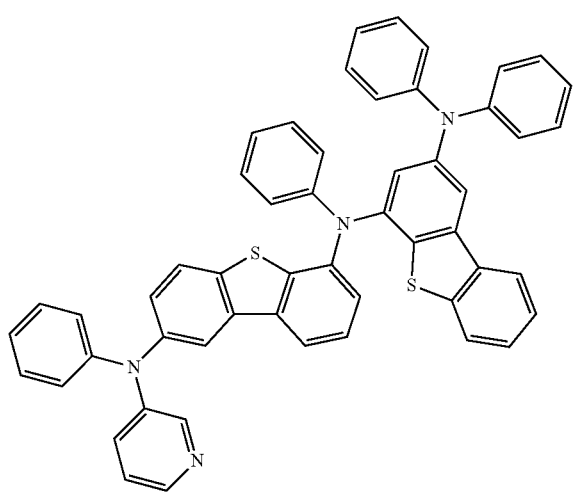
P-86
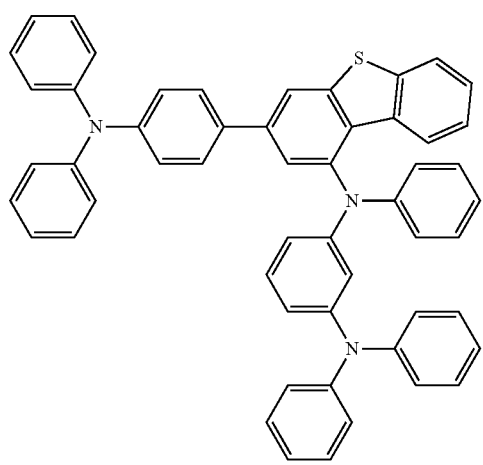
P-87
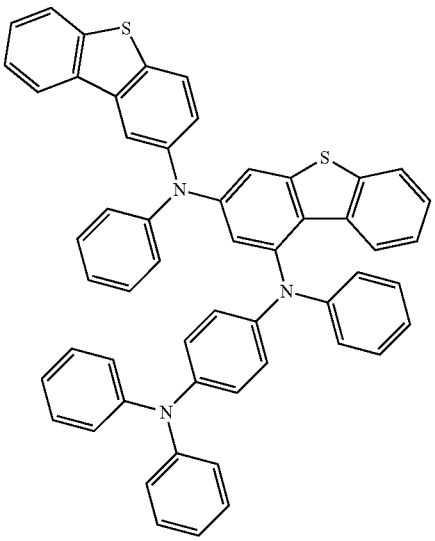
P-88
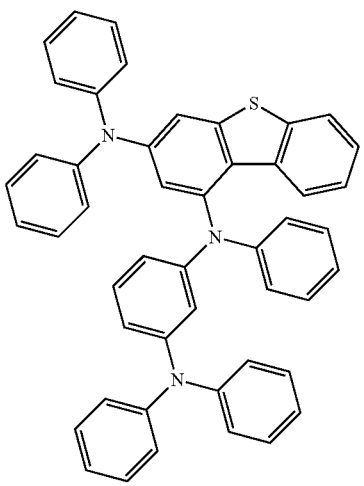
P-89
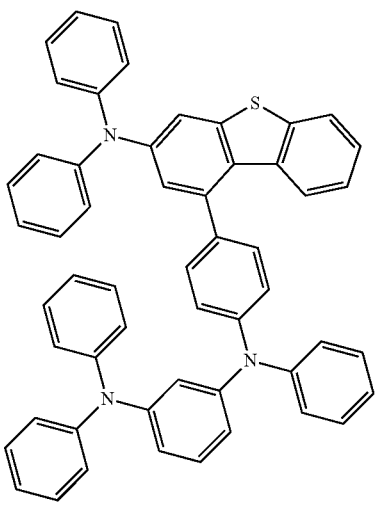

P-90
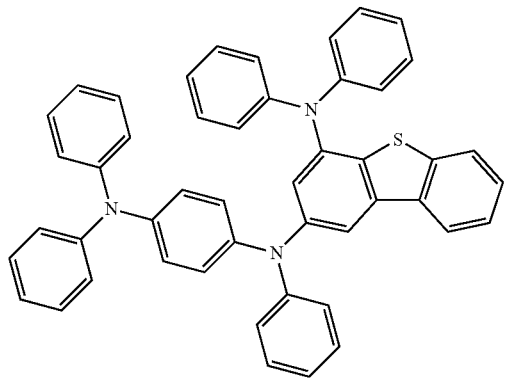
P-94
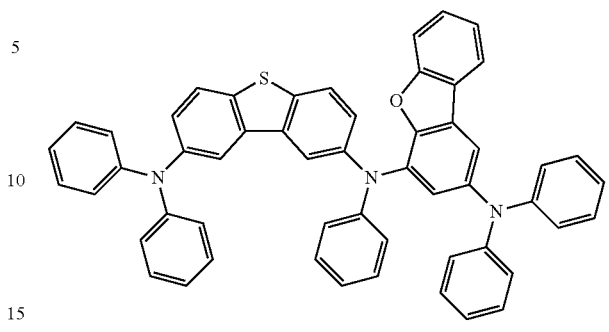
P-91
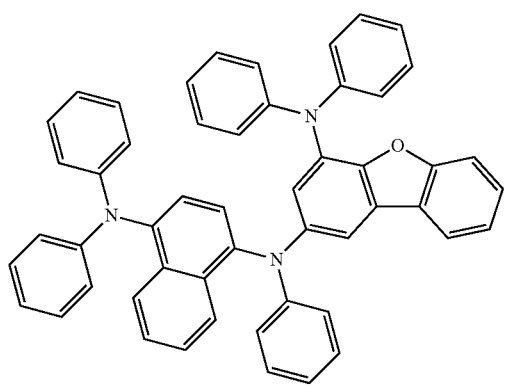
P-95
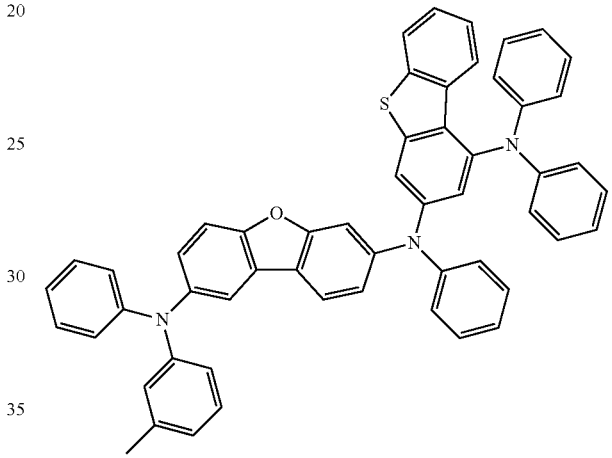
P-92
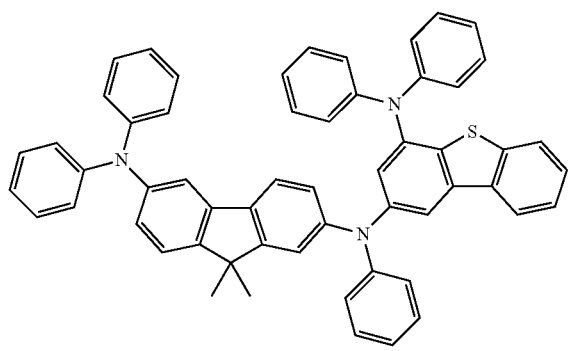
P-96
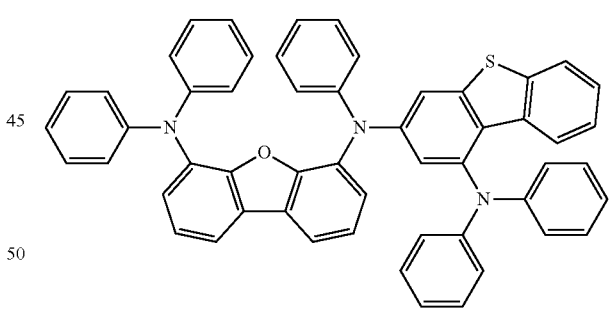
P-93
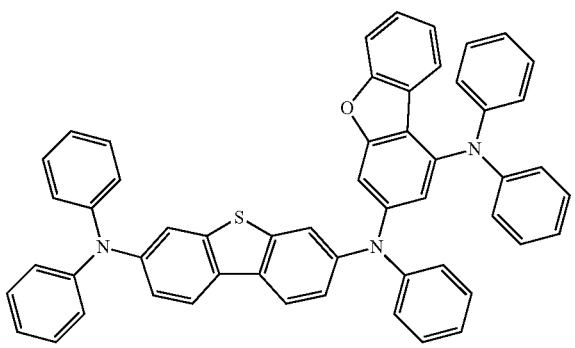
P-97
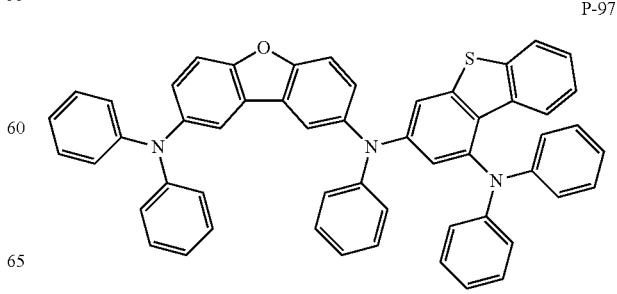

P-98
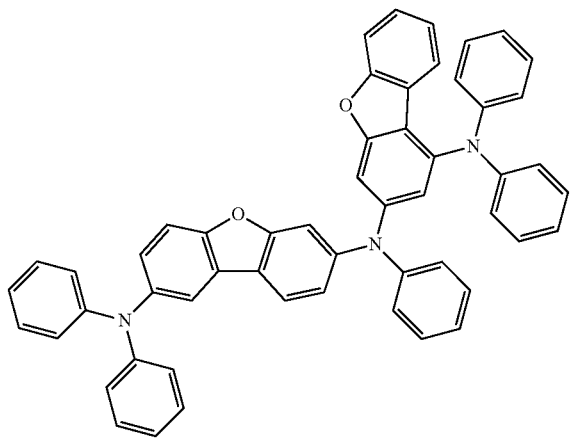
P-99
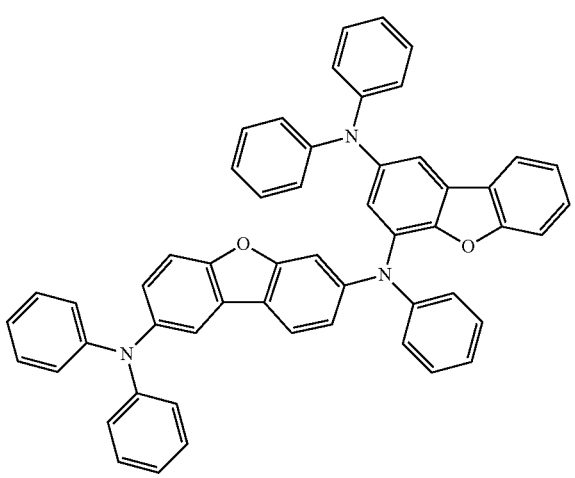
P-100
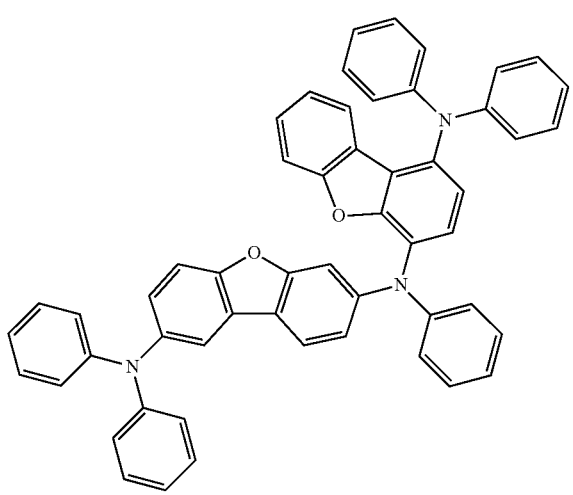
P-101
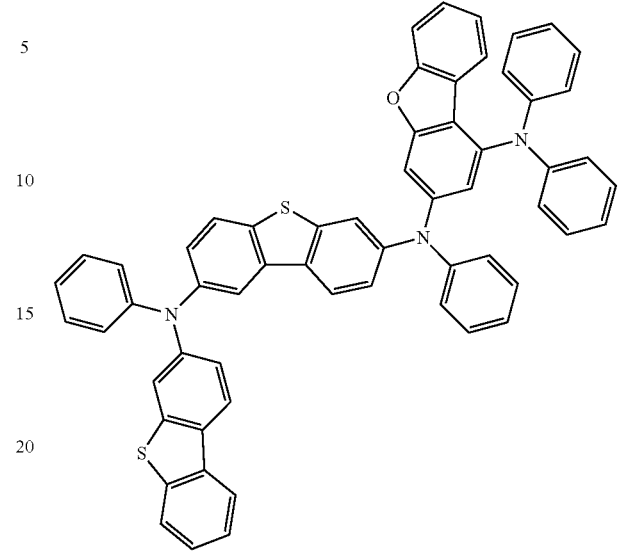
P-102
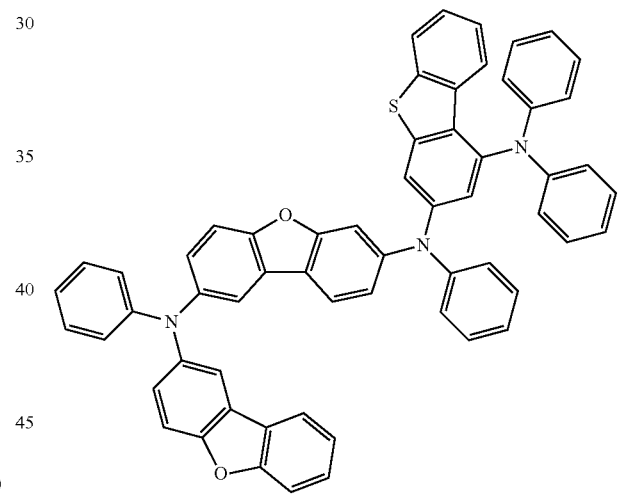
P-103
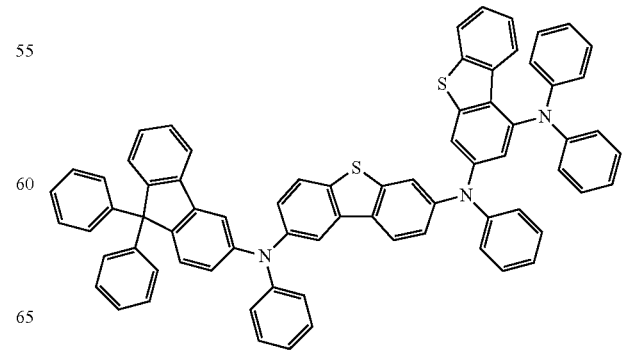

-continued
P-104
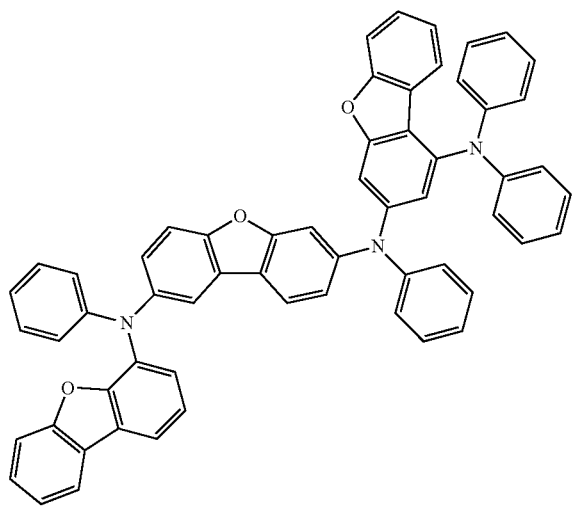
P-105
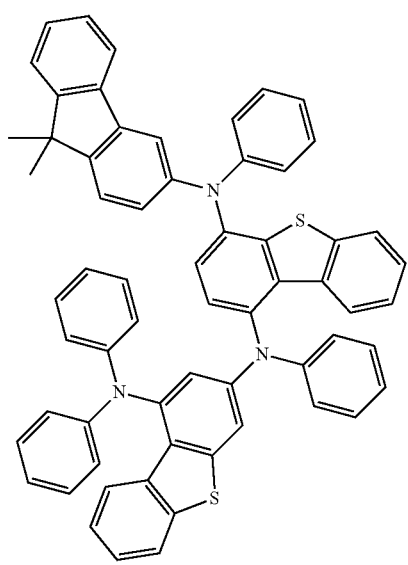
P-106
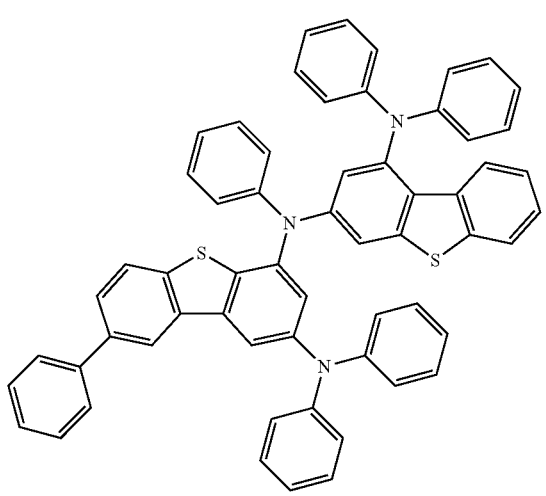
P-107
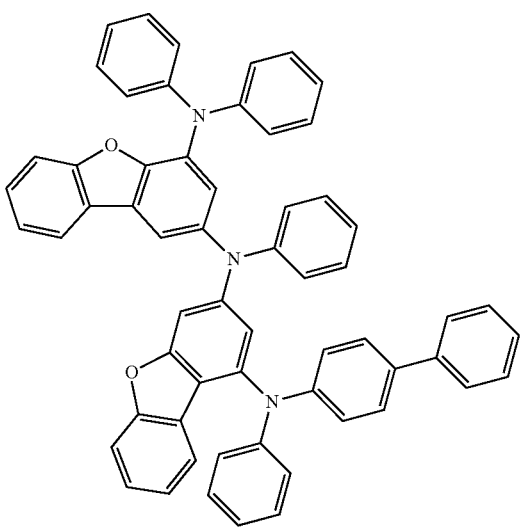
P-108
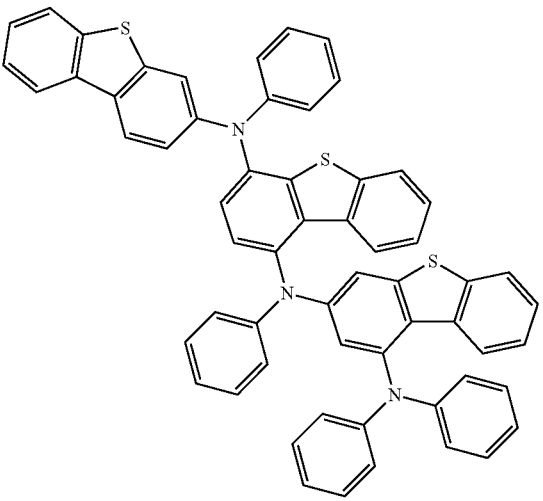

P-109
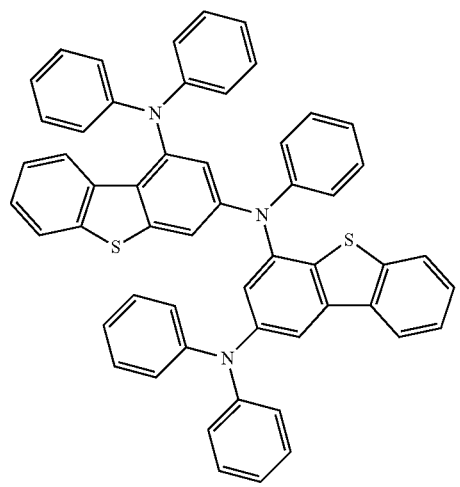
P-110
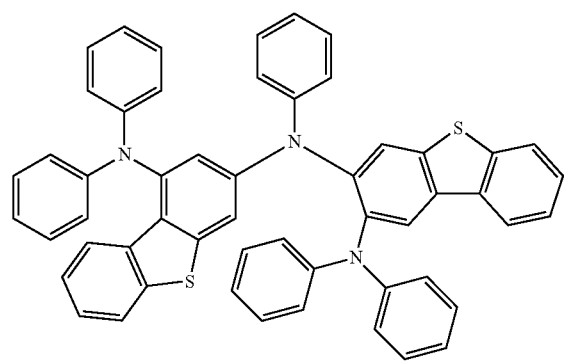
P-111
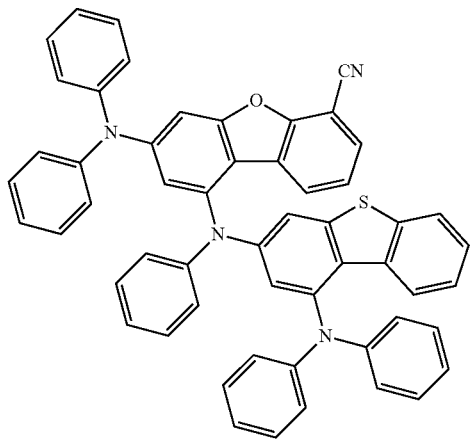
P-112
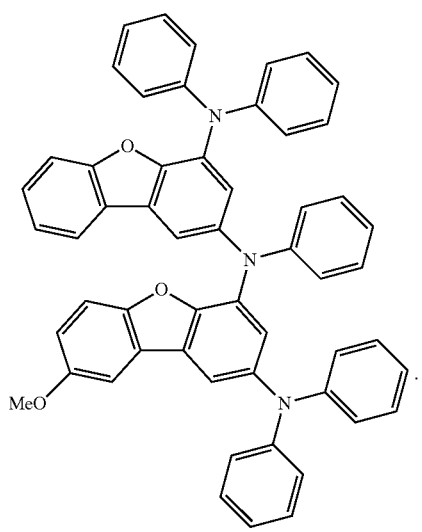
* * * * *